(12) United States Patent
Bartolozzi et al.

(10) Patent No.: US 9,174,980 B2
(45) Date of Patent: Nov. 3, 2015

(54) HETEROCYCLIC COMPOUNDS AS INHIBITORS OF LEUKOTRIENE PRODUCTION

(71) Applicants: Alessandra Bartolozzi, Norwalk, CT (US); Zhidong Chen, New Milford, CT (US); Jonathon Alan Dines, Abingdon (GB); Ho Yin Lo, Bethel, CT (US); Pui Leng Loke, Abingdon (GB); Alan Olague, Danbury, CT (US); Doris Riether, Biberach an der Riss (DE); Heather Tye, Abingdon (GB); Lifen Wu, New Milford, CT (US); Renee M. Zindell, New Milford, CT (US)

(72) Inventors: Alessandra Bartolozzi, Norwalk, CT (US); Zhidong Chen, New Milford, CT (US); Jonathon Alan Dines, Abingdon (GB); Ho Yin Lo, Bethel, CT (US); Pui Leng Loke, Abingdon (GB); Alan Olague, Danbury, CT (US); Doris Riether, Biberach an der Riss (DE); Heather Tye, Abingdon (GB); Lifen Wu, New Milford, CT (US); Renee M. Zindell, New Milford, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/752,640

(22) Filed: Jan. 29, 2013

(65) Prior Publication Data

US 2013/0196967 A1    Aug. 1, 2013

Related U.S. Application Data

(60) Provisional application No. 61/592,912, filed on Jan. 31, 2012.

(51) Int. Cl.

| | | |
|---|---|---|
| C07D 403/10 | (2006.01) |
| A61K 31/404 | (2006.01) |
| C07D 471/04 | (2006.01) |
| C07D 409/14 | (2006.01) |
| C07D 413/14 | (2006.01) |
| C07D 403/14 | (2006.01) |
| C07D 417/14 | (2006.01) |
| C07D 413/10 | (2006.01) |
| C07D 417/10 | (2006.01) |
| C07D 405/14 | (2006.01) |
| C07D 401/14 | (2006.01) |
| C07D 401/12 | (2006.01) |

(52) U.S. Cl.
CPC ........... *C07D 471/04* (2013.01); *A61K 31/404* (2013.01); *C07D 401/12* (2013.01); *C07D 401/14* (2013.01); *C07D 403/10* (2013.01); *C07D 403/14* (2013.01); *C07D 405/14* (2013.01); *C07D 409/14* (2013.01); *C07D 413/10* (2013.01); *C07D 413/14* (2013.01); *C07D 417/10* (2013.01); *C07D 417/14* (2013.01)

(58) Field of Classification Search
CPC .......................... C07D 403/10; A61K 31/404
USPC ......................................... 544/331; 514/275
See application file for complete search history.

(56) References Cited

U.S. PATENT DOCUMENTS

| | | | |
|---|---|---|---|
| 5,668,150 A | 9/1997 | Brooks et al. | |
| 8,580,829 B2 * | 11/2013 | Bartolozzi et al. | 514/364 |
| 8,658,661 B2 * | 2/2014 | Bartolozzi et al. | 514/275 |

FOREIGN PATENT DOCUMENTS

| | | |
|---|---|---|
| WO | 2006044602 A2 | 4/2006 |
| WO | 2006136829 A2 | 12/2006 |
| WO | 2007120574 A2 | 10/2007 |
| WO | 2008030369 A1 | 3/2008 |
| WO | 2008156721 A1 | 12/2008 |
| WO | WO 2012/027322 * | 3/2012 |

OTHER PUBLICATIONS

International Preliminary Report on Patentability for PCT/US2013/023539 filed on Jan. 29, 2013.

* cited by examiner

*Primary Examiner* — Deepak Rao
(74) *Attorney, Agent, or Firm* — Michael P. Morris; Usha R. Patel

(57) ABSTRACT

The present invention relates to compound of formula (I):

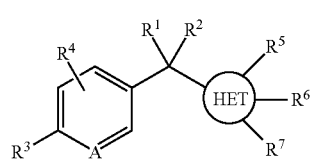

or pharmaceutically acceptable salts thereof, wherein $R^1$-$R^7$, A and HET are as defined herein. The invention also relates to pharmaceutical compositions comprising these compounds, methods of using these compounds in the treatment of various diseases and disorders, processes for preparing these compounds and intermediates useful in these processes.

9 Claims, No Drawings

HETEROCYCLIC COMPOUNDS AS INHIBITORS OF LEUKOTRIENE PRODUCTION

FIELD OF THE INVENTION

This invention relates to oxadiazoles that are useful as inhibitors of five lipoxygenase activating protein (FLAP) and are thus useful for treating a variety of diseases and disorders that are mediated or sustained through the activity of leukotrienes including asthma, allergy, rheumatoid arthritis, multiple sclerosis, inflammatory pain, acute chest syndrome and cardiovascular diseases including atherosclerosis, myocardial infarction and stroke. This invention also relates to pharmaceutical compositions comprising these compounds, methods of using these compounds in the treatment of various diseases and disorders, processes for preparing these compounds and intermediates useful in these processes.

BACKGROUND OF THE INVENTION

Leukotrienes (LTs) and the biosynthetic pathway from arachidonic acid leading to their production have been the targets of drug discovery efforts for over twenty years. LTs are produced by several cell types including neutrophils, mast cells, eosinophils, basophils monocytes and macrophages. The first committed step in the intracellular synthesis of LTs involves oxidation of arachidonic acid by 5-lipoxygenase (5-LO) to LTA4, a process requiring the presence of the 18 kD integral membrane protein 5-lipoxygenase-activating protein (FLAP) (D. K. Miller et al., Nature, 1990, 343, 278-281; R. A. F. Dixon et al., Nature, 1990, 343, 282-284). Subsequent metabolism of $LTA_4$ leads to $LTB_4$, and the cysteinyl LTs-$LTC_4$, $LTD_4$ and $LTE_4$ (B. Samuelsson, Science, 1983, 220, 568-575). The cysteinyl LTs have potent smooth muscle constricting and bronchoconstricting effects and they stimulate mucous secretion and vascular leakage. $LTB_4$ is a potent chemotactic agent for leukocytes, and stimulates adhesion, aggregation and enzyme release.

Much of the early drug discovery effort in the LT area was directed towards the treatment of allergy, asthma and other inflammatory conditions. Research efforts have been directed towards numerous targets in the pathway including antagonists of $LTB_4$ and the cysteinyl leukotrienes $LTC_4$, $LTD_4$ and $LTE_4$, as well as inhibitors of 5-lipoxygenase (5-LO), $LTA_4$ hydrolase and inhibitors of 5-lipoxygenase activating protein (FLAP) (R. W. Friesen and D. Riendeau, Leukotriene Biosynthesis Inhibitors, Ann. Rep. Med. Chem., 2005, 40, 199-214). Years of effort in the above areas have yielded a few marketed products for the treatment of asthma including a 5-LO inhibitor, zileuton, and LT antagonists, montelukast, pranlukast and zafirlukast.

More recent work has implicated LTs in cardiovascular disease, including myocardial infarction, stroke and atherosclerosis (G. Riccioni et al., J. Leukoc. Biol., 2008, 1374-1378). FLAP and 5-LO were among the components of the 5-LO and LT cascade found in atherosclerotic lesions, suggesting their involvement in atherogenesis (R. Spanbroek et al., Proc. Natl. Acad. Sci. U.S.A., 2003, 100, 1238-1243). Pharmacological inhibition of FLAP has been reported to decrease atherosclerotic lesion size in animal models. In one study, oral dosing of the FLAP inhibitor MK-886 to apoE/LDL-R double knockout mice fed a high-fat diet from 2 months of age to 6 months led to a 56% decrease in plaque coverage in the aorta and a 43% decrease in the aortic root (J. Jawien et al., Eur. J. Clin. Invest., 2006, 36, 141-146). This plaque effect was coupled with a decrease in plaque-macrophage content and a concomitant increase in collagen and smooth muscle content which suggests a conversion to a more stable plaque phenotype. In another study, it was reported that administration of MK-886 via infusion to $ApoE^{-/-}$ xCD4dnTβRII mice (apoE KO mice expressing a dominant-negative TGF-beta receptor which effectively removes all TGF-beta from the system) resulted in about a 40% decrease in plaque area in the aortic root (M. Back et al., Circ. Res., 2007, 100, 946-949). The mice were only treated for four weeks after plaque growth was already somewhat mature (12 weeks) thus raising the possibility of therapeutically treating atherosclerosis via this mechanism. In a study examining human atherosclerotic lesions, it was found that the expression of FLAP, 5-LO and $LTA_4$ hydrolase was significantly increased compared to healthy controls (H. Qiu et al., Proc. Natl. Acad. Sci. U.S.A., 103, 21, 8161-8166). Similar studies suggest that inhibition of the LT pathway, for example by inhibition of FLAP, would be useful for the treatment of atherosclerosis (for reviews, see M. Back Curr. Athero. Reports, 2008 10, 244-251 and Curr. Pharm. Des., 2009, 15, 3116-3132).

In addition to the work cited above, many other studies have been directed towards understanding the biological actions of LTs and the role of LTs in disease. These studies have implicated LTs as having a possible role in numerous diseases or conditions (for a review, see M. Peters-Golden and W. R. Henderson, Jr., M.D., N. Engl. J. Med., 2007, 357, 1841-1854). In addition to the specific diseases cited above, LTs have been implicated as having a possible role in numerous allergic, pulmonary, fibrotic, inflammatory and cardiovascular diseases, as well as cancer. Inhibition of FLAP is also reported to be useful for treating renal diseases such as diabetes-induced proteinuria (see for example J. M. Valdivieso et al., Journal of Nephrology, 2003, 16, 85-94 and A Montero et al., Journal of Nephrology, 2003, 16, 682-690).

A number of FLAP inhibitors have been reported in the scientific literature (see for example J. F. Evans et al., Trends in Pharmacological Sciences, 2008, 72-78) and in U.S. patents. Some have been evaluated in clinical trials for asthma, including MK-886, MK-591, and BAY X1005, also known as DG-031. More recently, the FLAP inhibitor AM-103 (J. H. Hutchinson et al., J. Med. Chem. 52, 5803-5815) has been evaluated in clinical trials, based on its anti-inflammatory properties (D. S. Lorrain et al., J. Pharm. Exp. Ther., 2009, DOI:10.1124/jpet.109.158089). Subsequently, it was replaced by the back-up compound AM-803 (GSK-2190915) for the treatment of respiratory diseases. DG-031 has also been in clinical trials to evaluate its effect on biomarkers for myocardial infarction risk and showed a dose-dependent suppression of several biomarkers for the disease (H. Hakonarson et al., JAMA, 2005, 293, 2245-2256). MK-591 was shown in a clinical trial to reduce proteinuria in human glomerulonephritis (see for example A. Guash et al., Kidney International, 1999, 56, 291-267).

However, to date, no FLAP inhibitor has been approved as a marketed drug.

BRIEF SUMMARY OF THE INVENTION

The present invention provides novel compounds which inhibit 5-lipoxygenase activating protein (FLAP) and are thus useful for treating a variety of diseases and disorders that are mediated or sustained through the activity of leukotrienes, including allergic, pulmonary, fibrotic, inflammatory and cardiovascular diseases and cancer. This invention also relates to pharmaceutical compositions comprising these compounds, methods of using these compounds in the treatment of various diseases and disorders, processes for preparing these compounds and intermediates useful in these processes.

DETAILED DESCRIPTION OF THE INVENTION

In its first broadest embodiment, the present invention relates to a compound of formula I:

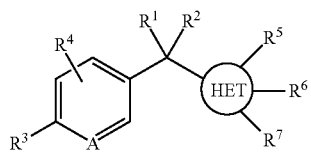

wherein:
A is carbon or nitrogen;
$R^1$ and $R^2$ are each independently hydrogen, $C_{1-7}$ alkyl or $C_{3-10}$carbocycle, with the proviso that both $R^1$ and $R^2$ are not simultaneously hydrogen;
or
$R^1$ and $R^2$ together with the carbon atom to which they are attached form a $C_{3-10}$ carbocyclic ring or a 5-11 membered heterocyclic ring, wherein each carbocycle or heterocycle is optionally independently substituted with one to two groups selected from $C_{1-6}$ alkyl and halogen;
or
$R^1$ and $R^2$ are each independently $C_{1-6}$ alkyl, hydroxy, $C_{1-3}$ alkyl-O—$C_{1-3}$ alkyl or —O—$C_{1-3}$alkyl;
$R^3$ is a 5-11 membered heteroaryl ring containing one to three heteroatoms selected from nitrogen, oxygen and sulfur, wherein the heteroaryl ring is optionally independently substituted with one to three groups selected from $C_{1-5}$alkyl, —O—$C_{1-5}$alkyl, $C_{1-3}$ alkylhydroxy, halogen, hydroxy, amino, $C_{1-6}$ alkylamino and $C_{1-3}$ dialkylamino;
or
$R^3$ is —O-heteroaryl or —O—$C_{1-3}$alkyl-heteroaryl;
$R^4$ is hydrogen, $C_{1-3}$ alkyl, halogen or nitrile;
HET is a 5-11 membered heteroaryl group selected from indolyl, pyrrolopyridinyl, indazolyl, benzimidazolyl, benzoxazolyl, benzothiazolyl, imidazopyridinyl, quinolinyl, isoquinolinyl, 3-pyridinyl, pyrimidinyl, pyridazinyl, pyrazinyl, pyrrolyl, imidazolyl, oxazolyl, thiazolyl, isoxazolyl, pyrazolyl, triazolyl, thiadiazolyl,

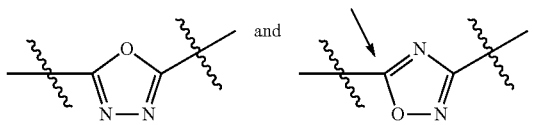 [SMILES: *c1nnc(*)o1 ; *c1noc(*)n1]

wherein the ring carbon atom identified in the oxadiazole ring, with an arrow, is attached to the carbon atom bearing $R^1$ and $R^2$;
$R^5$, $R^6$ and $R^7$ are each independently selected from
(a) —H,
(b) —OH,
(c) halogen,
(d) —CN,
(e) $C_{1-6}$alkyl optionally substituted with one to three —OH, —O—$C_{1-6}$alkyl, —N($R^8$)($R^9$), —O—$C_{1-6}$alkyl-OH, —$CO_2R^8$, —C(O)N($R^8$)($R^9$) or —S(O)$_n C_{1-6}$alkyl, aryl optionally substituted with halogen, 5-11 membered heteroaryl ring optionally substituted with $C_{1-4}$ alkyl-OH, 3-8 membered heterocycle optionally substituted with $C_{1-4}$ alkyl,
(f) —O—$C_{1-6}$alkyl optionally substituted with 5-11 membered heteroaryl ring,
(g) —O-heterocycle
(h) —N($R^8$)($R^9$),
(i) —S(O)$_n C_{1-6}$alkyl,
(j) —S(O)$_n$aryl,
(k) —$CO_2R^8$,
(l) —C(O)N($R^8$)($R^9$),
(m) —S(O)$_2$N($R^8$)($R^9$),
(n') oxo,
(o) —C(O)—$C_{1-3}$ alkyl
(p) $C_{3-10}$ carbocycle,
(q) a 3-10 membered heterocyclic group optionally substituted with one to three $C_{1-6}$ alkyl groups,
(r) a 5-11 membered heteroaryl group optionally substituted with one to three substituents selected from $C_{1-4}$ alkyl, $C_{1-4}$ alkyl-OH, —O—$C_{1-4}$ alkyl, $C_{1-4}$ alkyl-N($R^8$)($R^9$), $C_{1-4}$ alkyl-C(O)N($R^8$)($R^9$), —N($R^8$)($R^9$) and halogen,
(s) aryl optionally substituted with halogen;
$R^8$ and $R^9$ are each independently selected from —H, —$C_{1-6}$ alkyl, —C(O)$C_{1-6}$alkyl, and a 3-6 membered heterocyclic group, each of which is optionally independently substituted with one to three $C_{1-6}$alkyl groups, —OH, —O—$C_{1-6}$alkyl, —C(O)N($R^{10}$)($R^{11}$), —S(O)$_n C_{1-6}$alkyl, —S(O)$_n$N($R^{10}$)($R^{11}$), CN, a 3-6 membered heterocyclic group which is optionally substituted with one to two groups selected from $C_{1-3}$ alkyl, —O$C_{1-6}$alkyl, and oxo;
or
$R^8$ and $R^9$ taken together with the nitrogen ring to which they are attached form a heterocyclyl ring optionally substituted with one to three —OH, CN, —O$C_{1-6}$alkyl or oxo;
$R^{10}$ and $R^{11}$ are each independently selected from —H and —$C_{1-6}$alkyl;
n is 0, 1 or 2;
or a pharmaceutically acceptable salt thereof.

In a second embodiment, the present invention relates to a compound as described in the broadest embodiment above, wherein:
A is carbon or nitrogen;
$R^1$ and $R^2$ are each independently hydrogen, methyl, ethyl, propyl, isopropyl, butyl, isobutyl, tert. butyl, pentyl, hexyl, with the proviso that both $R^1$ and $R^2$ are not simultaneously hydrogen;
or
$R^1$ and $R^2$ together with the carbon atom to which they are attached form a cyclopropyl, cyclobutyl, cyclopentyl, cylohexyl or tetrahydropyranyl ring each optionally independently substituted with one to two groups selected from $C_{1-3}$ alkyl and halogen;
or
$R^1$ and $R^2$ are each independently $C_{1-4}$ alkyl, hydroxy, $C_{1-2}$ alkyl-O—$C_{1-2}$ alkyl or —O—$C_{1-3}$alkyl
$R^3$ is pyridinyl, pyrimidinyl, pyrazinyl, pyridazinyl, pyrrolopyridinyl, pyrrolyl, imidazolyl, thienyl, furanyl or thiazolyl, wherein each heteroaryl ring is optionally independently substituted with one to three groups selected from $C_{1-3}$ alkyl, —O—$C_{1-3}$ alkyl, $C_{1-3}$ alkylhydroxy, halogen, hydroxy, amino, $C_{1-3}$alkylamino and $C_{1-3}$dialkylamino;
or
$R^3$ is —O-pyridinyl or —O—$CH_2$-pyridinyl;
$R^4$ is hydrogen, methyl or fluoro;
HET is a 5-11 membered heteroaryl group selected from indolyl, pyrrolopyridinyl, indazolyl, benzimidazolyl, benzoxazolyl, benzothiazolyl, imidazopyridinyl, quinolinyl, isoquinolinyl, 3-pyridinyl, pyrimidinyl, pyridazinyl, pyrazinyl, pyrrolyl, imidazolyl, oxazolyl, thiazolyl, isoxazolyl, pyrazolyl, triazolyl, thiadiazolyl,

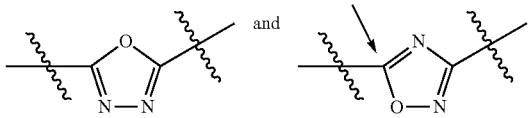 [SMILES: *c1nnc(*)o1 ; *c1noc(*)n1]

wherein the ring carbon atom identified in the oxadiazole ring, with an arrow, is attached to the carbon atom bearing $R^1$ and $R^2$;

$R^5$, $R^6$ and $R^7$ are each independently selected from
(a) —H,
(b) —OH,
(c) halogen,
(d) —CN,
(e) $C_{1-6}$alkyl optionally substituted with one to three —OH, —O—$C_{1-6}$alkyl, —N($R^8$)($R^9$), —O—$C_{1-6}$alkyl-OH, —$CO_2R^8$, —C(O)N($R^8$)($R^9$) or —S(O)$_n C_{1-6}$alkyl, aryl optionally substituted with halogen, 5-11 membered heteroaryl ring optionally substituted with $C_{1-4}$ alkyl-OH, 3-8 membered heterocycle optionally substituted with $C_{1-4}$ alkyl,
(f) —O—$C_{1-6}$alkyl optionally substituted with 5-11 membered heteroaryl ring,
(g) —O-heterocycle
(h) —N($R^8$)($R^9$),
(i) —S(O)$_n C_{1-6}$alkyl,
(j) —S(O)$_n$aryl,
(k) —$CO_2R^8$,
(l) —C(O)N($R^8$)($R^9$),
(m) —S(O)$_2$N($R^8$)($R^9$),
(n') oxo,
(o) —C(O)—$C_{1-3}$ alkyl
(p) $C_{3-10}$ carbocycle,
(q) a 3-10 membered heterocyclic group optionally substituted with one to three $C_{1-6}$ alkyl groups,
(r) a 5-11 membered heteroaryl group optionally substituted with one to three substituents selected from $C_{1-4}$ alkyl, $C_{1-4}$ alkyl-OH, —O—$C_{1-4}$ alkyl, $C_{1-4}$ alkyl-N($R^8$)($R^9$), $C_{1-4}$ alkyl-C(O)N($R^8$)($R^9$), —N($R^8$)($R^9$) and halogen,
(s) aryl optionally substituted with halogen;

$R^8$ and $R^9$ are each independently selected from —H, —$C_{1-6}$ alkyl, —C(O)$C_{1-6}$alkyl, and a 3-6 membered heterocyclic group, each of which is optionally independently substituted with one to three $C_{1-6}$alkyl groups, —OH, —O—$C_{1-6}$alkyl, —C(O)N($R^{10}$)($R^{11}$), —S(O)$_n C_{1-6}$alkyl, —S(O) N($R^{11}$), CN, S(O)N(R N a 3-6 membered heterocyclic group which is optionally substituted with one to two groups selected from $C_{1-3}$ alkyl, —O$C_{1-6}$alkyl, and oxo;
or
$R^8$ and $R^9$ taken together with the nitrogen ring to which they are attached form a heterocyclyl ring optionally substituted with one to three —OH, CN, —O$C_{1-6}$alkyl or oxo;
$R^{10}$ and $R^{11}$ are each independently selected from —H and —$C_{1-6}$alkyl;
n is 1 or 2;
or a pharmaceutically acceptable salt thereof.

In a third embodiment, the present invention relates to a compound as described in any of the preceding embodiments above, wherein:

A is carbon;
or a pharmaceutically acceptable salt thereof.

In a fourth embodiment there is provided a compound of formula (I) as described in any of the preceding embodiments above, wherein:
A is nitrogen;
or a pharmaceutically acceptable salt thereof.

In a fifth embodiment there is provided a compound as described in any of the preceding embodiments above, wherein:
$R^1$ and $R^2$ are each independently hydrogen, methyl, ethyl, propyl, isopropyl, butyl, isobutyl, tert. butyl, pentyl, hexyl, with the proviso that both $R^1$ and $R^2$ are not simultaneously hydrogen;
or a pharmaceutically acceptable salt thereof.

In a sixth embodiment there is provided a compound as described in any of the preceding embodiments above, wherein:
$R^1$ and $R^2$ together with the carbon atom to which they are attached form a cyclopropyl, cyclobutyl, cyclopentyl, cylohexyl or tetrahydropyranyl ring;
or a pharmaceutically acceptable salt thereof.

In a seventh embodiment there is provided a compound as described in any of the preceding embodiments above, wherein:
$R^1$ and $R^2$ are each independently $C_{1-4}$ alkyl, hydroxy, $C_{1-2}$ alkyl-O—$CH_3$ or —O—$C_{1-2}$alkyl or a pharmaceutically acceptable salt thereof.

In an eighth embodiment there is provided a compound as described in any of the preceding embodiments above, wherein:
$R^3$ is pyridinyl, pyrimidinyl, pyrazinyl, pyridazinyl or pyrrolopyridinyl, wherein each heteroaryl ring is optionally independently substituted with one to three groups selected from $C_{1-3}$ alkyl, —O—$C_{1-3}$ alkyl, $C_{1-3}$ alkylhydroxy, halogen, hydroxy, amino, $C_{1-3}$alkylamino and $C_{1-3}$dialkylamino;
or a pharmaceutically acceptable salt thereof.

In a ninth embodiment there is provided a compound as described in any of the preceding embodiments above, wherein:
$R^4$ is hydrogen or methyl;
or a pharmaceutically acceptable salt thereof.

In a tenth embodiment there is provided a compound as described in any of the preceding embodiments above, wherein:
HET is a 5-11 membered heteroaryl group selected from indolyl, pyrrolopyridinyl, indazolyl, benzimidazolyl, benzoxazolyl, benzothiazolyl, imidazopyridinyl, quinolinyl and isoquinolinyl;
or a pharmaceutically acceptable salt thereof.

In an eleventh embodiment there is provided a compound as described in any of the preceding embodiments above, wherein:
HET is a 5-11 membered heteroaryl group selected from 3-pyridinyl, pyrimidinyl, pyridazinyl, pyrazinyl, pyrrolyl, imidazolyl, oxazolyl, thiazolyl, isoxazolyl, pyrazolyl, triazolyl, thiadiazolyl,

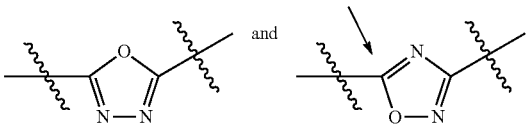

wherein the ring carbon atom identified in the oxadiazole ring, with an arrow, is attached to the carbon atom bearing $R^1$ and $R^2$;
or a pharmaceutically acceptable salt thereof.

In a twelfth embodiment there is provided a compound as described in any of the preceding embodiments above, wherein:

$R^5$, $R^6$ and $R^7$ are each independently selected from
- (a) —H,
- (b) —OH,
- (c) halogen,
- (d) —CN,
- (e) $C_{1-6}$alkyl optionally substituted with one to three —OH, —O—$C_{1-6}$alkyl, —N($R^8$)($R^9$), —O—$C_{1-6}$alkyl-OH, —$CO_2R^8$, —C(O)N($R^8$)($R^9$) or —S(O)$_2C_{1-3}$alkyl, phenyl optionally substituted with halogen, pyridinyl optionally substituted with $C_{1-4}$ alkyl-OH, tetrazolyl, piperazinyl optionally substituted with a methyl group,
- (f) —O—$C_{1-6}$alkyl optionally substituted with a quinolinyl or isoquinolinyl ring,
- (g) —O-heterocycle wherein the heterocycle is tetrahydrofuranyl or tetrahydropyranyl,
- (h) —N($R^8$)($R^9$),
- (i) —S(O)$_2C_{1-3}$alkyl,
- (j) —S(O)$_2$ phenyl,
- (k) —$CO_2R^8$,
- (l) —C(O)N($R^8$)($R^9$),
- (m) —S(O)$_2$N($R^8$)($R^9$),
- (n') oxo,
- (o) —C(O)—$C_{1-3}$ alkyl
- (p) $C_{3-10}$ carbocycle,
- (q) a piperazinyl group optionally substituted with a methyl group,
- (r) a 5-11 membered heteroaryl group selected from pyridinyl, pyrimidinyl, pyrazolyl, oxadiazolyl and tetrazolyl wherein each heteroaryl ring is optionally substituted with one to three substituents selected from $C_{1-4}$ alkyl, $C_{1-2}$ alkyl-OH, —O—$C_{1-2}$ alkyl, $C_{1-2}$alkyl-N($R^8$)($R^9$), $C_{1-4}$ alkyl-C(O)N($R^8$)($R^9$), —N($R^8$)($R^9$) and halogen,
- (s) phenyl ring optionally substituted with halogen;

$R^8$ and $R^9$ are each independently selected from —H, —$C_{1-6}$ alkyl, —C(O)$C_{1-6}$alkyl, and a 3-6 membered heterocyclic group, each of which is optionally independently substituted with one to three $C_{1-6}$alkyl groups, —OH, —O—$C_{1-6}$alkyl, —C(O)N($R^{10}$)($R^{11}$), —S(O)$_2C_{1-6}$alkyl, —S(O)$_2$N($R^{10}$)($R^{11}$), a 3-6 membered heterocyclic group which is optionally substituted with one to two groups selected from $C_{1-3}$ alkyl, —O$C_{1-3}$alkyl, and oxo;
or $R^8$ and $R^9$ taken together with the nitrogen ring to which they are attached form a heterocyclyl ring optionally substituted with one to three —OH, CN, —$OC_{1-3}$alkyl or oxo;

$R^{10}$ and $R^{11}$ are each independently selected from —H and —$C_{1-4}$alkyl;
or a pharmaceutically acceptable salt thereof.

In a thirteenth embodiment there is provided a compound, wherein:

A is carbon;

$R^1$ and $R^2$ are each independently methyl, ethyl, propyl, isopropyl, butyl, isobutyl, tert. butyl, pentyl or hexyl; or $R^1$ and $R^2$ together with the carbon atom to which they are attached form a cyclopropyl, cyclobutyl, cyclopentyl, cylohexyl or tetrahydropyranyl ring; or $R^1$ and $R^2$ are each independently $C_{1-4}$ alkyl, hydroxy, $C_{1-2}$ alkyl-O—$CH_3$ or —O—$C_{1-2}$alkyl;

$R^3$ is pyridinyl, pyrimidinyl or pyrrolopyridinyl, wherein each heteroaryl ring is optionally independently substituted with one to three groups selected from $C_{1-3}$ alkyl, —O—$C_{1-3}$ alkyl, $C_{1-3}$ alkylhydroxy, halogen, hydroxy, amino, $C_{1-3}$alkylamino and $C_{1-3}$dialkylamino;

$R^4$ is hydrogen;

HET is a 5-11 membered heteroaryl group selected from indolyl, pyrrolopyridinyl, indazolyl, benzimidazolyl, benzoxazolyl, benzothiazolyl, imidazopyridinyl, quinolinyl and isoquinolinyl;
or HET is a 5-11 membered heteroaryl group selected from 3-pyridinyl, pyrimidinyl, pyridazinyl, pyrazinyl, pyrrolyl, imidazolyl, oxazolyl, thiazolyl, isoxazolyl, pyrazolyl, triazolyl, thiadiazolyl,

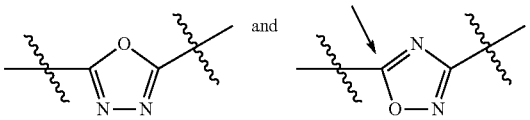 [SMILES: *c1nnc(*)o1 ; *c1noc(*)n1]

wherein the ring carbon atom identified in the oxadiazole ring, with an arrow, is attached to the carbon atom bearing $R^1$ and $R^2$;

$R^5$, $R^6$ and $R^7$ are each independently selected from
- (a) —H,
- (b) —OH,
- (c) halogen,
- (d) —CN,
- (e) $C_{1-6}$alkyl optionally substituted with one to three —OH, —O—$C_{1-6}$alkyl, —N($R^8$)($R^9$), —O—$C_{1-6}$alkyl-OH, —$CO_2R^8$, —C(O)N($R^8$)($R^9$) or —S(O)$_2C_{1-3}$alkyl, phenyl optionally substituted with halogen, pyridinyl optionally substituted with $C_{1-4}$ alkyl-OH, tetrazolyl, piperazinyl optionally substituted with a methyl group,
- (f) —O—$C_{1-6}$alkyl optionally substituted with a quinolinyl or isoquinolinyl ring,
- (g) —O-heterocycle wherein the heterocycle is tetrahydrofuranyl or tetrahydropyranyl,
- (h) —N($R^8$)($R^9$),
- (i) —S(O)$_2C_{1-3}$alkyl,
- (j) —S(O)$_2$ phenyl,
- (k) —$CO_2R^8$,
- (l) —C(O)N($R^8$)($R^9$),
- (m) —S(O)$_2$N($R^8$)($R^9$),
- (n') oxo,
- (o) —C(O)—$C_{1-3}$ alkyl
- (p) $C_{3-10}$ carbocycle,
- (q) a piperazinyl group optionally substituted with a methyl group,
- (r) a 5-11 membered heteroaryl group selected from pyridinyl, pyrimidinyl, pyrazolyl, oxadiazolyl and tetrazolyl wherein each heteroaryl ring is optionally substituted with one to three substituents selected from $C_{1-4}$ alkyl, $C_{1-2}$ alkyl-OH, —O—$C_{1-2}$ alkyl, $C_{1-2}$alkyl-N($R^8$)($R^9$), $C_{1-4}$ alkyl-C(O)N($R^8$)($R^9$), —N($R^8$)($R^9$) and halogen,
- (s) phenyl ring optionally substituted with halogen;

$R^8$ and $R^9$ are each independently selected from —H, —$C_{1-6}$ alkyl, —C(O)$C_{1-6}$alkyl, and a 3-6 membered heterocyclic group, each of which is optionally independently substituted with one to three $C_{1-6}$alkyl groups, —OH, —O—$C_{1-6}$alkyl, —C(O)N($R^{10}$)($R^{11}$), —S(O)$_2Cl\_6$alkyl, —S(O)$_2$N($R^{10}$)($R^{11}$), a 3-6 membered heterocyclic group which is optionally substituted with one to two groups selected from $C_{1-3}$ alkyl, —$OC_{1-3}$alkyl, and oxo;
or $R^8$ and $R^9$ taken together with the nitrogen ring to which they are attached form a heterocyclyl ring optionally substituted with one to three —OH, CN, —OC$_{1-3}$alkyl or oxo;

$R^{10}$ and $R^{11}$ are each independently selected from —H and —C$_{1-4}$alkyl;

or a pharmaceutically acceptable salt thereof.

In a fourteenth embodiment there is provided a compound as described in the thirteenth embodiment above, wherein:
HET is a 5-11 membered heteroaryl group selected from 3-pyridinyl, pyrimidinyl, pyridazinyl, pyrazinyl, pyrrolyl, imidazolyl, oxazolyl, thiazolyl, isoxazolyl, pyrazolyl, triazolyl, thiadiazolyl,

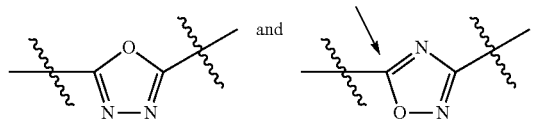 [SMILES: *c1nnc(*)o1 ; *c1noc(*)n1]

wherein the ring carbon atom identified in the oxadiazole ring, with an arrow, is attached to the carbon atom bearing $R^1$ and $R^2$;

or a pharmaceutically acceptable salt thereof.

In a fifteenth embodiment there is provided a compound as described in the thirteenth embodiment above, wherein:
HET is a 5-11 membered heteroaryl group selected from indolyl, pyrrolopyridinyl, indazolyl, benzimidazolyl, benzoxazolyl, benzothiazolyl, imidazopyridinyl, quinolinyl and isoquinolinyl;

or a pharmaceutically acceptable salt thereof.

In a sixteenth embodiment there is provided a compound as described in the fourteenth embodiment above, wherein:
HET is a 5-11 membered heteroaryl group selected from pyrrolyl, imidazolyl, oxazolyl, thiazolyl, isoxazolyl, pyrazolyl, triazolyl, thiadiazolyl,

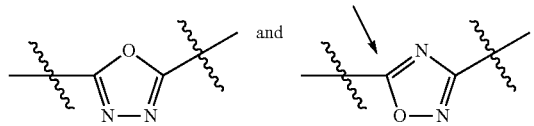 [SMILES: *c1nnc(*)o1 ; *c1noc(*)n1]

wherein the ring carbon atom identified in the oxadiazole ring, with an arrow, is attached to the carbon atom bearing $R^1$ and $R^2$;

or a pharmaceutically acceptable salt thereof.

In a seventeenth embodiment there is provided a compound, wherein:
A is nitrogen;
$R^1$ and $R^2$ are each independently methyl, ethyl, propyl, isopropyl, butyl, isobutyl, tert. butyl, pentyl or hexyl; or
$R^1$ and $R^2$ together with the carbon atom to which they are attached form a cyclopropyl, cyclobutyl, cyclopentyl, cylohexyl or tetrahydropyranyl ring; or
$R^1$ and $R^2$ are each independently C$_{1-4}$ alkyl, hydroxy, C$_{1-2}$ alkyl-O—CH$_3$ or —O—C$_{1-2}$alkyl;
$R^3$ is pyridinyl, pyrimidinyl or pyrrolopyridinyl, wherein each heteroaryl ring is optionally independently substituted with one to three groups selected from C$_{1-3}$ alkyl, —O—C$_{1-3}$ alkyl, C$_{1-3}$ alkylhydroxy, halogen, hydroxy, amino, C$_{1-3}$alkylamino and C$_{1-3}$dialkylamino;
$R^4$ is hydrogen;
HET is a 5-11 membered heteroaryl group selected from indolyl, pyrrolopyridinyl, indazolyl, benzimidazolyl, benzoxazolyl, benzothiazolyl, imidazopyridinyl, quinolinyl and isoquinolinyl;

or
HET is a 5-11 membered heteroaryl group selected from 3-pyridinyl, pyrimidinyl, pyridazinyl, pyrazinyl, pyrrolyl, imidazolyl, oxazolyl, thiazolyl, isoxazolyl, pyrazolyl, triazolyl, thiadiazolyl,

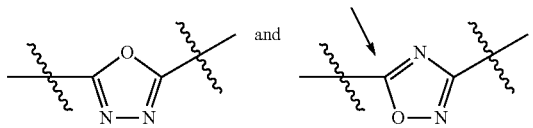

wherein the ring carbon atom identified in the oxadiazole ring, with an arrow, is attached to the carbon atom bearing $R^1$ and $R^2$;

$R^5$, $R^6$ and $R^7$ are each independently selected from
(a) —H,
(b) —OH,
(c) halogen,
(d) —CN,
(e) C$_{1-6}$alkyl optionally substituted with one to three —OH, —O—C$_{1-6}$alkyl, —N(R$^8$)(R$^9$), —O—C$_{1-6}$alkyl-OH, —CO$_2$R$^8$, —C(O)N(R$^8$)(R$^9$) or —S(O)$_2$C$_{1-3}$alkyl, phenyl optionally substituted with halogen, pyridinyl optionally substituted with C$_{1-4}$ alkyl-OH, tetrazolyl, piperazinyl optionally substituted with a methyl group,
(f) —O—C$_{1-6}$alkyl optionally substituted with a quinolinyl or isoquinolinyl ring,
(g) —O-heterocycle wherein the heterocycle is tetrahydrofuranyl or tetrahydropyranyl,
(h) —N(R$^8$)(R$^9$),
(i) —S(O)$_2$C$_{1-3}$alkyl,
(j) —S(O)$_2$ phenyl,
(k) —CO$_2$R$^8$,
(l) —C(O)N(R$^8$)(R$^9$),
(m) —S(O)$_2$N(R$^8$)(R$^9$),
(n') oxo,
(o) —C(O)—C$_{1-3}$ alkyl
(p) C$_{3-10}$ carbocycle,
(q) a piperazinyl group optionally substituted with a methyl group,
(r) a 5-11 membered heteroaryl group selected from pyridinyl, pyrimidinyl, pyrazolyl, oxadiazolyl and tetrazolyl wherein each heteroaryl ring is optionally substituted with one to three substituents selected from C$_{1-4}$ alkyl, C$_{1-2}$ alkyl-OH, —O—C$_{1-2}$ alkyl, C$_{1-2}$alkyl-N(R$^8$)(R$^9$), C$_{1-4}$ alkyl-C(O)N(R$^8$)(R$^9$), —N(R$^8$)(R$^9$) and halogen,
(s) phenyl ring optionally substituted with halogen;
$R^8$ and $R^9$ are each independently selected from —H, —C$_{1-6}$ alkyl, —C(O)C$_{1-6}$alkyl, and a 3-6 membered heterocyclic group, each of which is optionally independently substituted with one to three C$_{1-6}$alkyl groups, —OH, —O—C$_{1-6}$alkyl, —C(O)N(R$^{10}$)(R$^{11}$), —S(O)$_2$C$_{1-6}$alkyl, —S(O)$_2$N(R$^{10}$) (R$^{11}$), a 3-6 membered heterocyclic group which is optionally substituted with one to two groups selected from C$_{1-3}$ alkyl, —OC$_{1-3}$alkyl, and oxo;
or
$R^8$ and $R^9$ taken together with the nitrogen ring to which they are attached form a heterocyclyl ring optionally substituted with one to three —OH, CN, —OC$_{1-3}$alkyl or oxo;
$R^{10}$ and $R^{11}$ are each independently selected from —H and —C$_{1-4}$alkyl;
or a pharmaceutically acceptable salt thereof.

In an eighteenth embodiment there is provided a compound as described in the seventeenth embodiment above, wherein:

HET is a 5-11 membered heteroaryl group selected from 3-pyridinyl, pyrimidinyl, pyridazinyl, pyrazinyl, pyrrolyl, imidazolyl, oxazolyl, thiazolyl, isoxazolyl, pyrazolyl, triazolyl, thiadiazolyl,

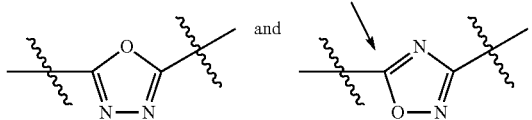

wherein the ring carbon atom identified in the oxadiazole ring, with an arrow, is attached to the carbon atom bearing $R^1$ and $R^2$;
or a pharmaceutically acceptable salt thereof.

In a nineteeth embodiment there is provided a compound as described in the seventeenth embodiment above, wherein:
HET is a 5-11 membered heteroaryl group selected from indolyl, pyrrolopyridinyl, indazolyl, benzimidazolyl, benzoxazolyl, benzothiazolyl, imidazopyridinyl, quinolinyl and isoquinolinyl;
or a pharmaceutically acceptable salt thereof.

In a twentieth embodiment there is provided a compound as described in the eighteenth embodiment above, wherein:
HET is a 5-11 membered heteroaryl group selected from pyrrolyl, imidazolyl, oxazolyl, thiazolyl, isoxazolyl, pyrazolyl, triazolyl, thiadiazolyl,

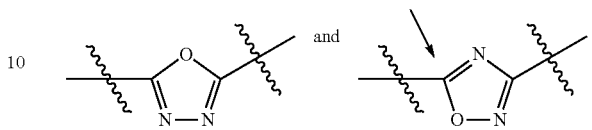

wherein the ring carbon atom identified in the oxadiazole ring, with an arrow, is attached to the carbon atom bearing $R^1$ and $R^2$;
or a pharmaceutically acceptable salt thereof.

The following are representative compounds of the invention which can be made by the general synthetic schemes, the examples, and known methods in the art.

TABLE 1

| Example | Structure | Name |
|---|---|---|
| 1 | 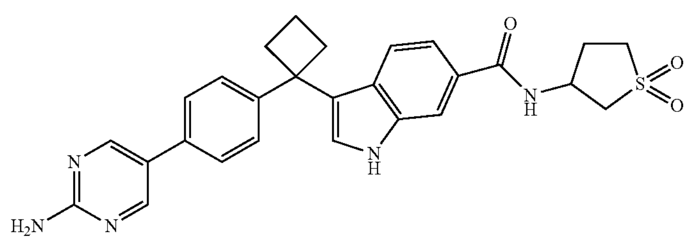 [SMILES: Nc1ncc(-c2ccc(C3(c4c[nH]c5cc(C(=O)NC6CCS(=O)(=O)C6)ccc45)CCC3)cc2)cn1] | 3-{1-[4-(2-aminopyrimidin-5-yl)phenyl]cyclobutyl}-N-(1,1-dioxidotetrahydrothiophen-3-yl)-1H-indole-6-carboxamide |
| 2 | 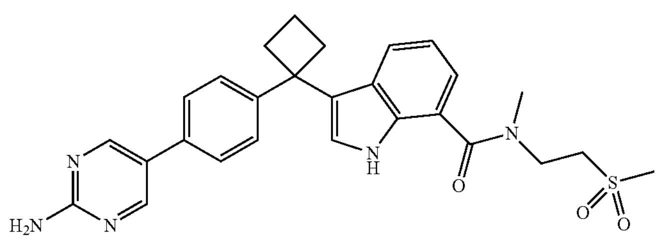 [SMILES: CN(CCS(C)(=O)=O)C(=O)c1cccc2c(C3(c4ccc(-c5cnc(N)nc5)cc4)CCC3)c[nH]c12] | 3-{1-[4-(2-aminopyrimidin-5-yl)phenyl]cyclobutyl}-N-methyl-N-[2-(methylsulfonyl)ethyl]-1H-indole-7-carboxamide |
| 3 | 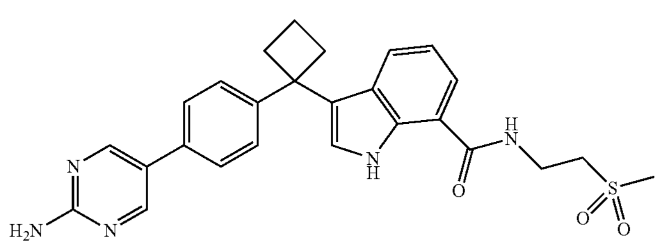 [SMILES: CS(=O)(=O)CCNC(=O)c1cccc2c(C3(c4ccc(-c5cnc(N)nc5)cc4)CCC3)c[nH]c12] | 3-{1-[4-(2-aminopyrimidin-5-yl)phenyl]cyclobutyl}-N-[2-(methylsulfonyl)ethyl]-1H-indole-7-carboxamide |
| 4 | 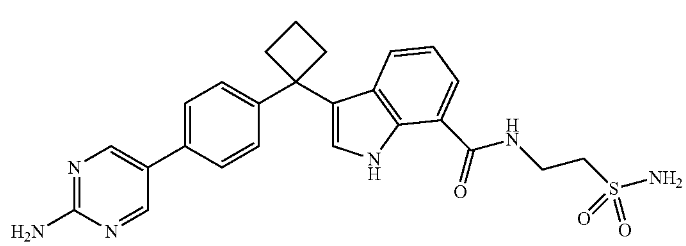 [SMILES: Nc1ncc(-c2ccc(C3(c4c[nH]c5c(C(=O)NCCS(N)(=O)=O)cccc45)CCC3)cc2)cn1] | 3-{1-[4-(2-aminopyrimidin-5-yl)phenyl]cyclobutyl}-N-(2-sulfamoylethyl)-1H-indole-7-carboxamide |

TABLE 1-continued

| Example | Structure | Name |
|---|---|---|
| 5 | 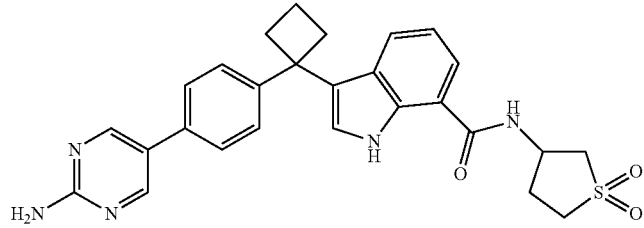 [SMILES: Nc1ncc(-c2ccc(C3(c4c[nH]c5c(C(=O)NC6CCS(=O)(=O)C6)cccc45)CCC3)cc2)cn1] | 3-{1-[4-(2-aminopyrimidin-5-yl)phenyl]cyclobutyl}-N-(1,1-dioxidotetrahydrothiophen-3-yl)-1H-indole-7-carboxamide |
| 6 | 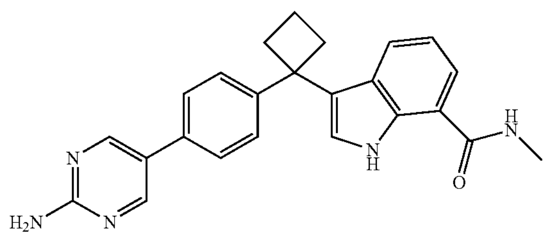 [SMILES: CNC(=O)c1cccc2c(C3(c4ccc(-c5cnc(N)nc5)cc4)CCC3)c[nH]c12] | 3-{1-[4-(2-aminopyrimidin-5-yl)phenyl]cyclobutyl}-N-methyl-1H-indole-7-carboxamide |
| 7 | 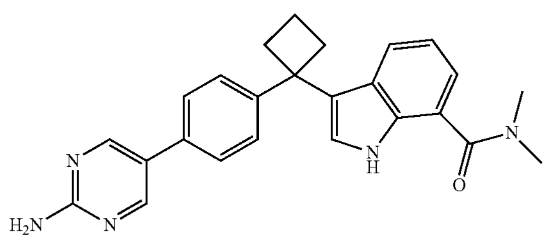 [SMILES: CN(C)C(=O)c1cccc2c(C3(c4ccc(-c5cnc(N)nc5)cc4)CCC3)c[nH]c12] | 3-{1-[4-(2-aminopyrimidin-5-yl)phenyl]cyclobutyl}-N,N-dimethyl-1H-indole-7-carboxamide |
| 8 | 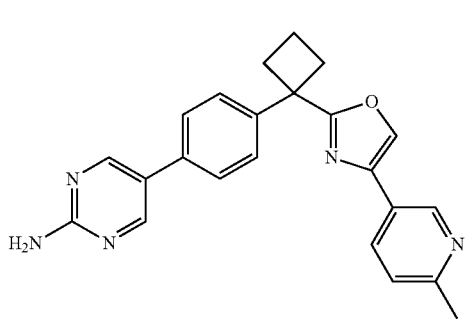 [SMILES: Cc1ccc(-c2coc(C3(c4ccc(-c5cnc(N)nc5)cc4)CCC3)n2)cn1] | 5-(4-{1-[4-(6-methylpyridin-3-yl)-1,3-oxazol-2-yl]cyclobutyl}phenyl)pyrimidin-2-amine |
| 9 | 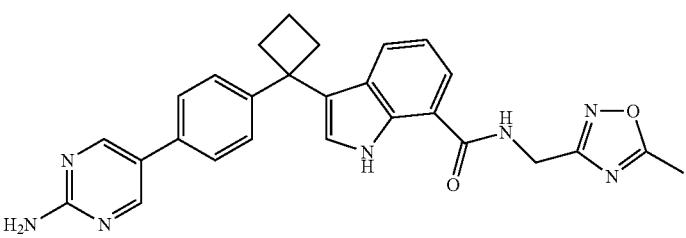 [SMILES: Cc1nc(CNC(=O)c2cccc3c(C4(c5ccc(-c6cnc(N)nc6)cc5)CCC4)c[nH]c23)no1] | 3-{1-[4-(2-aminopyrimidin-5-yl)phenyl]cyclobutyl}-N-[(5-methyl-1,2,4-oxadiazol-3-yl)methyl]-1H-indole-7-carboxamide |
| 10 | 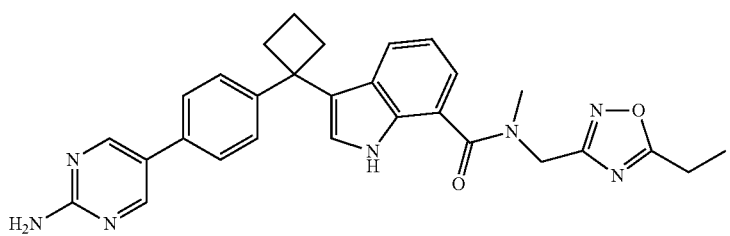 [SMILES: CCc1nc(CN(C)C(=O)c2cccc3c(C4(c5ccc(-c6cnc(N)nc6)cc5)CCC4)c[nH]c23)no1] | 3-{1-[4-(2-aminopyrimidin-5-yl)phenyl]cyclobutyl}-N-[(5-ethyl-1,2,4-oxadiazol-3-yl)methyl]-N-methyl-1H-indole-7-carboxamide |

TABLE 1-continued

| Example | Structure | Name |
|---|---|---|
| 11 | 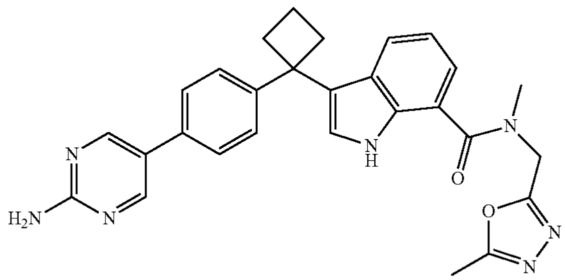 [SMILES: Cc1nnc(CN(C)C(=O)c2cccc3c(C4(c5ccc(-c6cnc(N)nc6)cc5)CCC4)c[nH]c23)o1] | 3-{1-[4-(2-aminopyrimidin-5-yl)phenyl]cyclobutyl}-N-methyl-N-[(5-methyl-1,3,4-oxadiazol-2-yl)methyl]-1H-indole-7-carboxamide |
| 12 | 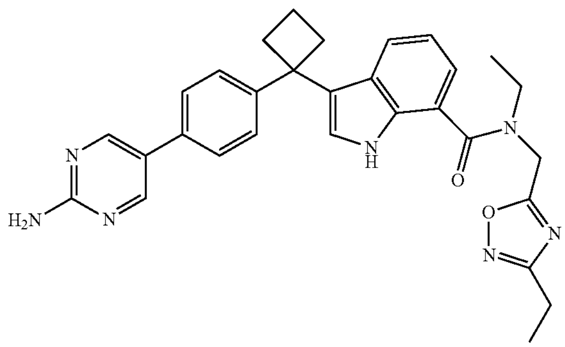 [SMILES: CCc1noc(CN(CC)C(=O)c2cccc3c(C4(c5ccc(-c6cnc(N)nc6)cc5)CCC4)c[nH]c23)n1] | 3-{1-[4-(2-aminopyrimidin-5-yl)phenyl]cyclobutyl}-N-ethyl-N-[(3-ethyl-1,2,4-oxadiazol-5-yl)methyl]-1H-indole-7-carboxamide |
| 13 | 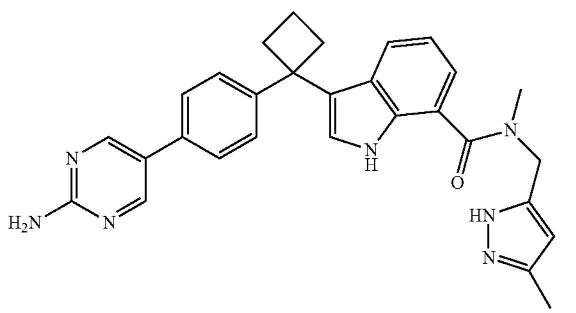 [SMILES: Cc1cc(CN(C)C(=O)c2cccc3c(C4(c5ccc(-c6cnc(N)nc6)cc5)CCC4)c[nH]c23)[nH]n1] | 3-{1-[4-(2-aminopyrimidin-5-yl)phenyl]cyclobutyl}-N-methyl-N-[(3-methyl-1H-pyrazol-5-yl)methyl]-1H-indole-7-carboxamide |
| 14 | 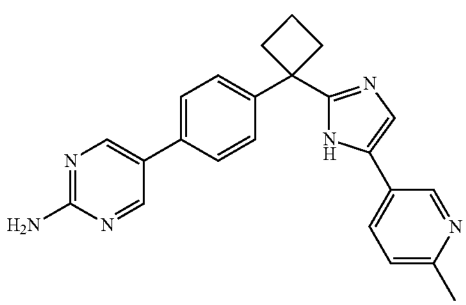 [SMILES: Cc1ccc(-c2cnc(C3(c4ccc(-c5cnc(N)nc5)cc4)CCC3)[nH]2)cn1] | 5-(4-{1-[5-(6-methylpyridin-3-yl)-1H-imidazol-2-yl]cyclobutyl}phenyl)pyrimidin-2-amine |
| 15 | 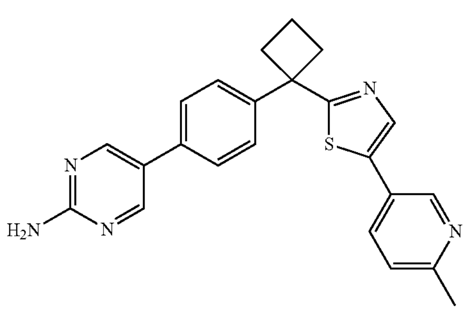 [SMILES: Cc1ccc(-c2cnc(C3(c4ccc(-c5cnc(N)nc5)cc4)CCC3)s2)cn1] | 5-(4-{1-[5-(6-methylpyridin-3-yl)-1,3-thiazol-2-yl]cyclobutyl}phenyl)pyrimidin-2-amine |

TABLE 1-continued

| Example | Structure | Name |
|---------|-----------|------|
| 16 | 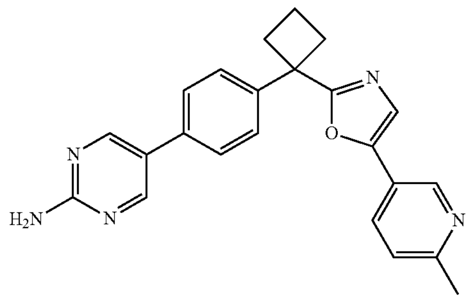 [SMILES: Cc1ccc(-c2cnc(C3(c4ccc(-c5cnc(N)nc5)cc4)CCC3)o2)cn1] | 5-(4-{1-[5-(6-methylpyridin-3-yl)-1,3-oxazol-2-yl]cyclobutyl}phenyl)pyrimidin-2-amine |
| 17 | 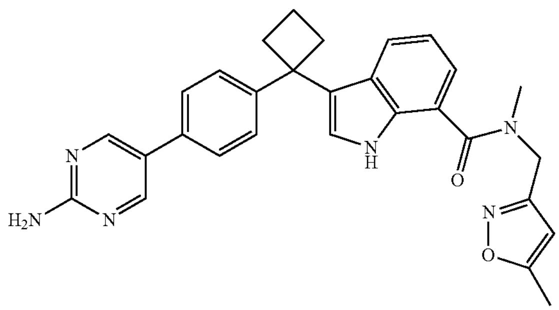 [SMILES: Cc1cc(CN(C)C(=O)c2cccc3c(C4(c5ccc(-c6cnc(N)nc6)cc5)CCC4)c[nH]c23)no1] | 3-{1-[4-(2-aminopyrimidin-5-yl)phenyl]cyclobutyl}-N-methyl-N-[(5-methyl-1,2-oxazol-3-yl)methyl]-1H-indole-7-carboxamide |
| 18 | 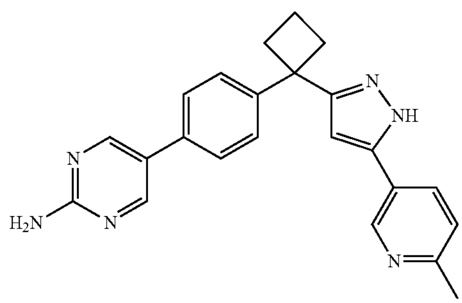 [SMILES: Cc1ccc(-c2cc(C3(c4ccc(-c5cnc(N)nc5)cc4)CCC3)n[nH]2)cn1] | 5-(4-{1-[5-(6-methylpyridin-3-yl)-1H-pyrazol-3-yl]cyclobutyl}phenyl)pyrimidin-2-amine |
| 19 | 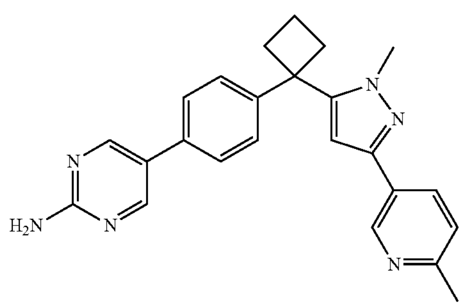 [SMILES: Cc1ccc(-c2cc(C3(c4ccc(-c5cnc(N)nc5)cc4)CCC3)n(C)n2)cn1] | 5-(4-{1-[1-methyl-3-(6-methylpyridin-3-yl)-1H-pyrazol-5-yl]cyclobutyl}phenyl)pyrimidin-2-amine |
| 20 | 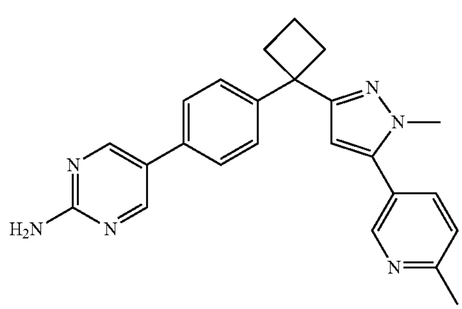 [SMILES: Cc1ccc(-c2cc(C3(c4ccc(-c5cnc(N)nc5)cc4)CCC3)nn2C)cn1] | 5-(4-{1-[1-methyl-5-(6-methylpyridin-3-yl)-1H-pyrazol-3-yl]cyclobutyl}phenyl)pyrimidin-2-amine |

TABLE 1-continued

| Example | Structure | Name |
|---|---|---|
| 21 | 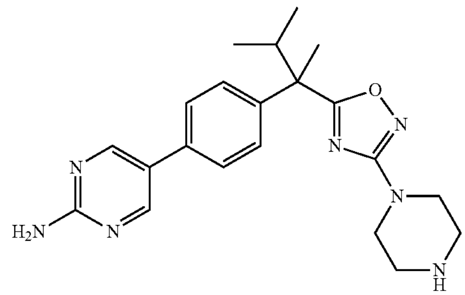 [SMILES: CC(C)C(C)(c1ccc(-c2cnc(N)nc2)cc1)c1nc(N2CCNCC2)no1] | 5-(4-{3-methyl-2-[3-(piperazin-1-yl)-1,2,4-oxadiazol-5-yl]butan-2-yl}phenyl)pyrimidin-2-amine |
| 22 | 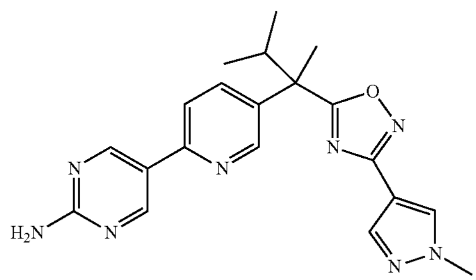 [SMILES: CC(C)C(C)(c1ccc(-c2cnc(N)nc2)nc1)c1nc(-c2cnn(C)c2)no1] | 5-(5-{3-methyl-2-[3-(1-methyl-1H-pyrazol-4-yl)-1,2,4-oxadiazol-5-yl]butan-2-yl}pyridin-2-yl)pyrimidin-2-amine |
| 24 | 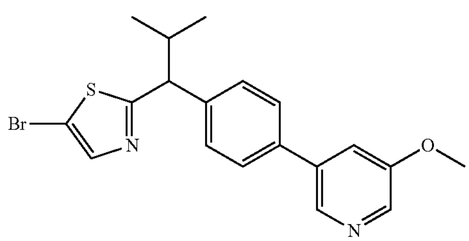 [SMILES: COc1cncc(-c2ccc(C(c3ncc(Br)s3)C(C)C)cc2)c1] | 3-{4-[1-(5-bromo-1,3-thiazol-2-yl)-2-methylpropyl]phenyl}-5-methoxypyridine |
| 25 | 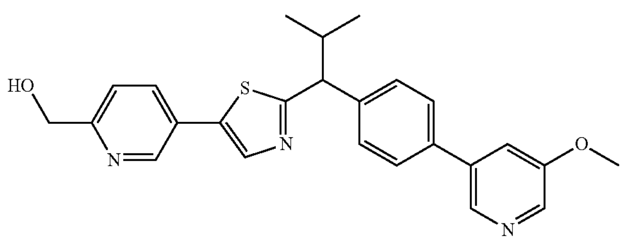 [SMILES: COc1cncc(-c2ccc(C(c3ncc(-c4ccc(CO)nc4)s3)C(C)C)cc2)c1] | [5-(2-{1-[4-(5-methoxypyridin-3-yl)phenyl]-2-methylpropyl}-1,3-thiazol-5-yl)pyridin-2-yl]methanol |
| 26 | Chiral | 5-{4-[(1R)-1-cyclopropyl-1-(5-{1-[2-(dimethylamino)ethyl]-1H-pyrazol-4-yl}-1,2-oxazol-3-yl)ethyl]phenyl}pyrimidin-2-amine |

TABLE 1-continued

| Example | Structure | Name |
|---|---|---|
| 27 | 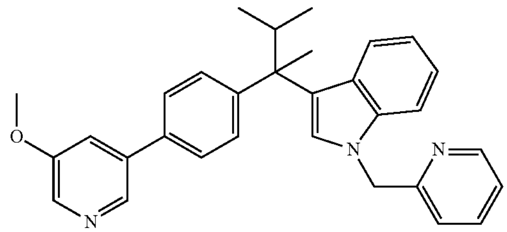 [SMILES: COc1cncc(-c2ccc(C(C)(c3cn(Cc4ccccn4)c4ccccc34)C(C)C)cc2)c1] | 3-{2-[4-(5-methoxypyridin-3-yl)phenyl]-3-methylbutan-2-yl}-1-(pyridin-2-ylmethyl)-1H-indole |
| 28 | 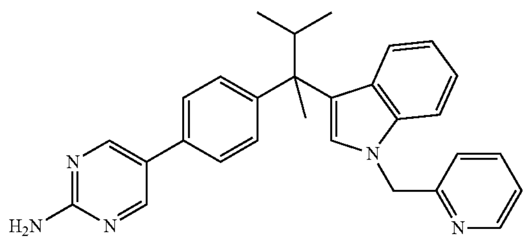 [SMILES: CC(C)C(C)(c1ccc(-c2cnc(N)nc2)cc1)c1cn(Cc2ccccn2)c2ccccc12] | 5-(4-{3-methyl-2-[1-(pyridin-2-ylmethyl)-1H-indol-3-yl]butan-2-yl}phenyl)pyrimidin-2-amine |
| 29 | 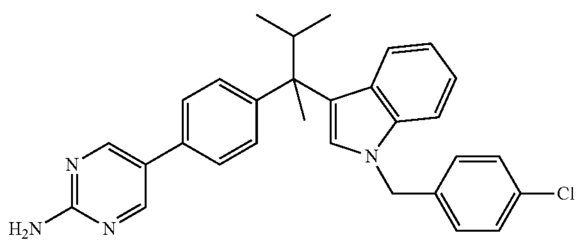 [SMILES: CC(C)C(C)(c1ccc(-c2cnc(N)nc2)cc1)c1cn(Cc2ccc(Cl)cc2)c2ccccc12] | 5-(4-{2-[1-(4-chlorobenzyl)-1H-indol-3-yl]-3-methylbutan-2-yl}phenyl)pyrimidin-2-amine |
| 30 | Chiral | 5-{4-[(1S)-1-cyclopropyl-1-(5-{1-[2-(dimethylamino)ethyl]-1H-pyrazol-4-yl}-1,2-oxazol-3-yl)ethyl]phenyl}pyrimidin-2-amine |
| 31 | 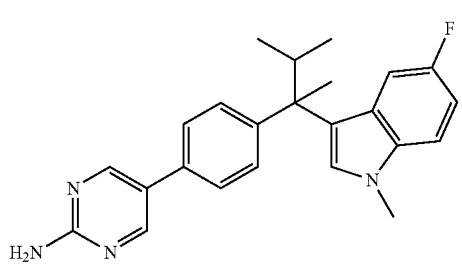 [SMILES: CC(C)C(C)(c1ccc(-c2cnc(N)nc2)cc1)c1cn(C)c2ccc(F)cc12] | 5-{4-[2-(5-fluoro-1-methyl-1H-indol-3-yl)-3-methylbutan-2-yl]phenyl}pyrimidin-2-amine |

TABLE 1-continued

| Example | Structure | Name |
|---|---|---|
| 32 | 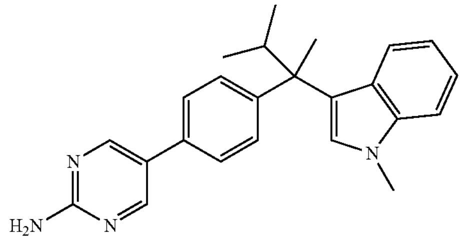 [SMILES: CC(C)C(C)(c1ccc(-c2cnc(N)nc2)cc1)c1cn(C)c2ccccc12] | 5-{4-[3-methyl-2-(1-methyl-1H-indol-3-yl)butan-2-yl]phenyl}pyrimidin-2-amine |
| 33 | 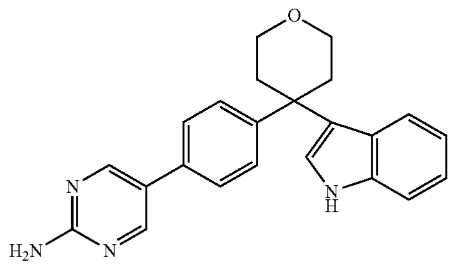 [SMILES: Nc1ncc(-c2ccc(C3(c4c[nH]c5ccccc45)CCOCC3)cc2)cn1] | 5-{4-[4-(1H-indol-3-yl)tetrahydro-2H-pyran-4-yl]phenyl}pyrimidin-2-amine |
| 34 | 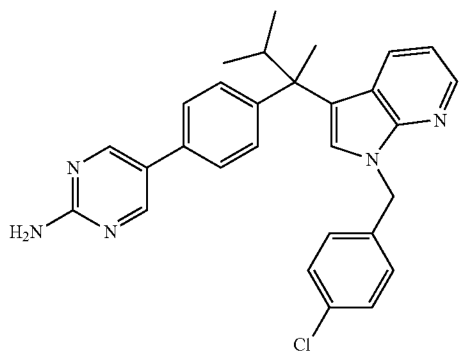 [SMILES: CC(C)C(C)(c1ccc(-c2cnc(N)nc2)cc1)c1cn(Cc2ccc(Cl)cc2)c2ncccc12] | 5-(4-{2-[1-(4-chlorobenzyl)-1H-pyrrolo[2,3-b]pyridin-3-yl]-3-methylbutan-2-yl}phenyl)pyrimidin-2-amine |
| 35 | 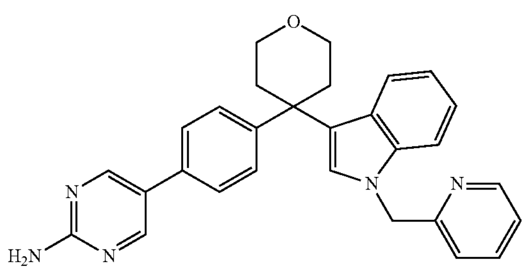 [SMILES: Nc1ncc(-c2ccc(C3(c4cn(Cc5ccccn5)c5ccccc45)CCOCC3)cc2)cn1] | 5-(4-{4-[1-(pyridin-2-ylmethyl)-1H-indol-3-yl]tetrahydro-2H-pyran-4-yl}phenyl)pyrimidin-2-amine |
| 36 | 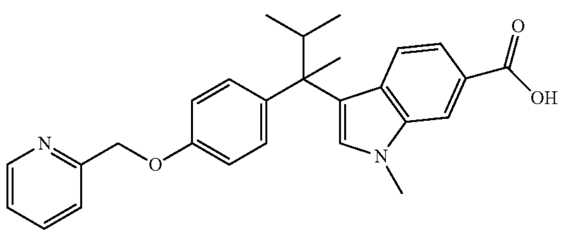 [SMILES: CC(C)C(C)(c1ccc(OCc2ccccn2)cc1)c1cn(C)c2cc(C(=O)O)ccc12] | 1-methyl-3-{3-methyl-2-[4-(pyridin-2-ylmethoxy)phenyl]butan-2-yl}-1H-indole-6-carboxylic acid |
| 37 | 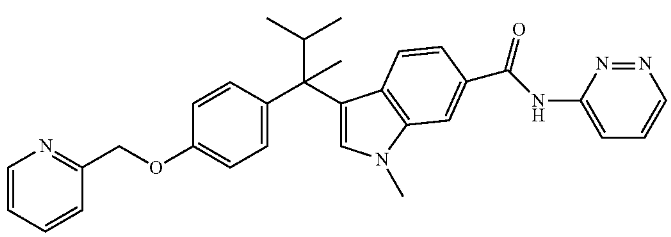 [SMILES: CC(C)C(C)(c1ccc(OCc2ccccn2)cc1)c1cn(C)c2cc(C(=O)Nc3cccnn3)ccc12] | 1-methyl-3-{3-methyl-2-[4-(pyridin-2-ylmethoxy)phenyl]butan-2-yl}-N-(pyridazin-3-yl)-1H-indole-6-carboxamide |

TABLE 1-continued

| Example | Structure | Name |
|---|---|---|
| 38 | 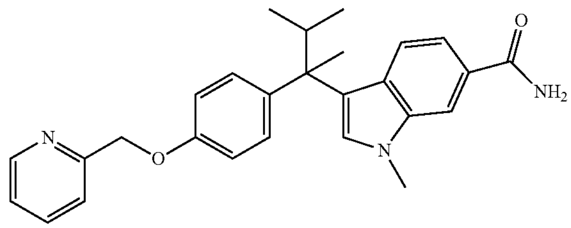 [SMILES: CC(C)C(C)(c1ccc(OCc2ccccn2)cc1)c1cn(C)c2cc(C(N)=O)ccc12] | 1-methyl-3-{3-methyl-2-[4-(pyridin-2-ylmethoxy)phenyl]butan-2-yl}-1H-indole-6-carboxamide |
| 39 | 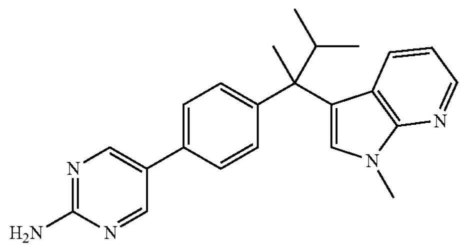 [SMILES: CC(C)C(C)(c1ccc(-c2cnc(N)nc2)cc1)c1cn(C)c2ncccc12] | 5-{4-[3-methyl-2-(1-methyl-1H-pyrrolo[2,3-b]pyridin-3-yl)butan-2-yl]phenyl}pyrimidin-2-amine |
| 40 | 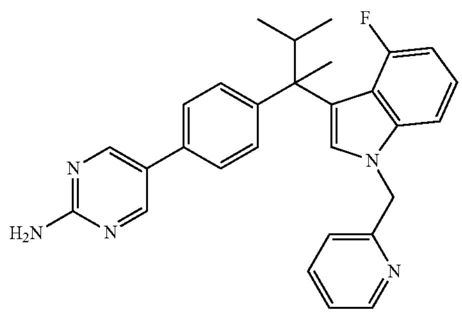 [SMILES: CC(C)C(C)(c1ccc(-c2cnc(N)nc2)cc1)c1cn(Cc2ccccn2)c2cccc(F)c12] | 5-(4-{2-[4-fluoro-1-(pyridin-2-ylmethyl)-1H-indol-3-yl]-3-methylbutan-2-yl}phenyl)pyrimidin-2-amine |
| 41 | 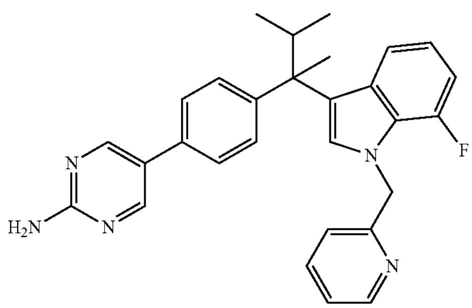 [SMILES: CC(C)C(C)(c1ccc(-c2cnc(N)nc2)cc1)c1cn(Cc2ccccn2)c2c(F)cccc12] | 5-(4-{2-[7-fluoro-1-(pyridin-2-ylmethyl)-1H-indol-3-yl]-3-methylbutan-2-yl}phenyl)pyrimidin-2-amine |
| 42 | 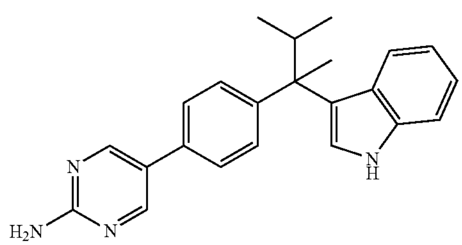 [SMILES: CC(C)C(C)(c1ccc(-c2cnc(N)nc2)cc1)c1c[nH]c2ccccc12] | 5-{4-[2-(1H-indol-3-yl)-3-methylbutan-2-yl]phenyl}pyrimidin-2-amine |
| 43 | 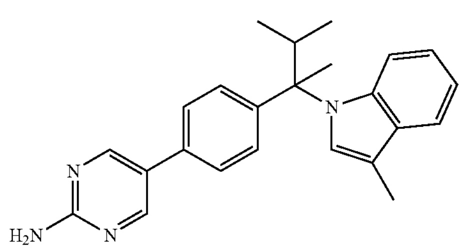 [SMILES: Cc1cn(C(C)(c2ccc(-c3cnc(N)nc3)cc2)C(C)C)c2ccccc12] | 5-{4-[3-methyl-2-(3-methyl-1H-indol-1-yl)butan-2-yl]phenyl}pyrimidin-2-amine |

TABLE 1-continued

| Example | Structure | Name |
|---|---|---|
| 44 | 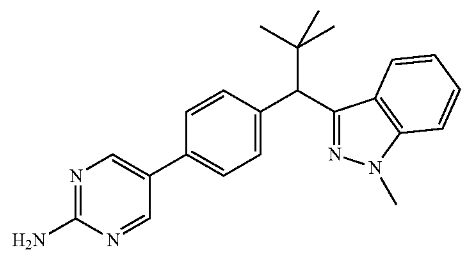 [SMILES: Cn1nc(C(c2ccc(-c3cnc(N)nc3)cc2)C(C)(C)C)c2ccccc21] | 5-{4-[2,2-dimethyl-1-(1-methyl-1H-indazol-3-yl)propyl]phenyl}pyrimidin-2-amine |
| 45 | 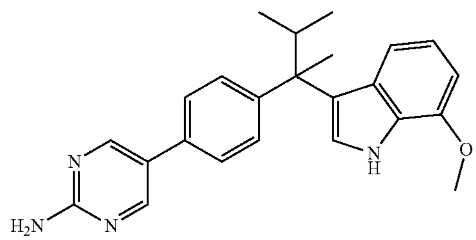 [SMILES: COc1cccc2c(C(C)(c3ccc(-c4cnc(N)nc4)cc3)C(C)C)c[nH]c12] | 5-{4-[2-(7-methoxy-1H-indol-3-yl)-3-methylbutan-2-yl]phenyl}pyrimidin-2-amine |
| 46 | 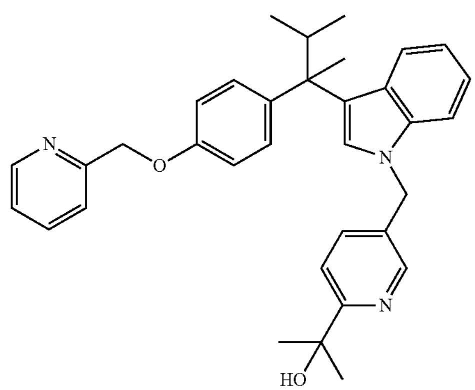 [SMILES: CC(C)C(C)(c1ccc(OCc2ccccn2)cc1)c1cn(Cc2ccc(C(C)(C)O)nc2)c2ccccc12] | 2-{5-[(3-{3-methyl-2-[4-(pyridin-2-ylmethoxy)phenyl]butan-2-yl}-1H-indol-1-yl)methyl]pyridin-2-yl}propan-2-ol |
| 47 | 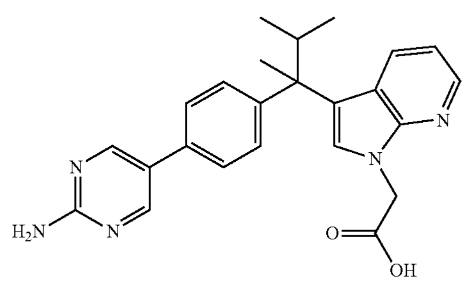 [SMILES: CC(C)C(C)(c1ccc(-c2cnc(N)nc2)cc1)c1cn(CC(=O)O)c2ncccc12] | (3-{2-[4-(2-aminopyrimidin-5-yl)phenyl]-3-methylbutan-2-yl}-1H-pyrrolo[2,3-b]pyridin-1-yl)acetic acid |
| 48 | 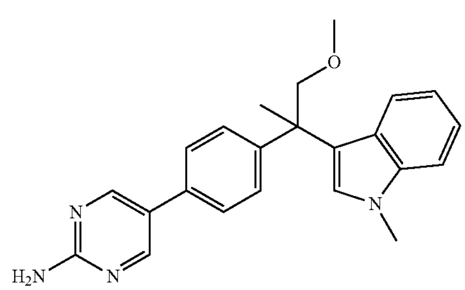 [SMILES: COCC(C)(c1ccc(-c2cnc(N)nc2)cc1)c1cn(C)c2ccccc12] | 5-{4-[1-methoxy-2-(1-methyl-1H-indol-2-yl)propan-2-yl]phenyl}pyrimidin-2-amine |

TABLE 1-continued

| Example | Structure | Name |
|---|---|---|
| 49 | 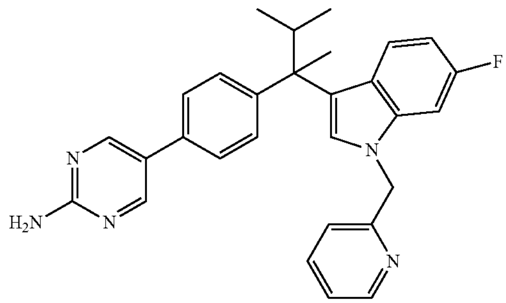 [SMILES: CC(C)C(C)(c1ccc(-c2cnc(N)nc2)cc1)c1cn(Cc2ccccn2)c2cc(F)ccc12] | 5-(4-{2-[6-fluoro-1-(pyridin-2-ylmethyl)-1H-indol-3-yl]-3-methylbutan-2-yl}phenyl)pyrimidin-2-amine |
| 50 | 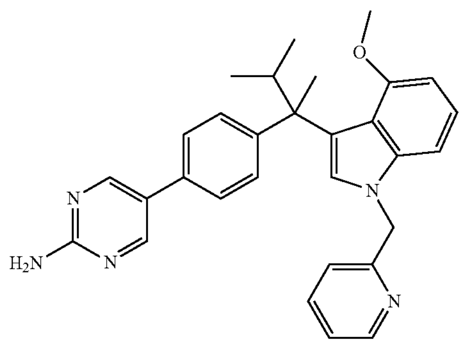 [SMILES: COc1cccc2c1c(C(C)(c1ccc(-c3cnc(N)nc3)cc1)C(C)C)cn2Cc1ccccn1] | 5-(4-{2-[4-methoxy-1-(pyridin-2-ylmethyl)-1H-indol-3-yl]-3-methylbutan-2-yl}phenyl)pyrimidin-2-amine |
| 51 | 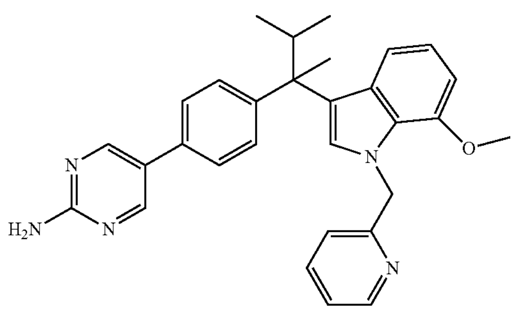 [SMILES: COc1cccc2c(C(C)(c3ccc(-c4cnc(N)nc4)cc3)C(C)C)cn(Cc3ccccn3)c12] | 5-(4-{2-[7-methoxy-1-(pyridin-2-ylmethyl)-1H-indol-3-yl]-3-methylbutan-2-yl}phenyl)pyrimidin-2-amine |
| 52 | 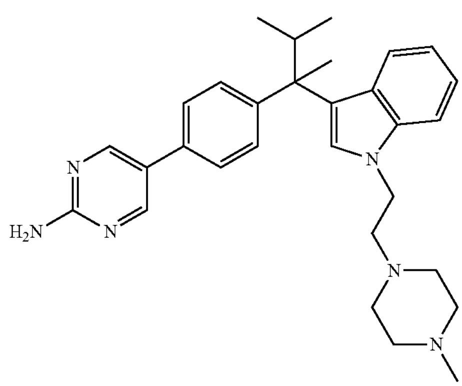 [SMILES: CC(C)C(C)(c1ccc(-c2cnc(N)nc2)cc1)c1cn(CCN2CCN(C)CC2)c2ccccc12] | 5-[4-(3-methyl-2-{1-[2-(4-methylpiperazin-1-yl)ethyl]-1H-indol-3-yl}butan-2-yl)phenyl]pyrimidin-2-amine |
| 53 | 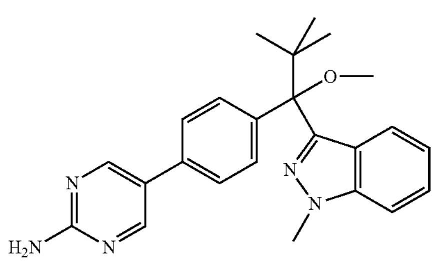 [SMILES: COC(c1ccc(-c2cnc(N)nc2)cc1)(c1nn(C)c2ccccc12)C(C)(C)C] | 5-{4-[1-methoxy-2,2-dimethyl-1-(1-methyl-1H-indazol-3-yl)propyl]phenyl}pyrimidin-2-amine |

TABLE 1-continued

| Example | Structure | Name |
|---|---|---|
| 54 | 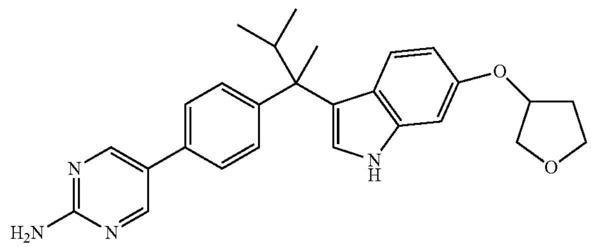 [SMILES: CC(C)C(C)(c1ccc(-c2cnc(N)nc2)cc1)c1c[nH]c2cc(OC3CCOC3)ccc12] | 5-(4-{3-methyl-2-[6-(tetrahydrofuran-3-yloxy)-1H-indol-3-yl]butan-2-yl}phenyl)pyrimidin-2-amine |
| 55 | 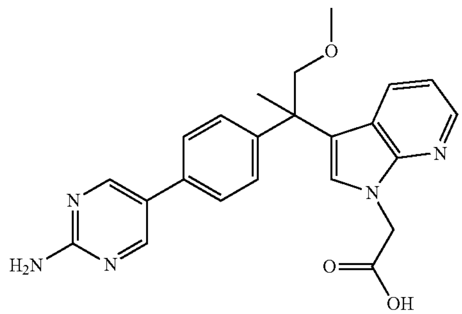 [SMILES: COCC(C)(c1ccc(-c2cnc(N)nc2)cc1)c1cn(CC(=O)O)c2ncccc12] | (3-{2-[4-(2-aminopyrimidin-5-yl)phenyl]-1-methoxypropan-2-yl}-1H-pyrrolo[2,3-b]pyridin-1-yl)acetic acid |
| 56 | 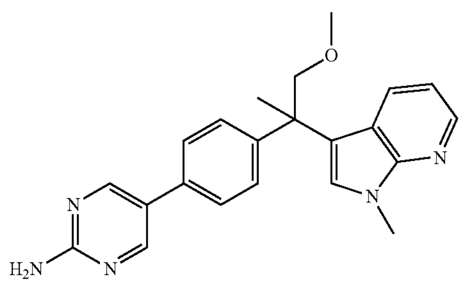 [SMILES: COCC(C)(c1ccc(-c2cnc(N)nc2)cc1)c1cn(C)c2ncccc12] | 5-{4-[1-methoxy-2-(1-methyl-1H-pyrrolo[2,3-b]pyridin-3-yl)propan-2-yl]phenyl}pyrimidin-2-amine |
| 57 | 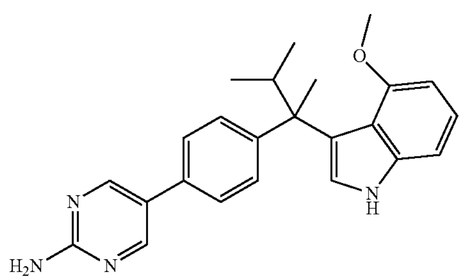 [SMILES: COc1cccc2[nH]cc(C(C)(c3ccc(-c4cnc(N)nc4)cc3)C(C)C)c12] | 5-{4-[2-(4-methoxy-1H-indol-3-yl)-3-methylbutan-2-yl]phenyl}pyrimidin-2-amine |
| 58 | 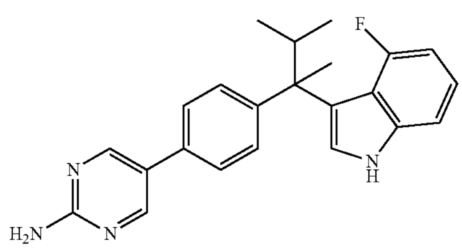 [SMILES: CC(C)C(C)(c1ccc(-c2cnc(N)nc2)cc1)c1c[nH]c2cccc(F)c12] | 5-{4-[2-(4-fluoro-1H-indol-3-yl)-3-methylbutan-2-yl]phenyl}pyrimidin-2-amine |
| 59 | 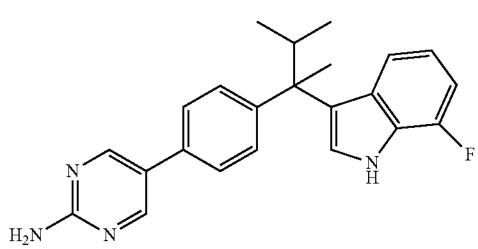 [SMILES: CC(C)C(C)(c1ccc(-c2cnc(N)nc2)cc1)c1c[nH]c2c(F)cccc12] | 5-{4-[2-(7-fluoro-1H-indol-3-yl)-3-methylbutan-2-yl]phenyl}pyrimidin-2-amine |

TABLE 1-continued

| Example | Structure | Name |
| --- | --- | --- |
| 60 | 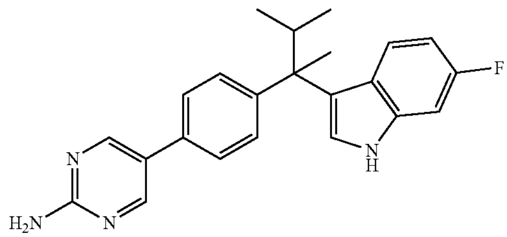 [SMILES: CC(C)C(C)(c1ccc(-c2cnc(N)nc2)cc1)c1c[nH]c2cc(F)ccc12] | 5-{4-[2-(6-fluoro-1H-indol-3-yl)-3-methylbutan-2-yl]phenyl}pyrimidin-2-amine |
| 61 | 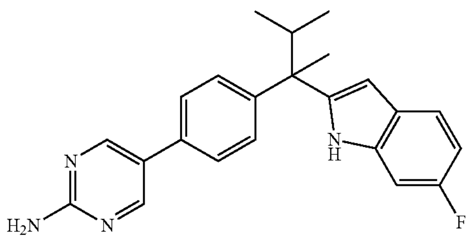 [SMILES: CC(C)C(C)(c1ccc(-c2cnc(N)nc2)cc1)c1cc2ccc(F)cc2[nH]1] | 5-{4-[2-(6-fluoro-1H-indol-2-yl)-3-methylbutan-2-yl]phenyl}pyrimidin-2-amine |
| 62 | 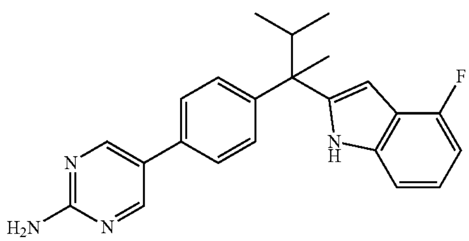 [SMILES: CC(C)C(C)(c1ccc(-c2cnc(N)nc2)cc1)c1cc2c(F)cccc2[nH]1] | 5-{4-[2-(4-fluoro-1H-indol-2-yl)-3-methylbutan-2-yl]phenyl}pyrimidin-2-amine |
| 63 | 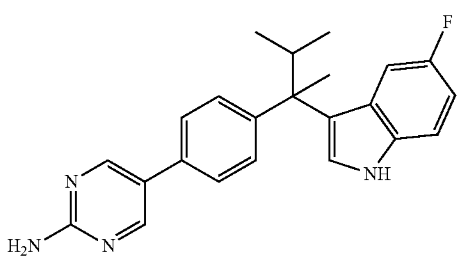 [SMILES: CC(C)C(C)(c1ccc(-c2cnc(N)nc2)cc1)c1c[nH]c2ccc(F)cc12] | 5-{4-[2-(5-fluoro-1H-indol-3-yl)-3-methylbutan-2-yl]phenyl}pyrimidin-2-amine |
| 64 | 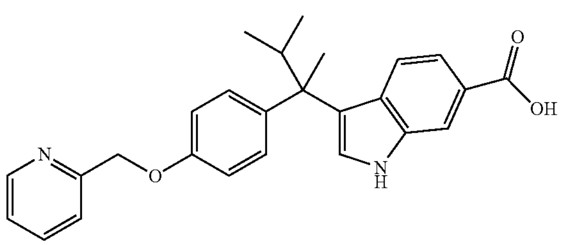 [SMILES: CC(C)C(C)(c1ccc(OCc2ccccn2)cc1)c1c[nH]c2cc(C(=O)O)ccc12] | 3-{3-methyl-2-[4-(pyridin-2-ylmethoxy)phenyl]butan-2-yl}-1H-indole-6-carboxylic acid |
| 65 | 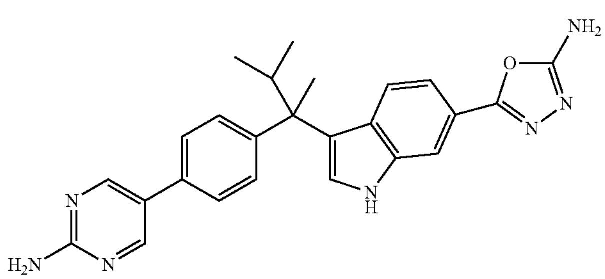 [SMILES: CC(C)C(C)(c1ccc(-c2cnc(N)nc2)cc1)c1c[nH]c2cc(-c3nnc(N)o3)ccc12] | 5-(4-{2-[6-(5-amino-1,3,4-oxadiazol-2-yl)-1H-indol-3-yl]-3-methylbutan-2-yl}phenyl)pyrimidin-2-amine |

TABLE 1-continued

| Example | Structure | Name |
|---|---|---|
| 66 | 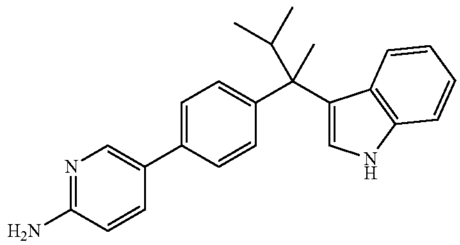 [SMILES: CC(C)C(C)(c1ccc(-c2ccc(N)nc2)cc1)c1c[nH]c2ccccc12] | 5-{4-[2-(1H-indol-3-yl)-3-methylbutan-2-yl]phenyl}pyridin-2-amine |
| 67 | 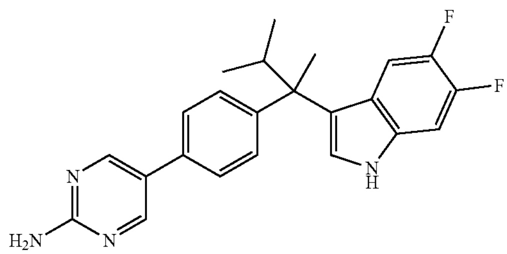 [SMILES: CC(C)C(C)(c1ccc(-c2cnc(N)nc2)cc1)c1c[nH]c2cc(F)c(F)cc12] | 5-{4-[2-(5,6-difluoro-1H-indol-3-yl)-3-methylbutan-2-yl]phenyl}pyrimidin-2-amine |
| 68 | 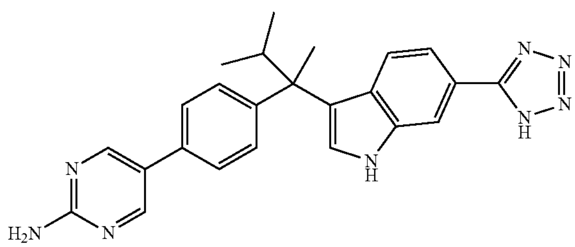 [SMILES: CC(C)C(C)(c1ccc(-c2cnc(N)nc2)cc1)c1c[nH]c2cc(-c3nnn[nH]3)ccc12] | 5-(4-[3-methyl-2-[6-(1H-tetrazol-5-yl)-1H-indol-3-yl]butan-2-yl}phenyl)pyrimidin-2-amine |
| 69 | 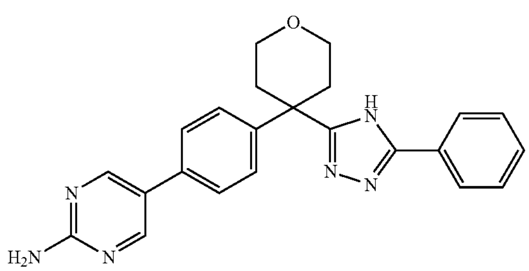 [SMILES: Nc1ncc(-c2ccc(C3(c4nnc(-c5ccccc5)[nH]4)CCOCC3)cc2)cn1] | 5-{4-[4-(5-phenyl-4H-1,2,4-triazol-3-yl)tetrahydro-2H-pyran-4-yl]phenyl}pyrimidin-2-amine |
| 70 | 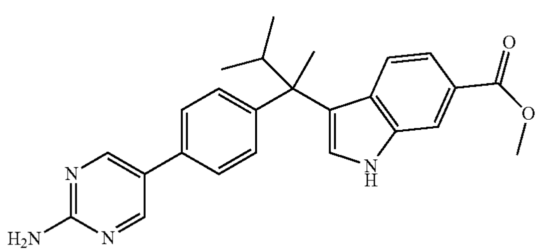 [SMILES: COC(=O)c1ccc2c(C(C)(c3ccc(-c4cnc(N)nc4)cc3)C(C)C)c[nH]c2c1] | methyl 3-{2-[4-(2-aminopyrimidin-5-yl)phenyl]-3-methylbutan-2-yl}-1H-indole-6-carboxylate |
| 71 | 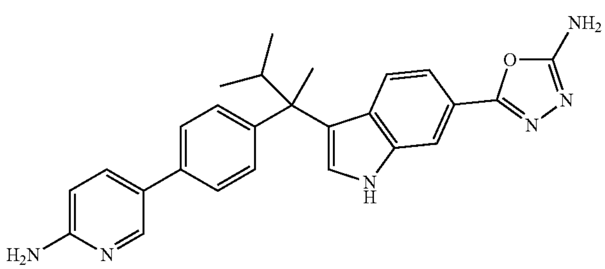 [SMILES: CC(C)C(C)(c1ccc(-c2ccc(N)nc2)cc1)c1c[nH]c2cc(-c3nnc(N)o3)ccc12] | 5-(4-{2-[6-(5-amino-1,3,4-oxadiazol-2-yl)-1H-indol-3-yl]-3-methylbutan-2-yl}phenyl)pyridin-2-amine |

TABLE 1-continued

| Example | Structure | Name |
|---|---|---|
| 72 | 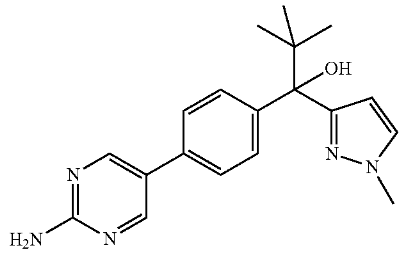 [SMILES: Cn1ccc(C(O)(c2ccc(-c3cnc(N)nc3)cc2)C(C)(C)C)n1] | 1-[4-(2-aminopyrimidin-5-yl)phenyl]-2,2-dimethyl-1-(1-methyl-1H-pyrazol-3-yl)propan-1-ol |
| 73 | 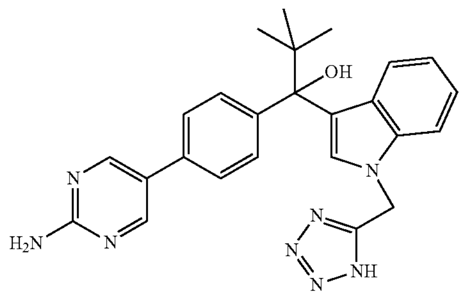 [SMILES: CC(C)(C)C(O)(c1ccc(-c2cnc(N)nc2)cc1)c1cn(Cc2nnn[nH]2)c2ccccc12] | 5-(4-{3-methyl-2-[1-(1H-tetrazol-5-ylmethyl)-1H-indol-3-yl]butan-2-yl}phenyl)pyrimidin-2-amine |
| 74 | 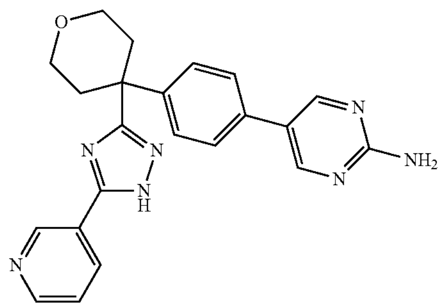 [SMILES: Nc1ncc(-c2ccc(C3(c4n[nH]c(-c5cccnc5)n4)CCOCC3)cc2)cn1] | 5-(4-{4-[5-(pyridin-3-yl)-1H-1,2,4-triazol-3-yl]tetrahydro-2H-pyran-4-yl}phenyl)pyrimidin-2-amine |
| 75 | 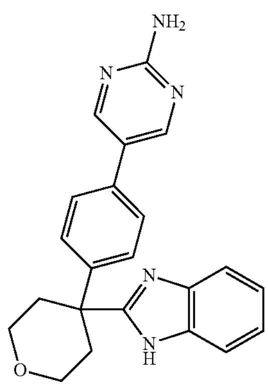 [SMILES: Nc1ncc(-c2ccc(C3(c4nc5ccccc5[nH]4)CCOCC3)cc2)cn1] | 5-{4-[4-(1H-benzimidazol-2-yl)tetrahydro-2H-pyran-4-yl]phenyl}pyrimidin-2-amine |
| 76 | 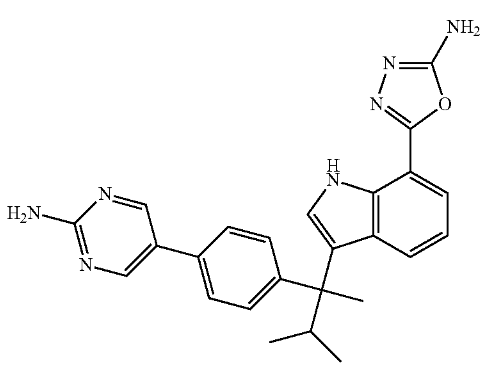 [SMILES: CC(C)C(C)(c1ccc(-c2cnc(N)nc2)cc1)c1c[nH]c2c(-c3nnc(N)o3)cccc12] | 5-(4-{2-[7-(5-amino-1,3,4-oxadiazol-2-yl)-1H-indol-3-yl]-3-methylbutan-2-yl}phenyl)pyrimidin-2-amine |

TABLE 1-continued

| Example | Structure | Name |
|---|---|---|
| 77 | 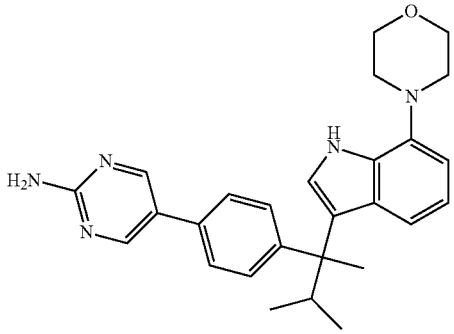 [SMILES: CC(C)C(C)(c1ccc(-c2cnc(N)nc2)cc1)c1c[nH]c2c(N3CCOCC3)cccc12] | (3-{2-[4-(2-aminopyrimidin-5-yl)phenyl]-3-methylbutan-2-yl}-1H-indol-6-yl)(morpholin-4-yl)methanone |
| 78 | 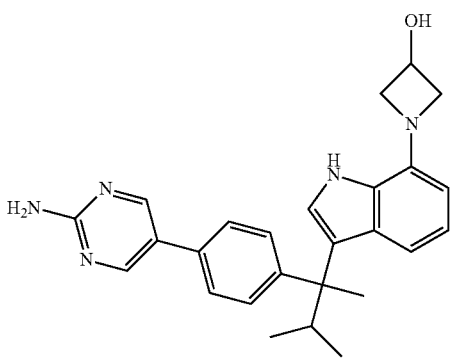 [SMILES: CC(C)C(C)(c1ccc(-c2cnc(N)nc2)cc1)c1c[nH]c2c(N3CC(O)C3)cccc12] | (3-{2-[4-(2-aminopyrimidin-5-yl)phenyl]-3-methylbutan-2-yl}-1H-indol-6-yl)(3-hydroxyazetidin-1-yl)methanone |
| 79 | 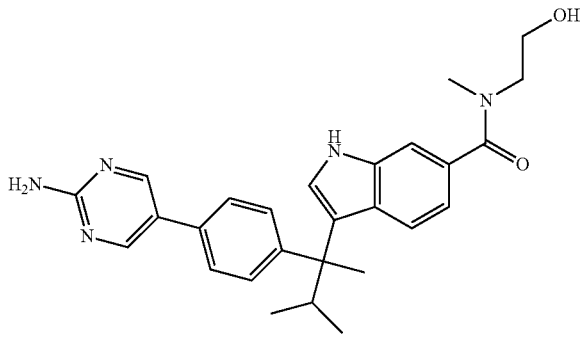 [SMILES: CC(C)C(C)(c1ccc(-c2cnc(N)nc2)cc1)c1c[nH]c2cc(C(=O)N(C)CCO)ccc12] | 3-{2-[4-(2-aminopyrimidin-5-yl)phenyl]-3-methylbutan-2-yl}-N-(2-hydroxyethyl)-N-methyl-1H-indole-6-carboxamide |
| 80 | 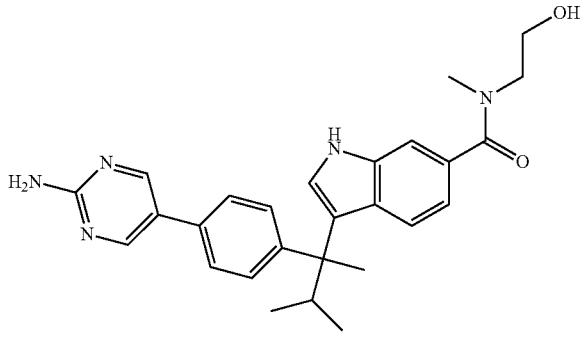 [SMILES: CC(C)C(C)(c1ccc(-c2cnc(N)nc2)cc1)c1c[nH]c2cc(C(=O)N(C)CCO)ccc12] | (3-{2-[4-(2-aminopyrimidin-5-yl)phenyl]-3-methylbutan-2-yl}-1H-indol-6-yl)(3-hydroxypyrrolidin-1-yl)methanone |
| 81 | 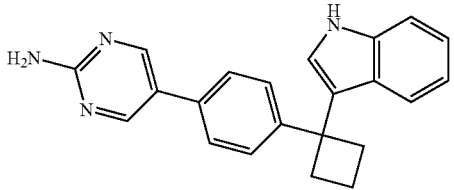 [SMILES: Nc1ncc(-c2ccc(C3(c4c[nH]c5ccccc45)CCC3)cc2)cn1] | 5-{4-[1-(1H-indol-3-yl)cyclobutyl]phenyl}pyrimidin-2-amine |

TABLE 1-continued

| Example | Structure | Name |
| --- | --- | --- |
| 82 | 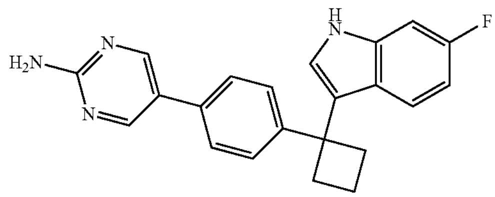 [SMILES: Nc1ncc(-c2ccc(C3(c4c[nH]c5cc(F)ccc45)CCC3)cc2)cn1] | 5-{4-[1-(6-fluoro-1H-indol-3-yl)cyclobutyl]phenyl}pyrimidin-2-amine |
| 83 | 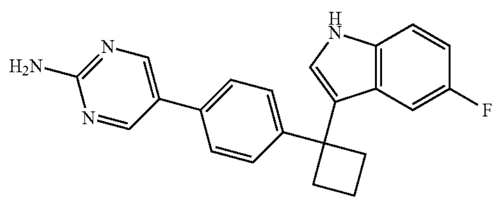 [SMILES: Nc1ncc(-c2ccc(C3(c4c[nH]c5ccc(F)cc45)CCC3)cc2)cn1] | 5-{4-[1-(5-fluoro-1H-indol-3-yl)cyclobutyl]phenyl}pyrimidin-2-amine |
| 84 | 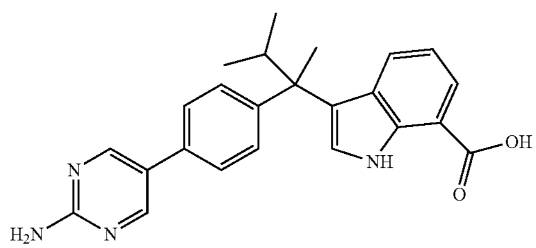 [SMILES: CC(C)C(C)(c1ccc(-c2cnc(N)nc2)cc1)c1c[nH]c2c(C(=O)O)cccc12] | 3-{2-[4-(2-aminopyrimidin-5-yl)phenyl]-3-methylbutan-2-yl}-1H-indole-7-carboxylic acid |
| 85 | 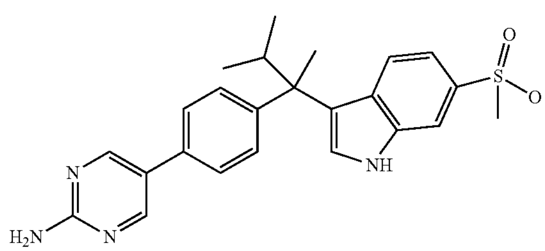 | 5-(4-{3-methyl-2-[6-(methylsulfonyl)-1H-indol-3-yl]butan-2-yl}phenyl)pyrimidin-2-amine |
| 86 | 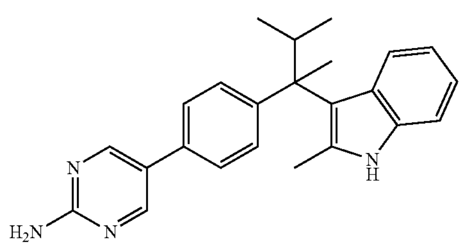 [SMILES: Cc1[nH]c2ccccc2c1C(C)(c1ccc(-c2cnc(N)nc2)cc1)C(C)C] | 5-{4-[3-methyl-2-(2-methyl-1H-indol-3-yl)butan-2-yl]phenyl}pyrimidin-2-amine |
| 87 | 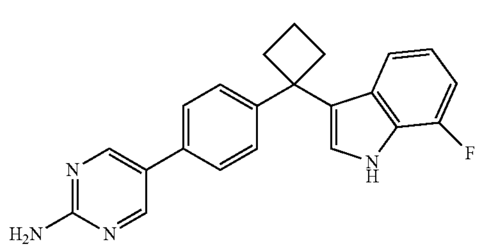 [SMILES: Nc1ncc(-c2ccc(C3(c4c[nH]c5c(F)cccc45)CCC3)cc2)cn1] | 5-{4-[1-(7-fluoro-1H-indol-3-yl)cyclobutyl]phenyl}pyrimidin-2-amine |

TABLE 1-continued

| Example | Structure | Name |
|---|---|---|
| 88 | 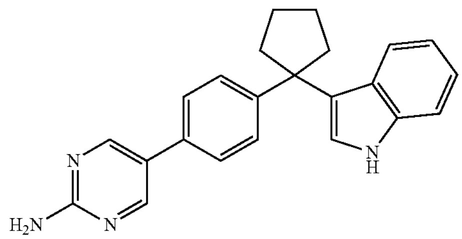 [SMILES: Nc1ncc(-c2ccc(C3(c4c[nH]c5ccccc45)CCCC3)cc2)cn1] | 5-{4-[1-(1H-indol-3-yl)cyclopentyl]phenyl}pyrimidin-2-amine |
| 89 | 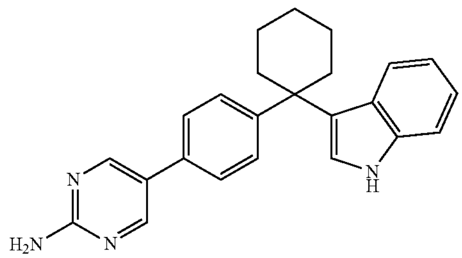 [SMILES: Nc1ncc(-c2ccc(C3(c4c[nH]c5ccccc45)CCCCC3)cc2)cn1] | 5-{4-[1-(1H-indol-3-yl)cyclohexyl]phenyl}pyrimidin-2-amine |
| 90 | 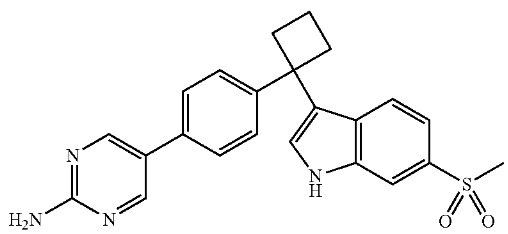 [SMILES: CS(=O)(=O)c1ccc2c(C3(c4ccc(-c5cnc(N)nc5)cc4)CCC3)c[nH]c2c1] | 5-(4-{1-[6-(methylsulfonyl)-1H-indol-3-yl]cyclobutyl}phenyl)pyrimidin-2-amine |
| 91 | 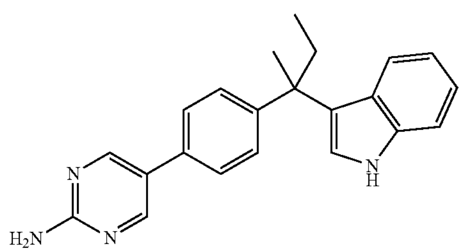 [SMILES: CCC(C)(c1ccc(-c2cnc(N)nc2)cc1)c1c[nH]c2ccccc12] | 5-{4-[2-(1H-indol-3-yl)butan-2-yl]phenyl}pyrimidin-2-amine |
| 92 | 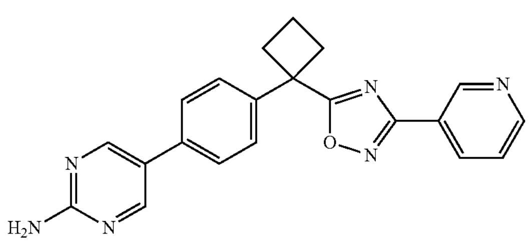 [SMILES: Nc1ncc(-c2ccc(C3(c4nc(-c5cccnc5)no4)CCC3)cc2)cn1] | 5-(4-{1-[3-(pyridin-3-yl)-1,2,4-oxadiazol-5-yl]cyclobutyl}phenyl)pyrimidin-2-amine |
| 93 | 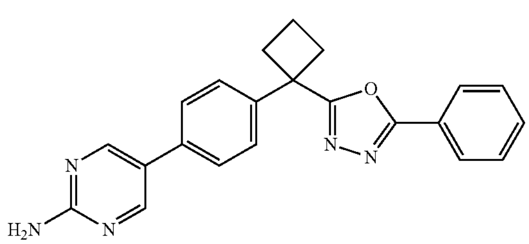 [SMILES: Nc1ncc(-c2ccc(C3(c4nnc(-c5ccccc5)o4)CCC3)cc2)cn1] | 5-{4-[1-(5-phenyl-1,3,4-oxadiazol-2-yl)cyclobutyl]phenyl}pyrimidin-2-amine |

TABLE 1-continued

| Example | Structure | Name |
|---|---|---|
| 94 | 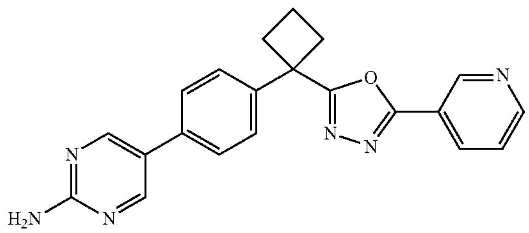 [SMILES: Nc1ncc(-c2ccc(C3(c4nnc(-c5cccnc5)o4)CCC3)cc2)cn1] | 5-(4-{1-[5-(pyridin-3-yl)-1,3,4-oxadiazol-2-yl]cyclobutyl}phenyl)pyrimidin-2-amine |
| 95 | 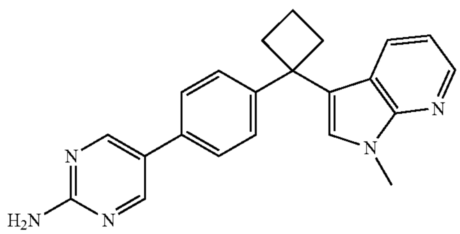 [SMILES: Cn1cc(C2(c3ccc(-c4cnc(N)nc4)cc3)CCC2)c2cccnc21] | 5-{4-[1-(1-methyl-1H-pyrrolo[2,3-b]pyridin-3-yl)cyclobutyl]phenyl}pyrimidin-2-amine |
| 96 | 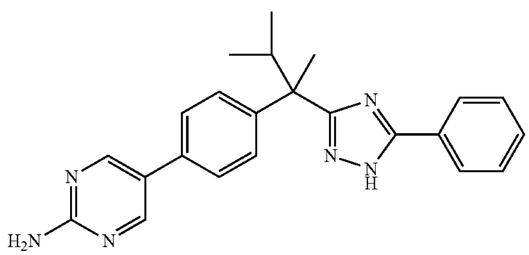 [SMILES: CC(C)C(C)(c1ccc(-c2cnc(N)nc2)cc1)c1n[nH]c(-c2ccccc2)n1] | 5-{4-[3-methyl-2-(5-phenyl-1H-1,2,4-triazol-3-yl)butan-2-yl]phenyl}pyrimidin-2-amine |
| 97 | 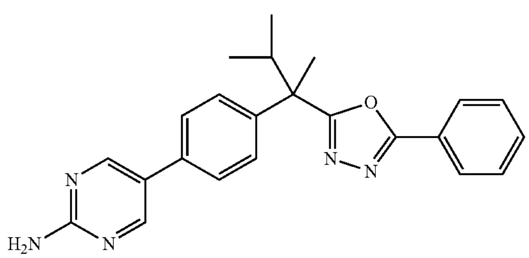 [SMILES: CC(C)C(C)(c1ccc(-c2cnc(N)nc2)cc1)c1nnc(-c2ccccc2)o1] | 5-{4-[3-methyl-2-(5-phenyl-1,3,4-oxadiazol-2-yl)butan-2-yl]phenyl}pyrimidin-2-amine |
| 98 | 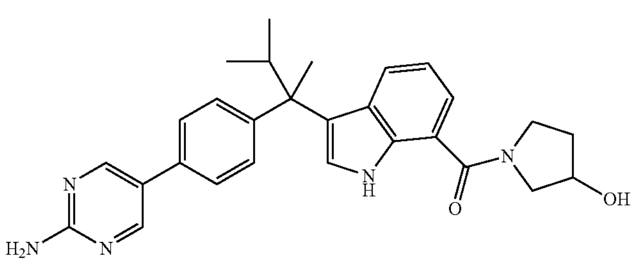 [SMILES: CC(C)C(C)(c1ccc(-c2cnc(N)nc2)cc1)c1c[nH]c2c(C(=O)N3CCC(O)C3)cccc12] | (3-{2-[4-(2-aminopyrimidin-5-yl)phenyl]-3-methylbutan-2-yl}-1H-indol-7-yl)(3-hydroxypyrrolidin-1-yl)methanone |
| 99 | 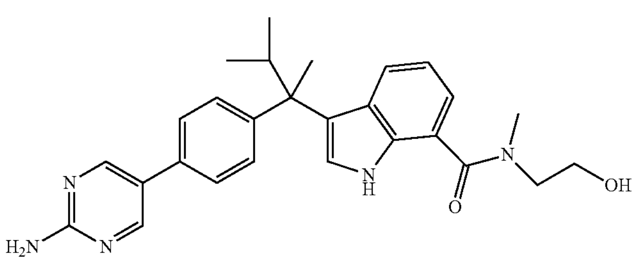 [SMILES: CC(C)C(C)(c1ccc(-c2cnc(N)nc2)cc1)c1c[nH]c2c(C(=O)N(C)CCO)cccc12] | 3-[1-[4-(2-aminopyrimidin-5-yl)phenyl]-1,2-dimethyl-propyl]-N-(2-hydroxyethyl)-N-methyl-1H-indole-7-carboxamide |

TABLE 1-continued

| Example | Structure | Name |
|---|---|---|
| 100 | 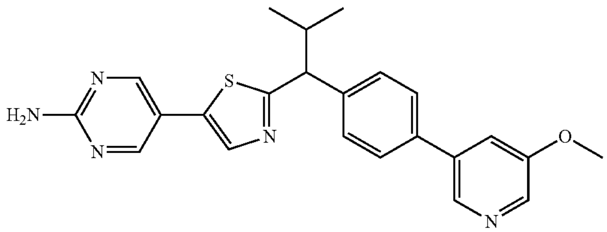 [SMILES: COc1cncc(-c2ccc(C(c3ncc(-c4cnc(N)nc4)s3)C(C)C)cc2)c1] | 5-(2-{1-[4-(5-methoxypyridin-3-yl)phenyl]-2-methoxypropyl}-1,3-thiazol-5-yl)pyrimidin-2-amine |
| 101 | 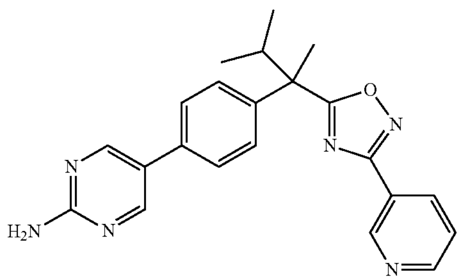 [SMILES: CC(C)C(C)(c1ccc(-c2cnc(N)nc2)cc1)c1nc(-c2cccnc2)no1] | 5-(4-{3-methyl-2-[3-(pyridin-3-yl)-1,2,4-oxadiazol-5-yl]butan-2-yl}phenyl)pyrimidin-2-amine |
| 102 | 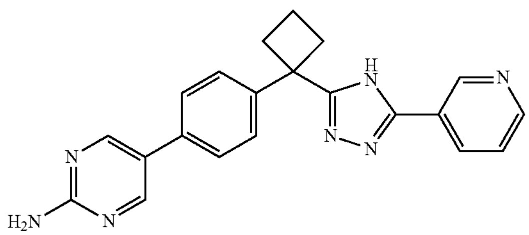 [SMILES: Nc1ncc(-c2ccc(C3(c4nnc(-c5cccnc5)[nH]4)CCC3)cc2)cn1] | 5-(4-{1-[5-(pyridin-3-yl)-4H-1,2,4-triazol-3-yl]cyclobutyl}phenyl)pyrimidin-2-amine |
| 103 | 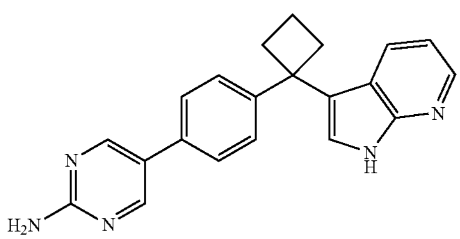 | 5-{4-[1-(1H-pyrrolo[2,3-b]pyridin-3-yl)cyclobutyl]phenyl}pyrimidin-2-amine |
| 104 | 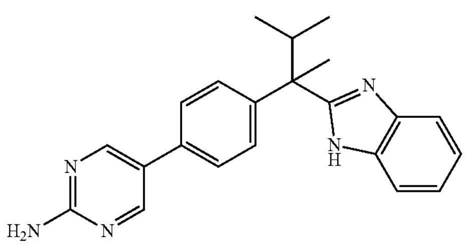 [SMILES: CC(C)C(C)(c1ccc(-c2cnc(N)nc2)cc1)c1nc2ccccc2[nH]1] | 5-{4-[2-(1H-benzimidazol-2-yl)-3-methylbutan-2-yl]phenyl}pyrimidin-2-amine |
| 105 | 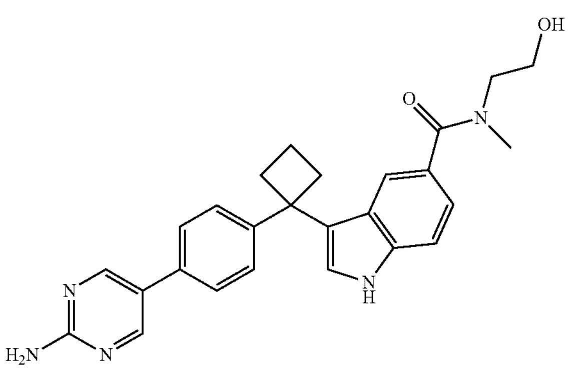 [SMILES: CN(CCO)C(=O)c1ccc2[nH]cc(C3(c4ccc(-c5cnc(N)nc5)cc4)CCC3)c2c1] | 3-{1-[4-(2-aminopyrimidin-5-yl)phenyl]cyclobutyl}-N-(2-hydroxyethyl)-N-methyl-1H-indole-5-carboxamide |

TABLE 1-continued

| Example | Structure | Name |
| --- | --- | --- |
| 106 | 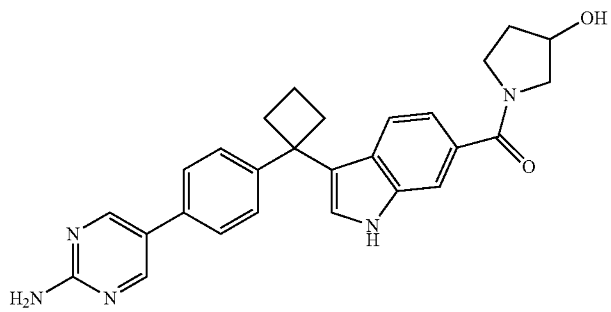 [SMILES: Nc1ncc(-c2ccc(C3(c4c[nH]c5cc(C(=O)N6CCC(O)C6)ccc45)CCC3)cc2)cn1] | (3-{1-[4-(2-aminopyrimidin-5-yl)phenyl]cyclobutyl}-1H-indol-6-yl)(3-hydroxypyrrolidin-1-yl)methanone |
| 107 | 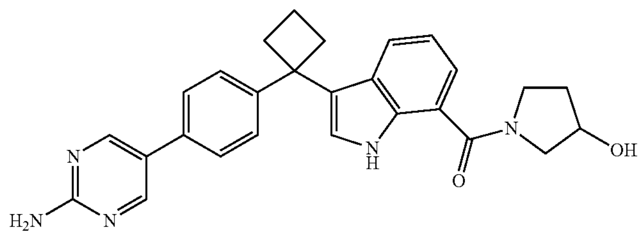 [SMILES: Nc1ncc(-c2ccc(C3(c4c[nH]c5c(C(=O)N6CCC(O)C6)cccc45)CCC3)cc2)cn1] | (3-{1-[4-(2-aminopyrimidin-5-yl)phenyl]cyclobutyl}-1H-indol-7-yl)(3-hydroxypyrrolidin-1-yl)methanone |
| 108 | 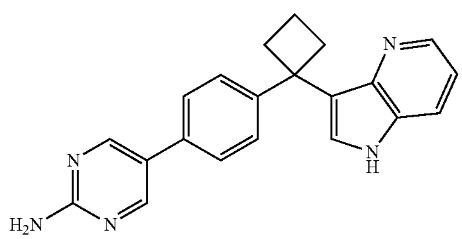 [SMILES: Nc1ncc(-c2ccc(C3(c4c[nH]c5cccnc45)CCC3)cc2)cn1] | 5-{4-[1-(1H-pyrrolo[3,2-b]pyridin-3-yl)cyclobutyl]phenyl}pyrimidin-2-amine |
| 109 | 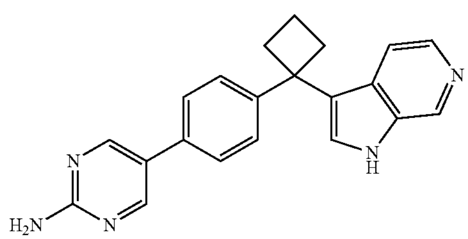 [SMILES: Nc1ncc(-c2ccc(C3(c4c[nH]c5cnccc45)CCC3)cc2)cn1] | 5-{4-[1-(1H-pyrrolo[2,3-c]pyridin-3-yl)cyclobutyl]phenyl}pyrimidin-2-amine |
| 110 | 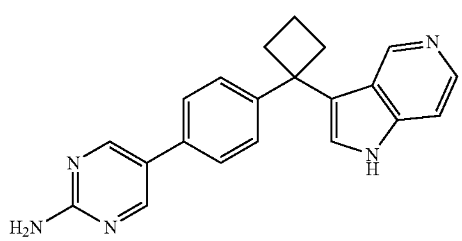 [SMILES: Nc1ncc(-c2ccc(C3(c4c[nH]c5ccncc45)CCC3)cc2)cn1] | 5-{4-[1-(1H-pyrrolo[3,2-c]pyridin-3-yl)cyclobutyl]phenyl}pyrimidin-2-amine |
| 111 | 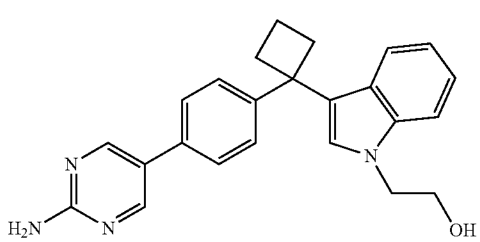 [SMILES: Nc1ncc(-c2ccc(C3(c4cn(CCO)c5ccccc45)CCC3)cc2)cn1] | 2-(3-{1-[4-(2-aminopyrimidin-5-yl)phenyl]cyclobutyl}-1H-indol-1-yl)ethanol |

TABLE 1-continued

| Example | Structure | Name |
|---|---|---|
| 112 | 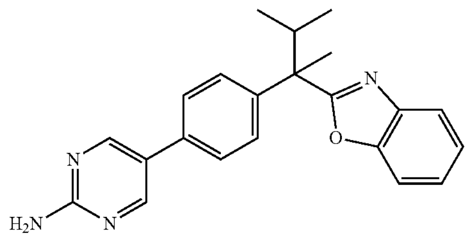 | 5-{4-[2-(1,3-benzoxazol-2-yl)-3-methylbutan-2-yl]phenyl}pyrimidin-2-amine |
| 113 | 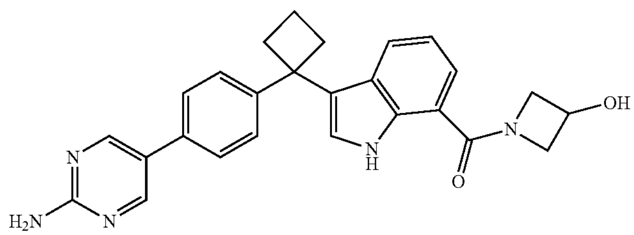 [SMILES: Nc1ncc(-c2ccc(C3(c4c[nH]c5c(C(=O)N6CC(O)C6)cccc45)CCC3)cc2)cn1] | (3-{1-[4-(2-aminopyrimidin-5-yl)phenyl]cyclobutyl}-1H-indol-7-yl)(3-hydroxyazetidin-1-yl)methanone |
| 114 | 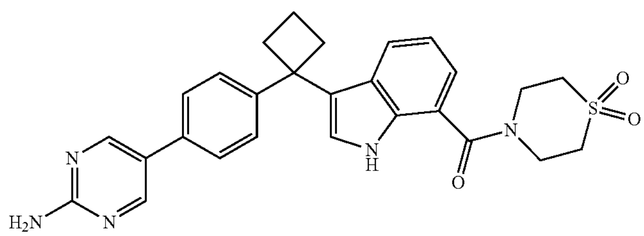 [SMILES: Nc1ncc(-c2ccc(C3(c4c[nH]c5c(C(=O)N6CCS(=O)(=O)CC6)cccc45)CCC3)cc2)cn1] | (3-{1-[4-(1-aminopyrimidin-5-yl)phenyl]cyclobutyl}-1H-indol-7-yl)(1,1-dioxidothiomorpholin-4-yl)methanone |
| 115 | 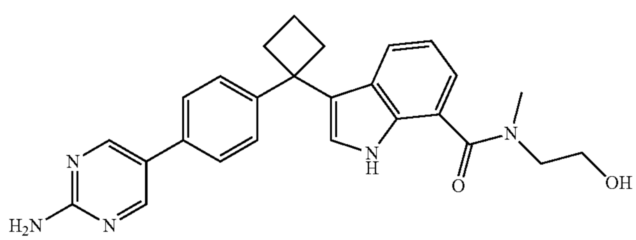 [SMILES: CN(CCO)C(=O)c1cccc2c(C3(c4ccc(-c5cnc(N)nc5)cc4)CCC3)c[nH]c12] | 3-{1-[4-(2-aminopyrimidin-5-yl)phenyl]cyclobutyl}-N-(2-hydroxyethyl)-N-methyl-1H-indole-7-carboxamide |
| 116 | 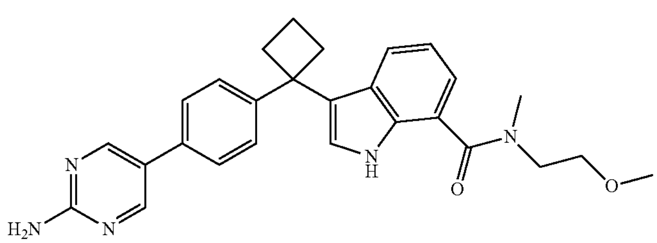 | 3-{1-[4-(2-aminopyrimidin-5-yl)phenyl]cyclobutyl}-N-(2-methoxyethyl)-N-methyl-1H-indole-7-carboxamide |
| 117 | 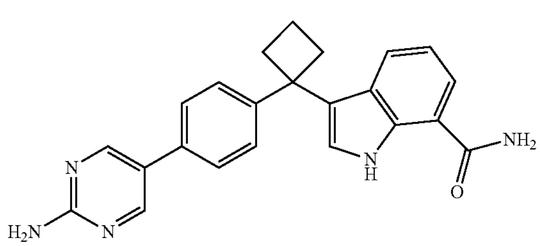 [SMILES: NC(=O)c1cccc2c(C3(c4ccc(-c5cnc(N)nc5)cc4)CCC3)c[nH]c12] | 3-{1-[4-(2-aminopyrimidin-5-yl)phenyl]cyclobutyl}-1H-indole-7-carboxamide |

TABLE 1-continued

| Example | Structure | Name |
|---|---|---|
| 118 | 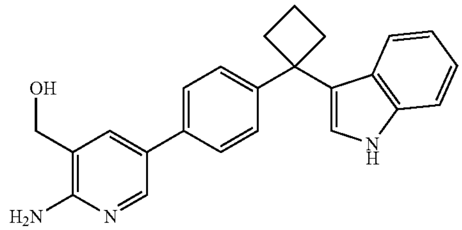 [SMILES: Nc1ncc(-c2ccc(C3(c4c[nH]c5ccccc45)CCC3)cc2)cc1CO] | (2-amino-5-{4-[1-(1H-indol-3-yl)cyclobutyl]phenyl}pyridin-3-yl)methanol |
| 119 | 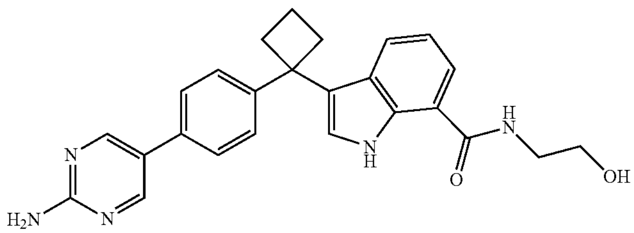 [SMILES: Nc1ncc(-c2ccc(C3(c4c[nH]c5c(C(=O)NCCO)cccc45)CCC3)cc2)cn1] | 3-{1-[4-(2-aminopyrimidin-5-yl)phenyl]cyclobutyl}-N-(2-hydroxyethyl)-1H-indole-7-carboxamide |
| 120 | 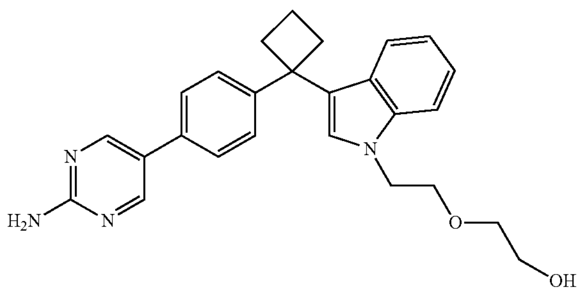 [SMILES: Nc1ncc(-c2ccc(C3(c4cn(CCOCCO)c5ccccc45)CCC3)cc2)cn1] | 2-[2-(3-{1-[4-(2-aminopyrimidin-5-yl)phenyl]cyclobutyl}-1H-indol-1-yl)ethoxy]ethanol |
| 121 | 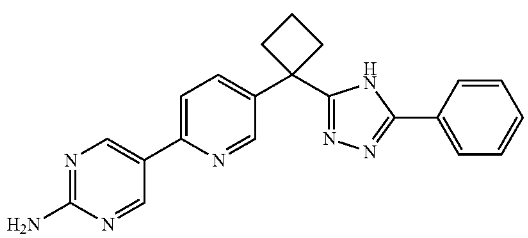 | 5-{5-[1-(5-phenyl-4H-1,2,4-triazol-3-yl)cyclobutyl]pyridin-2-yl}pyrimidin-2-amine |
| 122 | 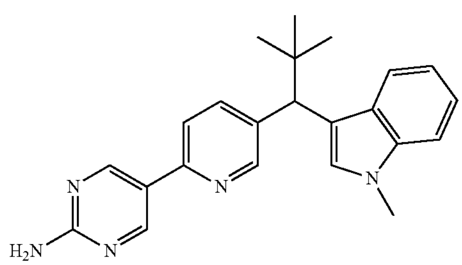 [SMILES: Cn1cc(C(c2ccc(-c3cnc(N)nc3)nc2)C(C)(C)C)c2ccccc21] | 5-{5-[2,2-dimethyl-1-(1-methyl-1H-indol-3-yl)propyl]pyridin-2-yl}pyrimidin-2-amine |
| 123 | 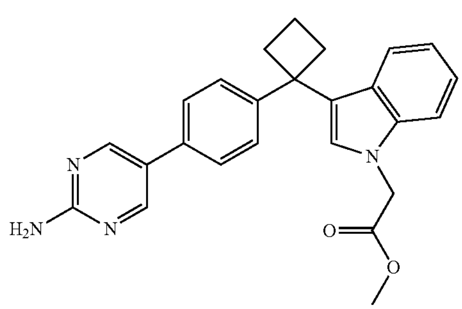 [SMILES: COC(=O)Cn1cc(C2(c3ccc(-c4cnc(N)nc4)cc3)CCC2)c2ccccc21] | methyl (3-{1-[4-(2-aminopyrimidin-5-yl)phenyl]cyclobutyl}-1H-indol-1-yl)-acetate |

TABLE 1-continued

| Example | Structure | Name |
|---|---|---|
| 124 | 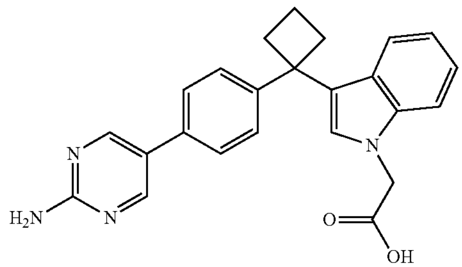 [SMILES: Nc1ncc(-c2ccc(C3(c4cn(CC(=O)O)c5ccccc45)CCC3)cc2)cn1] | (3-{1-[4-(2-aminopyrimidin-5-yl)phenyl]cyclobutyl}-1H-indol-1-yl)acetic acid |
| 125 | 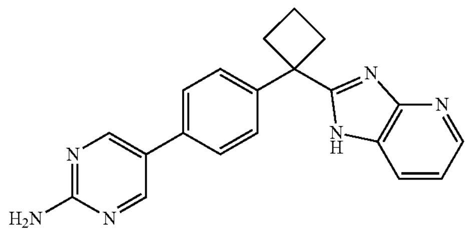 | 5-{4-[1-(1H-imidazo[4,5-b]pyridin-2-yl)cyclobutyl]phenyl}pyrimidin-2-amine |
| 126 | 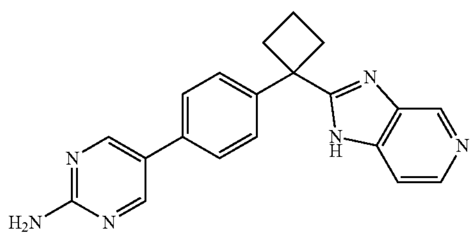 [SMILES: Nc1ncc(-c2ccc(C3(c4nc5cnccc5[nH]4)CCC3)cc2)cn1] | 5-{4-[1-(1H-imidazo[4,5-c]pyridin-2-yl)cyclobutyl]phenyl}pyrimidin-2-amine |
| 127 | 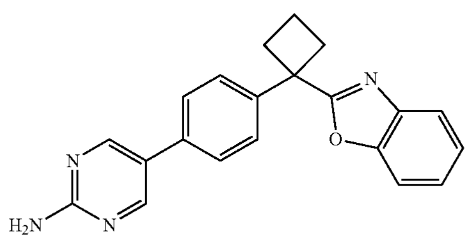 | 5-{4-[1-(1,3-benzoxazol-2-yl)cyclobutyl]phenyl}pyrimidin-2-amine |
| 128 | 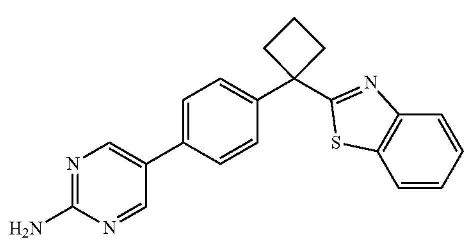 | 5-{4-[1-(1,3-benzothiazol-2-yl)cyclobutyl]phenyl}pyrimidin-2-amine |
| 129 | 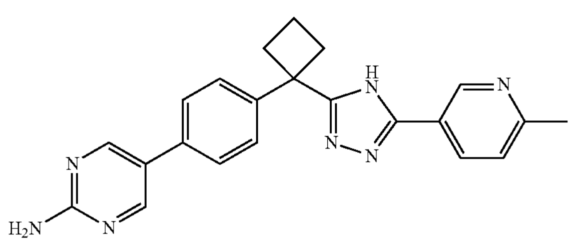 | 5-(4-{1-[5-(6-methylpyridin-3-yl)-4H-1,2,4-triazol-3-yl]cyclobutyl}phenyl)pyrimidin-2-amine |

TABLE 1-continued

| Example | Name |
|---------|------|
| 130 | 3-{1-[4-(1H-pyrrolo[2,3-b]pyridin-5-yl)phenyl]cyclobutyl}-1H-pyrrolo[2,3-b]pyridine |
| 131 | 5-(4-{1-[5-(6-methylpyridin-3-yl)-1,3,4-thiadiazol-2-yl]cyclobutyl}phenyl)pyrimidin-2-amine |
| 132 | 2-(3-{1-[4-(2-aminopyrimidin-5-yl)phenyl]cyclobutyl}-1H-indol-1-yl)-N-(2-hydroxyethyl)-N-methylacetamide |
| 133 | 2-(3-{1-[4-(2-aminopyrimidin-5-yl)phenyl]cyclobutyl}-1H-indol-1-yl)-1-(3-hydroxyazetidin-1-yl)ethanone |
| 134 | (3-{1-[4-(2-aminopyrimidin-5-yl)phenyl]cyclobutyl}-1H-indol-7-yl)[(3R)-3-hydroxypyrrolidin-1-yl]methanone |
| 135 | (3-{1-[4-(2-aminopyrimidin-5-yl)phenyl]cyclobutyl}-1H-indol-7-yl)[(3S)-3-hydroxypyrrolidin-1-yl]methanone |

TABLE 1-continued

| Example | Structure | Name |
|---|---|---|
| 136 | 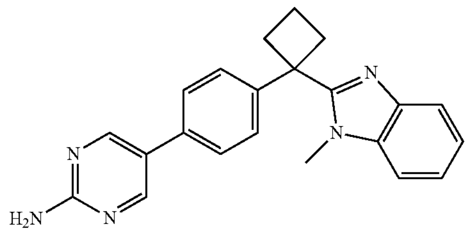 [SMILES: Cn1c(C2(c3ccc(-c4cnc(N)nc4)cc3)CCC2)nc2ccccc21] | 5-{4-[1-(1-methyl-1H-benzimidazol-2-yl)cyclobutyl]phenyl}pyrimidin-2-amine |
| 137 | 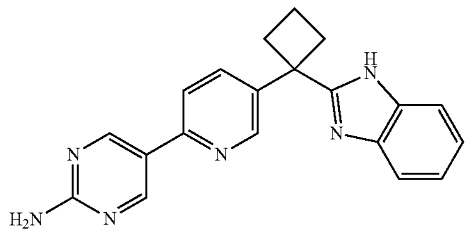 | 5-{5-[1-(1H-benzimidazol-2-yl)cyclobutyl]pyridin-2-yl}pyrimidin-2-amine |
| 138 | 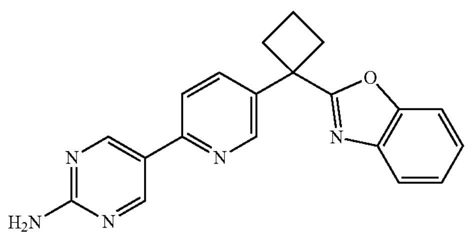 [SMILES: Nc1ncc(-c2ccc(C3(c4nc5ccccc5o4)CCC3)cn2)cn1] | 5-{5-[1-(1,3-benzoxazol-2-yl)cyclobutyl]pyridin-2-yl}pyrimidin-2-amine |
| 139 | 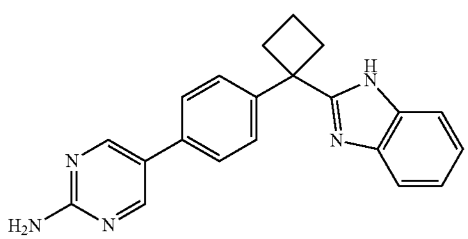 [SMILES: Nc1ncc(-c2ccc(C3(c4nc5ccccc5[nH]4)CCC3)cc2)cn1] | 5-{4-[1-(1H-benzimidazol-2-yl)cyclobutyl]phenyl}pyrimidin-2-amine |
| 140 | 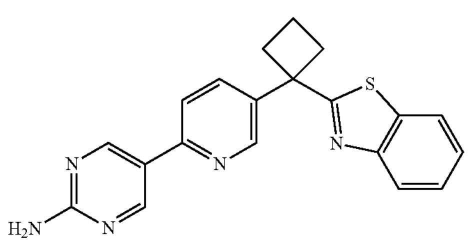 | 5-{5-[1-(1,3-benzothiazol-2-yl)cyclobutyl]pyridin-2-yl}pyrimidin-2-amine |
| 141 | 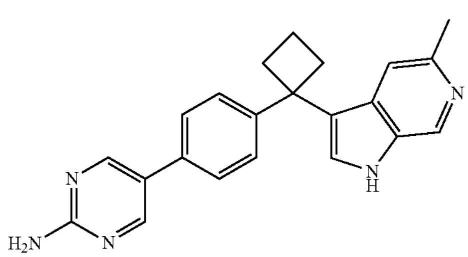 [SMILES: Cc1cc2c(C3(c4ccc(-c5cnc(N)nc5)cc4)CCC3)c[nH]c2cn1] | 5-{4-[1-(5-methyl-1H-pyrrolo[2,3-c]pyridin-3-yl)cyclobutyl]phenyl}pyrimidin-2-amine |

TABLE 1-continued

| Example | Structure | Name |
|---|---|---|
| 142 | 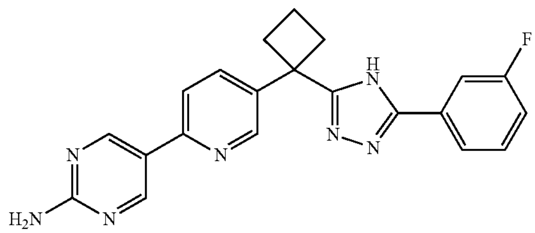 [SMILES: Nc1ncc(-c2ccc(C3(c4nnc(-c5cccc(F)c5)[nH]4)CCC3)cn2)cn1] | 5-(5-{1-[5-(3-fluorophenyl)-4H-1,2,4-triazol-3-yl]cyclobutyl}pyridin-3-yl)pyrimidin-2-amine |
| 143 | 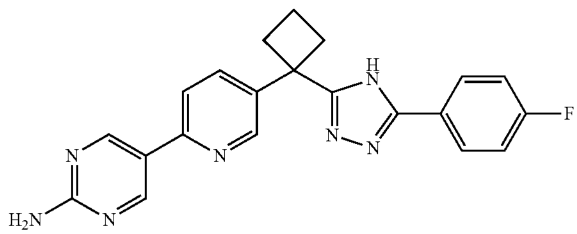 [SMILES: Nc1ncc(-c2ccc(C3(c4nnc(-c5ccc(F)cc5)[nH]4)CCC3)cn2)cn1] | 5-(5-{1-[5-(4-fluorophenyl)-4H-1,2,4-triazol-3-yl]cyclobutyl}pyridin-2-yl)pyrimidin-2-amine |
| 144 | 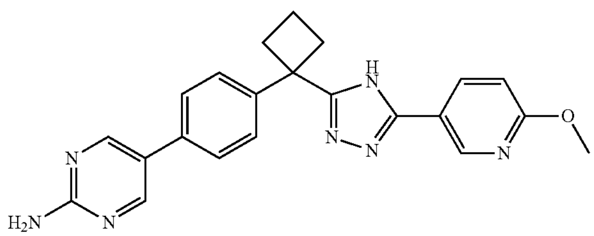 [SMILES: COc1ccc(-c2nnc(C3(c4ccc(-c5cnc(N)nc5)cc4)CCC3)[nH]2)cn1] | 5-(4-{1-[5-(6-methoxypyridin-3-yl)-4H-1,2,4-triazol-3-yl]cyclobutyl}phenyl)pyrimidin-2-amine |
| 145 | 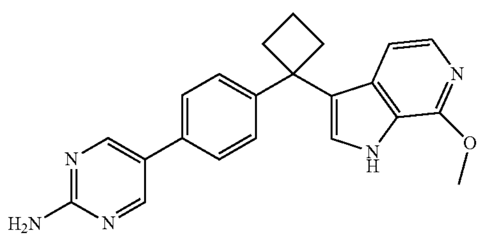 | 5-{4-[1-(7-methoxy-1H-pyrrolo[2,3-b]pyridin-3-yl)cyclobutyl]phenyl}pyrimidin-2-amine |
| 146 | 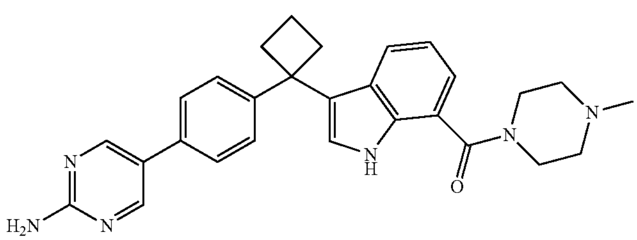 [SMILES: CN1CCN(C(=O)c2cccc3c(C4(c5ccc(-c6cnc(N)nc6)cc5)CCC4)c[nH]c23)CC1] | (3-{1-[4-(2-aminopyridin-5-yl)phenyl]cyclobutyl}-1H-indol-7-yl)(4-methylpiperazin-1-yl)methanone |
| 147 | 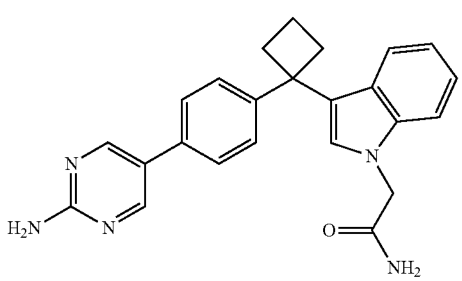 [SMILES: NC(=O)Cn1cc(C2(c3ccc(-c4cnc(N)nc4)cc3)CCC2)c2ccccc21] | 2-(3-{1-[4-(2-aminopyridin-5-yl)phenyl]cyclobutyl}-1H-indol-1-yl)acetamide |

TABLE 1-continued

| Example | Structure | Name |
|---|---|---|
| 148 | 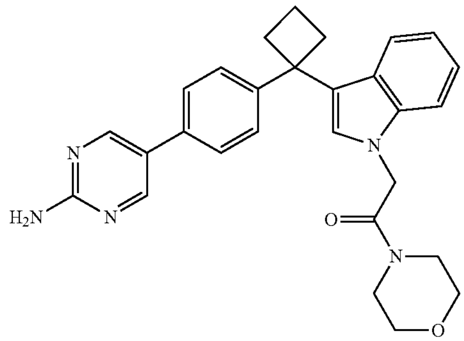 [SMILES: Nc1ncc(-c2ccc(C3(c4cn(CC(=O)N5CCOCC5)c5ccccc45)CCC3)cc2)cn1] | 2-(3-{1-[4-(2-aminopyrimidin-5-yl)phenyl]cyclobutyl}-1H-indol-1-yl)-1-(morpholin-4-yl)ethanone |
| 149 | 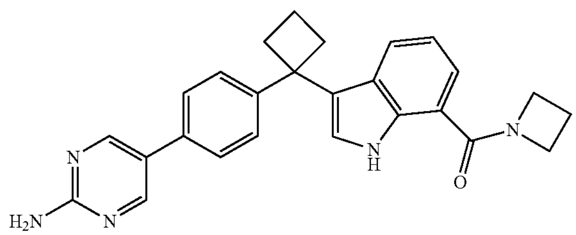 [SMILES: Nc1ncc(-c2ccc(C3(c4c[nH]c5c(C(=O)N6CCC6)cccc45)CCC3)cc2)cn1] | (3-{1-[4-(2-aminopyrimidin-5-yl)phenyl]cyclobutyl}-1H-indol-7-yl)(azetidin-1-yl)methanone |
| 150 | 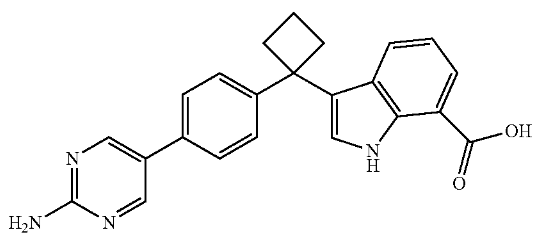 [SMILES: Nc1ncc(-c2ccc(C3(c4c[nH]c5c(C(=O)O)cccc45)CCC3)cc2)cn1] | 3-{1-[4-(2-aminopyrimidin-5-yl)phenyl]cyclobutyl}-1H-indole-7-carboxylic acid |
| 151 | 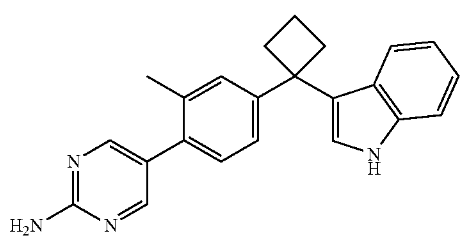 [SMILES: Cc1cc(C2(c3c[nH]c4ccccc34)CCC2)ccc1-c1cnc(N)nc1] | 5-{4-[1-(1H-indol-3-yl)cyclobutyl]-2-methylphenyl}pyrimidin-2-amine |
| 152 | 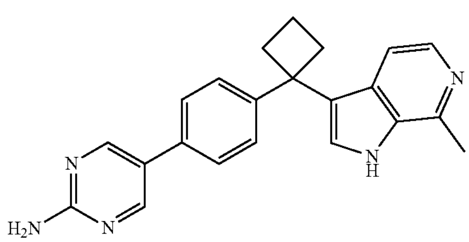 [SMILES: Cc1nccc2c(C3(c4ccc(-c5cnc(N)nc5)cc4)CCC3)c[nH]c12] | 5-{4-[1-(7-methyl-1H-pyrrolo[2,3-c]pyridin-3-yl)cyclobutyl]phenyl}pyrimidin-2-amine |
| 153 | 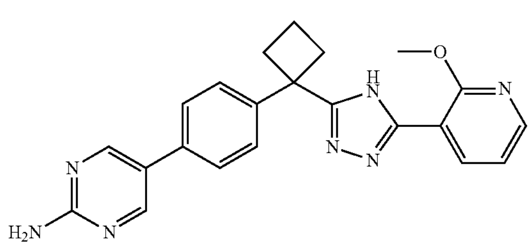 [SMILES: COc1ncccc1-c1nnc(C2(c3ccc(-c4cnc(N)nc4)cc3)CCC2)[nH]1] | 5-(4-{1-[5-(2-methoxypyridin-3-yl)-4H-1,2,4-triazol-3-yl]cyclobutyl}phenyl)pyrimidin-2-amine |

TABLE 1-continued

| Example | Structure | Name |
|---|---|---|
| 154 | 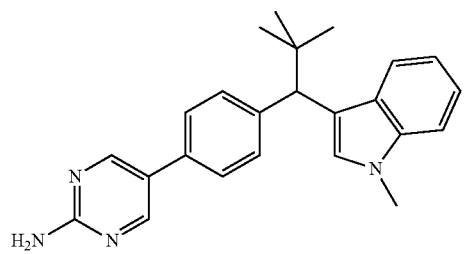 [SMILES: Cn1cc(C(c2ccc(-c3cnc(N)nc3)cc2)C(C)(C)C)c2ccccc21] | 5-{4-[2,2-dimethyl-1-(1-methyl-1H-indol-3-yl)propyl]phenyl}pyrimidin-2-amine |
| 155 | 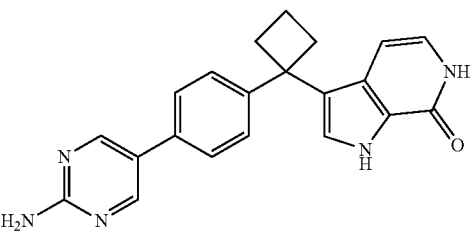 [SMILES: Nc1ncc(-c2ccc(C3(c4c[nH]c5c(=O)[nH]ccc45)CCC3)cc2)cn1] | 3-{1-[4-(2-aminopyridin-5-yl)phenyl]cyclobutyl}-1,6-dihydro-7H-pyrrolo[2,3-c]pyridin-7-one |
| 156 | 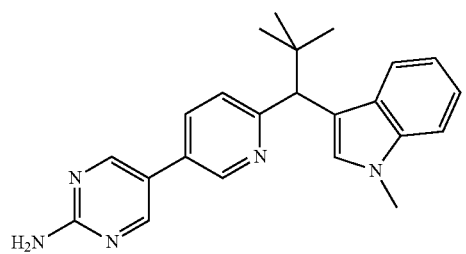 [SMILES: Cn1cc(C(c2ccc(-c3cnc(N)nc3)cn2)C(C)(C)C)c2ccccc21] | 5-{6-[2,2-dimethyl-1-(1-methyl-1H-indol-3-yl)propyl]pyridin-3-yl}pyrimidin-2-amine |
| 157 | 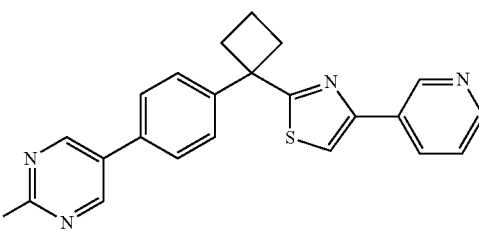 | 5-(4-{1-[4-(6-methylpyridin-3-yl)-1,3-thiazol-2-yl]cyclobutyl}phenyl)pyrimidin-2-amine |
| 158 | 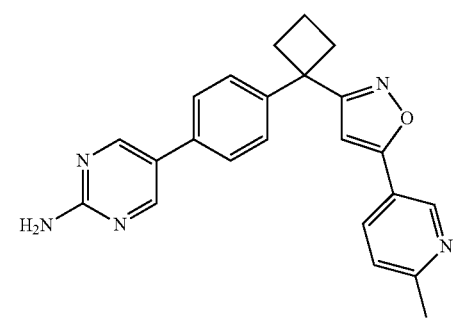 | 5-(4-{1-[5-(6-methylpyridin-3-yl)-1,2-oxazol-3-yl]cyclobutyl}phenyl)pyrimidin-2-amine |
| 159 | 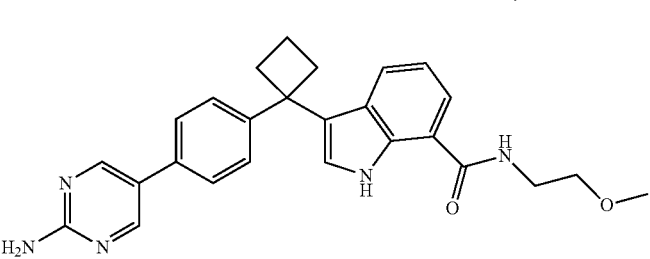 | 3-{1-[4-(2-aminopyridin-5-yl)phenyl]cyclobutyl}-N-(2-methoxyethyl)-1H-indole-7-carboxamide |

TABLE 1-continued

| Example | Structure | Name |
|---|---|---|
| 160 | 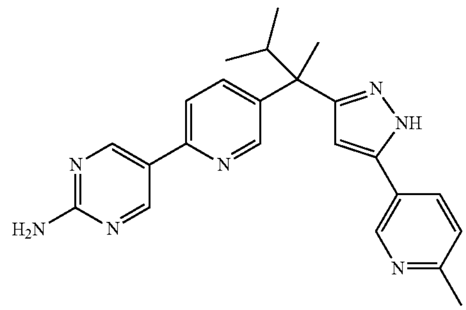 [SMILES: Cc1ccc(-c2cc(C(C)(c3ccc(-c4cnc(N)nc4)nc3)C(C)C)n[nH]2)cn1] | 5-(5-{3-methyl-2-[5-(6-methylpyridin-3-yl)-1H-pyrazol-3-yl]butan-2-yl}pyridin-2-yl)pyrimidin-2-amine |
| 161 | 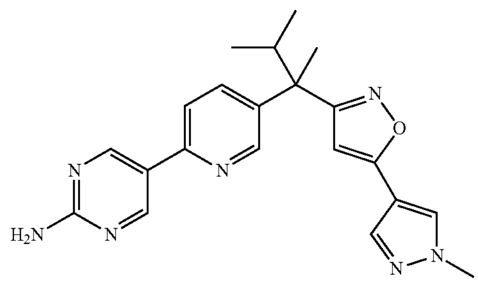 [SMILES: CC(C)C(C)(c1ccc(-c2cnc(N)nc2)nc1)c1cc(-c2cnn(C)c2)on1] | 5-(5-{3-methyl-2-[5-(1-methyl-1H-pyrazol-4-yl)-1,2-oxazol-3-yl]butan-2-yl}pyridin-2-yl)pyrimidin-2-amine |
| 162 | 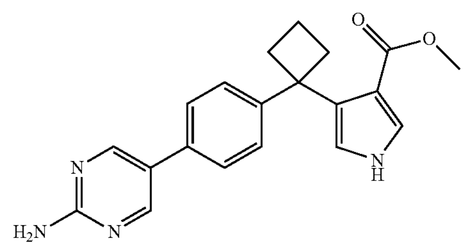 [SMILES: COC(=O)c1c[nH]cc1C1(c2ccc(-c3cnc(N)nc3)cc2)CCC1] | methyl 4-{1-[4-(2-aminopyrimidin-5-yl)phenyl]cyclobutyl}-1H-pyrrole-3-carboxylate |
| 163 | 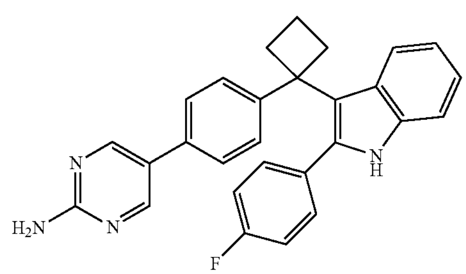 [SMILES: Nc1ncc(-c2ccc(C3(c4c(-c5ccc(F)cc5)[nH]c5ccccc45)CCC3)cc2)cn1] | 5-(4-{1-[2-(4-fluorophenyl)-1H-indol-3-yl]cyclobutyl}phenyl)pyrimidin-2-amine |
| 164 | 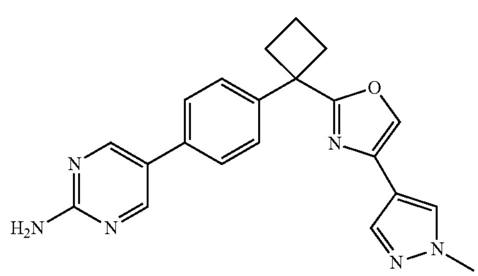 [SMILES: Cn1cc(-c2coc(C3(c4ccc(-c5cnc(N)nc5)cc4)CCC3)n2)cn1] | 5-(4-{1-[4-(1-methyl-1H-pyrazol-4-yl)-1,3-oxazol-2-yl]cyclobutyl}phenyl)pyrimidin-2-amine |

TABLE 1-continued

| Example | Structure | Name |
|---|---|---|
| 165 | 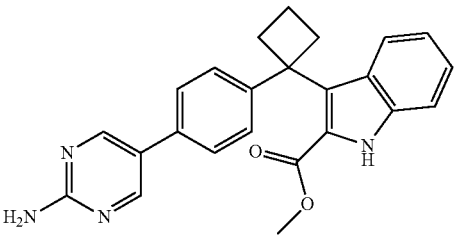 [SMILES: COC(=O)c1[nH]c2ccccc2c1C1(c2ccc(-c3cnc(N)nc3)cc2)CCC1] | methyl 3-{1-[4-(2-aminopyrimidin-5-yl)phenyl]cyclobutyl}-1H-indole-2-carboxylate |
| 166 | 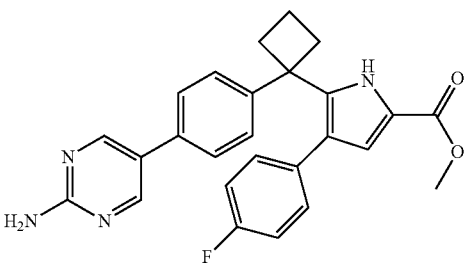 [SMILES: COC(=O)c1cc(-c2ccc(F)cc2)c(C2(c3ccc(-c4cnc(N)nc4)cc3)CCC2)[nH]1] | methyl 5-{1-[4-(2-aminopyrimidin-5-yl)phenyl]cyclobutyl}-4-(4-fluorophenyl)-1H-pyrrole-2-carboxylate |
| 167 | 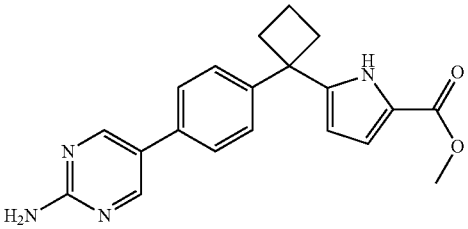 | methyl 5-{1-[4-(2-aminopyrimidin-5-yl)phenyl]cyclobutyl}-1H-pyrrole-2-carboxylate |
| 168 | 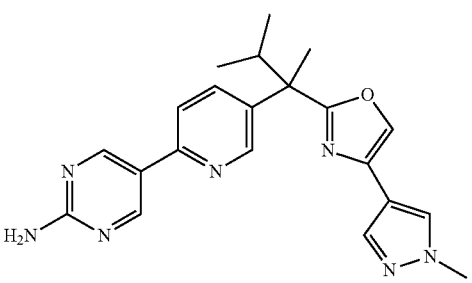 [SMILES: CC(C)C(C)(c1ccc(-c2cnc(N)nc2)nc1)c1nc(-c2cnn(C)c2)co1] | 5-(5-{3-methyl-2-[4-(1-methyl-1H-pyrazol-4-yl)-1,3-oxazol-2-yl]butan-2-yl}pyridin-2-yl)pyrimidin-2-amine |
| 169 | 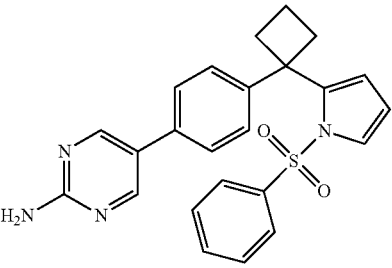 [SMILES: Nc1ncc(-c2ccc(C3(c4cccn4S(=O)(=O)c4ccccc4)CCC3)cc2)cn1] | 5-(4-{1-[1-(phenylsulfonyl)-1H-pyrrol-2-yl]cyclobutyl}phenyl)pyrimidin-2-amine |

TABLE 1-continued

| Example | Structure | Name |
|---|---|---|
| 170 | 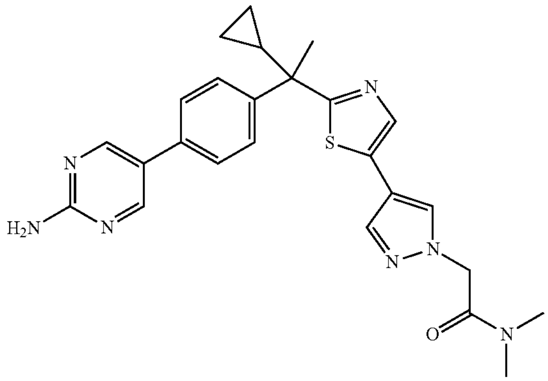 [SMILES: CN(C)C(=O)Cn1cc(-c2cnc(C(C)(c3ccc(-c4cnc(N)nc4)cc3)C3CC3)s2)cn1] | 2-[4-(2-{1-[4-(2-aminopyrimidin-5-yl)phenyl]-1-cyclopropylethyl}-1,3-thiazol-5-yl)-1H-pyrazol-1-yl]-N,N-dimethylacetamide |
| 171 | 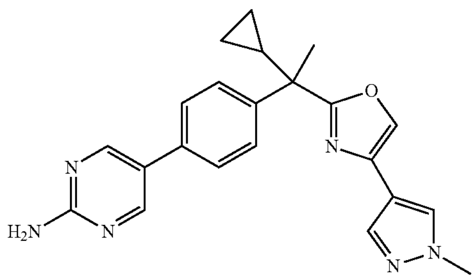 [SMILES: Cn1cc(-c2coc(C(C)(c3ccc(-c4cnc(N)nc4)cc3)C3CC3)n2)cn1] | 5-(4-{1-cyclopropyl-1-[4-(1-methyl-1H-pyrazol-4-yl)-1,3-oxazol-2-yl]ethyl}phenyl)pyrimidin-2-amine |
| 172 | 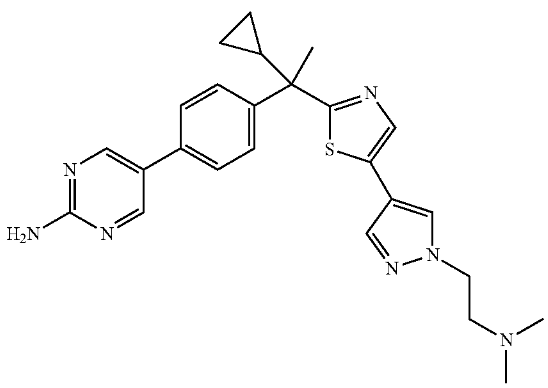 [SMILES: CN(C)CCn1cc(-c2cnc(C(C)(c3ccc(-c4cnc(N)nc4)cc3)C3CC3)s2)cn1] | 5-{4-[1-cyclopropyl-1-(5-{1-[2-(dimethylamino)ethyl]-1H-pyrazol-4-yl}-1,3-thiazol-2-yl)ethyl]phenyl}pyrimidin-2-amine |
| 173 | 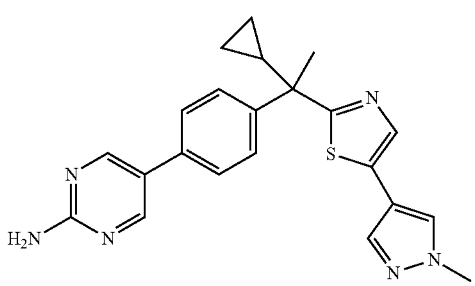 [SMILES: Cn1cc(-c2cnc(C(C)(c3ccc(-c4cnc(N)nc4)cc3)C3CC3)s2)cn1] | 5-(4-{1-cyclopropyl-1-[5-(1-methyl-1H-pyrazol-4-yl)-1,3-thiazol-2-yl]ethyl}phenyl)pyrimidin-2-amine |
| 174 | 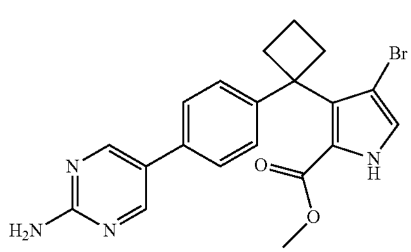 [SMILES: COC(=O)c1[nH]cc(Br)c1C1(c2ccc(-c3cnc(N)nc3)cc2)CCC1] | methyl 3-{1-[4-(2-aminopyrimidin-5-yl)phenyl]cyclobutyl}-4-bromo-1H-pyrrole-2-carboxylate |

TABLE 1-continued

| Example | Structure | Name |
|---|---|---|
| 175 | 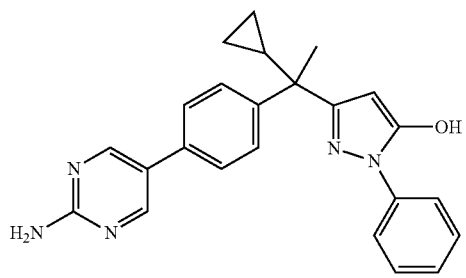 [SMILES: CC(c1ccc(-c2cnc(N)nc2)cc1)(c1cc(O)n(-c2ccccc2)n1)C1CC1] | 3-{1-[4-(2-aminopyrimidin-5-yl)phenyl]-1-cyclopropylethyl}-1-phenyl-1H-pyrazol-5-ol |
| 176 | 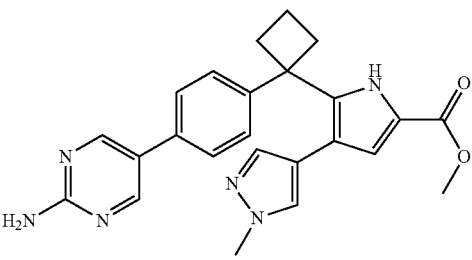 [SMILES: COC(=O)c1cc(-c2cnn(C)c2)c(C2(c3ccc(-c4cnc(N)nc4)cc3)CCC2)[nH]1] | methyl 5-{1-[4-(2-aminopyrimidin-5-yl)phenyl]cyclobutyl}-4-(1-methyl-1H-pyrazol-4-yl)-1H-pyrrole-2-carboxylate |
| 177 | 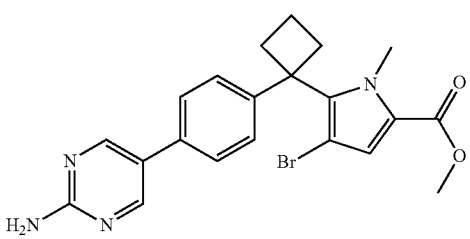 [SMILES: COC(=O)c1cc(Br)c(C2(c3ccc(-c4cnc(N)nc4)cc3)CCC2)n1C] | methyl 5-{1-[4-(2-aminopyrimidin-5-yl)phenyl]cyclobutyl}-4-bromo-1-methyl-1H-pyrrole-2-carboxylate |
| 178 | 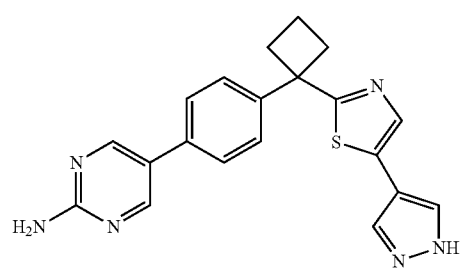 [SMILES: Nc1ncc(-c2ccc(C3(c4ncc(-c5cn[nH]c5)s4)CCC3)cc2)cn1] | 5-(4-{1-[5-(1H-pyrazol-4-yl)-1,3-thiazol-2-yl]cyclobutyl}phenyl)pyrimidin-2-amine |
| 179 | 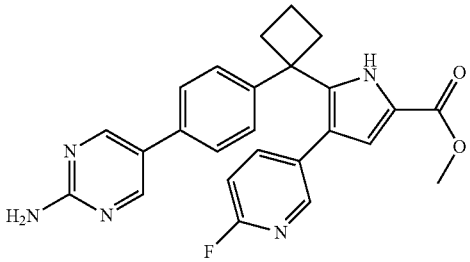 [SMILES: COC(=O)c1cc(-c2ccc(F)nc2)c(C2(c3ccc(-c4cnc(N)nc4)cc3)CCC2)[nH]1] | methyl 5-{1-[4-(2-aminopyrimidin-5-yl)phenyl]cyclobutyl}-4-(6-fluoropyridin-3-yl)-1H-pyrrole-2-carboxylate |

TABLE 1-continued

| Example | Structure | Name |
|---|---|---|
| 180 | 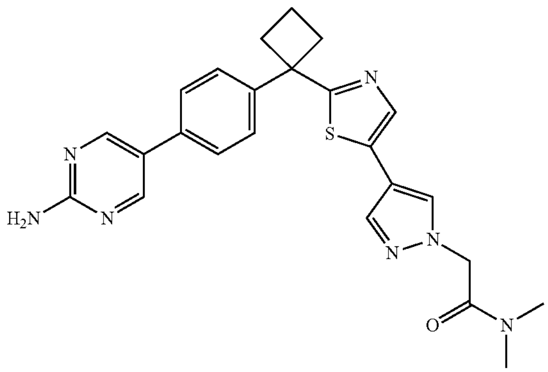 [SMILES: CN(C)C(=O)Cn1cc(-c2cnc(C3(c4ccc(-c5cnc(N)nc5)cc4)CCC3)s2)cn1] | 2-[4-(2-{1-[4-(2-aminopyrimidin-5-yl)phenyl]cyclobutyl}-1,3-thiazol-5-yl)-1H-pyrazol-1-yl]-N,N-dimethylacetamide |
| 181 | 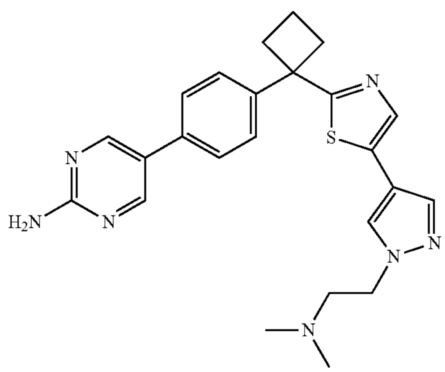 [SMILES: CN(C)CCn1cc(-c2cnc(C3(c4ccc(-c5cnc(N)nc5)cc4)CCC3)s2)cn1] | 5-{4-[1-(5-{1-[2-(dimethylamino)ethyl]-1H-pyrazol-4-yl}-1,3-thiazol-2-yl)cyclobutyl]phenyl}pyrimidin-2-amine |
| 182 | 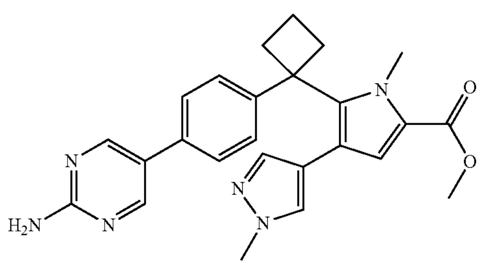 [SMILES: COC(=O)c1cc(-c2cnn(C)c2)c(C2(c3ccc(-c4cnc(N)nc4)cc3)CCC2)n1C] | methyl 5-{1-[4-(2-aminopyrimidin-5-yl)phenyl]cyclobutyl}-1-methyl-4-(1-methyl-1H-pyrazol-4-yl)-1H-pyrrole-2-carboxylate |
| 183 | 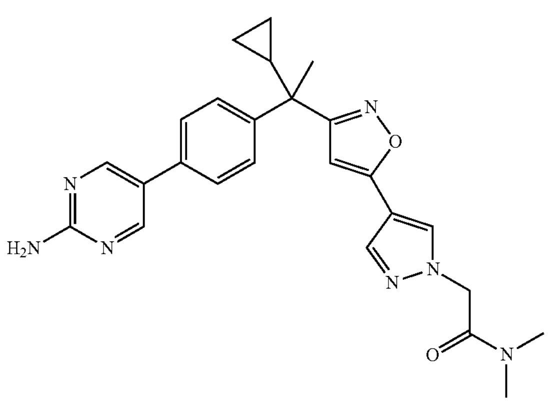 [SMILES: CN(C)C(=O)Cn1cc(-c2cc(C(C)(c3ccc(-c4cnc(N)nc4)cc3)C3CC3)no2)cn1] | 2-[4-(3-{1-[4-(2-aminopyrimidin-5-yl)phenyl]-1-cyclopropylethyl}-1,2-oxazol-5-yl)-1H-pyrazol-1-yl]-N,N-dimethylacetamide |

TABLE 1-continued

| Example | Structure | Name |
|---|---|---|
| 184 | 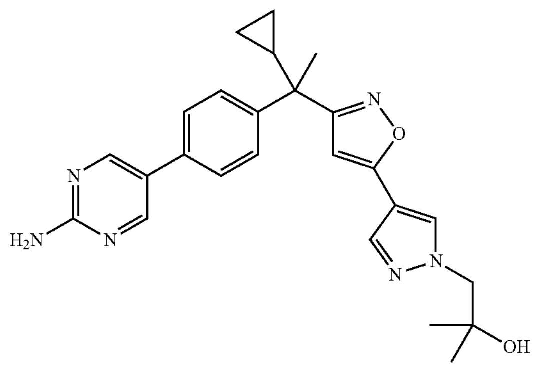 [SMILES: CC(C)(O)Cn1cc(-c2cc(C(C)(c3ccc(-c4cnc(N)nc4)cc3)C3CC3)no2)cn1] | 1-[4-(3-{1-[4-(2-aminopyrimidin-5-yl)phenyl]-1-cyclopropylethyl}-1,2-oxazol-5-yl)-1H-pyrazol-1-yl]-2-methylpropan-2-ol |
| 185 | Chiral | 5-(4-{(1R)-1-cyclopropyl-1-[4-(1-methyl-1H-pyrazol-4-yl)-1,3-oxazol-2-yl]ethyl}phenyl)pyrimidin-2-amine |
| 186 | Chiral | 5-(4-{(1S)-1-cyclopropyl-1-[4-(1-methyl-1H-pyrazol-4-yl)-1,3-oxazol-2-yl]ethyl}phenyl)pyrimidin-2-amine |
| 187 | 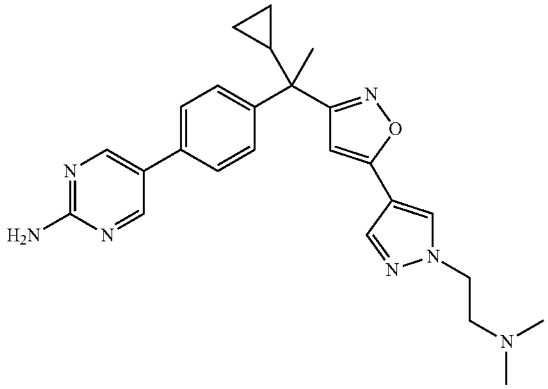 [SMILES: CN(C)CCn1cc(-c2cc(C(C)(c3ccc(-c4cnc(N)nc4)cc3)C3CC3)no2)cn1] | 5-{4-[1-cyclopropyl-1-(5-{1-[2-(dimethylamino)ethyl]-1H-pyrazol-4-yl}-1,2-oxazol-3-yl)ethyl]phenyl}pyrimidin-2-amine |

TABLE 1-continued

| Example | Structure | Name |
|---|---|---|
| 188 | 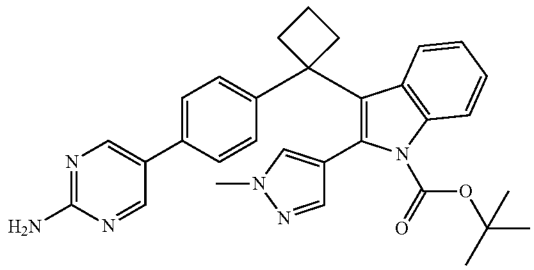 [SMILES: Cn1cc(-c2c(C3(c4ccc(-c5cnc(N)nc5)cc4)CCC3)c3ccccc3n2C(=O)OC(C)(C)C)cn1] | tert-butyl 3-{1-[4-(2-aminopyrimidin-5-yl)phenyl]cyclobutyl}-2-(1-methyl-1H-pyrazol-4-yl)-1H-indole-1-carboxylate |
| 189 | 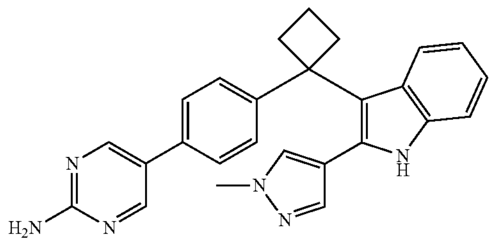 [SMILES: Cn1cc(-c2[nH]c3ccccc3c2C2(c3ccc(-c4cnc(N)nc4)cc3)CCC2)cn1] | 5-(4-{2-(1-methyl-1H-pyrazol-4-yl)-1H-indol-3-yl]cyclobutyl}phenyl)pyrimidin-2-amine |
| 190 | 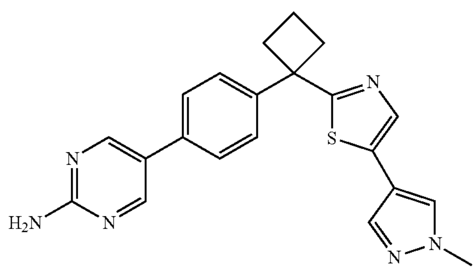 [SMILES: Cn1cc(-c2cnc(C3(c4ccc(-c5cnc(N)nc5)cc4)CCC3)s2)cn1] | 5-(4-{1-[5-(1-methyl-1H-pyrazol-4-yl)-1,3-thiazol-2-yl]cyclobutyl}phenyl)pyrimidin-2-amine |
| 191 | Chiral | 5-(5-{(2R)-3-methyl-2-[5-(1-methyl-1H-pyrazol-4-yl)-1,2-oxazol-3-yl]butan-2-yl}pyridin-2-yl)pyrimidin-2-amine |
| 192 | Chiral | 5-(5-{(2S)-3-methyl-2-[5-(1-methyl-1H-pyrazol-4-yl)-1,2-oxazol-3-yl]butan-2-yl}pyridin-2-yl)pyrimidin-2-amine |

TABLE 1-continued

| Example | Structure | Name |
|---|---|---|
| 193 | 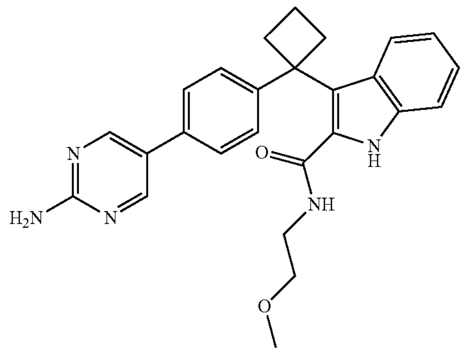 [SMILES: COCCNC(=O)c1[nH]c2ccccc2c1C1(c2ccc(-c3cnc(N)nc3)cc2)CCC1] | 3-{1-[4-(2-aminopyrimidin-5-yl)phenyl]cyclobutyl}-N-(2-methoxyethyl)-1H-indole-2-carboxylate |
| 194 | 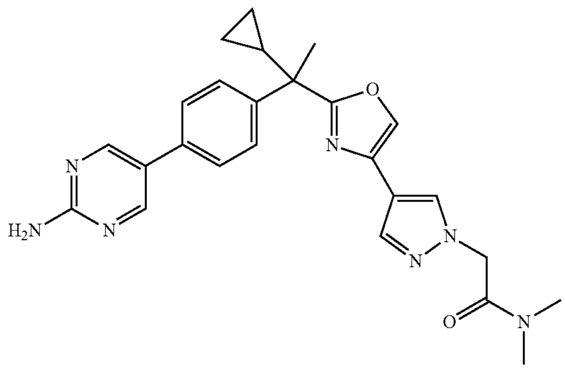 [SMILES: CN(C)C(=O)Cn1cc(-c2coc(C(C)(c3ccc(-c4cnc(N)nc4)cc3)C3CC3)n2)cn1] | 2-[4-(2-{1-[4-(2-aminopyrimidin-5-yl)phenyl]-1-cyclopropylethyl}-1,3-oxazol-4-yl)-1H-pyrazol-1-yl]-N,N-dimethylacetamide |
| 195 | Chiral | 2-[4-(2-{(1R)-1-[4-(2-aminopyrimidin-5-yl)phenyl]-1-cyclopropylethyl}-1,3-oxazol-4-yl)-1H-pyrazol-1-yl]-N,N-dimethylacetamide |
| 196 | Chiral | 2-[4-(2-{(1S)-1-[4-(2-aminopyrimidin-5-yl)phenyl]-1-cyclopropylethyl}-1,3-oxazol-4-yl)-1H-pyrazol-1-yl]-N,N-dimethylacetamide |

TABLE 1-continued

| Example | Structure | Name |
|---|---|---|
| 197 | Chiral | 2-[4-(3-{(1R)-1-[4-(2-aminopyrimidin-5-yl)phenyl]-1-cyclopropylethyl}-1,2-oxazol-5-yl)-1H-pyrazol-1-yl]-N,N-dimethylacetamide |
| 198 | Chiral | 2-[4-(3-{(1S)-1-[4-(2-aminopyrimidin-5-yl)phenyl]-1-cyclopropylethyl}-1,2-oxazol-5-yl)-1H-pyrazol-1-yl]-N,N-dimethylacetamide |
| 199 | 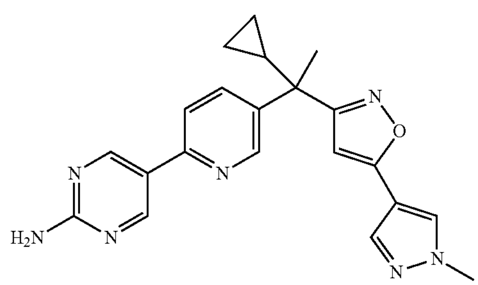 [SMILES: Cn1cc(-c2cc(C(C)(c3ccc(-c4cnc(N)nc4)nc3)C3CC3)no2)cn1] | 5-(5-{1-Cyclopropyl-1-[5-(1-methyl-1H-pyrazol-4-yl)-isoxazol-3-yl]-ethyl}-pyridin-2-yl)-pyrimidin-2-ylamine |
| 200 | 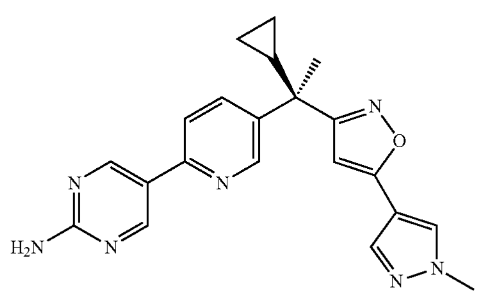 [SMILES: Cn1cc(-c2cc([C@@](C)(c3ccc(-c4cnc(N)nc4)nc3)C3CC3)no2)cn1] | 5-{(1R)-1-Cyclopropyl-1-[5-(1-methyl-1H-pyrazol-4-yl)-isoxazol-3-yl]-ethyl}-[2,3']bipyridinyl-6'-ylamine |

TABLE 1-continued

| Example | Structure | Name |
|---|---|---|
| 201 | 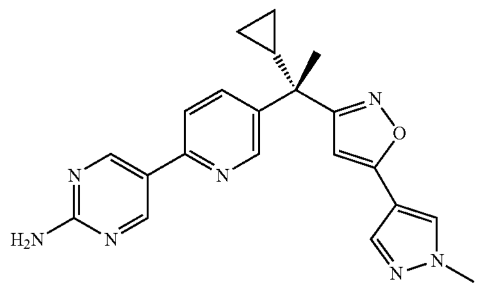 [SMILES: Cn1cc(-c2cc([C@](C)(c3ccc(-c4cnc(N)nc4)nc3)C3CC3)no2)cn1] | 5-(5-{(S)-1-Cyclopropyl-1-[5-(1-methyl-1H-pyrazol-4-yl)-isoxazol-3-yl]-ethyl}-pyridin-2-yl)-pyrimidin-2-ylamine |
| 202 | 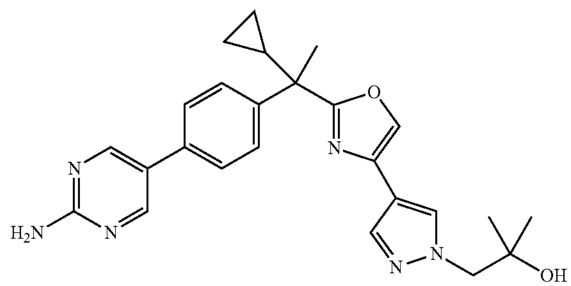 [SMILES: CC(C)(O)Cn1cc(-c2coc(C(C)(c3ccc(-c4cnc(N)nc4)cc3)C3CC3)n2)cn1] | 1-[4-(2-{1-[4-(2-Amino-pyrimidin-5-yl)-phenyl]-1-cyclopropyl-ethyl}-oxazol-4-yl)-pyrazol-1-yl]-2-methyl-propan-2-ol |
| 203 | 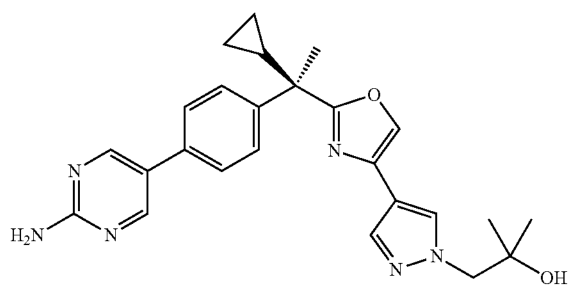 [SMILES: CC(C)(O)Cn1cc(-c2coc([C@@](C)(c3ccc(-c4cnc(N)nc4)cc3)C3CC3)n2)cn1] | 1-[4-(2-{(R)-1-[4-(2-Amino-pyrimidin-5-yl)-phenyl]-1-cyclopropyl-ethyl}-oxazol-4-yl)-pyrazol-1-yl]-2-methyl-propan-2-ol |
| 204 | 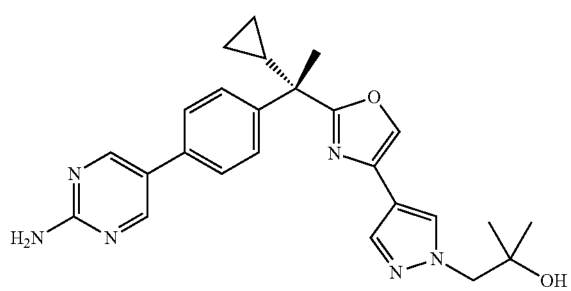 [SMILES: CC(C)(O)Cn1cc(-c2coc([C@](C)(c3ccc(-c4cnc(N)nc4)cc3)C3CC3)n2)cn1] | 1-[4-(2-{(S)-1-[4-(2-Amino-pyrimidin-5-yl)-phenyl]-1-cyclopropyl-ethyl}-oxazol-4-yl)-pyrazol-1-yl]-2-methyl-propan-2-ol |
| 205 | 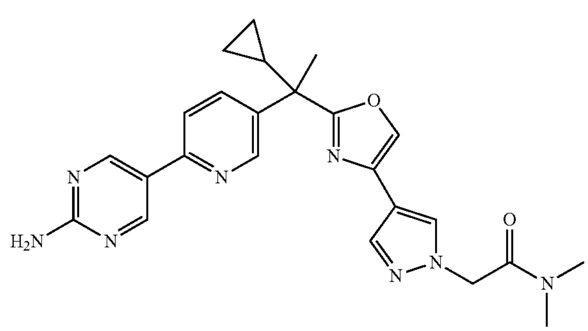 [SMILES: CN(C)C(=O)Cn1cc(-c2coc(C(C)(c3ccc(-c4cnc(N)nc4)nc3)C3CC3)n2)cn1] | 2-[4-(2-{1-[6-(2-Amino-pyrimidin-5-yl)-pyridin-3-yl]-1-cyclopropyl-ethyl}-oxazol-4-yl)-pyrazol-1-yl]-N,N-dimethyl-acetamide |

TABLE 1-continued

| Example | Structure | Name |
|---|---|---|
| 206 | 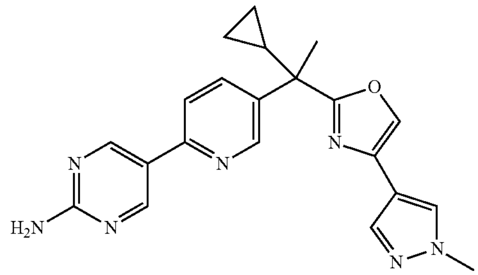 [SMILES: Cn1cc(-c2coc(C(C)(c3ccc(-c4cnc(N)nc4)nc3)C3CC3)n2)cn1] | 5-(5-{1-Cyclopropyl-1-[4-(1-methyl-1H-pyrazol-4-yl)-oxazol-2-yl]-ethyl}-pyridin-2-yl)-pyrimidin-2-ylamine |
| 207 | 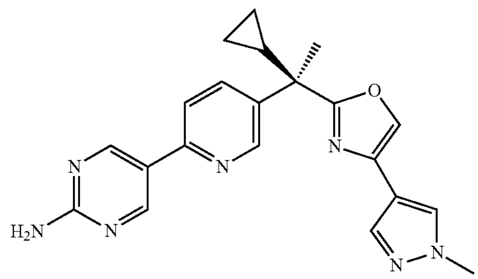 [SMILES: Cn1cc(-c2coc([C@@](C)(c3ccc(-c4cnc(N)nc4)nc3)C3CC3)n2)cn1] | 5-(5-{(R)-1-Cyclopropyl-1-[4-(1-methyl-1H-pyrazol-4-yl)-oxazol-2-yl]-ethyl}-pyridin-2-yl)-pyrimidin-2-ylamine |
| 208 | 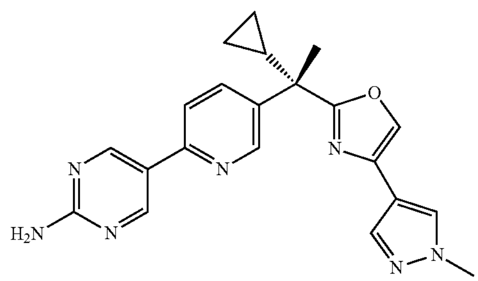 [SMILES: Cn1cc(-c2coc([C@](C)(c3ccc(-c4cnc(N)nc4)nc3)C3CC3)n2)cn1] | 5-(5-{(S)-1-Cyclopropyl-1-[4-(1-methyl-1H-pyrazol-4-yl)-oxazol-2-yl]-ethyl}-pyridin-2-yl)-pyrimidin-2-ylamine |
| 209 | 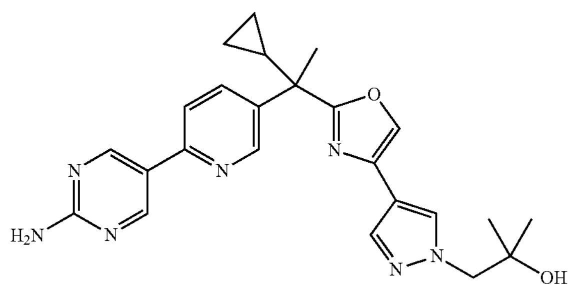 [SMILES: CC(C)(O)Cn1cc(-c2coc(C(C)(c3ccc(-c4cnc(N)nc4)nc3)C3CC3)n2)cn1] | 1-[4-(2-{1-[6-(2-Amino-pyrimidin-5-yl)-pyridin-3-yl]-1-cyclopropyl-ethyl}-oxazol-4-yl)-pyrazol-1-yl]-2-methyl-propan-2-ol |
| 210 | 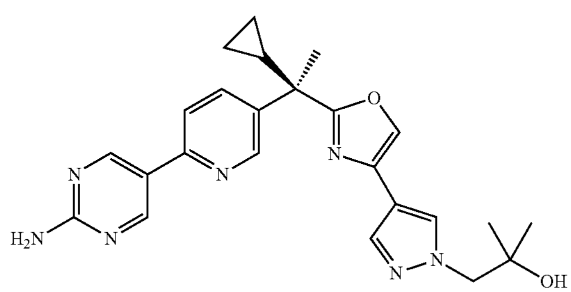 [SMILES: CC(C)(O)Cn1cc(-c2coc([C@@](C)(c3ccc(-c4cnc(N)nc4)nc3)C3CC3)n2)cn1] | 1-[4-(2-{(R)-1-[6-(2-Amino-pyrimidin-5-yl)-pyridin-3-yl]-1-cyclopropyl-ethyl}-oxazol-4-yl)-pyrazol-1-yl]-2-methyl-propan-2-ol |

TABLE 1-continued

| Example | Structure | Name |
|---|---|---|
| 211 | 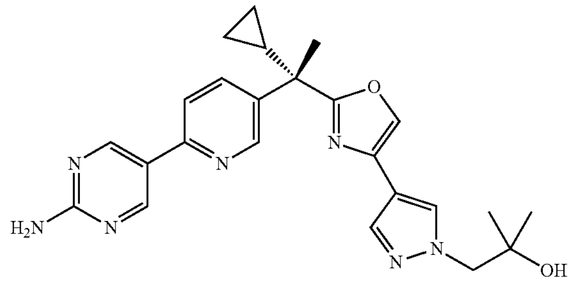 [SMILES: CC(C)(O)Cn1cc(-c2coc([C@](C)(c3ccc(-c4cnc(N)nc4)nc3)C3CC3)n2)cn1] | 1-[4-(2-{(S)-1-[6-(2-Amino-pyrimidin-5-yl)-pyridin-3-yl]-1-cyclopropyl-ethyl}-oxazol-4-yl)-pyrazol-1-yl]-2-methyl-propan-2-ol |
| 212 | 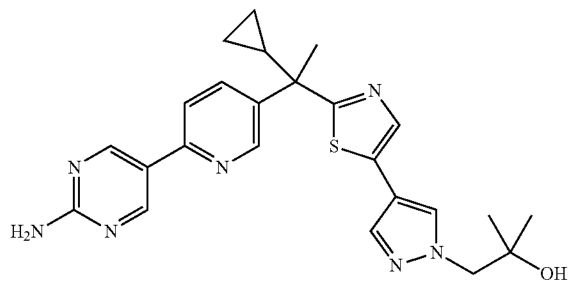 [SMILES: CC(C)(O)Cn1cc(-c2cnc(C(C)(c3ccc(-c4cnc(N)nc4)nc3)C3CC3)s2)cn1] | 1-[4-(2-{1-[6-(2-Amino-pyrimidin-5-yl)-pyridin-3-yl]-1-cyclopropyl-ethyl}-thiazol-5-yl)-pyrazol-1-yl]-2-methyl-propan-2-ol |

In one embodiment, the invention relates to any of the compounds depicted in Table 1 above or pharmaceutically acceptable salts thereof.

Representative compounds of the invention show activity in the FLAP binding assay and the human whole blood assay, described in the assessment of biological properties section, as shown in Table 2.

TABLE 2

| Example | Human FLAP SPA Binding (IC50 nM) | Human Whole Blood LTB4 Assay for FLAP (IC50 nM) |
|---|---|---|
| 1 | 1.3 | 1300 |
| 2 | 1.9 | 490 |
| 3 | 1.4 | 490 |
| 4 | 1.2 | 2800 |
| 5 | 0.72 | 220 |
| 6 | 1.5 | 29 |
| 7 | 2.1 | 210 |
| 8 | 2.8 | 410 |
| 9 | 2.2 | 27 |
| 10 | 2.4 | 340 |
| 11 | 3.3 | 230 |
| 12 | 2.7 | 680 |
| 13 | 1.4 | 320 |
| 14 | 30 | >5000 |
| 15 | 1.8 | 220 |
| 16 | 7.1 | 1400 |
| 17 | 3.4 | 250 |
| 18 | 4.0 | 680 |
| 19 | 510 | >5000 |
| 20 | 5.1 | 430 |
| 21 | 38 | 1600 |
| 22 | 44 | 710 |
| 24 | 890 | >5000 |
| 25 | 36 | >5000 |
| 26 | 4.6 | 39 |
| 27 | 20 | 1800 |
| 28 | 3.3 | 610 |
| 29 | 5.1 | 2700 |
| 30 | 330 | 1200 |
| 31 | 7.1 | 1200 |
| 32 | 3.3 | 650 |
| 33 | 290 | >5000 |
| 34 | 3.4 | 460 |
| 35 | 150 | >5000 |
| 36 | 1.8 | 1900 |
| 37 | 1.4 | 150 |
| 38 | 1.4 | 240 |
| 39 | 3.3 | 290 |
| 40 | 2.6 | 540 |
| 41 | 3.4 | 1300 |
| 42 | 2.5 | 170 |
| 43 | 30 | 1500 |
| 44 | 21 | >5000 |
| 45 | 1.4 | 260 |
| 46 | 3.2 | 550 |
| 47 | 4.6 | >5000 |
| 48 | 72 | >5000 |
| 49 | 2.0 | 810 |
| 50 | 260 | >5000 |
| 51 | 2.7 | 840 |
| 52 | 3.1 | 2200 |
| 53 | 400 | >5000 |
| 54 | 8.3 | 840 |
| 55 | 1100 | >5000 |
| 56 | 160 | >5000 |
| 57 | 37 | 2600 |
| 58 | 1.1 | 69 |
| 59 | 0.65 | 330 |
| 60 | 0.86 | 170 |
| 61 | 9.3 | 1200 |
| 62 | 18 | 2300 |
| 63 | 3.0 | 440 |
| 64 | 0.85 | 1400 |
| 65 | 0.57 | 1800 |
| 66 | 1.2 | 170 |
| 67 | 3.0 | 340 |
| 68 | 1.0 | >5000 |
| 69 | 120 | 3100 |
| 70 | 0.9 | 240 |
| 71 | 0.72 | 1900 |
| 72 | 110 | 2100 |
| 73 | 1.3 | >5000 |
| 74 | 780 | 3500 |
| 75 | 380 | >5000 |

TABLE 2-continued

| Example | Human FLAP SPA Binding (IC50 nM) | Human Whole Blood LTB4 Assay for FLAP (IC50 nM) |
|---|---|---|
| 76 | 1.1 | 250 |
| 77 | 1.7 | 640 |
| 78 | 1.6 | >5000 |
| 79 | 8.5 | 2600 |
| 80 | 1.6 | >5000 |
| 81 | 5.1 | 370 |
| 82 | 0.94 | 160 |
| 83 | 5.0 | 460 |
| 84 | 0.7 | 3000 |
| 85 | 0.97 | 300 |
| 86 | 1.4 | 230 |
| 87 | 1.6 | 400 |
| 88 | 1.7 | 430 |
| 89 | 12 | 2200 |
| 90 | 0.75 | 170 |
| 91 | 2.7 | 230 |
| 92 | 9.1 | 840 |
| 93 | 29 | >5000 |
| 94 | 120 | 2800 |
| 95 | 5.0 | 960 |
| 96 | 1.4 | 240 |
| 97 | 14 | 4100 |
| 98 | 0.6 | 360 |
| 99 | 0.93 | 1600 |
| 100 | 18 | 2100 |
| 101 | 12 | 1400 |
| 102 | 3.7 | 900 |
| 103 | 2.5 | 160 |
| 104 | 8.6 | 1900 |
| 105 | 91 | >5000 |
| 106 | 0.91 | 4100 |
| 107 | 1.2 | 180 |
| 108 | 3.0 | 360 |
| 109 | 1.3 | 71 |
| 110 | 87 | 1500 |
| 111 | 1.5 | >5000 |
| 112 | 3.2 | 570 |
| 113 | 1.1 | 100 |
| 114 | 2.3 | 380 |
| 115 | 2.6 | 1100 |
| 116 | 2.5 | 270 |
| 117 | 1.1 | 30 |
| 118 | 1.6 | 69 |
| 119 | 1.5 | 170 |
| 120 | 4.7 | >5000 |
| 121 | 8.7 | 810 |
| 122 | 75 | >5000 |
| 123 | 7.9 | >5000 |
| 124 | 5.5 | >5000 |
| 125 | 250 | 3400 |
| 126 | 71 | 1800 |
| 127 | 7.2 | 1900 |
| 128 | 8.1 | 2300 |
| 129 | 7.6 | 4000 |
| 130 | 1.5 | 140 |
| 131 | 5.5 | 920 |
| 132 | 7.2 | >5000 |
| 133 | 7.5 | >5000 |
| 134 | 1.8 | 270 |
| 135 | 2.3 | 500 |
| 136 | 190 | >5000 |
| 137 | 410 | >5000 |
| 138 | 18 | 990 |
| 139 | 27 | >5000 |
| 140 | 10 | >5000 |
| 141 | 5.8 | 350 |
| 142 | 7.5 | 1400 |
| 143 | 12 | 1500 |
| 144 | 4.0 | 2500 |
| 145 | 1.7 | 150 |
| 146 | 1.7 | 310 |
| 147 | 7.9 | >5000 |
| 148 | 9.0 | 3100 |
| 149 | 2.0 | 110 |
| 150 | 1.5 | >5000 |
| 151 | 7.0 | 890 |
| 152 | 1.7 | 55 |
| 153 | 3.1 | 1100 |
| 154 | 22 | >5000 |
| 155 | 2.5 | 370 |
| 156 | 260 | >5000 |
| 157 | 16 | 2600 |
| 158 | 5.2 | 430 |
| 159 | 1.9 | 43 |
| 160 | 8.4 | 1400 |
| 161 | 8.2 | 160 |
| 162 | 210 | 1500 |
| 163 | 5.7 | 590 |
| 164 | 3.7 | 93 |
| 165 | 6.1 | 160 |
| 166 | 72 | 3600 |
| 167 | 59 | 3200 |
| 168 | 87 | 390 |
| 169 | 110 | 2000 |
| 170 | 10 | 120 |
| 171 | 7.4 | 140 |
| 172 | 8.2 | 73 |
| 173 | 7.7 | 89 |
| 174 | 17 | 650 |
| 175 | 10 | 1100 |
| 176 | 150 | 2900 |
| 177 | 42 | 1800 |
| 178 | 2.9 | 81 |
| 179 | 200 | 4400 |
| 180 | 8.9 | 270 |
| 181 | 6.1 | 110 |
| 182 | 38 | 1400 |
| 183 | 9.0 | 200 |
| 184 | 8.4 | 97 |
| 185 | 3.3 | 54 |
| 186 | 87 | 2000 |
| 187 | 9.9 | 67 |
| 188 | 270 | >5000 |
| 189 | 5.3 | 280 |
| 190 | 4.9 | 80 |
| 191 | 7.5 | 56 |
| 192 | 210 | 1900 |
| 193 | 7.9 | 450 |
| 194 | 40 | 560 |
| 195 | 18 | 280 |
| 196 | 380 | 2000 |
| 197 | 5.3 | 93 |
| 198 | 350 | 1600 |
| 199 | 230 | 590 |
| 200 | 140 | 450 |
| 201 | >2000 | 3500 |
| 202 | 69 | 230 |
| 203 | 36 | 190 |
| 204 | 560 | 1500 |
| 205 | 1500 | 1600 |
| 206 | 180 | 930 |
| 207 | 110 | 220 |
| 208 | >2000 | 1300 |
| 209 | 300 | 560 |
| 210 | 180 | 530 |
| 211 | >2000 | >5000 |
| 212 | 130 | 410 |

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g. $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$C_{1-6}$ alkoxy" is a $C_{1-6}$ alkyl with a terminal oxygen, such as methoxy, ethoxy, propoxy, butoxy. All alkyl, alkenyl, and alkynyl groups shall be understood as being branched or unbranched where structurally possible and unless otherwise specified. Other more specific definitions are as follows:

The term "alkyl" refers to both branched and unbranched alkyl groups. It should be understood that any combination term using an "alk" or "alkyl" prefix refers to analogs according to the above definition of "alkyl". For example, terms such as "alkoxy", "alkylhio" refer to alkyl groups linked to a second group via an oxygen or sulfur atom. "Alkanoyl" refers to an alkyl group linked to a carbonyl group (C=O).

In all alkyl groups or carbon chains, one or more carbon atoms can be optionally replaced by heteroatoms such as O, S or N. It shall be understood that if N is not substituted then it is NH. It shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo. As used herein, "nitrogen" and "sulfur" include any oxidized form of nitrogen and sulfur and the quaternized form of any basic nitrogen. For example, for a —S—$C_{1-6}$ alkyl radical, unless otherwise specified, shall be understood to include —S(O)—$C_{1-6}$ alkyl and —S(O)$_2$—$C_{1-6}$ alkyl.

The term "$C_{3-10}$ carbocycle" refers to a nonaromatic 3 to 10-membered (but preferably, 3 to 6-membered) monocyclic carbocyclic radical or a nonaromatic 6 to 10-membered fused bicyclic, bridged bicyclic, or spirocyclic carbocyclic radical. The $C_{3-10}$ carbocycle may be either saturated or partially unsaturated, and the carbocycle may be attached by any atom of the cycle which results in the creation of a stable structure. Non-limiting examples of 3 to 10-membered monocyclic carbocycles include cyclopropyl, cyclobutyl, cyclopentyl, cyclopentenyl, cyclohexyl, cyclohexenyl, cycloheptanyl, cycloheptenyl, and cyclohexanone. Non-limiting examples of 6 to 10-membered fused bicyclic carbocyclic radicals include bicyclo[3.3.0]octane, bicyclo[4.3.0]nonane, and bicyclo [4.4.0]decanyl (decahydronaphthalenyl). Non-limiting examples of 6 to 10-membered bridged bicyclic carbocyclic radicals include bicyclo[2.2.2]heptanyl, bicyclo[2.2.2]octanyl, and bicyclo[3.2.1]octanyl. Non-limiting examples of 6 to 10-membered spirocyclic carbocyclic radicals include but are not limited to spiro[3,3]heptanyl, spiro[3,4]octanyl and spiro [4,4]heptanyl.

The term "$C_{6-10}$ aryl" or "aryl" refers to aromatic hydrocarbon rings containing from six to ten carbon ring atoms. The term $C_{6-10}$ aryl includes monocyclic rings and bicyclic rings where at least one of the rings is aromatic. Non-limiting examples of $C_{6-10}$ aryls include phenyl, indanyl, indenyl, benzocyclobutanyl, dihydronaphthyl, tetrahydronaphthyl, naphthyl, benzocycloheptanyl and benzocycloheptenyl.

The term "5 to 11-membered heterocycle" refers to a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, tetrahydropyranyl, oxetanyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3] heptanyl, 7-spiro[3,4]octanyl, and 7-aza-spiro[3,4]octanyl.

The term "5 to 11-membered heteroaryl" shall be understood to mean an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl, benzodioxolyl, benzoxazolyl, pyridooxazinyl, dihydro-pyridooxazinyl, dihydro-pyrrolopyridinyl, pyrrolopyridinyl, pyrrolopyrazinyl, and benzothiazolyl.

It will be understood that one to three carbon ring moieties in the each of the $C_{3-10}$ carbocyclic rings, the 5 to 11-membered heterocyclic rings, the nonaromatic portion of the bicyclic aryl rings, and the nonaromatic portion of the bicyclic heteroaryl rings can independently be replaced with a carbonyl, thiocarbonyl, or iminyl moiety, i.e., —C(=O)—, —C(=S)— and —C(=NR$^8$)—, respectively, where R$^8$ is as defined above. The term "heteroatom" as used herein shall be understood to mean atoms other than carbon such as O, N, and S.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —CH$_2$CHF$_2$, —CF$_3$ etc.

Each alkyl, carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining patient, the prodrug may be transformed into a compound disclosed hereinabove, thereby imparting the desired pharmacological effect.

The compounds of formula I may be made using the general synthetic methods described below, which also constitute part of the invention.

General Synthetic Methods

The invention also provides processes for making compounds of Formula (I). In all Schemes, unless specified otherwise, R$^1$, R$^2$, R$^3$, R$^4$, R$^5$, R$^6$, R$^7$, A and HET in the Formulas below shall have the meaning of R$^1$, R$^2$, R$^3$, R$^4$, R$^5$, R$^6$, R$^7$, A and HET in Formula (I) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC) or LC-MS, if desired, and intermediates and products may be purified by chromatography on silica gel, recrystallization and/or preparative HPLC.

The examples which follow are illustrative and, as recognized by one skilled in the art, particular reagents or conditions could be modified as needed for individual compounds without undue experimentation. Starting materials and intermediates used, in the Schemes below, are either commercially available or easily prepared from commercially available materials by methods known to those skilled in the art.

The compounds of Formula (I) may be synthesized according to Scheme 1:

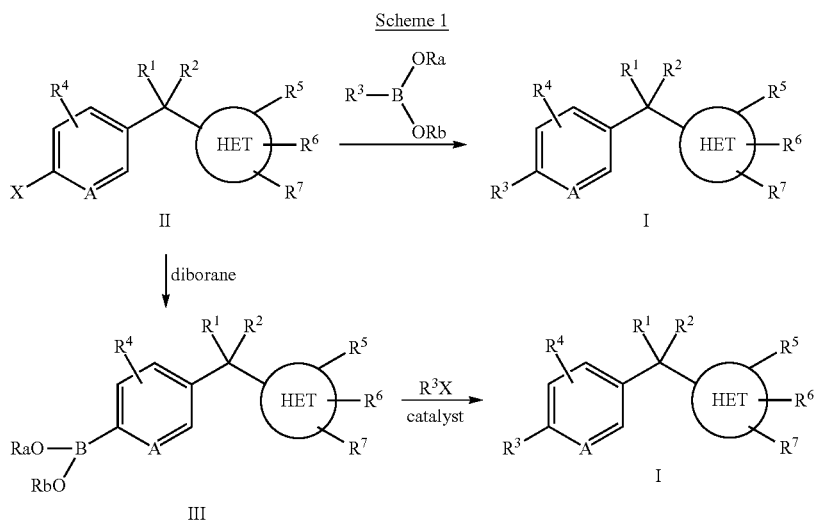

the compounds and their pharmaceutically acceptable acid addition salts. Salts derived from appropriate bases include alkali metal (e.g., sodium), alkaline earth metal (e.g., magnesium), ammonium and N—(C$_1$-C$_4$ alkyl)$_4$$^+$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a As illustrated in scheme 1, reaction of a compound of formula II with a boronic acid or the corresponding boronic acid ester shown in the above scheme, in a suitable solvent, in the presence of a suitable catalyst, provides a compound of formula (I). Ra and Rb are hydrogen or Ra and Rb together with the oxygen atoms to which they are attached form a 5-6 membered ring optionally substituted with 2-4 methyl groups.

Alternatively, reaction of a compound of formula II with a diborane, under standard reaction conditions, provides a compound of formula III. Coupling the intermediate of formula III with a halide or triflate $R^3X$, in a suitable solvent, in the presence of a suitable catalyst, provides a compound of formula (I). X is chloro, bromo, triflate, or iodo.

The intermediate of formula II may be synthesized as outlined in Scheme 2:

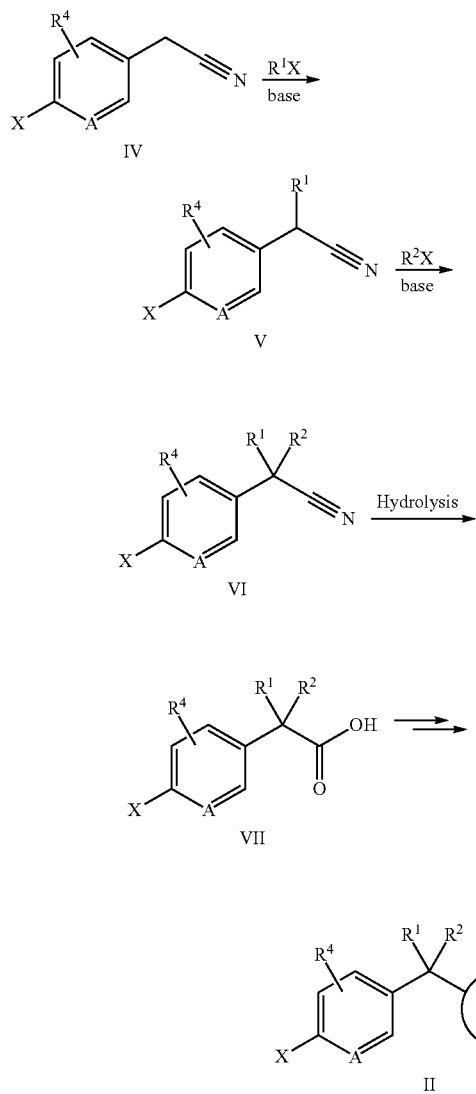

As illustrated in scheme 2, reaction of a nitrile of formula IV with a halide $R^1X$, in a suitable solvent, in the presence of a suitable base such as sodium hydride or potassium t-butoxide, provides a substituted nitrile of formula V. Further reaction of the intermediate of formula V with a halide $R^2X$, in a suitable solvent, in the presence of a suitable base, provides the corresponding disubstituted nitrile of formula VI. X is chloro, bromo, or iodo. Hydrolysis of the compound of formula VI, under standard reaction conditions, provides a compound of formula VII. Reaction of the compound of formula VII with appropriate reagents, as exemplified in the Examples section, provides an intermediate of formula II.

The intermediate of formula II may also be synthesized as shown in Scheme 3:

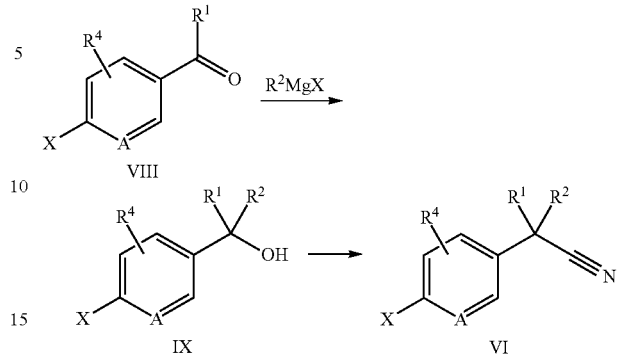

As shown in scheme 3, reaction of a carbonyl compound of formula VIII with a grignard reagent $R^2MgX$, in a suitable solvent, provides a hydroxy compound of formula IX. Conversion of the hydroxyl group in compound of formula IX to a cyano group, using standard procedures, provides a compound of formula VI. The compound of formula VI may be converted to the intermediate of formula II as in scheme 2. X in $R^2MgX$ is chloro, bromo or iodo.

Nitrile intermediate VI may be synthesized as shown in scheme 4, wherein $R^1$ and $R^2$ form a cyclic ring

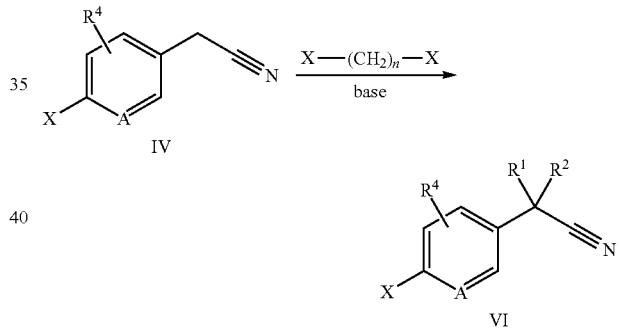

As illustrated in scheme 4, reaction of a nitrile of formula V with a dihalide wherein one of the carbon atoms in the alkyl chain may be optionally substituted with O, S or N, in a suitable solvent, in the presence of a suitable base such as sodium hydride, provides a substituted nitrile of formula VII. $R^1$ and $R^2$ together with the carbon atom to which they are attached form a $C_{3-8}$ carbocyclic or heterocyclic ring. X is chloro, bromo, or iodo.

The intermediate of formula II may be synthesized according to Scheme 5:

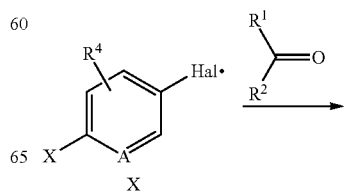

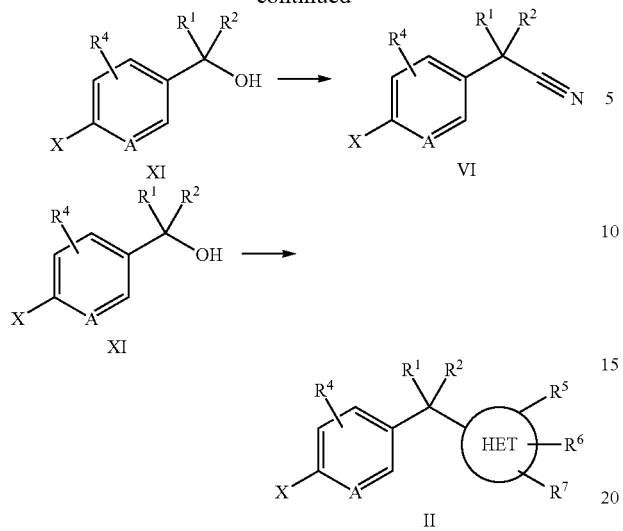

As shown in scheme 5, when A=C, reaction of a compound of formula X with a carbonyl compound, in a suitable solvent, provides a hydroxy compound of formula XI. Conversion of the hydroxyl group in compound of formula XI to a cyano group, using standard procedures, provides a compound of formula VI.

Alternatively, reaction of the hydroxy compound of formula XI, with suitable reagents, as exemplified in the Examples section, provides an intermediate of formula II.

Compounds of formula I as well as intermediates prepared by the above methods may be further converted to additional intermediates or compounds of formula I by methods known in the art and exemplified in the Synthetic Examples section below.

Synthetic Examples

LCMS Methods

| LC-MS Method A | | |
|---|---|---|
| Column | Waters Atlantis dC18 | |
| | 3 μm, 100 × 2.1 mm | |
| | 40° C. | |
| Mobile phase | A—0.1% Formic acid (water) | |
| | B—0.1% Formic acid (acetonitrile) | |
| Flow rate | 0.6 ml/min | |
| Injection volume | 3 μl | |
| Detector | 215 nm (nominal) | |
| | Time (mins) | % B |
| Gradient | 0 | 5 |
| | 5 | 100 |
| | 5.4 | 100 |
| | 5.42 | 5 |
| | 7.00 | 5 |

| LC-MS Method B | | |
|---|---|---|
| Column | Waters Atlantis dC18 | |
| | 3 μm, 50 × 2.1 mm | |
| | 40° C. | |
| Mobile phase | A—0.1% Formic acid (water) | |
| | B—0.1% Formic acid (acetonitrile) | |
| Flow rate | 1.0 ml/min | |
| Injection volume | 3 μl | |
| Detector | 215 nm (nominal) | |
| | Time (mins) | % B |
| Gradient | 0 | 5 |
| | 2.50 | 100 |
| | 2.70 | 100 |
| | 2.71 | 5 |
| | 3.50 | 5 |

| LC-MS Method C | | |
|---|---|---|
| Column | Waters Atlantis dC18 | |
| | 3 μm, 30 × 2.1 mm | |
| | 40° C. | |
| Mobile phase | A—0.1% Formic acid (water) | |
| | B—0.1% Formic acid (acetonitrile) | |
| Flow rate | 1.0 ml/min | |
| Injection volume | 3 μl | |
| Detector | 215 nm (nominal) | |
| | Time (mins) | % B |
| Gradient | 0 | 5 |
| | 1.50 | 100 |
| | 1.60 | 100 |
| | 1.61 | 5 |
| | 2.0 | 5 |

| LC-MS Method D | | |
|---|---|---|
| Column | Agilent SB-C18 | |
| | 1.8 μm, 3 × 50 mm column | |
| | Ambient temperature | |
| Mobile phase | A = Formic acid (aq) 0.1% | |
| | B = Formic acid (acetonitrile) 0.1% | |
| Flow rate | 1.5 ml/min | |
| Injection volume | 3 μl | |
| Detector | 220 nm and 254 nm | |
| | Time (mins) | % B |
| Gradient | 0 | 5 |
| | 3.8 | 90 |
| | 4.5 | 100 |

| LC-MS Method E | | |
|---|---|---|
| Column | Agilent SB-C18 | |
| | 1.8 μm, 3 × 50 mm column | |
| | Ambient temperature | |
| Mobile phase | A = Formic acid (aq) 0.1% | |
| | B = Formic acid (acetonitrile) 0.1% | |
| Flow rate | 1.5 ml/min | |
| Injection volume | 3 μl | |
| Detector | 220 nm and 254 nm | |
| | Time (mins) | % B |
| Gradient | 0 | 12 |
| | 0.25 | 30 |
| | 0.3 | 40 |
| | 1.19 | 95 |
| | 1.75 | 100 |

| LC-MS Method F | |
|---|---|
| Column | Agilent Zorbax C18 SB |
| | 3.5 μm, 4.6 × 30 mm column |
| | Ambient temperature |
| Mobile phase | A = Formic acid (aq) 0.1% |
| | B = Formic acid (acetonitrile) 0.1% |
| Flow rate | 2.5 ml/min |
| Injection volume | 7 μl |
| Detector | 210 nm-400 nm |
| | Time (mins)   % B |
| Gradient | 0              5 |
| | 1.7           95 |
| | 2             95 |
| | 2.1            5 |
| | 2.3            5 |

HPLC purification methods used anywhere from 0-100% acetonitrile in water and may contain 0.1% formic acid, 0.1% TFA or 0.2% ammonium hydroxide and used one of the following columns:

a) Waters Sunfire OBD C18 5 μm 30×150 mm column
b) Waters XBridge OBD C18 5 μm 30×150 mm column
c) Waters ODB C8 5 μm 19×150 mm column
d) Waters Atlantis ODB C18 5 μm 19×50 mm column
e) Waters Atlantis T3 OBD 5 μM 30×100 mm column
f) Phenomenex Gemini Axia C18 5 μm 30×100 mm column
g) Waters SunFire C18 Prep OBD 5 μm 19×100 mm column
h) Waters XBridge Prep C18 5 μm 19×100 mm column Starting materials and reagents are either commercially available or may be prepared by one skilled in the art using methods described in the chemical literature.

Method 1

Synthesis of 5-fluoro-1-methyl-indole (Intermediate 1)

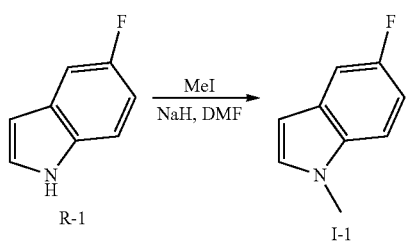

To a solution of R-1 (1 g, 7.40 mmol) in anhydrous DMF (30 mL) under $N_2$ is added sodium hydride (355 mg of a 60% suspension in mineral oil, 8.88 mmol) and stirred for 1 h. Iodomethane (510 μL, 8.14 mmol) is slowly added and the reaction stirred for 2 h at room temperature. The reaction is quenched with a mixture of MeOH—$NH_3$-water and diluted with water before extracting with DCM. The combined extracts are washed with water and brine then dried over anhydrous $Na_2SO_4$. The solvent is removed in vacuo to give the title intermediate I-1 (973 mg) m/z 150.1 [M+H].

The following intermediates are also prepared according to the methods described in Method 1:

| Structures | Name | m/z [M + H] |
|---|---|---|
| 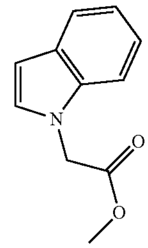 | I-1.1 | 190.0 |
| 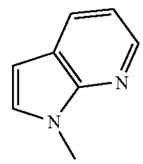 | I-1.2 | 133.0 |
| 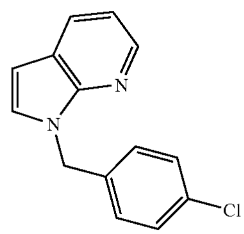 [SMILES: Clc1ccc(Cn2ccc3cccnc32)cc1] | I-1.3 | 243.0, 245.0 |
| 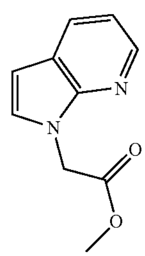 | I-1.4 | 191.0 |

Method 2

Synthesis of 2-indol-1-ylethanol (Intermediate 2) and 2-(2-indol-1-ylethoxy)ethanol (Intermediate 3)

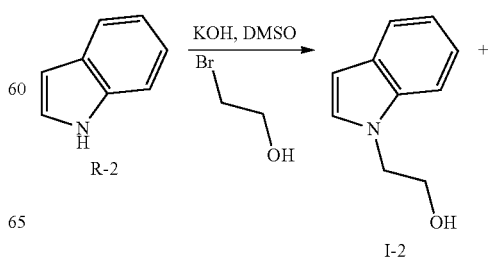

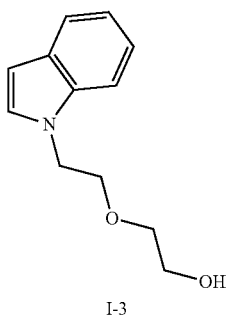

I-3

To a suspension of KOH (4.48 g, 80.0 mmol) in DMSO (20 mL) is added R-2 (2.34 g, 20.0 mmol) under N$_2$ and the suspension is stirred at room temperature for 1 h. 2-Bromoethanol (1.8 mL, 25.0 mmol) is then added and stirring continued for 18 h. The reaction is diluted with EtOAc and washed with water, and the organic phase dried over anhydrous Na$_2$SO$_4$. The solvent is removed in vacuo and the crude material purified by flash chromatography (SiO$_2$, 1% MeOH in DCM) to give I-2 (300 mg) m/z 162.0 [M+H] and I-3 (75 mg) m/z 206.0 [M+H].

Method 3

Synthesis of methyl 1-methylindole-6-carboxylate (Intermediate 4)

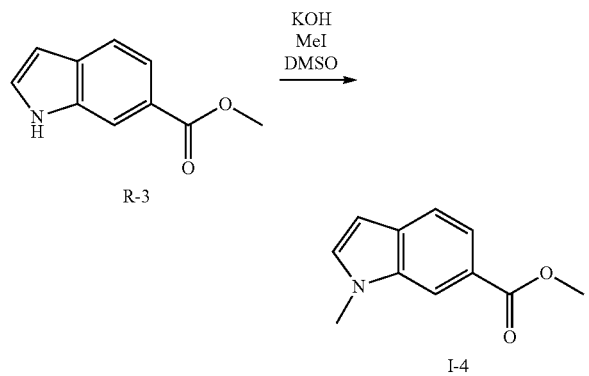

To a solution of R-3 (1 g, 5.7 mmol) in DMSO (10 mL) is added KOH (800 mg, 14.3 mmol) and iodomethane (0.534 mL, 8.6 mmol). After stirring at room temperature for 1 h the reaction mixture is diluted with water (50 mL) and the resultant suspension filtered and washed with more water. The solid is dried in vacuo to give the title intermediate I-4 (1.16 g) m/z 190.0 [M+H].

Method 4

Synthesis of 7-methoxy-1H-pyrrolo[2,3-c]pyridine (Intermediate 5)

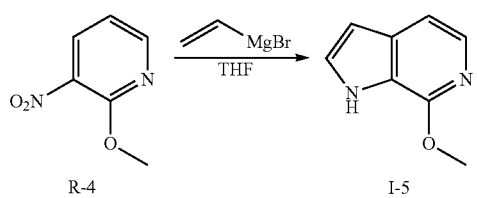

A solution of R-4 (500 mg, 3.24 mmol) in anhydrous THF (20 mL) is cooled to −78° C. and vinylmagnesium bromide (9.73 mL of a 1 M solution in THF, 9.73 mmol) added. The reaction is stirred at −20° C. for 6 h then quenched with saturated aqueous NH$_4$Cl solution and extracted with EtOAc. The organic phase is concentrated in vacuo and the crude material purified by flash chromatography (SiO$_2$, 2% to 10% MeOH in DCM) to give the title intermediate I-5 (100 mg) m/z 148.9 [M+H].

Method 5

Synthesis of N-(2-hydroxyethyl)-N-methyl-1H-indole-5-carboxamide (Intermediate 6)

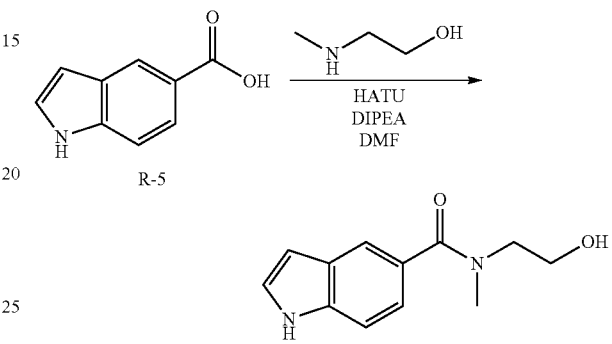

To a stirred solution of R-5 (100 mg, 0.62 mmol) in anhydrous DMF (3 mL) is added HATU (472 mg, 1.24 mmol) and DIPEA (322 mL, 1.86 mmol) and the reaction is stirred at room temperature for 1 h. 2-(Methylamino)ethanol (100 mL, 1.24 mmol) is added and the mixture is stirred at room temperature for 16 h. The reaction is diluted with DCM and saturated aqueous NaHCO$_3$, the layers separated, and the aqueous solution extracted with further DCM. Combined organics are washed with saturated aqueous NaHCO$_3$, and brine. NaCl is then added to the combined aqueous phases and then the aqueous solution extracted with EtOAc. Combined organics are washed with brine, dried over anhydrous Na$_2$SO$_4$ and concentrated in vacuo to give the title intermediate I-6 (379.4 mg) m/z 219.0 [M+H].

Method 6

Synthesis of 2-(4-iodophenyl)-3-methyl-butan-2-ol (Intermediate 7)

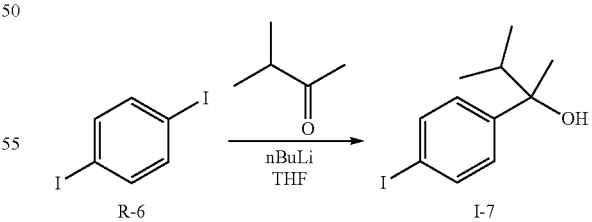

A solution of R-6 (30 g, 90.93 mmol) in THF (200 mL) under N$_2$ is cooled to −78° C. and n-butyl lithium (37.1 mL of a 2.5 M solution in hexanes, 92.75 mmol) added slowly. On completion of addition the solution is stirred for a further 20 min then 3-methyl-2-butanone (8.22 g, 95.48 mmol) added and stifling continued for 1.5 h at −78° C. The reaction is quenched by dropwise addition of 1 M HCl (50 mL) and the THF is removed in vacuo. A further 50 mL of 1 M HCl is added and the aqueous phase extracted with EtOAc. The combined extracts are washed with brine and dried over anhydrous Na$_2$SO$_4$. The solvent is removed in vacuo and purification by flash chromatography (SiO$_2$, heptane to EtOAc) gives the title intermediate I-7 (23.05 g) m/z 273.0 [M+H—H$_2$O].

The following intermediates are also prepared according to the methods described in Method 6:

| Structures | Name | m/z [M + H − H$_2$O] |
|---|---|---|
| 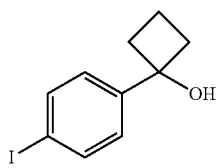 | I-7.1 | 256.9 |
| 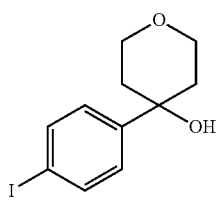 [SMILES: OC1(c2ccc(I)cc2)CCOCC1] | I-7.2 | 287.0 |
| 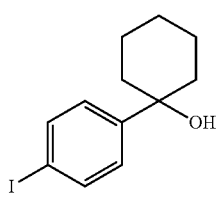 [SMILES: OC1(c2ccc(I)cc2)CCCCC1] | I-7.3 | 284.9 |
| 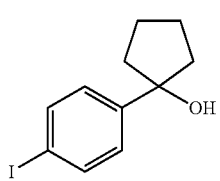 [SMILES: OC1(c2ccc(I)cc2)CCCC1] | I-7.4 | 271.0 |
| 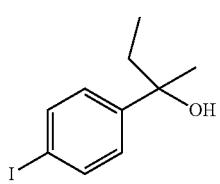 | I-7.5 | 258.9 |
| 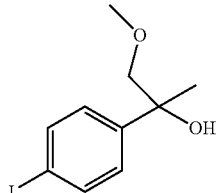 | I-7.6 | 274.9 |

-continued

| Structures | Name | m/z [M + H − H$_2$O] |
|---|---|---|
| 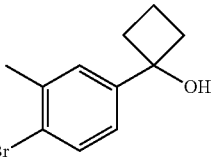 | I-7.7 | 222.9, 224.9 |

Method 7

Synthesis of 3-methyl-2-[4-(2-pyridylmethoxy)phenyl]butan-2-ol (Intermediate 10)

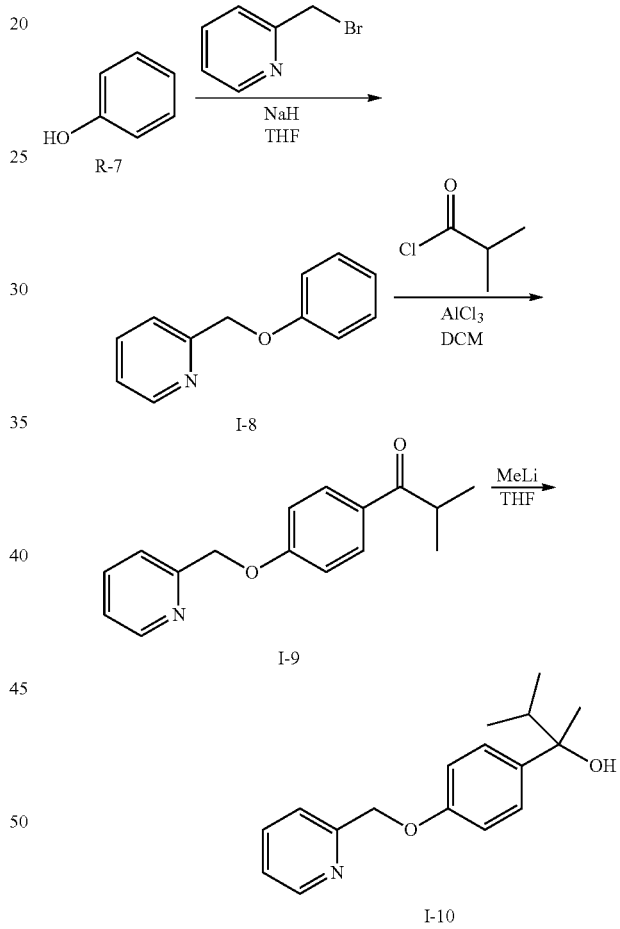

To a suspension of NaH (60% dispersion in mineral oil) (5.22 g, 130.5 mmol) in anhydrous THF (300 mL) at 0° C. under N$_2$ is slowly added phenol (5.58 g, 59.3 mmol). On completion of addition the suspension is allowed to warm to room temperature for 15 min before being cooled to 0° C. and 2-(bromomethyl)pyridine hydrobromide (15 g, 59.3 mmol) added slowly. Stirring is continued at 70° C. for 4 h then allowed to cool to room temperature and quenched by dropwise addition to ice-water. The organic solvent is removed in vacuo and the remaining suspension further diluted with water before extracting with EtOAc. The combined extracts are washed with brine and dried over anhydrous MgSO$_4$. The solvent is removed in vacuo to leave a residue which is purified by flash chromatography (SiO$_2$, 30% EtOAc in cyclohexane) to give I-8 (9.94 g) m/z 186.0 [M+H].

To a solution of I-8 (8.0 g, 43.19 mmol) in DCM (215 mL) at 0° C. under N$_2$ is slowly added AlCl$_3$ (11.52 g, 86.38 mmol) followed by dropwise addition of isobutyryl chloride (9.02 g, 86.38 mmol). The solution is stirred at room temperature for 18 h then a further portion of AlCl$_3$ (5.75 g, 43.17 mmol) added. Stirring is continued for 30 min at room temperature then the reaction cooled to 0° C. and quenched by dropwise addition of water (100 mL). The organic phase is separated and the aqueous phase neutralized with saturated aqueous NaHCO$_3$ and extracted with DCM. The combined organic phases are washed with saturated aqueous NaHCO$_3$ and brine then dried over anhydrous MgSO$_4$. The solvent is removed in vacuo and is purified by flash chromatography (SiO$_2$, 20% to 30% EtOAc in cyclohexane) to give I-9 (7.18 g) m/z 256.1 [M+H].

A solution of I-9 (6.92 g, 27.10 mmol) in anhydrous THF under N$_2$ is cooled to 0° C. and methyl lithium (20.3 mL of a 1.6 M solution in Et$_2$O, 32.52 mmol) added dropwise. The deep-orange solution is allowed to warm to room temperature and stirred for 30 min. A further aliquot of methyl lithium (8.46 mL) is added and stirred for 10 min. The reaction is quenched by dropwise addition of water at 0° C. and the THF evaporated. The aqueous mixture is extracted with EtOAc and the combined extracts washed with brine, then dried over anhydrous MgSO$_4$ and concentrated in vacuo. The residue is purified by flash chromatography (SiO$_2$, 40% EtOAc in cyclohexane) to give the title intermediate I-10 (6.48 g) m/z 272.2 [M+H].

Method 8

Synthesis of 3-[1-(4-iodophenyl)-1,2-dimethyl-propyl]-1H-indole (Intermediate 11)

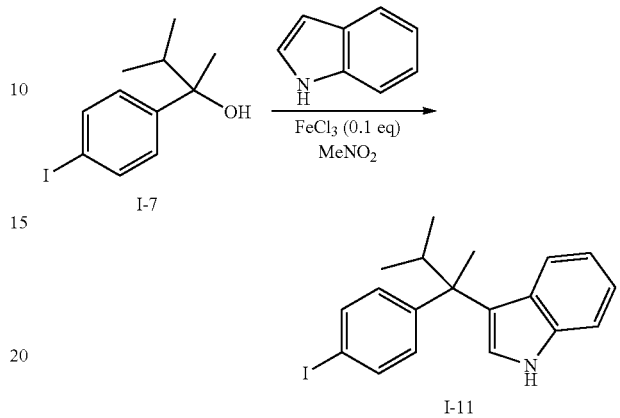

To a solution of I-7 (800 mg, 2.76 mmol) and indole (323 mg, 2.76 mmol) in nitromethane (8 mL) is added anhydrous FeCl$_3$ (45 mg, 0.28 mmol) and the resultant solution stirred at room temperature for 1 h. The suspension is concentrated in vacuo and purified by flash chromatography (SiO$_2$, 10% EtOAc in heptane) to give the title intermediate I-11 (972 mg, 90%) m/z 390.0 [M+H].

The following intermediates are also prepared according to the methods described in Method 8:

| Structures | Name | m/z [M + H] |
|---|---|---|
| 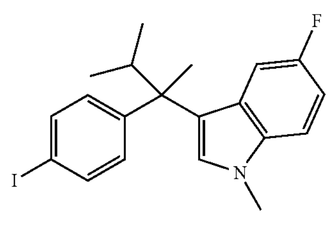 [SMILES: CC(C)C(C)(c1ccc(I)cc1)c1cn(C)c2ccc(F)cc12] | I-11.1 | NA |
| 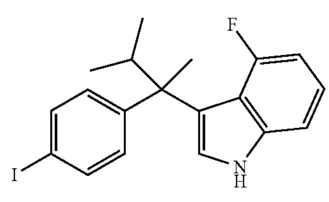 [SMILES: CC(C)C(C)(c1ccc(I)cc1)c1c[nH]c2cccc(F)c12] | I-11.2 | 408.0 |
| 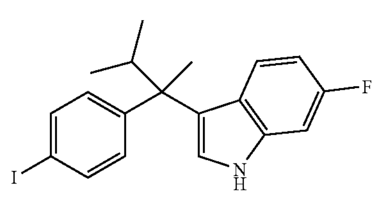 [SMILES: CC(C)C(C)(c1ccc(I)cc1)c1c[nH]c2cc(F)ccc12] | I-11.3 | 408.0 |

-continued

| Structures | Name | m/z [M + H] |
|---|---|---|
| 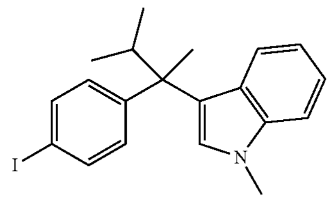 [SMILES: CC(C)C(C)(c1ccc(I)cc1)c1cn(C)c2ccccc12] | I-11.4 | NA |
| 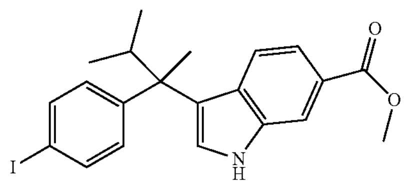 [SMILES: COC(=O)c1ccc2c(C(C)(c3ccc(I)cc3)C(C)C)c[nH]c2c1] | I-11.5 | 447.9 |
| 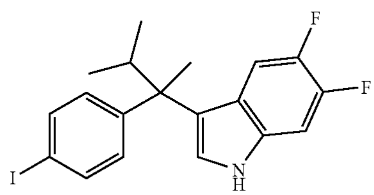 [SMILES: CC(C)C(C)(c1ccc(I)cc1)c1c[nH]c2cc(F)c(F)cc12] | I-11.6 | 426.1 |
| 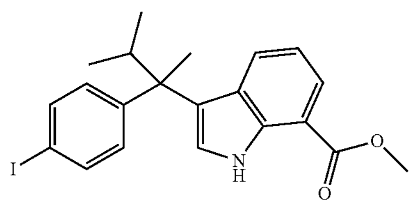 [SMILES: COC(=O)c1cccc2c(C(C)(c3ccc(I)cc3)C(C)C)c[nH]c12] | I-11.7 | NA |
| 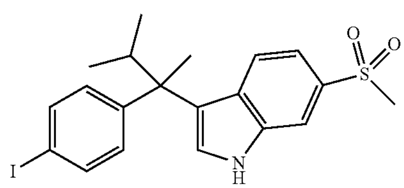 [SMILES: CC(C)C(C)(c1ccc(I)cc1)c1c[nH]c2cc(S(C)(=O)=O)ccc12] | I-11.8 | 468.0 |
| 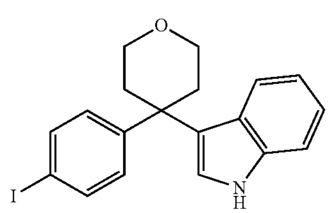 [SMILES: Ic1ccc(C2(c3c[nH]c4ccccc34)CCOCC2)cc1] | I-11.9 | 403.9 |
| 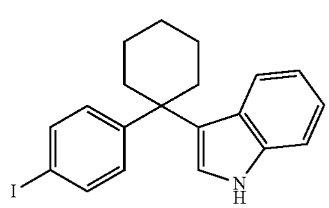 [SMILES: Ic1ccc(C2(c3c[nH]c4ccccc34)CCCCC2)cc1] | I-11.10 | NA |
| 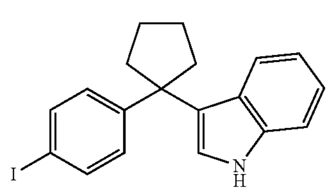 [SMILES: Ic1ccc(C2(c3c[nH]c4ccccc34)CCCC2)cc1] | I-11.11 | 387.9 |

-continued

| Structures | Name | m/z [M + H] |
|---|---|---|
| 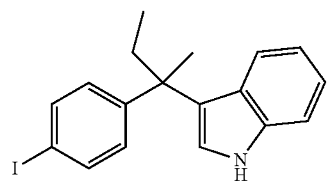 [SMILES: CCC(C)(c1ccc(I)cc1)c1c[nH]c2ccccc12] | I-11.12 | 375.9 |
| 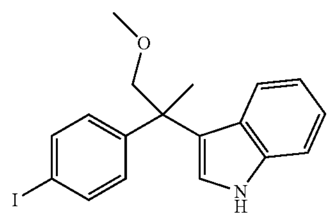 [SMILES: COCC(C)(c1ccc(I)cc1)c1c[nH]c2ccccc12] | I-11.13 | 391.9 |
| 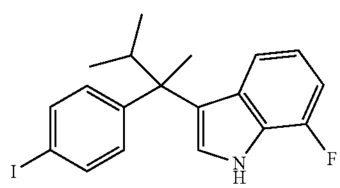 [SMILES: CC(C)C(C)(c1ccc(I)cc1)c1c[nH]c2c(F)cccc12] | I-11.14 | 407.8 |
| 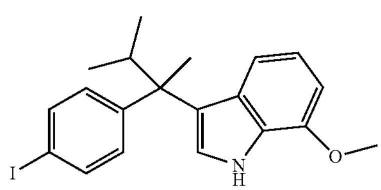 [SMILES: COc1cccc2c(C(C)(c3ccc(I)cc3)C(C)C)c[nH]c12] | I-11.15 | 420.0 |
| 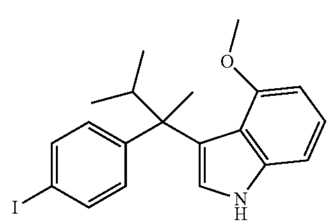 [SMILES: COc1cccc2[nH]cc(C(C)(c3ccc(I)cc3)C(C)C)c12] | I-11.16 | 420.0 |
| 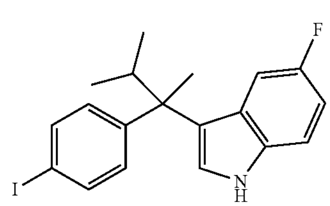 [SMILES: CC(C)C(C)(c1ccc(I)cc1)c1c[nH]c2ccc(F)cc12] | I-11.17 | 408.0 |
| 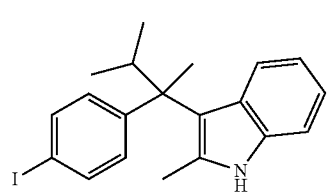 [SMILES: Cc1[nH]c2ccccc2c1C(C)(c1ccc(I)cc1)C(C)C] | I-11.18 | 404.0 |

| Structures | Name | m/z [M + H] |
|---|---|---|
| 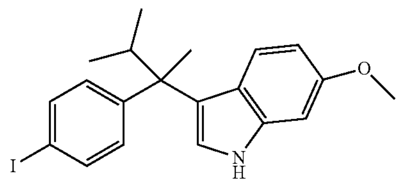 [SMILES: COc1ccc2c(C(C)(c3ccc(I)cc3)C(C)C)c[nH]c2c1] | I-11.19 | 420.0 |
| 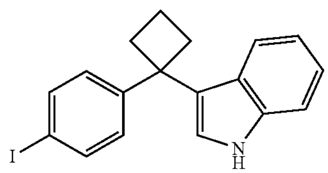 [SMILES: Ic1ccc(C2(c3c[nH]c4ccccc34)CCC2)cc1] | I-11.20 | 373.9 |
| 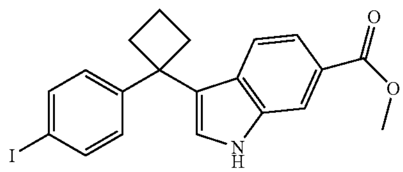 [SMILES: COC(=O)c1ccc2c(C3(c4ccc(I)cc4)CCC3)c[nH]c2c1] | I-11.21 | 431.9 |
| 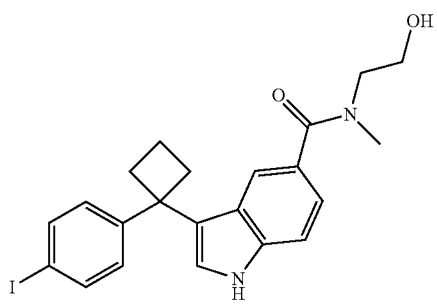 [SMILES: CN(CCO)C(=O)c1ccc2[nH]cc(C3(c4ccc(I)cc4)CCC3)c2c1] | I-11.22 | 486.9 |
| 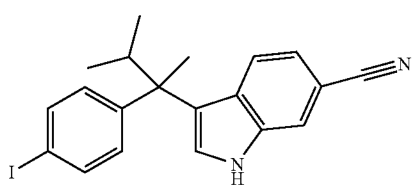 [SMILES: CC(C)C(C)(c1ccc(I)cc1)c1c[nH]c2cc(C#N)ccc12] | I-11.23 | 414.9 |
| 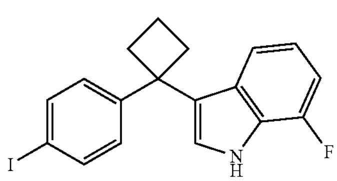 [SMILES: Fc1cccc2c(C3(c4ccc(I)cc4)CCC3)c[nH]c12] | I-11.24 | 391.8 |
| 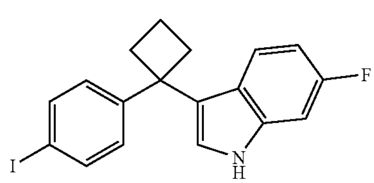 [SMILES: Fc1ccc2c(C3(c4ccc(I)cc4)CCC3)c[nH]c2c1] | I-11.25 | 391.8 |

-continued

| Structures | Name | m/z [M + H] |
|---|---|---|
| 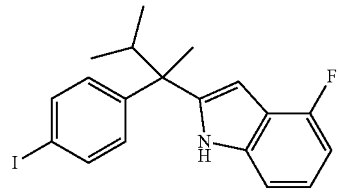 [SMILES: CC(C)C(C)(c1ccc(I)cc1)c1cc2c(F)cccc2[nH]1] | I-11.26 | 408.0 |
| 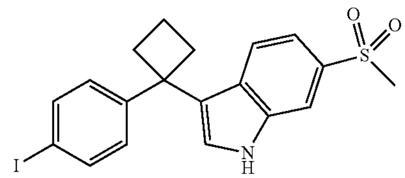 [SMILES: CS(=O)(=O)c1ccc2c(C3(c4ccc(I)cc4)CCC3)c[nH]c2c1] | I-11.27 | 451.7 |
| 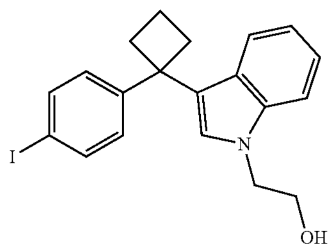 [SMILES: OCCn1cc(C2(c3ccc(I)cc3)CCC2)c2ccccc21] | I-11.28 | 418.0 |
| 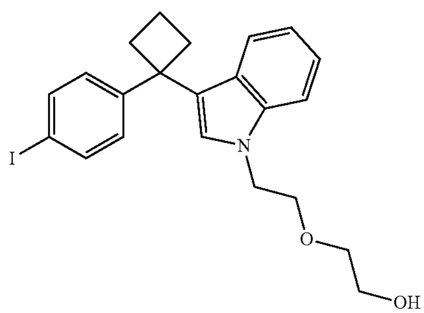 [SMILES: OCCOCCn1cc(C2(c3ccc(I)cc3)CCC2)c2ccccc21] | I-11.29 | 483.9 [M + Na] |
| 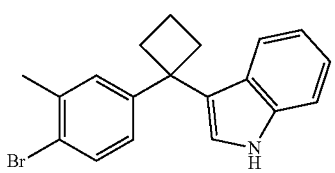 [SMILES: Cc1cc(C2(c3c[nH]c4ccccc34)CCC2)ccc1Br] | I-11.30 | NA |
| 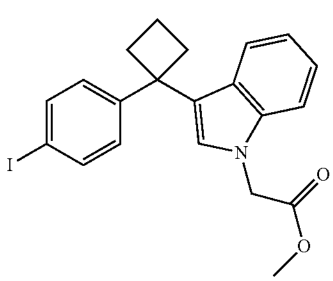 [SMILES: COC(=O)Cn1cc(C2(c3ccc(I)cc3)CCC2)c2ccccc21] | I-11.31 | 445.9 |
| 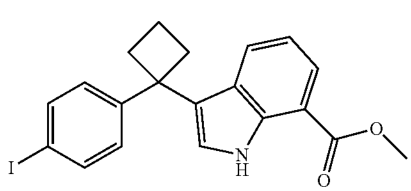 [SMILES: COC(=O)c1cccc2c(C3(c4ccc(I)cc4)CCC3)c[nH]c12] | I-11.32 | NA |

-continued

| Structures | Name | m/z [M + H] |
|---|---|---|
| | I-11.33<sup>a</sup> | 374.9 |
| | I-11.34<sup>a</sup> | 374.9 |
| | I-11.35<sup>a</sup> | 388.9 |
| | I-11.36<sup>a</sup> | 388.9 |
| | I-11.37<sup>a</sup> | 405.3 |
| | I-11.38<sup>a</sup> | 374.9 |
| | I-11.39<sup>a</sup> | 374.9 |
| | I-11.40<sup>b</sup> | 371.3 |

-continued

| Structures | Name | m/z [M + H] |
|---|---|---|
| | I-11.41ᶜ | 388.9 |
| | I-11.42ᶜ | 405.0 |
| | I-11.43ᶜ | 515.0, 517.0 [M, M + 2] |
| | I-11.44ᶜ | 463.0 |
| | I-11.45ᶜ | 407.4 |
| | I-11.46ᶜ | 465.4 |

-continued
| Structures | Name | m/z [M + H] |
|---|---|---|
| 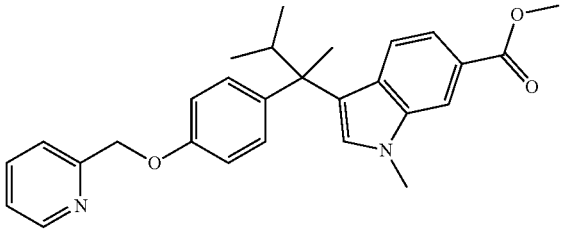 [SMILES: COC(=O)c1ccc2c(C(C)(c3ccc(OCc4ccccn4)cc3)C(C)C)cn(C)c2c1] | I-11.47 | NA |
| 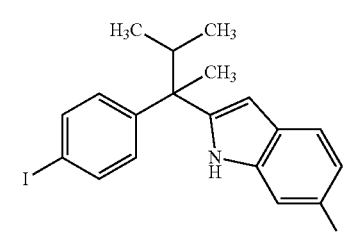 | 11.48 | NA |
| 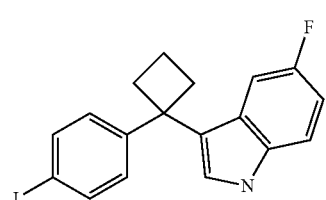 | 11.49 | NA |
$^a$= The reaction is run using 3 equivalents of FeCl$_3$
$^b$= The reaction is run using 0.5 equivalents of FeCl$_3$ at 50° C.
$^c$= The reaction is run using 0.3 equivalents of FeCl$_3$ at 90° C. in a sealed tube
Method 9
Synthesis of methyl 6-[[3-[1,2-dimethyl-1-[4-(2-pyridylmethoxy)phenyl]propyl]indol-1-yl]methyl]pyridine-3-carboxylate (Intermediate 13)
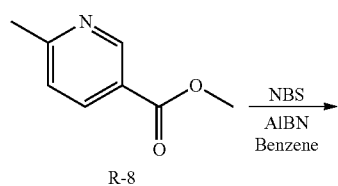
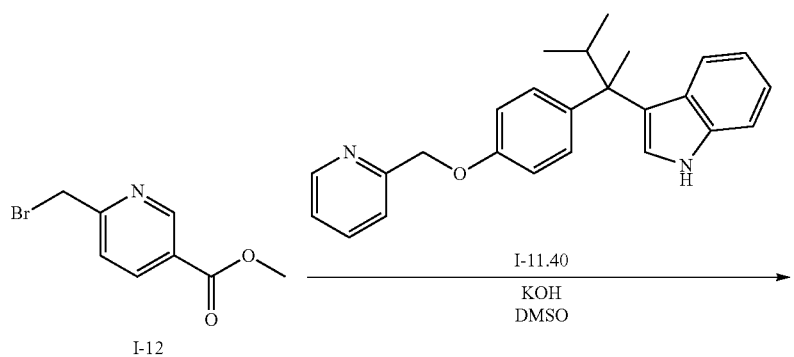

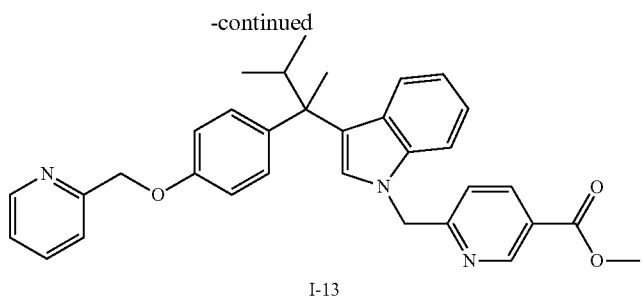

I-13

To a solution of methyl-6-methyl nicotinate R-8 (1 g, 6.63 mmol) in anhydrous benzene (75 mL) is added N-bromosuccinimide (1.77 g, 9.95 mmol) and azobis(isobutyronitrile) (0.217 g, 1.32 mmol). The mixture is stirred at 90° C. for 4 h, then saturated aqueous $NaHCO_3$ is added and the organic layer separated, dried over anhydrous $Na_2SO_4$, and concentrated in vacuo. The residue is purified by flash chromatography ($SiO_2$, 50% DCM in heptane) to give I-12 (493 mg).

A mixture of I-12 (75 mg, 0.33 mmol), I-11.40 (0.27 mmol) and KOH (30 mg, 0.54 mmol) in DMSO (1 mL) is stirred at room temperature for 18 h. The mixture is purified by preparative HPLC (Low pH method) to give I-13 (5 mg).

Method 10

Synthesis of 3-[1-(4-iodophenyl)-1,2-dimethyl-propyl]-1-(2-pyridylmethyl)indole (Intermediate 14)

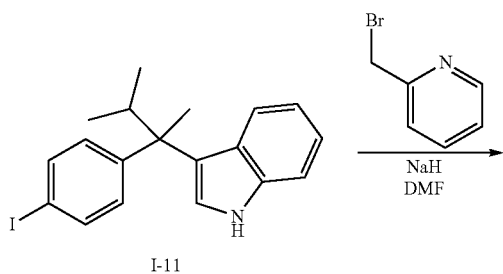

I-11

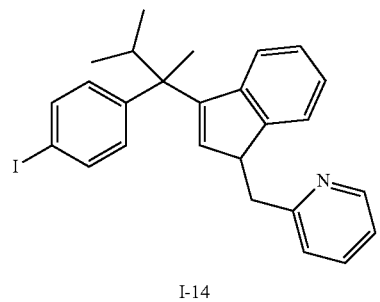

I-14

To a solution of I-11 (680 mg, 1.75 mmol) in anhydrous DMF (18 mL) under $N_2$ is slowly added NaH (60% dispersion in mineral oil) (210 mg, 5.24 mmol) and the resultant suspension stirred at room temperature for 10 min. 2-(Bromomethyl)pyridine hydrobromide (487 mg, 1.93 mmol) is added slowly and stifling continued for 1 h at room temperature. The reaction is quenched by dropwise addition of water (40 mL) and the suspension extracted with EtOAc. The combined organics are washed with water and brine before drying over anhydrous $MgSO_4$. The solvent is removed in vacuo and the crude product purified by flash chromatography ($SiO_2$, 30% EtOAc in heptane) to give I-14 (728 mg) m/z 481.0 [M+H].

The following intermediates are also prepared according to the method described in Method 10:

| Structure | Name | m/z [M + H] |
|---|---|---|
| 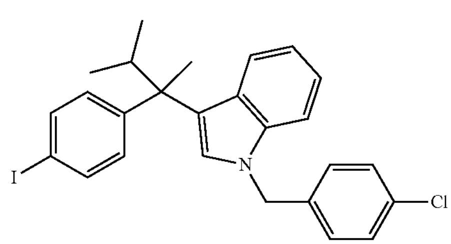 [SMILES: CC(C)C(C)(c1ccc(I)cc1)c1cn(Cc2ccc(Cl)cc2)c2ccccc12] | I-14.1 | NA |

-continued
| Structure | Name | m/z [M + H] |
|---|---|---|
| 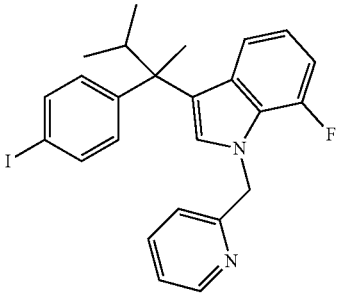 [SMILES: CC(C)C(C)(c1ccc(I)cc1)c1cn(Cc2ccccn2)c2c(F)cccc12] | I-14.2 | 499.1 |
| 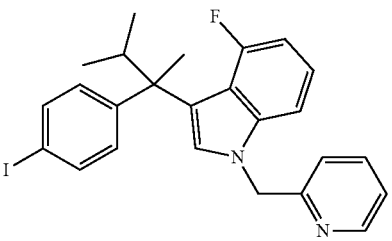 [SMILES: CC(C)C(C)(c1ccc(I)cc1)c1cn(Cc2ccccn2)c2cccc(F)c12] | I-14.3 | 499.0 |
| 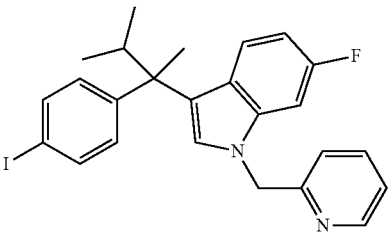 [SMILES: CC(C)C(C)(c1ccc(I)cc1)c1cn(Cc2ccccn2)c2cc(F)ccc12] | I-14.4 | 499.1 |
| 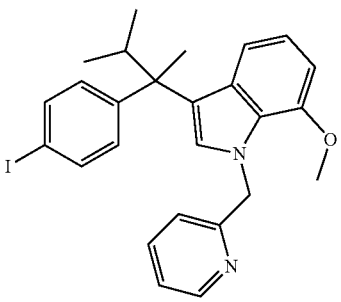 [SMILES: COc1cccc2c(C(C)(c3ccc(I)cc3)C(C)C)cn(Cc3ccccn3)c12] | I-14.5 | 511.2 |
| 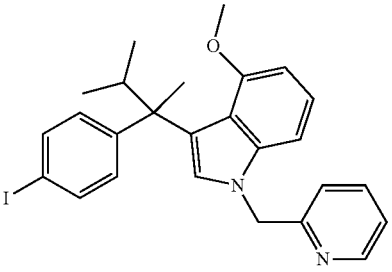 [SMILES: COc1cccc2c1c(C(C)(c1ccc(I)cc1)C(C)C)cn2Cc1ccccn1] | I-14.6 | 511.1 |

-continued
| Structure | Name | m/z [M + H] |
|---|---|---|
| 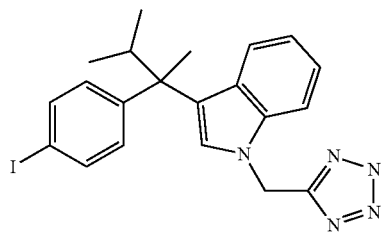 [SMILES: CC(C)C(C)(c1ccc(I)cc1)c1cn(Cc2nn[nH]n2)c2ccccc12] | I-14.7 | 472.9 |
| 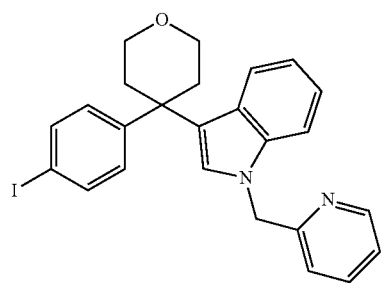 [SMILES: Ic1ccc(C2(c3cn(Cc4ccccn4)c4ccccc34)CCOCC2)cc1] | I-14.8 | 495.0 |
| 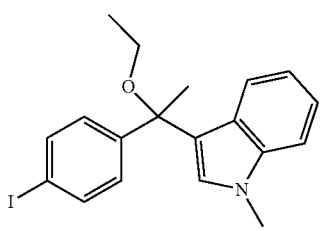 [SMILES: CCOC(C)(c1ccc(I)cc1)c1cn(C)c2ccccc12] | I-14.9 | 406.0 |
| 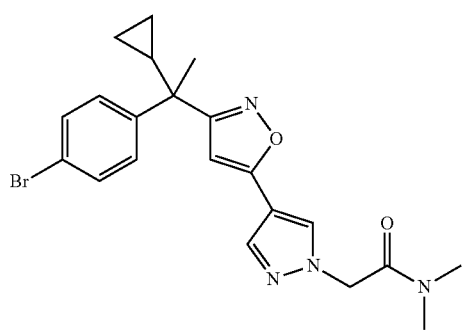 [SMILES: CN(C)C(=O)Cn1cc(-c2cc(C(C)(c3ccc(Br)cc3)C3CC3)no2)cn1] | I-14.10[a] | NA |
| 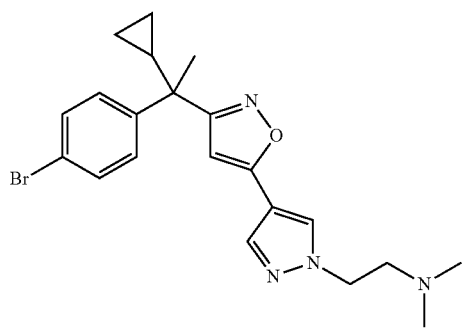 [SMILES: CN(C)CCn1cc(-c2cc(C(C)(c3ccc(Br)cc3)C3CC3)no2)cn1] | I-14.11[a] | NA |

|Structure|Name|m/z [M + H]|
|---|---|---|
| 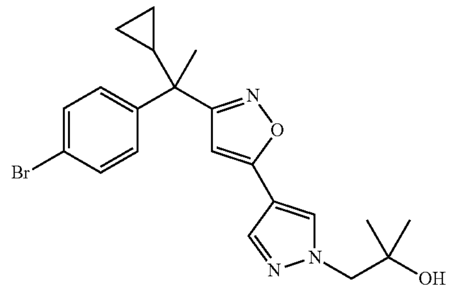 [SMILES: CC(C)(O)Cn1cc(-c2cc(C(C)(c3ccc(Br)cc3)C3CC3)no2)cn1] |I-14.12[a]|NA|

[a] = Reaction is run using K₂CO₃ (2 eq) instead of NaH

Method 11

Synthesis of 3-[1-(4-iodophenyl)-1,2-dimethyl-propyl]-1H-indole-7-carboxylic acid (Intermediate 13)

To a solution of I-11.7 (1.03 g, 2.39 mmol) in a mixture of MeOH (12 mL) and THF (6 mL) is added 5 M NaOH (2.9 mL) and the solution stirred at room temperature for 1 d. The solvent is removed in vacuo and the residue diluted in water. The aqueous phase is acidified with 6 M HCl and extracted with EtOAc. The combined aqueous phases are washed with brine and dried over anhydrous Na₂SO₄. The solvent is removed in vacuo to give the title intermediate I-15 (946 mg) m/z 433.9 [M+H].

The following intermediates are also prepared according to the method described in Method 11:

|Structure|Name|m/z [M + H]|
|---|---|---|
| |I-15.1|433.9|
| 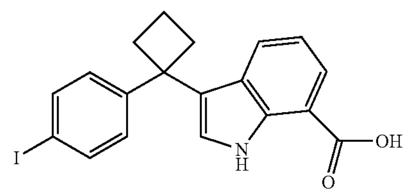 [SMILES: O=C(O)c1cccc2c(C3(c4ccc(I)cc4)CCC3)c[nH]c12] |I-15.2|416.0|
| 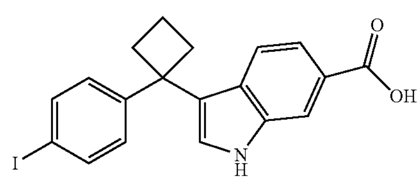 [SMILES: O=C(O)c1ccc2c(C3(c4ccc(I)cc4)CCC3)c[nH]c2c1] |I-15.3|416.0|
| 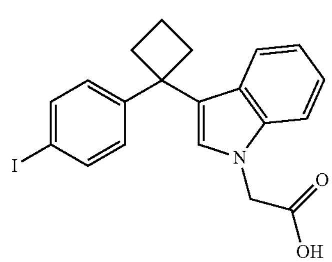 [SMILES: O=C(O)Cn1cc(C2(c3ccc(I)cc3)CCC2)c2ccccc21] |I-15.4[a]|431.7|

[a] = LiOH was used in place of NaOH

Method 12

Synthesis of N-(2-hydroxyethyl)-3-[1-(4-iodophenyl)-1,2-dimethyl-propyl]-N-methyl-1H-indole-7-carboxamide (Intermediate 16)

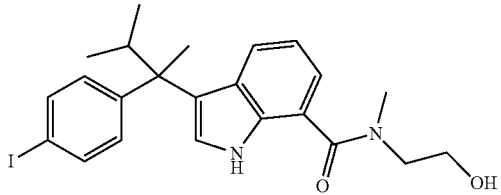

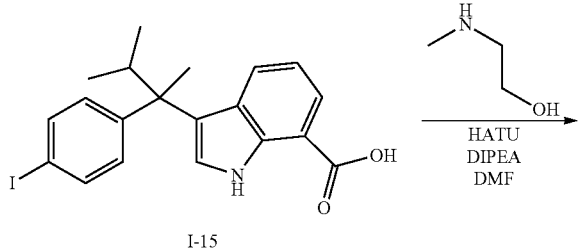

To a solution of crude I-15 (100 mg, 0.24 mmol) in anhydrous DMF (3 mL) is added HATU (182 mg, 0.48 mmol) and DIPEA (124 μL, 0.48 mmol) and the solution stirred at room temperature for 5 min. 2-(Methylamino)ethanol (38 μL, 0.24 mmol) is then added and stifling continued for 2 h. The reaction is diluted with saturated aqueous $NaHCO_3$ solution and extracted with EtOAc. The combined extracts are washed with saturated aqueous $NaHCO_3$, water and brine, and dried over anhydrous $Na_2SO_4$. The solvent is removed in vacuo to give the title intermediate I-16 (132 mg) m/z 491.0 [M+H].

The following intermediates are also prepared according to the method described in Method 12:

| Structure | Name | m/z [M + H] |
|---|---|---|
| 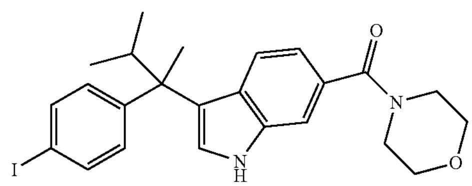 [SMILES: CC(C)C(C)(c1ccc(I)cc1)c1c[nH]c2cc(C(=O)N3CCOCC3)ccc12] | I-16.1 | 503.2 |
| 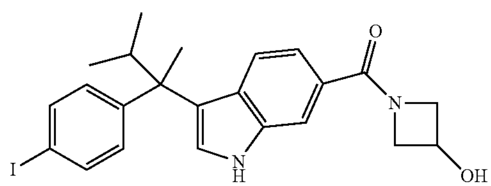 [SMILES: CC(C)C(C)(c1ccc(I)cc1)c1c[nH]c2cc(C(=O)N3CC(O)C3)ccc12] | I-16.2 | 489.0 |
| 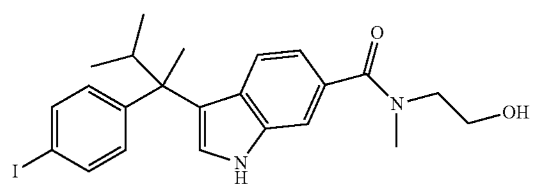 [SMILES: CC(C)C(C)(c1ccc(I)cc1)c1c[nH]c2cc(C(=O)N(C)CCO)ccc12] | I-16.3 | 491.0 |
| 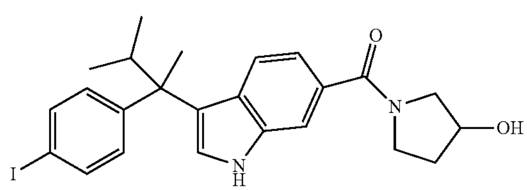 [SMILES: CC(C)C(C)(c1ccc(I)cc1)c1c[nH]c2cc(C(=O)N3CCC(O)C3)ccc12] | I-16.4 | 503.0 |
| 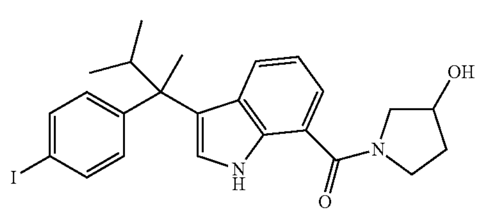 [SMILES: CC(C)C(C)(c1ccc(I)cc1)c1c[nH]c2c(C(=O)N3CCC(O)C3)cccc12] | I-16.5 | 503.0 |

-continued

| Structure | Name | m/z [M + H] |
|---|---|---|
| 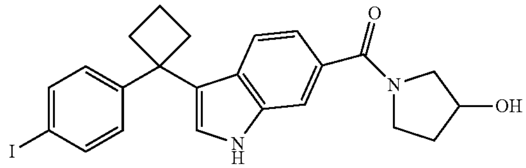 [SMILES: O=C(c1ccc2c(C3(c4ccc(I)cc4)CCC3)c[nH]c2c1)N1CCC(O)C1] | I-16.6 | 487.0 |
| 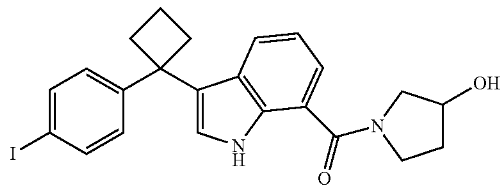 [SMILES: O=C(c1cccc2c(C3(c4ccc(I)cc4)CCC3)c[nH]c12)N1CCC(O)C1] | I-16.7 | 487.0 |
| 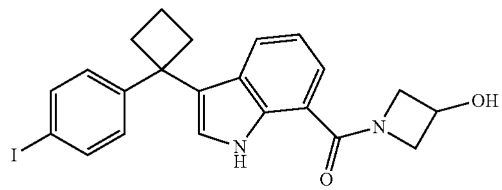 [SMILES: O=C(c1cccc2c(C3(c4ccc(I)cc4)CCC3)c[nH]c12)N1CC(O)C1] | I-16.8 | 473.0 |
| 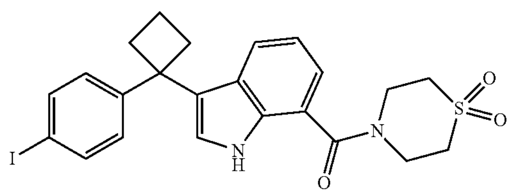 [SMILES: O=C(c1cccc2c(C3(c4ccc(I)cc4)CCC3)c[nH]c12)N1CCS(=O)(=O)CC1] | I-16.9 | 534.9 |
| 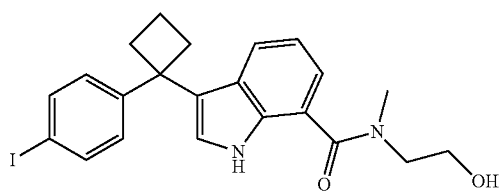 [SMILES: CN(CCO)C(=O)c1cccc2c(C3(c4ccc(I)cc4)CCC3)c[nH]c12] | I-16.10 | 474.9 |
| 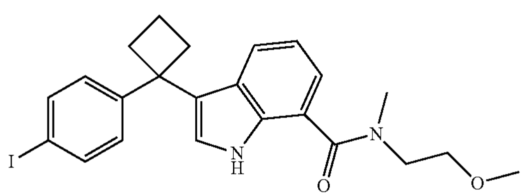 [SMILES: COCCN(C)C(=O)c1cccc2c(C3(c4ccc(I)cc4)CCC3)c[nH]c12] | I-16.11 | 488.9 |
| 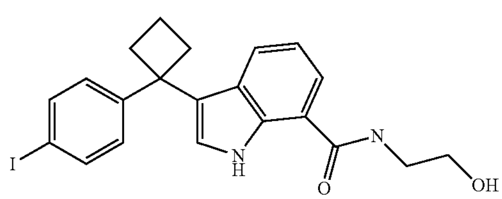 [SMILES: O=C(NCCO)c1cccc2c(C3(c4ccc(I)cc4)CCC3)c[nH]c12] | I-16.12 | 460.9 |
| 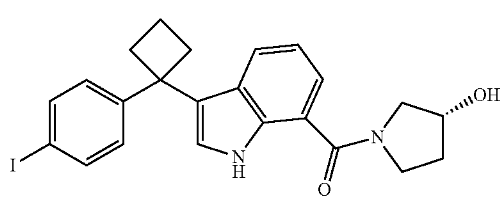 [SMILES: O=C(c1cccc2c(C3(c4ccc(I)cc4)CCC3)c[nH]c12)N1CC[C@@H](O)C1] | I-16.13 | 487.0 |

-continued

| Structure | Name | m/z [M + H] |
|---|---|---|
| 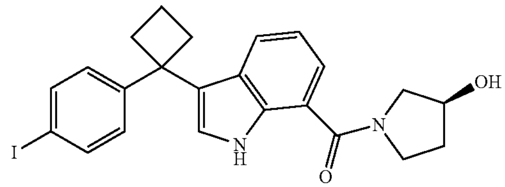 [SMILES: O=C(c1cccc2c(C3(c4ccc(I)cc4)CCC3)c[nH]c12)N1CC[C@H](O)C1] | I-16.14 | 487.0 |
| 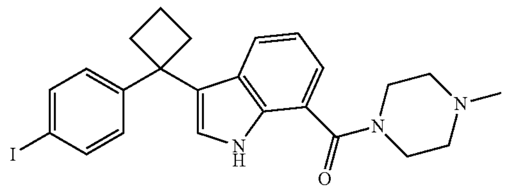 [SMILES: CN1CCN(C(=O)c2cccc3c(C4(c5ccc(I)cc5)CCC4)c[nH]c23)CC1] | I-16.15 | 500.0 |
| | I-16.16<sup>a</sup> | 508.9 |
| | I-16.17<sup>a</sup> | 510.9 |

<sup>a</sup> = 5 equivalents of DIPEA and 2 equivalents of amine were used in the reaction Method 13

Synthesis of 1-(4-bromophenyl)-N-methoxy-N-methyl-cyclobutanecarboxamide (Intermediate 16)

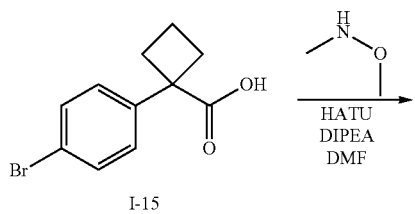

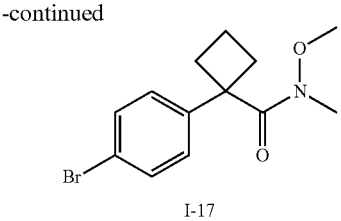

I-17

To a solution of I-15 (30 g, 117.5 mmol) in DMF (300 mL) is added N,O-dimethylhydroxylamine hydrochloride (12.62 g, 129.4 mmol), HATU (53.68 g, 141.2 mmol) and DIPEA (60.82 g, 470.6 mmol) and stirred at room temperature for 5 hours. The reaction mixture is quenched with water, extracted with EtOAc. The organic layer is separated, washed with brine, dried over anhydrous $Na_2SO_4$, filtered and concentrated.

The residue is purified by flash chromatography (SiO$_2$, 0-5% EtOAc/petether) to give the title intermediate I-17 (32 g), m/z: 298, 300 [M, M+2].

The following intermediates are also prepared according to the method described in Method XX:

| Structure | Name | m/z [M, M + 2] |
|---|---|---|
| 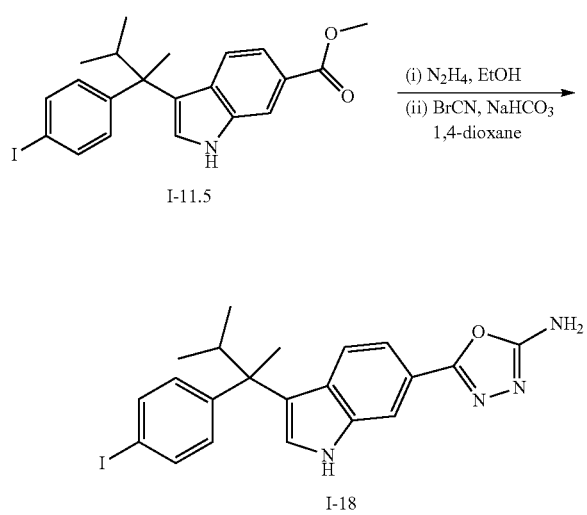 | I-17.1[a] | 377.1, 379.1 |

[a]= Et$_3$N (5 eq) was used in place of DIPEA, 1.2 eq of HATU used in the reaction

Method 14

Synthesis of 5-[3-[1-(4-iodophenyl)-1,2-dimethyl-propyl]-1H-indol-6-yl]-1,3,4-oxadiazol-2-amine (Intermediate 18)

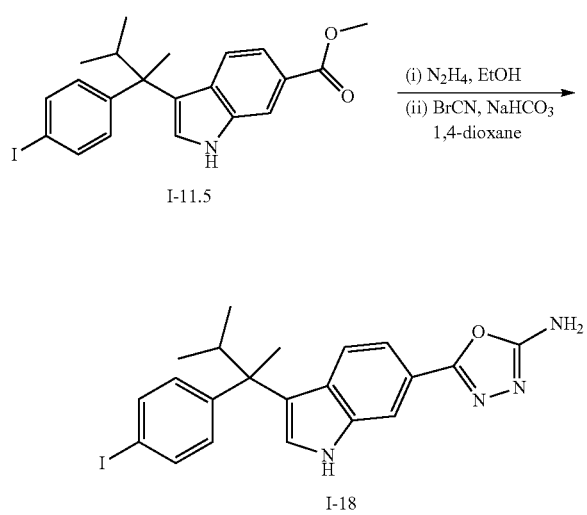

To a solution of I-11.5 (400 mg, 0.894 mmol) in EtOH (5 mL) is added hydrazine hydrate (258 mg, 8.07 mmol) and the solution heated to reflux for 2.5 h. The solvent is removed in vacuo and the residue re-dissolved in 1,4-dioxane (10 mL). NaHCO$_3$ (104 mg, 0.98 mmol) is added followed by BrCN (104 mg, 0.98 mmol) and the reaction stirred at room temperature for 18 h. The mixture is then poured onto saturated aqueous NaHCO$_3$ and extracted with EtOAc. The combined organics are washed with brine, dried over anhydrous Na$_2$SO$_4$, and the solvent removed in vacuo to give the title compound I-18 (469 mg, 93%) m/z 473.3 [M+H].

Method 15

Synthesis of azetidin-1-yl-[3-[1-(4-iodophenyl)cyclobutyl]-1H-indol-7-yl]methanone (Intermediate 19)

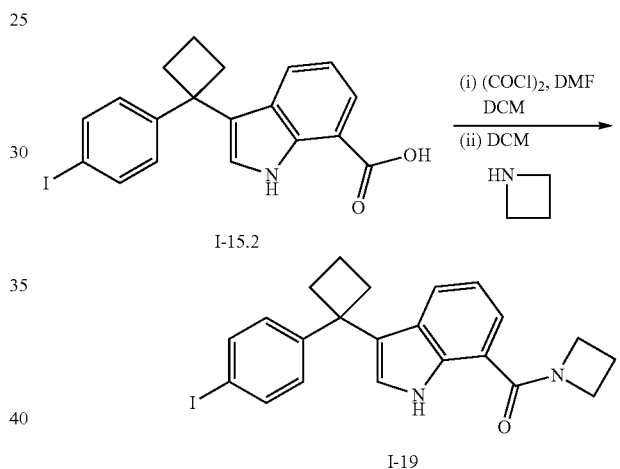

To a solution of I-15.2 (200 mg, 0.48 mmol) in DCM (4 mL) is added oxalyl chloride (165 µL, 1.92 mmol) followed by DMF (100 µL) and the solution stirred under N$_2$ at room temperature for 30 min. The solvent is removed in vacuo and the residue re-dissolved in DCM (4 mL). The solution is cooled to 0° C. and azetidine (129 µL, 1.92 mmol) added dropwise. Stirring is continued at room temperature for 1 h then a further 2 eq of azetidine added. After stifling for a further 1 h the reaction is quenched with saturated aqueous NH$_4$Cl and extracted with DCM. The combined extracts are washed with saturated aqueous NaHCO$_3$ and brine, and dried over anhydrous Na$_2$SO$_4$. The solvent is removed in vacuo to leave a brown solid which is recrystallised from EtOAc to give the title intermediate I-19 (183 mg) m/z 456.9 [M+H].

The following intermediates are also prepared according to the method described in Method 14.

| Structure | Name | m/z [M + H] |
|---|---|---|
| 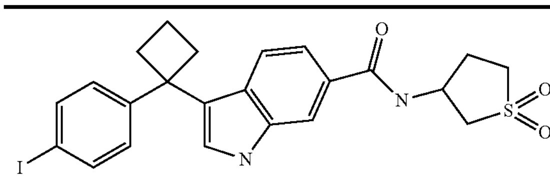 | I-19.1 | 534.9 |

| Structure | Name | m/z [M + H] |
|---|---|---|
| 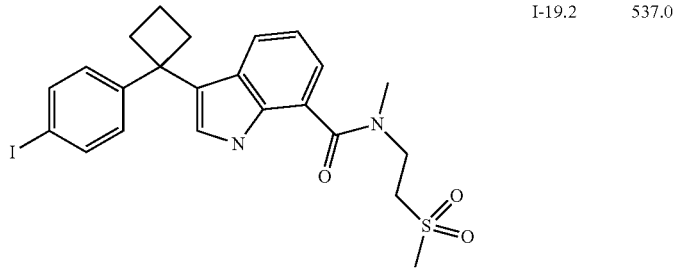 | I-19.2 | 537.0 |
| 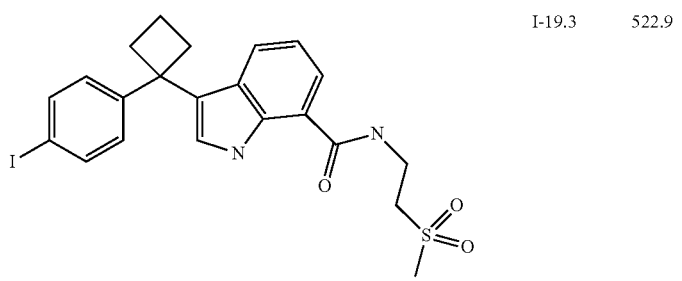 | I-19.3 | 522.9 |
| 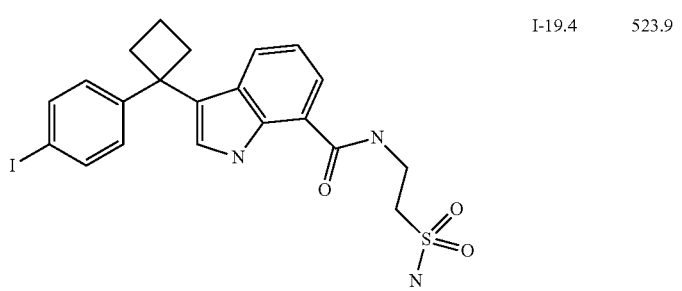 | I-19.4 | 523.9 |
| 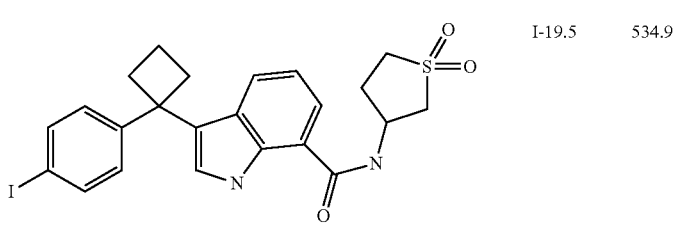 | I-19.5 | 534.9 |
| 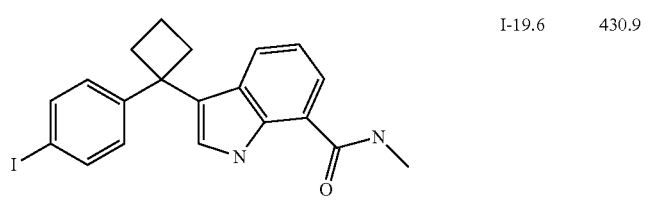 | I-19.6 | 430.9 |
| 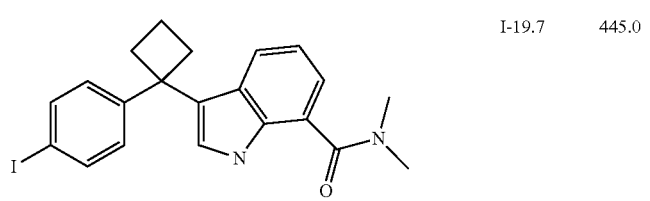 | I-19.7 | 445.0 |

-continued

| Structure | Name | m/z [M + H] |
|---|---|---|
| 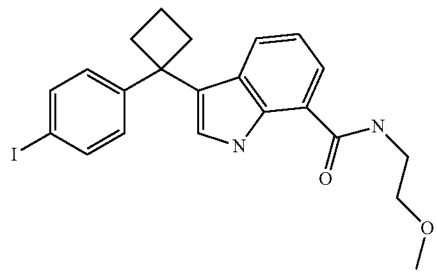 [SMILES: COCCNC(=O)c1cccc2c(C3(c4ccc(I)cc4)CCC3)c[nH]c12] | I-19.8 | 475.1 |
| 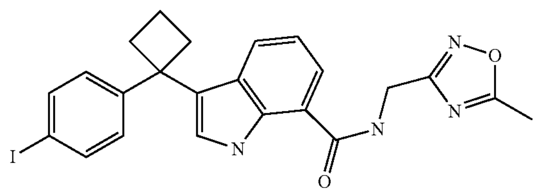 [SMILES: Cc1nc(CNC(=O)c2cccc3c(C4(c5ccc(I)cc5)CCC4)c[nH]c23)no1] | I-19.9 | 513.0 |
| 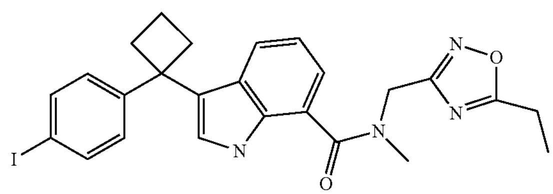 [SMILES: CCc1nc(CN(C)C(=O)c2cccc3c(C4(c5ccc(I)cc5)CCC4)c[nH]c23)no1] | I-19.10 | 541.0 |
| 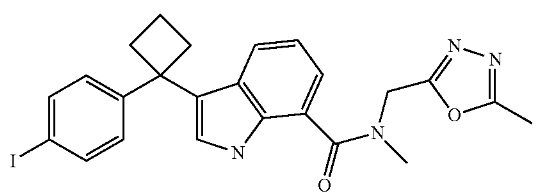 [SMILES: Cc1nnc(CN(C)C(=O)c2cccc3c(C4(c5ccc(I)cc5)CCC4)c[nH]c23)o1] | I-19.11 | 526.9 |
| 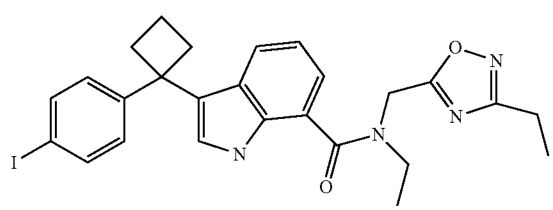 [SMILES: CCc1noc(CN(CC)C(=O)c2cccc3c(C4(c5ccc(I)cc5)CCC4)c[nH]c23)n1] | I-19.12 | 555.0 |
| 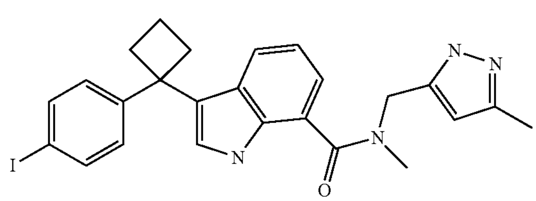 [SMILES: Cc1cc(CN(C)C(=O)c2cccc3c(C4(c5ccc(I)cc5)CCC4)c[nH]c23)[nH]n1] | I-19.13 | 525.1 |
| 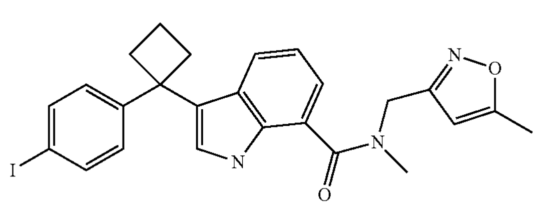 [SMILES: Cc1cc(CN(C)C(=O)c2cccc3c(C4(c5ccc(I)cc5)CCC4)c[nH]c23)no1] | I-19.14 | 526.1 |

Method 16

Synthesis of 3-[1-(4-iodophenyl)cyclobutyl]-1H-indole-7-carboxamide (Intermediate 20)

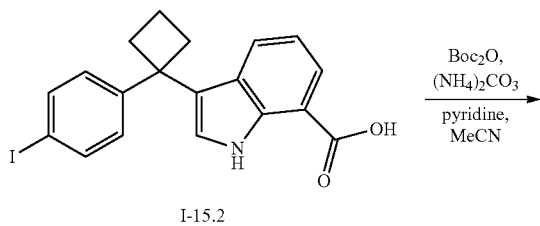

I-15.2

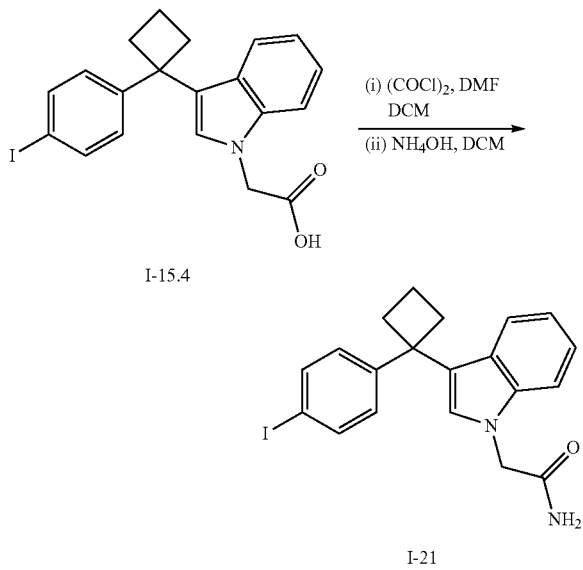

To a suspension of I-15.2 (112 mg, 0.27 mmol) in anhydrous MeCN (3 mL) is added di-tert-butyl dicarbonate (76 mg, 0.35 mmol), ammonium carbonate (31 mg, 0.32 mmol) and pyridine (27 µL, 0.32 mmol). The reaction is stirred at room temperature for 1 d then re-treated with a further 0.8 equivalents of the reagents and warmed to 40° C. for 5 h. The solvent is removed in vacuo and the residue taken up in saturated aqueous NH₄Cl and extracted with EtOAc. The combined organics are washed with saturated aqueous NaHCO₃ and brine, and dried over anhydrous Na₂SO₄. The solvent is removed in vacuo to give the title intermediate I-20 (128 mg) m/z 416.8 [M+H].

Method 17

Synthesis of 2-[3-[1-(4-iodophenyl)cyclobutyl]indol-1-yl]acetamide (Intermediate 21)

To a solution of I-15.4 (50 mg, 0.12 mmol) in DCM (2 mL) is added oxalyl chloride (30 µL, 0.35 mmol) and DMF (100 µL) and the resultant solution stirred at room temperature for 30 min. The solvent is removed in vacuo and the residue taken up in DCM (2 mL). The solution is added dropwise to ammonium hydroxide (1 mL) at 0° C. The solution is allowed to warm to room temperature then stirred for 2 d. The organic phase is separated and added to 1 M HCl. The acidic aqueous phase is extracted with DCM and the combined extracts are washed with brine and dried over anhydrous Na₂SO₄. The solvent is removed in vacuo and the crude material purified by flash chromatography (SiO₂, 70% EtOAc in heptane) to give the title intermediate I-21 (25 mg) m/z 452.9 [M+Na].

The following intermediates are also prepared according to the method described in Method 16:

| Structure | Name | m/z [M + H] |
|---|---|---|
| 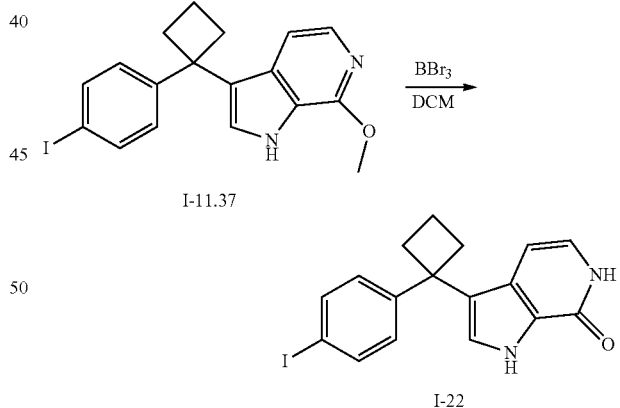 | I-21.1 | 500.9 |

Method 18

Synthesis of 3-[1-(4-iodophenyl)cyclobutyl]-1,6-dihydropyrrolo[2,3-c]pyridin-7-one (Intermediate 22)

I-11.37

I-22

To a solution of I-11.37 (200 mg, 0.495 mmol) in DCM at −78° C. is added dropwise a BBr₃ (2.97 mL of a 1M solution in DCM, 2.968 mmol) and the reaction stirred at −70° C. for 15 minutes and at room temperature for 16 h. The reaction is cooled to −70° C. and further BBr₃ (2.97 mL of a 1 M solution in DCM, 2.968 mmol) is added. The reaction is stirred at room temperature for 4.5 hours and then is poured over ice and neutralised to pH 7.5 with saturated aqueous NaHCO₃. The aqueous solution is extracted into DCM and the organics dried over anhydrous Na₂SO₄, and concentrated in vacuo to give the title intermediate I-22 (85 mg) m/z 390.9 [M+H].

Method 19

Synthesis of 3-[1-(4-iodophenyl)-1,2-dimethyl-propyl]-6-tetrahydrofuran-3-yloxy-1H-indole (Intermediate 24)

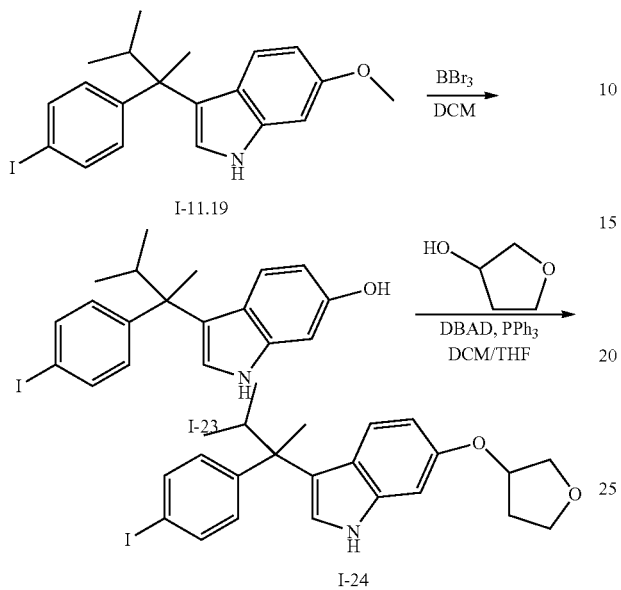

To a solution of I-11.19 (150 mg, 0.36 mmol) in DCM (0.5 mL) at 0° C. is added a solution of BBr₃ (133 mg, 0.53 mmol) in DCM (1 mL) dropwise. The solution is stirred for 2 h then the reaction quenched by dropwise addition of ice-water. The mixture is extracted with DCM and the combined organics washed with brine then dried over anhydrous $Na_2SO_4$. The solvent is removed in vacuo to give I-23 (110 mg) m/z 405.9 [M+H].

To a solution of I-23 (110 mg, 0.27 mmol), 3-hydroxytetrahydrofuran (28 mg, 0.32 mmol) and triphenylphosphine (85 mg, 0.32 mmol) in a mixture of DCM (2.5 mL) and THF (2.5 mL) is added di-tert-butyl azodicarboxylate (74 mg, 0.32 mmol) and the resultant solution stirred at room temperature for 18 h. The solvent is removed in vacuo and the residue taken up in DCM. The organics are washed with water then dried over anhdrous $Na_2SO_4$ and the solvent is removed in vacuo. The crude material is purified by preparative HPLC (Low pH method: water-acetonitrile, containing 0.1% TFA) to give the title compound I-24 (14 mg, 11%) m/z 476.0 [M+H].

Method 20

Synthesis of 3-[1-(4-iodophenyl)-1,2-dimethyl-propyl]-1-[2-(4-methylpiperazin-1-yl)ethyl]indole (Intermediate 26)

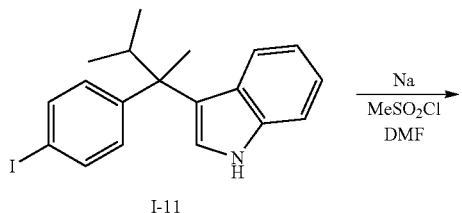

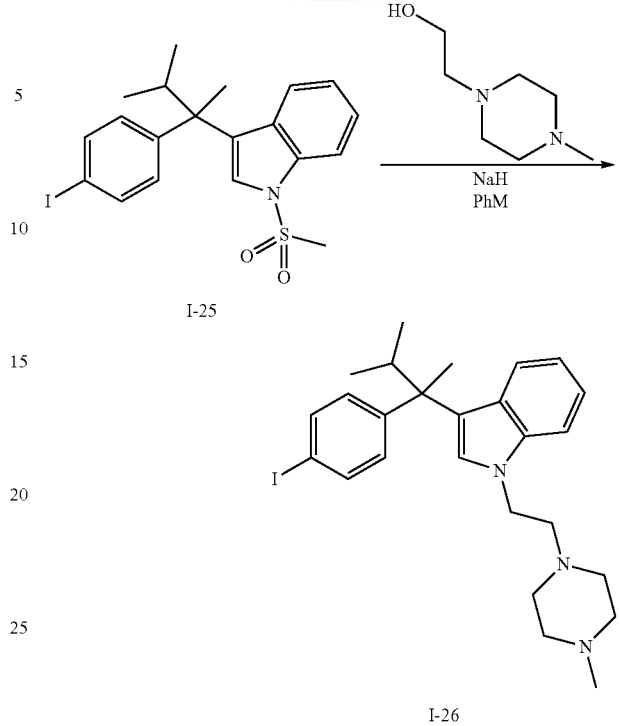

To a solution of I-11 (150 mg, 0.39 mmol) in anhydrous DMF (4.5 mL) is added NaH (60% dispersion in mineral oil) (18 mg, 0.46 mmol). The mixture is stirred at room temperature for 10 minutes and then methanesulfonyl chloride (0.032 mL, 0.42 mmol) is added and stifling continued for 18 h. The reaction is retreated with more methane sulfonyl chloride (0.03 mL) and NaH (60% dispersion in mineral oil) (18 mg) and stirring is continued for another 2 h before quenching with water. The reaction is partitioned between saturated aqueous $NaHCO_3$ and DCM. The combined organics are washed with brine, dried over anhydrous $Na_2SO_4$, and concentrated in vacuo to give I-25 (193 mg).

To a solution of 1-(2-hydroxyethyl)-4-methylpiperazine (54 mg, 0.37 mmol) in toluene (3 mL) is added NaH (60% dispersion in mineral oil) (18 mg, 0.45 mmol) and the suspension stirred at room temperature for 10 min. A solution of I-25 (175 mg, 0.37 mmol) in toluene (1.5 mL) is added and the reaction heated to 110° C. for 3 h. A further 1 eq of 1-(2-hydroxyethyl)-4-methylpiperazine and 1.2 eq of NaH are added and heating continued for 3 h. The reaction is quenched by dropwise addition of water and extracted with DCM. The combined organics are washed with water and brine, and dried over anhydrous $Na_2SO_4$. The solvent is removed in vacuo and the crude material purified by flash chromatography ($SiO_2$, 2% MeOH in DCM) to give the title intermediate I-26 (52 mg) m/z 516.1 [M+H].

Method 21

Synthesis of 3-[1-(4-iodophenyl)-1,2-dimethyl-propyl]-6-(1H-tetrazol-5-yl)-1H-indole (Intermediate 27)

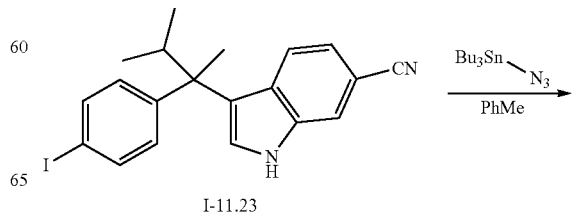

-continued

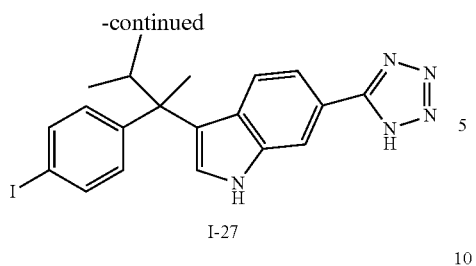

I-27

To a solution of I-11.23 (200 mg, 0.48 mmol) in toluene (10 mL) is added 3-(tributylstannanyl)triaza-1,2-dien-2-ium-1-ide (0.32 g, 0.96 mmol) and the reaction heated to 85° C. for 18 h. The reaction is allowed to cool to room temperature, diluted with EtOAc and washed with saturated aqueous Rochelle's salt. The organic phase is dried over anhydrous Na$_2$SO$_4$ and the solvent removed in vacuo. The compound was dissolved in EtOAc (2 mL) and loaded onto an Isolute SCX-2 column. The column was then eluted with EtOAc followed by 5% MeOH in EtOAc to give the title intermediate I-27 (216 mg) m/z 457.9 [M+H].

Method 22

Synthesis of 1-[1-(4-iodophenyl)-1,2-dimethyl-propyl]-3-methyl-indole (Intermediate 28)

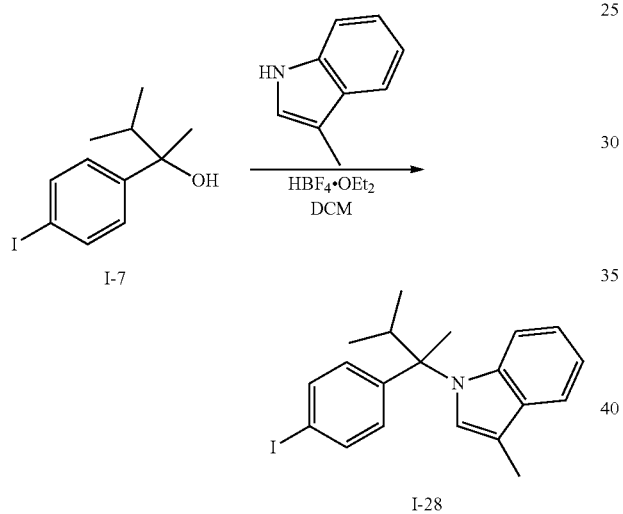

To a mixture of I-7 (50 mg, 0.17 mmol) and 3-methylindole (22 mg, 0.17 mmol) in DCM (1 mL) is added HBF$_4$.OEt$_2$ (0.028 mL, 0.20 mmol). The mixture is stirred at room temperature for 1 h then quenched with saturated aqueous NaHCO$_3$. The organics are separated and the aqueous phase is extracted with further DCM. The combined organics are dried over anhydrous MgSO$_4$ and concentrated in vacuo. The residue is purified by flash chromatography (SiO$_2$, 5% EtOAc in cyclohexane) to give I-28 (69 mg). LCMS (ESMS): Rt 2.81 min (Method G) m/z 404.0 (M+H)$^+$.

Method 23

Synthesis of (5-bromo-2-pyridyl)-(1-methylindol-3-yl)methanone (Intermediate 33)

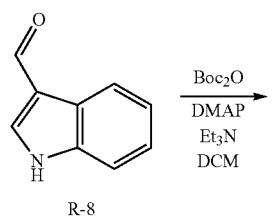

-continued

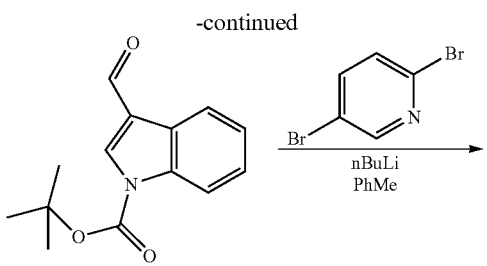

I-29

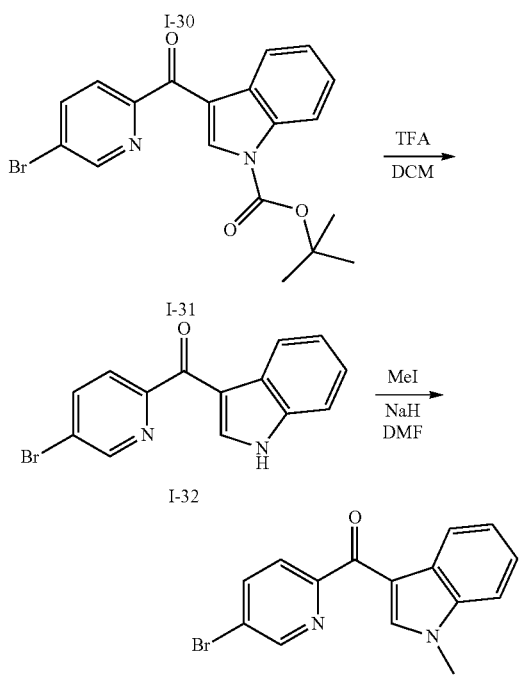

To a solution of R-8 (5.00 g, 34.45 mmol), DMAP (0.42 g, 3.44 mmol) and triethylamine (9.6 mL, 68.89 mmol) in DCM (300 mL) is added di-tert-butyl dicarbonate (8.27 g, 37.89 mmol) and the resultant solution stirred at room temperature for 1 h. The solution is washed with saturated aqueous NH$_4$Cl and brine then dried over anhydrous Na$_2$SO$_4$. The solvent is removed in vacuo to give I-29 (8.04 g).

To a solution of 2,5-dibromopyridine (2.0 g, 8.44 mmol) in anhydrous toluene (400 mL) at −78° C. under N$_2$ is slowly added n-butyl lithium (4.05 mL of a 2.5 M solution in hexanes, 10.13 mmol) and the reaction aged for 4 h. I-29 (2.17 g, 8.86 mmol) is added and stirring continued for 1 h. The mixture is warmed to −10° C. and quenched with saturated aqueous NH$_4$Cl. On warming to room temperature the organic phase is separated and dried over anhydrous Na$_2$SO$_4$. The solvent is removed in vacuo and the crude material purified by flash chromatography (SiO$_2$, 15% EtOAc in heptane) to give I-30 (2.60 g) m/z 424.9, 426.9 [M+Na].

To a solution of I-30 (1.50 g, 3.72 mmol) in DCM (30 mL) is added manganese (IV) oxide (1.62 g, 18.60 mmol) and the reaction stirred at room temperature for 3 d. The suspension is filtered through Celite and the solvent removed in vacuo to give I-31 (1.10 g) m/z 401.1, 402.9 [M+H].

I-31 (1.0 g, 2.49 mmol) is dissolved in a solution of TFA (7 mL) in DCM (23 mL) and the solution is left to stand for 3 h. The solvent is removed in vacuo and the residue taken up in saturated aqueous NaHCO$_3$. The mixture is extracted with EtOAc, the combined organics dried over anhydrous Na$_2$SO$_4$ and the solvent removed in vacuo to give I-32 (770 mg) m/z 300.9, 302.8 [M+H].

I-32 (770 mg, 1.46 mmol) is dissolved in DMF (10 mL) and cooled to 0° C. NaH (60% dispersion in mineral oil) (87 mg, 2.19 mmol) is added portionwise and the mixture allowed to warm to room temperature. Iodomethane (0.11 mL, 1.75 mmol) is added dropwise and the reaction stirred for a further 1 h. The reaction is quenched by cautious addition of saturated aqueous NaHCO$_3$ and the mixture extracted with EtOAc. The combined organics are washed with water and brine then dried over anhydrous Na$_2$SO$_4$ and the solvent removed in vacuo to give the title intermediate I-33 (778 mg) m/z 314.9, 316.9 [M+H].

Method 24

Synthesis of (6-chloro-3-pyridyl)-(1-methylindol-3-yl)methanone (Intermediate 34)

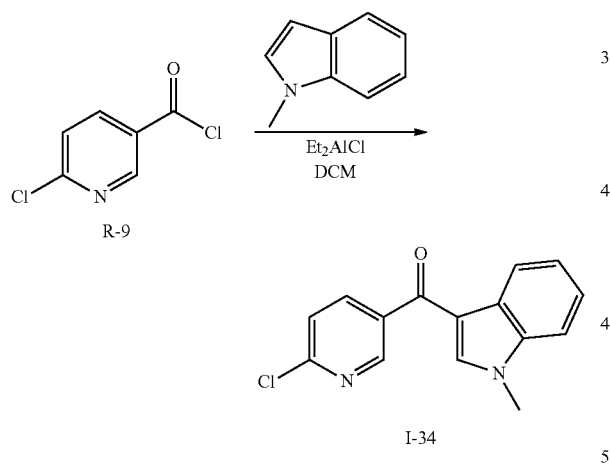

I-34

To a solution of 1-methylindole (2.0 g, 15.25 mmol) in DCM (50 mL) is added diethylaluminium chloride (15.25 mL of a 1 M solution in hexanes, 15.25 mmol) dropwise at −78° C. under N$_2$. After stirring for 15 min, R-9 (1.12 g, 4.19 mmol) is added portionwise. The resultant suspension is allowed to warm to room temperature, and stirred for a further 2 h. The reaction is quenched by slow addition of MeOH, and the solvent is removed in vacuo. The residue is taken up in DCM and washed with saturated aqueous NaHCO$_3$ and brine, and dried over anhydrous Na$_2$SO$_4$. The solvent is removed in vacuo and the crude material purified by flash chromatography (SiO$_2$, 1% to 4% EtOAc in DCM) to give the title intermediate I-34 (1.77 g) m/z 271.0, 273.0 [M+H].

The following intermediates are also prepared according to the method described in Method 24:

| Structure | Name | m/z [M + H] |
|---|---|---|
| 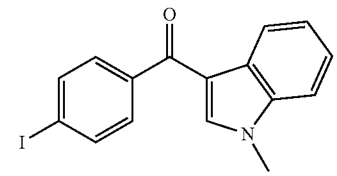 [SMILES: Cn1cc(C(=O)c2ccc(I)cc2)c2ccccc21] | I-34.1 | 361.8 |

Method 25

Synthesis of (4-iodophenyl)-(1-methylindazol-3-yl)methanone (Intermediate 36)

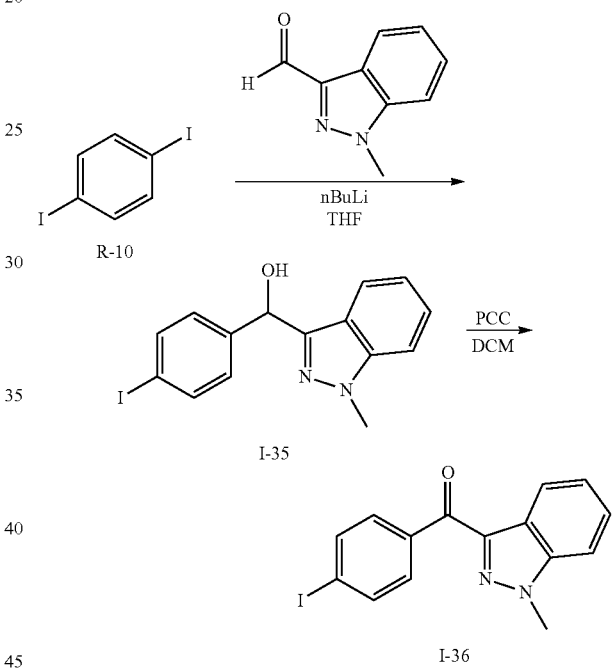

To a solution of R-10 (500 mg, 1.51 mmol) in anhydrous THF (5 mL) at −78° C. is added n-butyl lithium (0.994 mL of a 1.6 M solution in hexanes, 1.59 mmol). After stirring for 20 minutes at this temperature 1-methyl-1H-indazole-3-carbaldehyde (242 mg, 1.51 mmol) is added and the reaction is allowed to warm to room temperature. After 30 minutes the reaction is partitioned between aqueous NH$_4$Cl and EtOAc. The organics are dried over Na$_2$SO$_4$ and concentrated in vacuo to give I-35 (534 mg) m/z 364.9 [M+H].

To a solution of I-35 (534 mg, 1.47 mmol) in DCM (5 mL) is added pyridinium chlorochromate (632 mg, 2.93 mmol). The mixture is stirred at room temperature for 1 h and is then decanted to remove the solid residue. The solid residue is washed with more DCM. The combined organics are washed with saturated aqueous NaHCO$_3$, dried over Na$_2$SO$_4$, and concentrated in vacuo to give the title intermediate I-36 (527 mg) m/z 362.9 [M+H].

The following intermediates are also prepared according to the method described in Method 25:

| Structure | Name | m/z [M + H] |
|---|---|---|
| 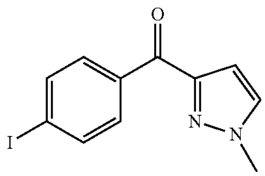 | I-36.1 | 312.8 |

Method 26

Synthesis of [4-(2-aminopyrimidin-5-yl)phenyl]-(1-methylindazol-3-yl)methanone (Intermediate 37)

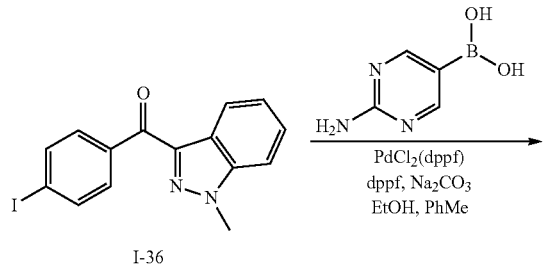

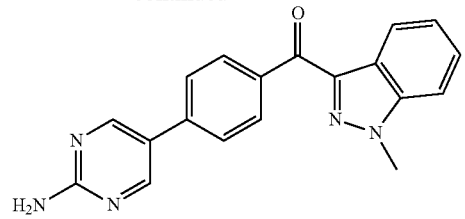

A suspension of the I-36 (250 mg, 0.69 mmol), 2-aminopyrimidine-5-boronic acid (115 mg, 0.83 mmol), 1,1-(bisdiphenylphosphino)ferrocene (11 mg, 20 µmol) and 2 M aqueous $Na_2CO_3$ (1.04 mL, 2.08 mmol) in a 4:1 mixture of EtOH:toluene (2.5 mL) is degassed for 5 min then [1,1-(bisdiphenylphosphino)ferrocene]dichloropalladium(II) (8 mg, 11 µmol) is added. The reaction vessel is sealed under $N_2$ and heated to 95° C. for 18 h. On cooling to room temperature the mixture is diluted with DCM and washed with saturated aqueous $NaHCO_3$. The organic phase is dried over anhydrous $Na_2SO_4$ and the solvent removed in vacuo to give I-37 (97 mg).

The following intermediates are also prepared according to the method described in Method 26:

| Structure | Name | m/z [M + H] |
|---|---|---|
| 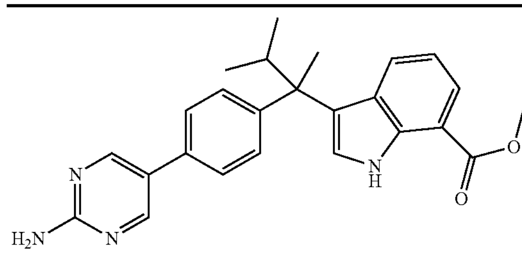 | I-37.1 | NA |
| 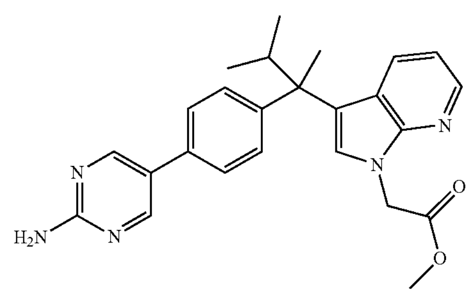 [SMILES: COC(=O)Cn1cc(C(C)(c2ccc(-c3cnc(N)nc3)cc2)C(C)C)c2cccnc21] | I-37.2 | NA |

Method 27

Synthesis of 3-[1-[4-(4,4,5,5-tetramethyl-1,3,2-dioxaborolan-2-yl)phenyl]cyclobutyl]-1H-indole (Intermediate 38)

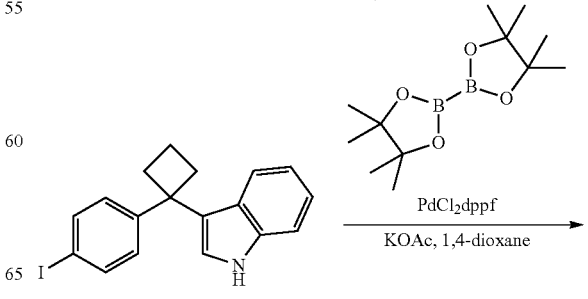

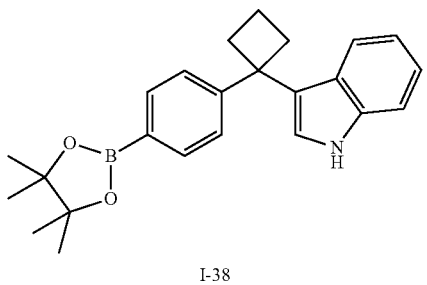

I-38

To a de-gassed solution of I-11.20 (290 mg, 0.77 mmol), KOAc (300 mg, 3.11 mmol) and bis(pinacolato)diboron (240 mg, 0.93 mmol) in 1,4-dioxane (3 mL) is added [1,1-(bis-diphenylphosphino)ferrocene]dichloropalladium (II) (63 mg, 0.08 mmol) and the sealed reaction vessel heated to 100° C. for 8 h. On cooling to room temperature the reaction is diluted with EtOAc and washed with water. The organic phase is dried over anhydrous Na$_2$SO$_4$ and the solvent removed in vacuo. The crude material is purified by flash chromatography (SiO$_2$, 5% EtOAc in heptane) to give I-38 (108 mg).

Method 28

Synthesis of 1-(6-chloro-3-pyridyl)-2,2-dimethyl-1-(1-methylindol-3-yl)propan-1-ol (Intermediate 39)

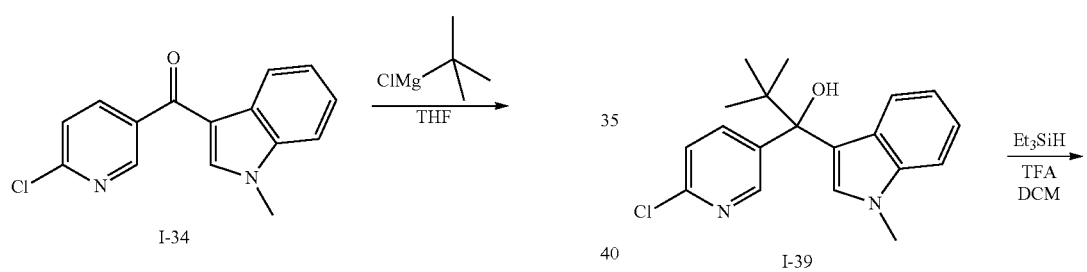

A solution of I-34 (700 mg, 2.59 mmol) in anhydrous THF (14 mL) is cooled to 0° C. under N$_2$ and tert-butylmagnesium chloride (1.29 mL of a 2 M solution in Et$_2$O, 2.59 mmol) added. The resultant solution is stirred at 0° C. for 5 min then allowed to warm to room temperature. After a further 2 h, the reaction is cooled to 0° C. and a further 0.2 eq of tert-butylmagnesium chloride added. The reaction is stirred for 1 h then quenched with saturated aqueous NH$_4$Cl and extracted with EtOAc. The combined organics are washed with water and brine then dried over anhydrous Na$_2$SO$_4$. The solvent is removed in vacuo and the crude material is purified by flash chromatography (SiO$_2$, DCM to 1% EtOAc in DCM) to give I-39 (340 mg) m/z 329.0, 331.0 [M+H].

The following intermediates are also prepared according to the method described in Method 28:

| Structure | Name | m/z [M + H] |
|---|---|---|
| 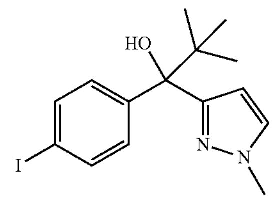 [SMILES: Cn1ccc(C(O)(c2ccc(I)cc2)C(C)(C)C)n1] | I-39.1 | 353.3 [M + H − H$_2$O] |
| 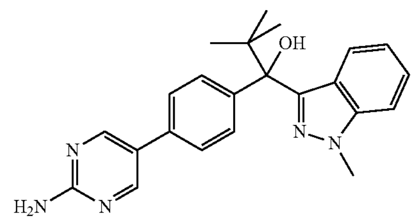 [SMILES: Cn1nc(C(O)(c2ccc(-c3cnc(N)nc3)cc2)C(C)(C)C)c2ccccc21] | I-39.2 | 371.18 |

Method 29

Synthesis of 3-[1-(6-chloro-3-pyridyl)-2,2-dimethyl-propyl]-1-methyl-indole (Intermediate 40)

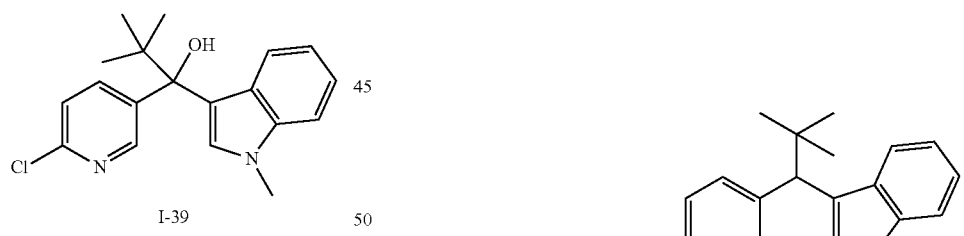

To a solution of I-39 (282 mg, 0.86 mmol) in DCM (8 mL) is added triethylsilane (151 μL, 0.84 mmol), followed by dropwise addition of TFA (0.66 mL, 8.58 mmol). The reaction is stirred at room temperature for 2 h, and quenched with saturated aqueous NaHCO$_3$. The mixture is extracted with DCM and the combined organics washed with saturated aqueous NaHCO$_3$ and brine, then dried over anhydrous Na$_2$SO$_4$. The solvent is removed in vacuo to give the title intermediate I-40 (286 mg) m/z 313.0, 315.0 [M+H].

The following intermediates are also prepared according to the method described in Method 29:

| Structure | Name | m/z [M + H] |
|---|---|---|
| 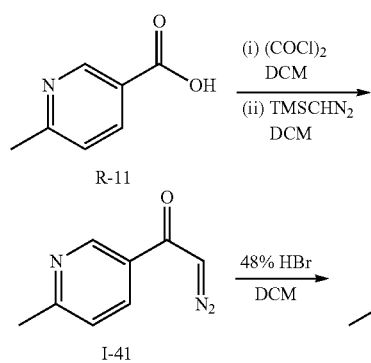 | I-40.1 | 404.0 |
| 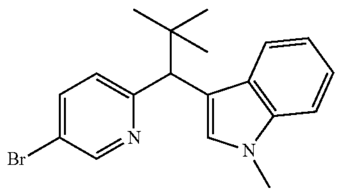 [SMILES: Cn1cc(C(c2ccc(Br)cn2)C(C)(C)C)c2ccccc21] | I-40.2 | 357.0, 358.9 [M, M + 2] |

Method 30

Synthesis of 2-bromo-1-(6-methyl-3-pyridyl)ethanone (Intermediate 42)

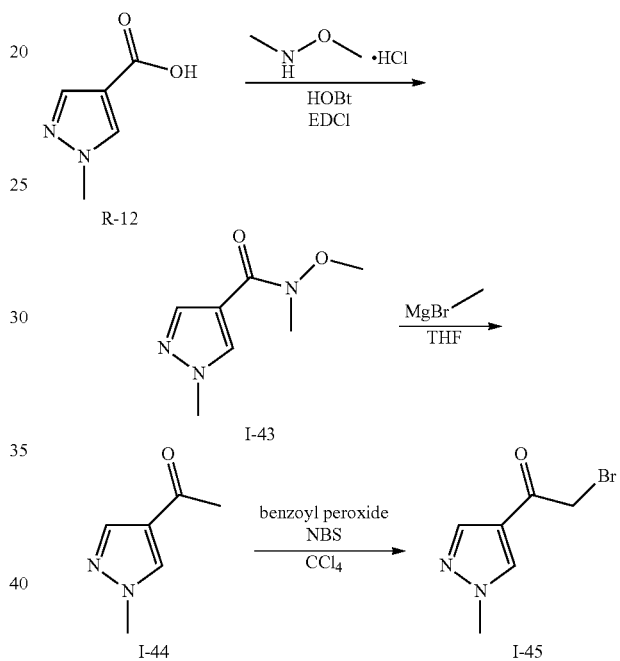

To a solution of R-11 (2.46 g, 17.9 mmol) in anhydrous DCM (60 mL) is added oxalyl chloride (15 g, 116 mmol). The mixture is stirred at room temperature for 1 h then concentrated in vacuo. The residue is dissolved in toluene (20 mL) and concentration in vacuo is repeated. The residue is redissolved in anhydrous DCM (50 mL) and TMS-diazomethane (45 mL of a 2 M solution in Et$_2$O, 90 mmol) is added dropwise at 0° C. The mixture is stirred at room temperature for 1 h then quenched in saturated aqueous NaHCO$_3$. The DCM layer is concentrated in vacuo and the crude material purified by flash chromatography (SiO$_2$, 80% EtOAc in heptane to 100% EtOAc) to give the I-41 (2.21 g).

A solution of I-40 (92.1 g, 13.0 mmol) in DCM (20 mL) is added dropwise to ice-cold 48% aqueous HBr (20 mL). The mixture is stirred at 0° C. for 10 min and is then neutralized by careful addition of 1 M aqueous NaHCO$_3$ at 0° C. The mixture is extracted with DCM and the combined organics dried over anhydrous Na$_2$SO$_4$ and concentrated in vacuo to give the I-42 (2.27 g, 81%) m/z 2143.9, 215.9 [M+H].

The following intermediates are also prepared according to the method described in Method 30:

Method 31

Synthesis of 2-bromo-1-(6-methyl-3-pyridyl)ethanone (Intermediate 45)

To a solution of R-12 (10 g, 79.3 mmol) in MeCN (200 mL) at 0° C. is added N,O-dimethylhydroxylaminehydrochloride (8.5 g, 87.2 mmol), EDCI (18.2 g, 95.2 mmol), 1-hydroxybenzotriazole (3.2 g, 23.8 mmol) followed by triethylamine (20.5 mL, 158 mmol) and stirred at room temperature 15 h. The reaction mixture is partitioned between water and EtOAc. The collected organics are dried with anhydrous Na$_2$SO$_4$, filtered, and concentrated in vacuo to give I-43 (12 g) m/z 170.0 [M+H].

To a solution of I-43 (12 g, 70.9 mmol) in THF (200 mL) cooled to −78° C. is slowly added methylmagnesium bromide 2.0 M sol. in THF (50 mL, 160 mmol) and stirred at room temperature for 14 h. The reaction mixture is quenched with sat. aq. NH$_4$Cl and is extracted with ethyl acetate. The organic layers are combined and washed with brine, dried with anhydrous Na$_2$SO$_4$, filtered and concentrated in vacuo to give I-44 (8.0 g) m/z 125 [M+H].

To a solution of I-44 (8.0 g, 64.4 mmol) in CCl$_4$ at room temperature is added benzoyl peroxide (3.8 g, 16.1 mmol) and N-bromosuccinimide (31.5 g, 177 mmol) and stirred at 80° C. for 14 h. After cooling to room temperature, the reaction mixture is partitioned between water and EtOAc. The combined organics are washed with brine, dried with anhy- Method 32

Synthesis of
2-amino-1-(6-methyl-3-pyridyl)ethanone
(Intermediate 46)

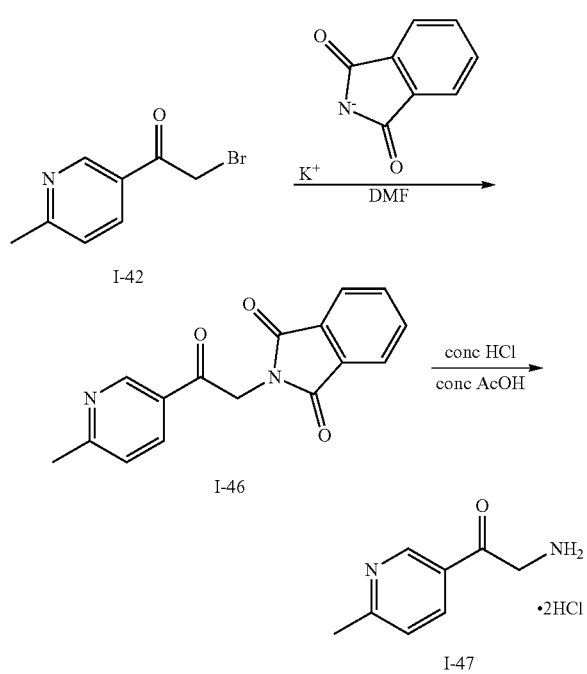

To a solution of I-42 (2.37 g, 11.1 mmol) in anhydrous DMF (30 mL) at 0° C. is added dropwise a solution of potassium phthalimide (2.05 g, 11.1 mmol) in DMF (20 mL). The reaction is allowed to warm to room temperature then concentrated in vacuo. The residue is taken up in DCM and insoluble material removed. The organics are concentrated in vacuo and the crude material purified by flash chromatography (SiO$_2$, EtOAc) to give the I-46 (1.86 g) m/z 281.4 [M+H].

A mixture of I-46 (1.86 g, 6.64 mmol), concentrated HCl (40 mL) and concentrated AcOH (20 mL) is heated at 120° C. for 18 h. The reaction mixture is concentrated in vacuo and the resultant residue is taken up in MeOH (100 mL). The solution is stirred with Ambersep 900 OH$^-$ resin (3 mmol/g, 25 g) for 15 min and then filtered. The filtrate is re-acidified with 4M HCl in dioxane (6 mL) then concentrated in vacuo to give the title intermediate I-47 (as 2HCl salt) (1.18 g) m/z 151.0 [M+H].

The following intermediates are also prepared according to the method described in Method 32:

| Structure | Name | m/z [M + H] |
|---|---|---|
| (pyrazole-NH$_2$ ketone, 2HCl) | I-47.1 | NA |

Method 33

Synthesis of
2-(4-Bromo-phenyl)-2-cyclopropylpropionitrile
(Intermediate 49)

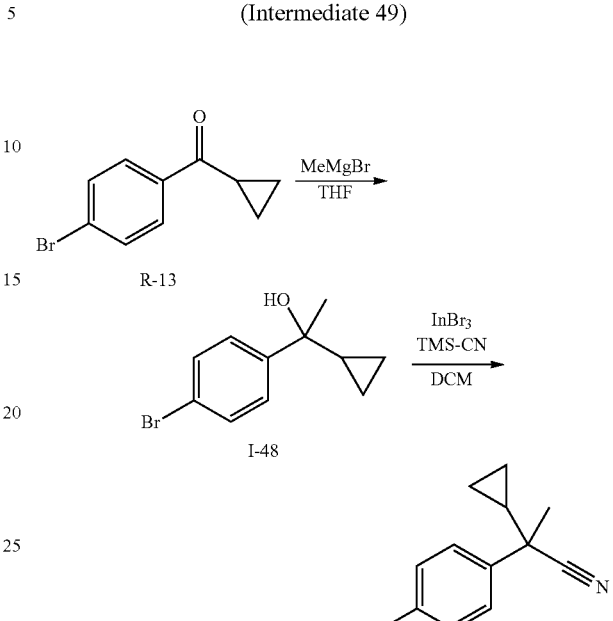

To a stirred solution of R-13 (50 g, 222 mmol) in THF (400 mL) at −78° C. is added methylmagnesium bromide (3M in ether) (222 mL, 666 mmol) slowly. The reaction mixture is stirred at −78° C. for 1 hour, then at room temperature for 2 hours. To the reaction mixture is added saturated aqueous NH$_4$Cl, and extracted with EtOAc. The organic layer is separated, washed with brine, dried over anhydrous Na$_2$SO$_4$, filtered and concentrated in vacuo to give I-48 (50 g).

To a solution I-48 (20 g, 82.9 mmol) in DCM (400 mL) at −60° C. is added indium (III) bromide (5.87 g, 16.6 mmol). The reaction mixture is stirred at −60° C. for 30 minutes, followed by the addition of trimethylsilyl cyanide (22.2 mL, 165.9 mmol) dropwise over a period of 15 minutes at −60° C. The reaction mixture is allowed to warm to 0° C. and is stirred at 0° C. for 2 hours. To the reaction mixture is added with 20% Na$_2$CO$_3$ and is filtered through a pad of Celite. The filtrate is extracted with DCM, and the combined organic layer is dried over anhydrous Na$_2$SO$_4$, filtered and concentrated in vacuo. The residue is purified by flash chromatography (SiO$_2$, 5% EtOAc/petether) to give the title intermediate I-49 (12 g).

2-(4-Bromo-phenyl)-2-cyclopropylpropionitrile can Also be Prepared in the Following Manner To a solution of R-13 (309 g, 1.37 mol) in THF (3.0 L) is added dropwise MeMgBr (3M in Et$_2$O 1.37 L, 4.12 mol) at −78° C. The mixture is stirred at −78° C. for 10 min and then at room temperature for 2 h. The reaction mixture is quenched with saturated aqueous NH$_4$Cl and extracted with EtOAc. The combined organic layers are washed with brine, dried over anhydrous Na$_2$SO$_4$ and concentrated to afford the crude compound I-48 (330 g) which is used in the next step without further purification. To a solution of I-48 (330 g, 1.37 mol) in CH$_2$Cl$_2$ (2.4 L) is added dropwise BF$_3$.EtO$_2$ (198 g, 1.37 mol) at −78° C. The mixture is stirred at the same temperature for 30 min. TMSCN (272 g, 2.74 mol) is added drop-wise at −78°

C. After addition, the mixture is allowed to stir at room temperature for 2 h. The reaction mixture is quenched with chilled water and the organic layer is separated. The aqueous phase is extracted with DCM. The organic layer is washed with brine, dried over anhydrus Na₂SO₄ and concentrated. The residue is purified by chromatography on silica gel with petroleum ether/EtOAc (50:1) to give the title intermediate I-49 (160 g).

Method 34

Synthesis of 1-(4-bromophenyl)cyclobutanecarbonitrile (Intermediate 50)

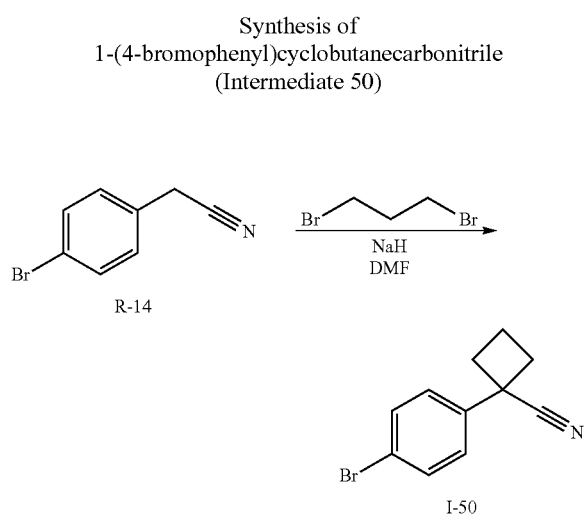

To a solution of R-14 (30.0 g, 0.153 mol) in DMF (400 mL) at 0° C. is added NaH (60% dispersion in mineral oil) (613.5 g, 0.337 mol) portionwise over 20 minutes. The mixture is then stirred for a further 20 minutes and 1,3-dibromopropane (15.8 mL, 0.156 mol) is added. The reaction mixture is stirred at 0° C. to room temperature for 1 hour and then quenched by the addition of water (100 mL). The mixture is concentrated in vacuo and partitioned between EtOAc and saturated NaHCO₃. The combined organics are dried over anhydrous Na₂SO₄ and concentrated in vacuo. The residue is purified by flash column chromatography (SiO₂, 20% to 60% EtOAc in heptane) to give I-50 (25.1 g).

The following intermediates are also prepared according to the method described in Method 34:

| Structure | Name | m/z [M + H] |
|---|---|---|
| 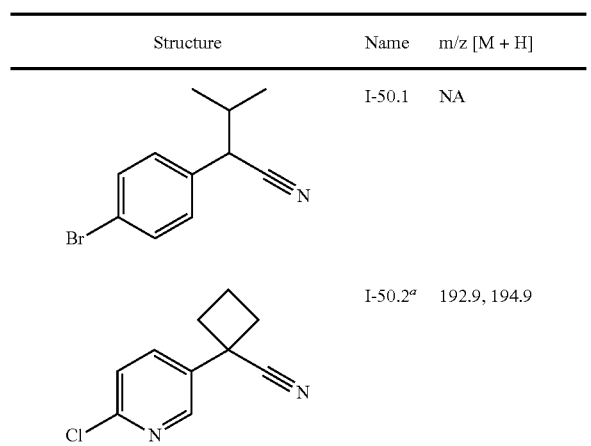 | I-50.1 | NA |
| | I-50.2$^a$ | 192.9, 194.9 |
| | I-50.3 | 195.2 |
| | I-50.4$^b$ | NA |
| | I-50.5$^b$ | 209.2 |
| | I-50.6$^a$ | 312.9, 314.9 [M, M + 2] |

$^a$= The reaction was run with 0.05 eq of 15-crown-5 ether
$^b$= IprBr was reacted first, followed by MeI Method 35

Synthesis of 1-(4-bromophenyl)cyclobutanecarboxylic acid (Intermediate 51)

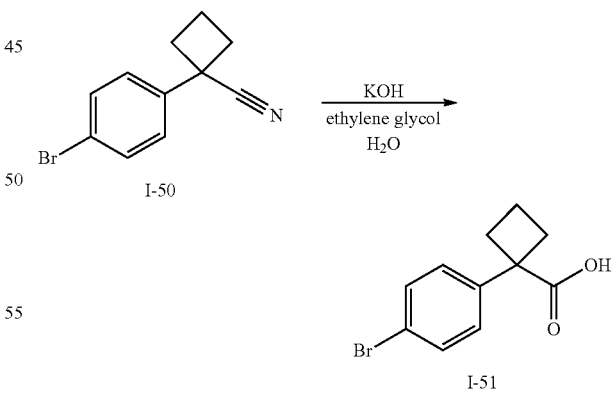

To a solution of I-50 (1.5 g, 6.25 mmol) in a mixture of ethylene glycol (7.5 mL) and water (4 mL) is added KOH (1.5 g, 26 mmol). The mixture is stirred at 120° C. for 18 h, before cooling to room temperature and pouring into 1M HCl (100 mL). The resultant precipitate is filtered and washed with water to give the title intermediate I-51 (1.3 g).

The following intermediates are also prepared according to the method described in Method 35:

| Structure | Name | m/z [M + H] |
|---|---|---|
| 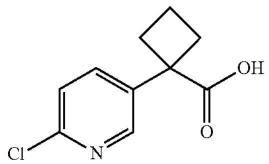 [SMILES: O=C(O)C1(c2ccc(Cl)nc2)CCC1] | I-51.1[a] | 211.9, 214.0 [M, M + 2] |
| 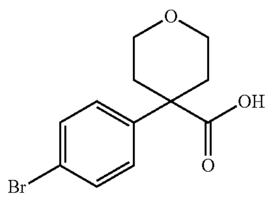 [SMILES: O=C(O)C1(c2ccc(Br)cc2)CCOCC1] | I-51.2[b] | 282.9, 284.9 [M, M + 2] |
| 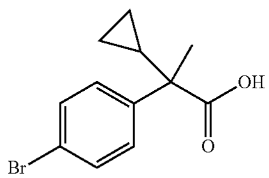 | I-51.3[c] | 325.7 |
| 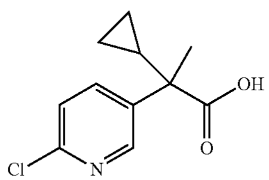 | I-51.4[c] | N/A |

[a] = No ethylene glycol was used
[b] = LiOH was used in place of KOH, with the addition of THF/MeOH as co-solvents, and the starting material was an ethyl ester instead of CN
[c] = The reaction was run in a pressure vessel at 100° C. for 60 hrs using EtOH as co-solvent Method 36

Synthesis of 2-(4-bromophenyl)-2,3-dimethyl-butanoic acid (Intermediate 52)

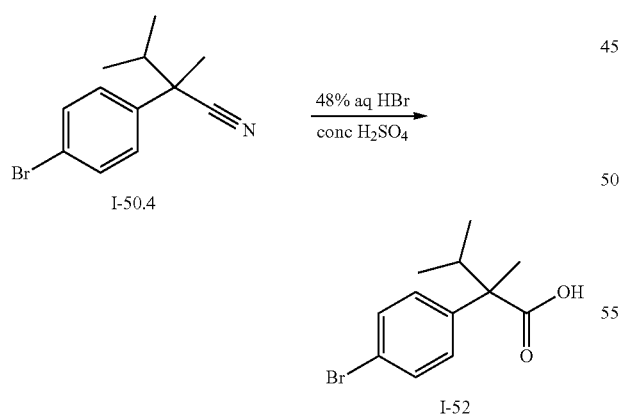

A mixture of I-50.4 (2.0 g, 7.93 mmol), concentrated $H_2SO_4$ (2.5 mL) and 48% aqueous HBr (5.0 mL) is heated at 110° C. for 18 h then at 145° C. for 24 h. The reaction is cooled to room temperature, partitioned between DCM and water, and the organics dried over $Na_2SO_4$. The solvent is removed in vacuo and the crude material triturated with heptane to give the title intermediate I-52 (1.3 g) m/z 268.9, 270.7 [M–H].

The following intermediates are also prepared according to the method described in Method 36:

| Structure | Name | m/z [M + H] |
|---|---|---|
| 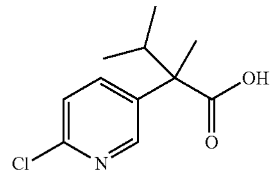 | I-52.1[a] | 228.1 |

[a] = Glacial acetic acid was used in place of 48% aq. HBr

Method 37

Synthesis of 5-[5-[1-(4-bromophenyl)cyclobutyl]-1H-pyrazol-3-yl]-2-methyl-pyridine (Intermediate 55)

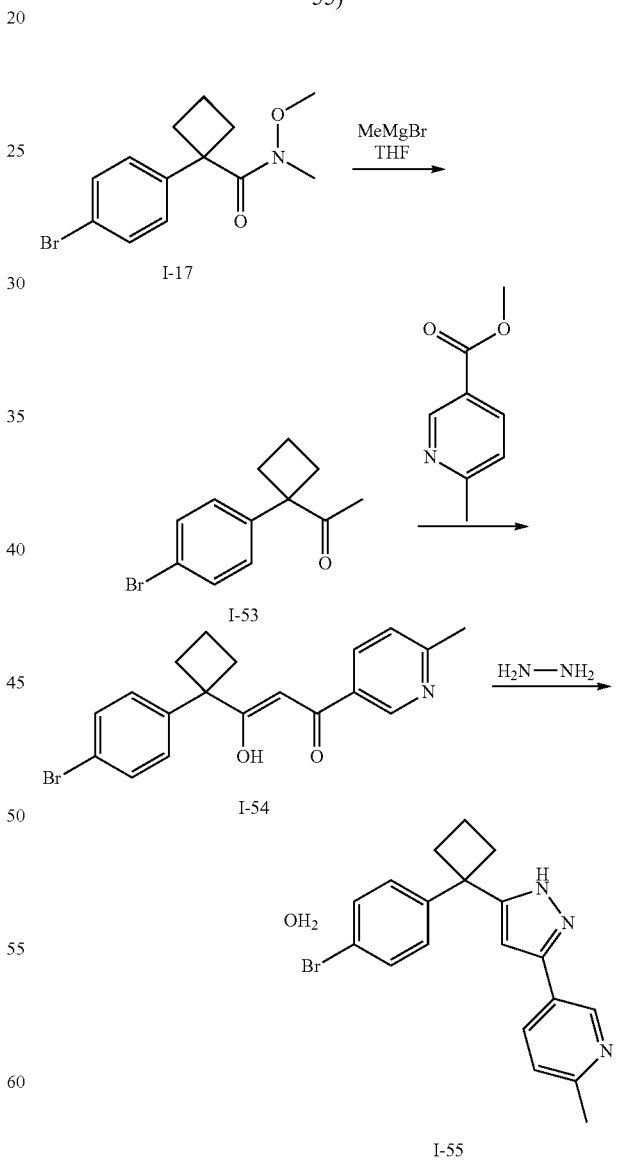

To a solution of I-17 (32 g, 107.3 mmol) in THF (1000 mL) at −20° C. is added methylmagnesium bromide (3.0 M in diethylether) (89.4 mL, 268.5 mmol) and is stirred at room temperature for 24 hours. To the reaction mixture is added saturated aqueous NH₄Cl and is extracted with EtOAc. The organic layer is separated, washed with brine, dried over anhydrous Na₂SO₄, filtered and concentrated to give the titile intermediate I-53 (22 g), m/z: 253, 255 [M, M+2].

To a solution of I-53 (22 g, 86.91 mmol) in THF (75 mL) at 0° C. is added potassium bis(trimethylsilyl)amide, 0.5M in toluene (208.7 mL, 104.34 mmol) and is stirred at 0° C. for 30 minutes, followed by the addition of methyl-6-methylnicotanate (14.5 g, 95.65 mmol). The reaction mixture is stirred at room temperature for 4 hours. To the reaction mixture is added water and extracted with EtOAc. The organic layer is separated, washed with brine, dried over anhydrous Na₂SO₄, filtered and concentrated in vacuo. The residue is purified by flash chromatography (SiO₂, 0-10% EtOAc/petether) to give the title intermediate I-54 (7.5 g), m/z: 372, 374 [M, M+2].

To a solution of I-54 (4 g, 10.7 mmol) in ethanol (50 mL) is added hydrazine hydrate (2.688 g, 53.8 mmol) and is heated at 75° C. for 4 hours. The reaction mixture is concentrated in vacuo. To the residue is added water, extracted with EtOAc. The organic layer is separated, washed with brine, dried over anhydrous Na₂SO₄, filtered and concentrated. The residue is purified by flash chromatography (SiO₂, 70% EtOAc/petether) to give the title intermediate I-55 (0.9 g), m/z: 368,370 [M, M+2].

The following intermediates are also prepared according to the method described in Method 37:

| Structure | Name | m/z [M + H] |
|---|---|---|
| 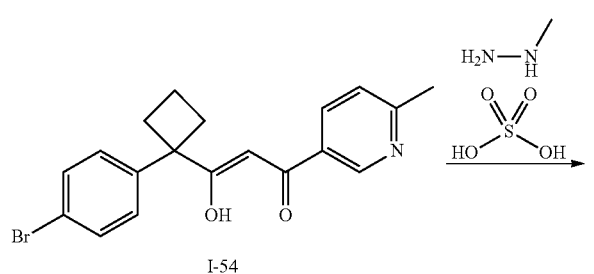 | I-55.1 | NA |

Method 38

Synthesis of 5-[5-[1-(4-bromophenyl)cyclobutyl]-1-methyl-pyrazol-3-yl]-2-methyl-pyridine (Intermediate 56) and 5-[5-[1-(4-bromophenyl)cyclobutyl]-2-methyl-pyrazol-3-yl]-2-methyl-pyridine (Intermediate 57)

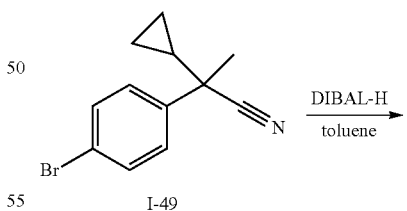

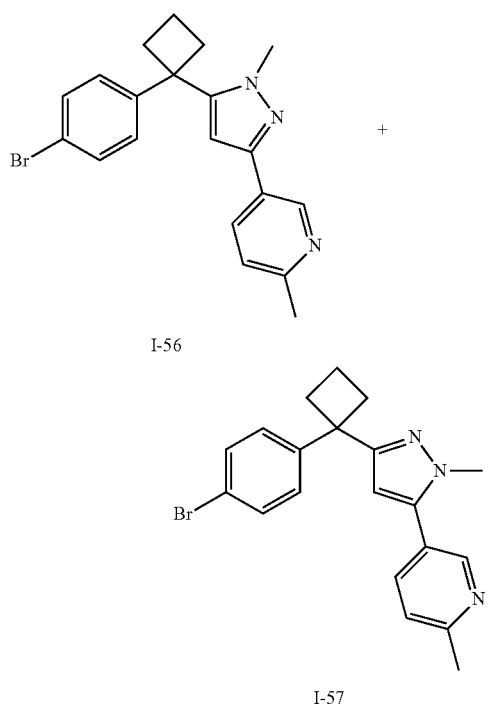

To a solution of I-54 (4 g, 10.7 mmol) in ethanol (40 mL) is added methyl hydrazinesulfate (7.75 g, 53.8 mmol) and heated at 75° C. for 4 hours. The reaction mixture is concentrated in vacuo and to the residue is added water, extracted with EtOAc. The organic layer is separated, washed with brine, dried over anhydrous Na₂SO₄, filtered and concentrated. The crude material is purified by a prep HPLC to give the title intermediate of I-56 (0.4 g), m/z: 382,384 [M, M+2], and I-57 (0.8 g), m/z: 382,384 [M, M+2].

Method 39

Synthesis of 5-[1-(4-bromophenyl)-1-cyclopropyl-ethyl]-2-phenyl-pyrazol-3-ol (Intermediate 61)

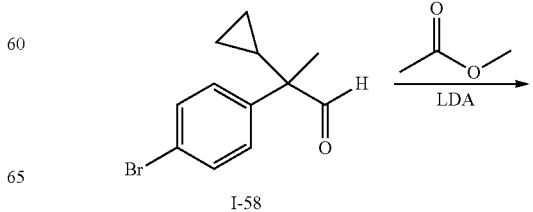

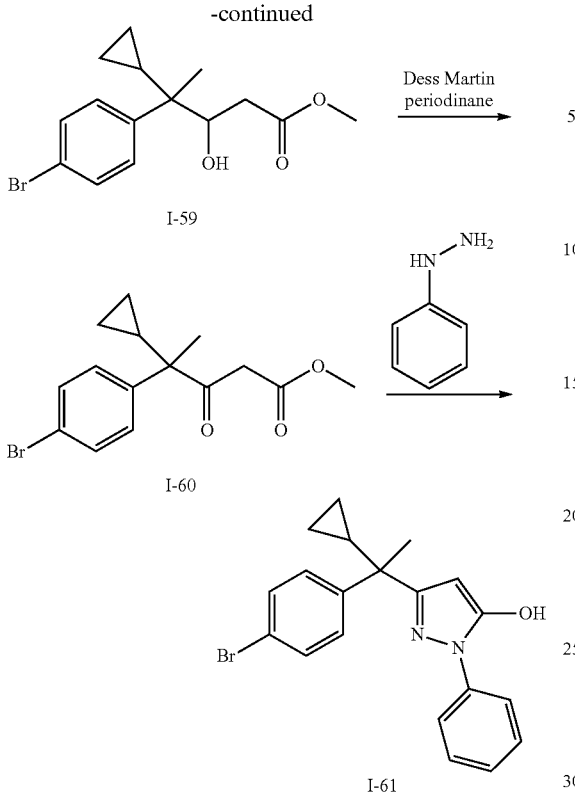

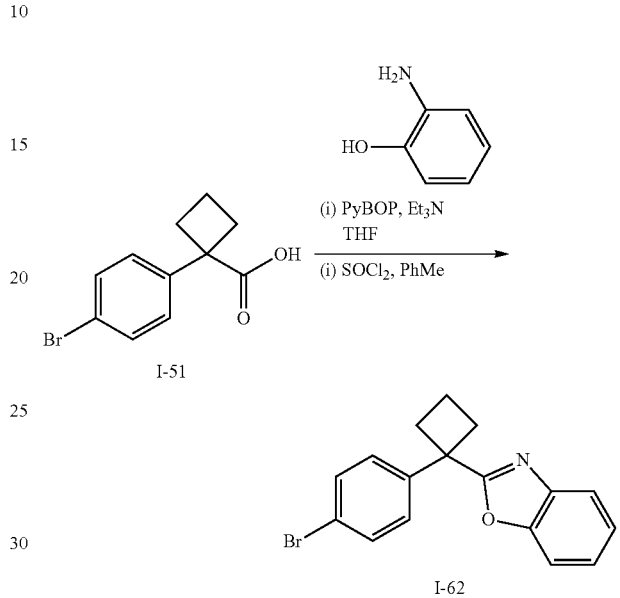

Method 40

Synthesis of 2-[1-(4-bromophenyl)cyclobutyl]-1,3-benzoxazole (Intermediate 62)

To a solution I-49 (16 g, 64 mmol) in dry toluene (400 mL) at −78° C. is added DIBAL-H (1.0 M in toluene) (128 mL, 128 mmol) and stirred at −78° C. for 1 hour. To the reaction mixture is added 1M $H_2SO_4$ (200 mL) and extracted with EtOAc. The combined organic layer is washed with brine, dried over anhydrous $Na_2SO_4$, filtered and concentrated. The residue is purified by flash chromatography ($SiO_2$, 5% EtOAc/petether) to give the title intermediate I-58 (14 g).

To a solution of acetic acid methyl ester (6.83 ml, 83 mmol) in THF (40 mL) at −78° C. is added freshly prepared LDA (THF 80 mL; diisopropylamine 11.6 ml, 83 mmol; n-butyl-lithium, 1.6M solution in hexane 52 mL, 83 mmol at −78° C. for 1 hour) slowly over 15 minutes. The reaction mixture is stirred at −78° C. for 30 minutes, followed by the addition of I-58 (14 g, 55.3 mmol) in THF (40 mL) at −78° C. for over 10 minutes and stirred at −78° C. for 1 hour. The reaction mixture is quenched with saturated aqueous $NH_4Cl$ and extracted with EtOAc. The organic layer is dried over anhydrous $Na_2SO_4$, filtered and concentrated. The residue is purified by flash chromatography ($SiO_2$, 25% EtOAc/petether) to give the title intermediate I-59 (14 g), m/z: 327, 329 [M, M+2].

To a solution of I-59 (14 g, 42.8 mmol) in toluene (200 mL) at 0° C. is added Dess Martin periodinane (27.2 g, 64.2 mmol) in one portion and stirred at room temperature for 2 hours. The reaction mixture is filtered through Celite and washed with EtOAc. The filtrate is washed with saturated aqueous $NaHCO_3$, dried over anhydrous $Na_2SO_4$, filtered and concentrated in vacuo. The residue is purified by flash chromatography ($SiO_2$, 10% EtOAc/petether) to give the title intermediate I-60 (11.2 g), m/z: 325, 327 [M, M+2].

To a solution of the I-60 (500 mg, 1.54 mmol) in ethanol (10 mL) is added phenyl hydrazine (0.15 mL, 1.54 mmol) and triethylamine (0.5 mL). The reaction mixture is heated in a sealed reactor at 85° C. for three days. The reaction mixture is concentrated in vacuo. The residue is purified by flash chromatography ($SiO_2$, 5-50% EtOAc/heptane) to give the title intermediate I-61 (200 mg), m/z: [M, M+2].

A suspension of I-51 (150 mg, 0.588 mmol), 2-aminophenol (76 mg, 0.706 mmol), triethylamine (123 μL, 0.882 mmol), and PyBOP (459 mg, 0.882 mmol) in THF (2 mL) is heated at 70° C. in a sealed vessel for 18 h. After cooling to room temperature the reaction is diluted with DCM and washed with saturated aqueous $NaHCO_3$. The organics are dried over anhydrous $Na_2SO_4$, concentrated in vacuo and the residue re-dissolved in toluene (10 mL). Thionyl chloride (47 μL, 647 mmol) is added and the reaction heated at 80° C. for 1 h. Further thionyl chloride (47 μL, 647 mmol) is added and the reaction heated at 100° C. for 1 h. After cooling to room temperature, the reaction is diluted with water and EtOAc and the organics dried over anhydrous $Na_2SO_4$. The solvent is removed in vacuo and the crude material purified by flash chromatography ($SiO_2$, DCM) to give the title intermediate I-62 (112 mg) m/z 343.9, 329.9 [M,M+2].

The following intermediates are also prepared according to the method described in Method 38:

| Structure | Name | m/z [M, M + 2] |
|---|---|---|
| 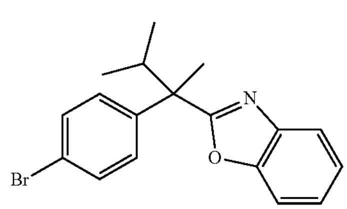 [SMILES: CC(C)C(C)(c1ccc(Br)cc1)c1nc2ccccc2o1] | I-62.1 | 343.9, 345.9 |

| Structure | Name | m/z [M, M + 2] |
|---|---|---|
| 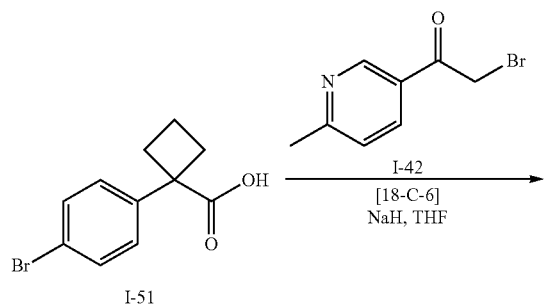 | I-62.2 | 285.0, 286.9 |

Method 41

Synthesis of 2-[1-(4-bromophenyl)cyclobutyl]-4-(6-methyl-3-pyridyl)oxazole (Intermediate 64)

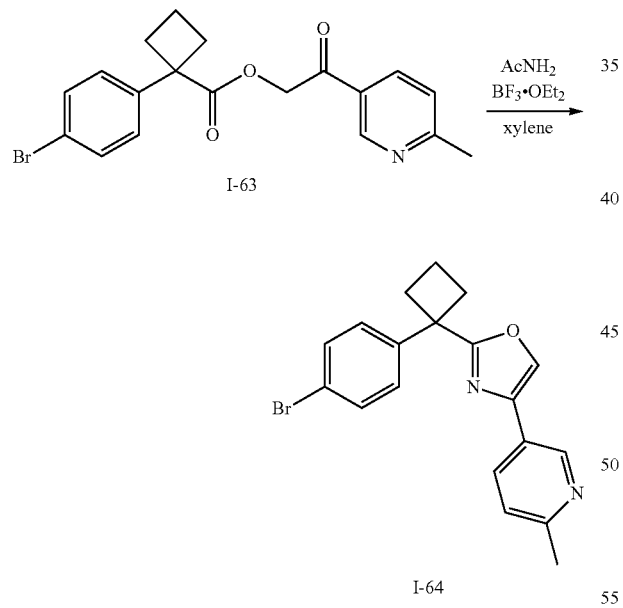

To a solution of I-51 (169 mg, 0.663 mmol) in anhydrous THF (8 mL) is added NaH (32 mg of a 60% dispersion in mineral oil, 0.795 mmol), 18-crown-6 (88 mg, 0.33 mmol) and I-42 (213 mg, 0.995 mmol). The mixture is heated at 80° C. under $N_2$ for 3 h then quenched with 0.1 M aqueous citric acid. The mixture is neutralised with saturated aqueous NaHCO₃, extracted with DCM, and the combined organics are dried over anhydrous Na₂SO₄. The solvent is removed in vacuo and the crude material purified by flash chromatography (SiO₂, 40% to 50% EtOAc in heptane) to give the I-63 (200 mg, 78%) m/z 388.0, 389.8 [M+H].

A mixture of I-63 (188 mg, 0.485 mmol), acetamide (146 mg, 2.42 mmol) and boron trifluoride diethyl etherate (0.030 mL, 0.243 mmol) in anhydrous xylene (5 mL) is stirred at 130° C. under $N_2$ for 6 h. Stirring is continued at 140° C. for another 18 h. Additional portions of acetamide and boron trifluoride diethyl etherate are added and stirring is continued at 160° C. for 18 h. The reaction is partitioned between EtOAc and 1 M aqueous NaHCO₃. The organics are washed with saturated brine, dried over anhydrous Na₂SO₄ and concentrated in vacuo. The residue is purified by flash chromatography (SiO₂, heptane to 50% EtOAc in heptane) to give the 1-64 (60 mg, 34%) m/z 369.0, 370.8 [M+H].

The following intermediates are also prepared according to the method described in Method 41:

| Structure | Name | m/z [M, M + 2] |
|---|---|---|
| 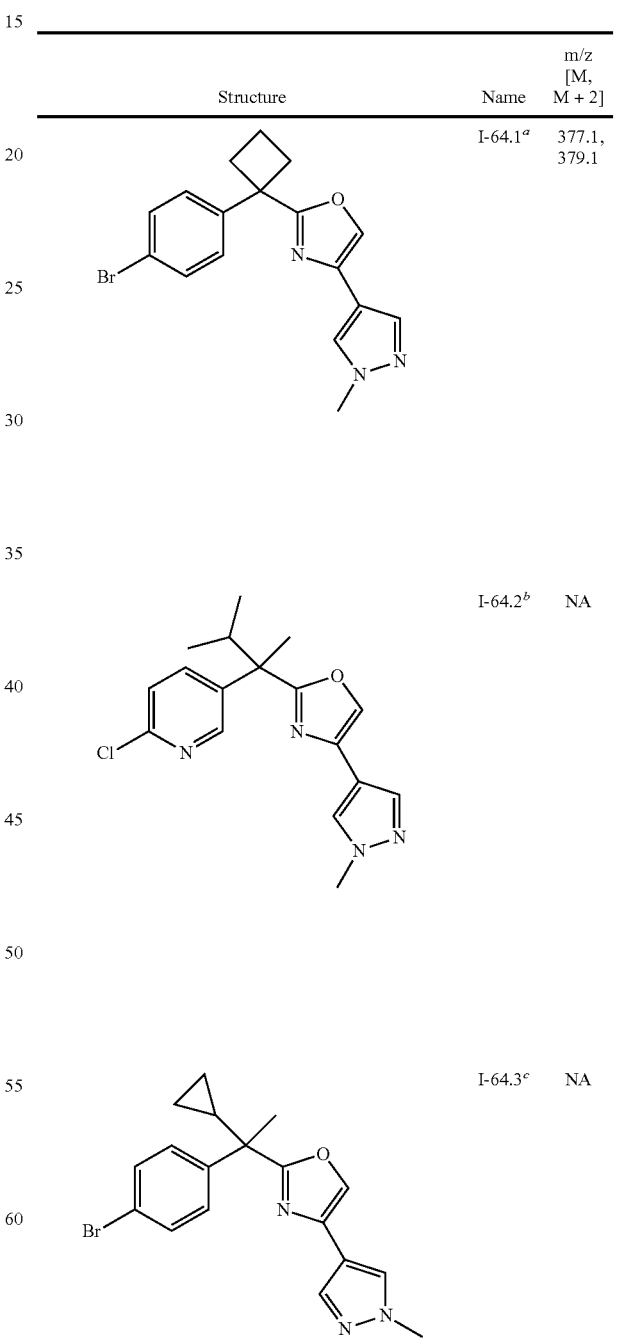 | I-64.1[a] | 377.1, 379.1 |
| 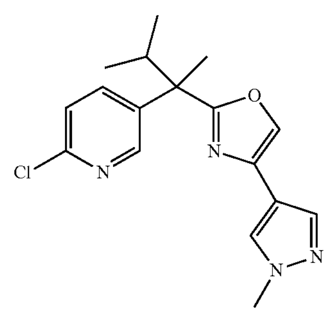 [SMILES: CC(C)C(C)(c1ccc(Cl)nc1)c1nc(-c2cnn(C)c2)co1] | I-64.2[b] | NA |
| 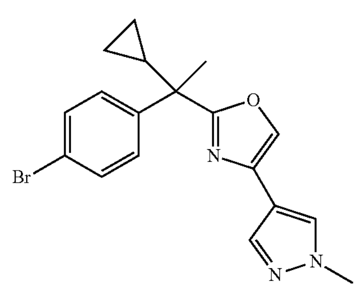 [SMILES: Cn1cc(-c2coc(C(C)(c3ccc(Br)cc3)C3CC3)n2)cn1] | I-64.3[c] | NA |

-continued

| Structure | Name | m/z [M, M + 2] |
|---|---|---|
| 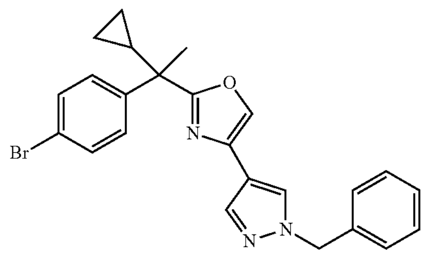 [SMILES: CC(c1ccc(Br)cc1)(c1nc(-c2cnn(Cc3ccccc3)c2)co1)C1CC1] | I-64.4[d] | NA |
| 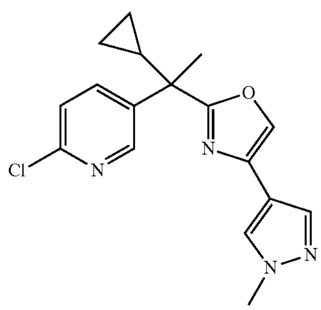 [SMILES: Cn1cc(-c2coc(C(C)(c3ccc(Cl)nc3)C3CC3)n2)cn1] | I-64.5[e] | NA |

[a] = Starting materials come from I-51 and I-45
[b] = Starting materials come from I-51.1 and I-45
[c] = Starting materials come from I-51.3 and I-45
[d] = Starting materials come from I-51.3 and I-42.1
[e] = Starting materials come from I-51.4 and I-45

Method 42

Synthesis of 1-(4-bromophenyl)-N-[2-(6-methyl-3-pyridyl)-2-oxo-ethyl]cyclobutanecarboxamide (Intermediate 65)

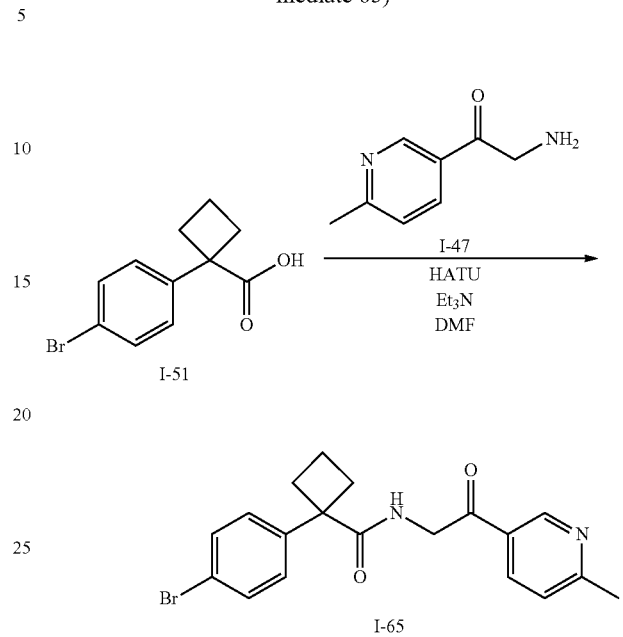

A mixture of I-51 (750 mg, 2.94 mmol) and HATU (1.34 g, 3.52 mmol) in anhydrous DMF (2 mL) is stirred at room temperature for 0.5 h. Triethylamine (2.1 mL, 15.4 mmol) and I-47 (852 mg, 3.82 mmol) are added and stifling is continued for another 2 h. The reaction is quenched with 0.5 M NaOH, and then extracted with EtOAc. The combined organics are washed with water, dried over $Na_2SO_4$, and concentrated in vacuo. The residue is purified by flash chromatography ($SiO_2$, 100% EtOAc) to give the title compound I-65 (854 mg). m/z 387.0, 388.8 [M+H].

Method 43

Synthesis of 5-[4-[1-[4-(1-benzylpyrazol-4-yl)oxazol-2-yl]-1-cyclopropyl-ethyl]phenyl]pyrimidin-2-amine (Intermediate 66)

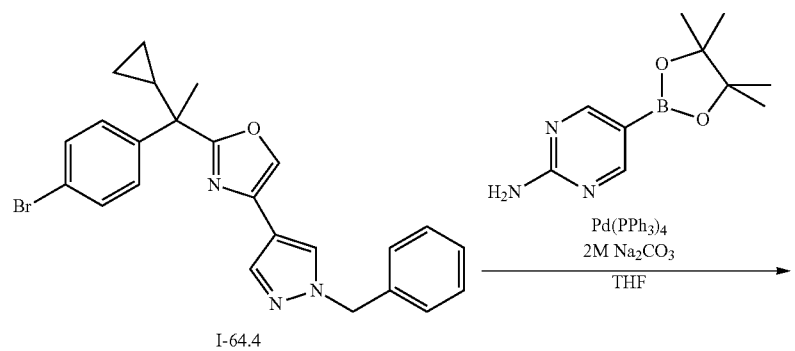

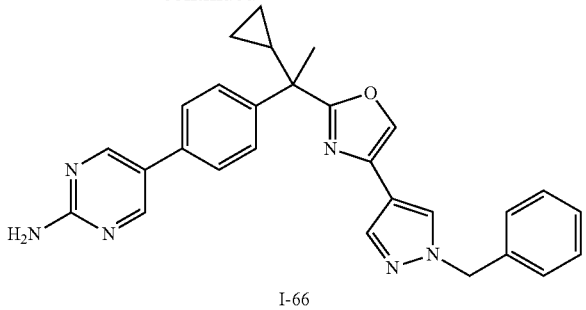

I-66

To a sealed vial is added I-64.4 (207 mg, 0.462 mmol) in THF (5 mL), followed by the addition of 2-aminopyrimidine-5-boronic acid pinacol ester (122 mg, 0.552 mmol), tetrakis(triphenylphosphine)palladium(0) (53 mg, 0.046 mmol) and 2M aq. $Na_2CO_3$ (0.9 mL, 1.8 mmol). The reaction mixture is heated under Ar at 75° C. for 18 hours. The reaction mixture is concentrated in vacuo, and dissolved in EtOAc, washed with water, brine, dried under anhydrous $Na_2SO_4$, filtered and concentrated. The residue is purified by flash chromatography ($SiO_2$, 0-4% MeOH/$CH_2Cl_2$) to give the title intermediate I-66 (209 mg), m/z: 463.3 [M+H].

The following intermediates are also prepared according to the method described in Method 43:

| Structure | Name | m/z [M + H] |
|---|---|---|
| 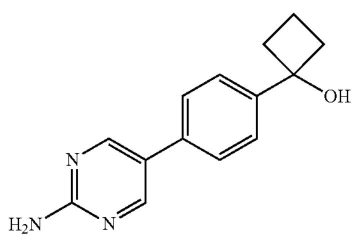 [SMILES: Nc1ncc(-c2ccc(C3(O)CCC3)cc2)cn1] | I-66.1[a] | NA |
| 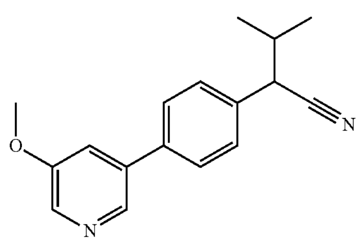 [SMILES: COc1cncc(-c2ccc(C(C#N)C(C)C)cc2)c1] | I-66.2 | 267.7 |
| 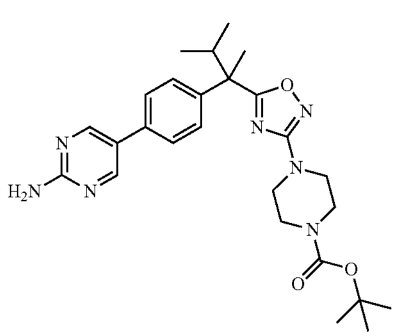 [SMILES: CC(C)C(C)(c1ccc(-c2cnc(N)nc2)cc1)c1nc(N2CCN(C(=O)OC(C)(C)C)CC2)no1] | I-66.3 | NA |

[a] = starting material comes from I-7.1, an iodo group instead of Br

Method 44

Synthesis of 5-[4-[1-cyclopropyl-1-[4-(1H-pyrazol-4-yl)oxazol-2-yl]ethyl]phenyl]pyrimidin-2-amine (Intermediate 67)

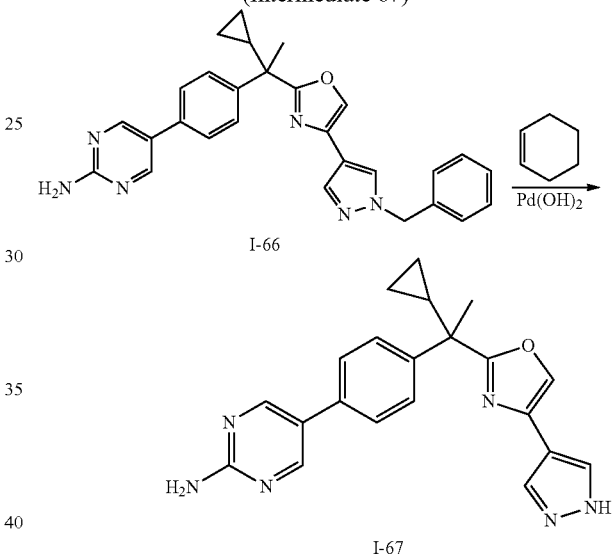

To a sealed vial is added I-66 (200 mg, 0.432 mmol) in EtOH (6 mL), followed by the addition of Pd(OH)$_2$ (20% Wt %) (320 mg) and cyclohexene (9 mL). The reaction mixture is stirred at 80° C. for 4 days. The reaction mixture is concentrated in vacuo and the residue is purified by flash chromatography ($SiO_2$, 0-5% MeOH/$CH_2Cl_2$) to give the title intermediate I-67 (25 mg), m/z: 373.2 [M+H].

Method 45

Synthesis of 2-[1-(4-bromophenyl)cyclobutyl]-1,3-benzothiazole (Intermediate 68)

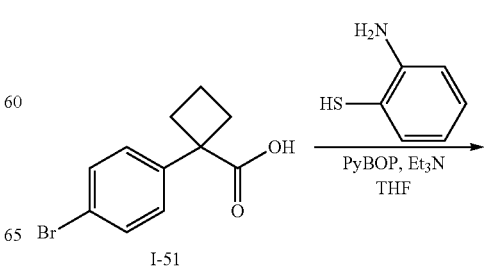

I-51

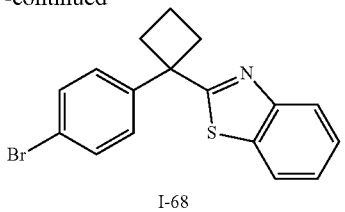

I-68

A suspension of I-51 (150 mg, 0.588 mmol), 2-aminothiophenol (76 μL, 0.706 mmol), triethylamine (123 μL, 0.882 mmol), and PyBOP (459 mg, 0.882 mmol) in THF (2 mL) is heated at 70° C. in a sealed vessel for 18 h. After cooling to room temperature the reaction is diluted with DCM and washed with saturated aqueous NaHCO₃. The organics are dried over Na₂SO₄ and concentrated in vacuo. Purification is by flash chromatography (SiO₂, DCM) to give the title intermediate I-68 (223 mg) m/z 343.9, 345 [M+H].

The following intermediates are also prepared according to the method described in Method 45:

| Structure | Name | m/z [M, M + 2] |
|---|---|---|
| 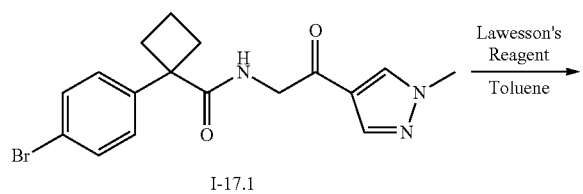 | I-68.1 | 300.9, 302.9 |

Method 46

Synthesis of 2-[1-(4-bromophenyl)cyclobutyl]-5-(1-methylpyrazol-4-yl)thiazole (Intermediate 69)

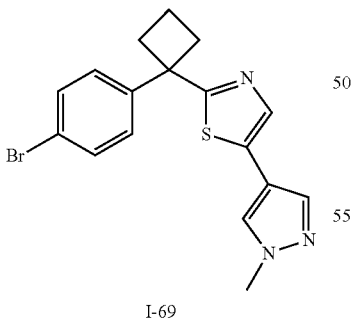

I-17.1

I-69

To the stirred solution of I-17.1 (500 mg, 2.67 mmol) in toluene (10 mL) at room temperature is added Lawesson's Reagent (1.08 g, 2.67 mmol) and stirred at reflux for 14 h. The reaction mixture is quenched with bicarbonate, and the organic layer is separated and washed with brine, dried with Na₂SO₄, filtered and concentrated in vacuo. The residue is purified by flash chromatography giving I-69 (400 mg).

Method 47

Synthesis of 5-bromo-2-[1-[4-(5-methoxy-3-pyridyl)phenyl]-2-methyl-propyl]thiazole (Intermediate 70)

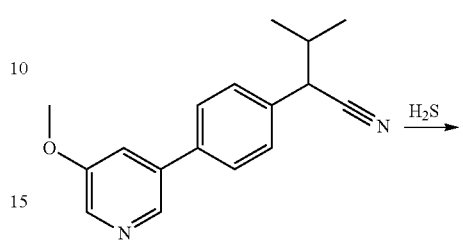

I-66.2

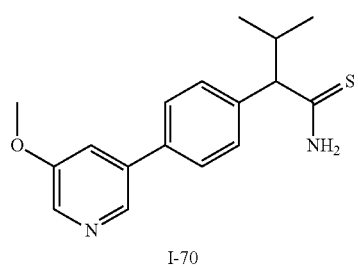

I-70

To a round bottom flask was added I-66.2 (1.22 g, 4.58 mmol) in Et₃N (7 mL) and pyridine (15 mL). The reaction mixture was stirred at room temperature for 60 minutes. The reaction mixture was cooled to −20° C., and H₂S gas was bubbled to the reaction mixture for 60 minutes. The reaction mixture was stirred at room temperature for 48 hours. The reaction solvent was blown out by nitrogen. The residue was diluted with EtOAc and sat. NaHCO₃. The organic layer was separated, washed with brine, dried under anhydrous Na₂SO₄, filtered and concentrated. The residue was purified by flash chromatography (SiO₂, 10-50% EtOAc/heptane) to give the title intermediate I-70 (991 mg), m/z: 301.7 [M+H].

Method 48

Synthesis of 5-[4-[1-cyclopropyl-1-[5-(1H-pyrazol-4-yl)thiazol-2-yl]ethyl]phenyl]pyrimidin-2-amine (Intermediate 72)

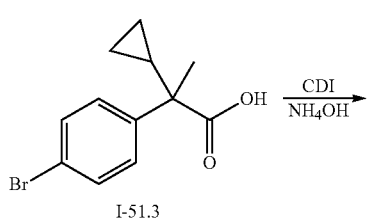

I-51.3

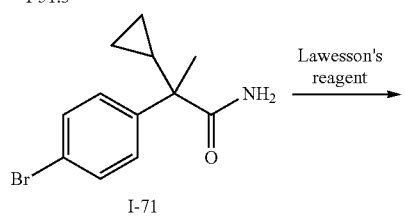

I-71

-continued

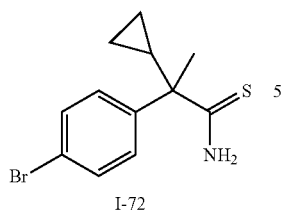
I-72

To a solution of I-51.3 (1775 mg, 6.60 mmol) in THF (20 mL) is added 1,1'-carbonyldiimidazole (1176 mg, 7.253 mmol) and stirred at 55° C. for 1 hour, followed by the addition of ammonium hydroxide (5 mL). The reaction mixture is stirred at 75° C. for 3 hours. The reaction mixture is concentrated in vacuo. The residue is diluted with EtOAc, washed with water, brine, dried under anhydrous $Na_2SO_4$, filtered and concentrated. The residue is purified by flash chromatography ($SiO_2$, 0-5% MeOH/$CH_2Cl_2$) to give the title intermediate I-71 (1363 mg), m/z: 268, 270 [M, M+2].

To a solution of I-71 (1363 mg, 5.083 mmol) in THF (15 mL), is added Lawesson's reagent (3084 mg, 7.625 mmol) and stirred at 50° C. for 3 hours. The reaction mixture is diluted with EtOAc, washed with water, brine, dried under anhydrous $Na_2SO_4$, filtered and concentrated. The residue is purified by flash chromatography ($SiO_2$, 0-35% EtOAc/heptane) to give the title intermediate I-72 (725 mg), m/z: 284, 286 [M, M+2].

The following intermediates are also prepared according to the method described in Method 48:

| Structure | Name | m/z [M, M + 2] |
|---|---|---|
| 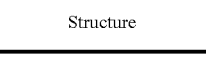 | I-72.1[a] | 270, 272 |

[a] = $P_2S_5$ was used in place of Lawesson's reagent

Method 49

Synthesis of 2-[1-(4-bromophenyl)cyclobutyl]-4-(6-methyl-3-pyridyl)thiazole (Intermediate 73)

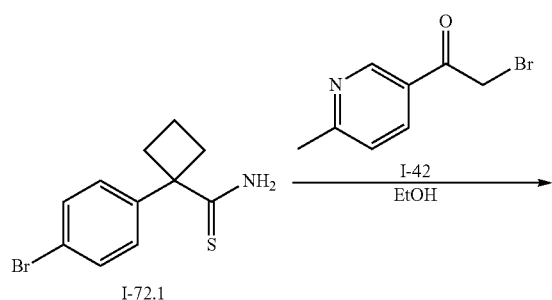

-continued

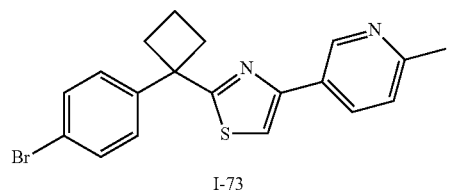
I-73

A solution of I-72.1 (122 mg, 0.45 mmol) and 1-42 (254 mg, 0.86 mmol) in ethanol (3 mL) is stirred at 90° C. for 3 h. The reaction mixture is then concentrated in vacuo and partitioned between DCM and saturated aqueous $NaHCO_3$. The organics are dried over $Na_2SO_4$ and concentrated in vacuo. The residue is purified by flash chromatography ($SiO_2$, 40% EtOAc in heptane) to give I-73 (116 mg).

Method 50

Synthesis of 5-[4-[1-cyclopropyl-1-[5-(1H-pyrazol-4-yl)thiazol-2-yl]ethyl]phenyl]pyrimidin-2-amine (Intermediate 77)

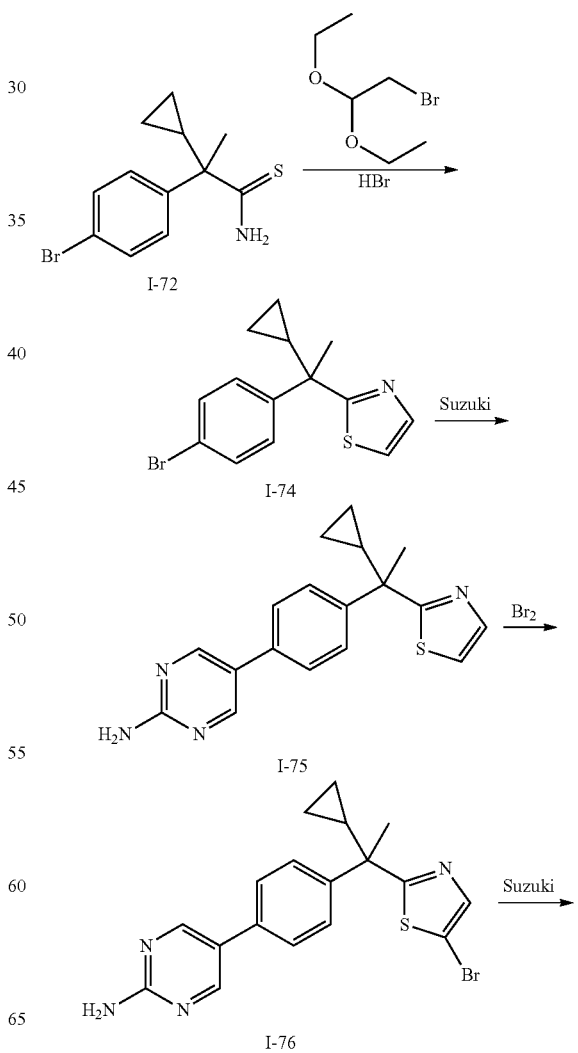

177

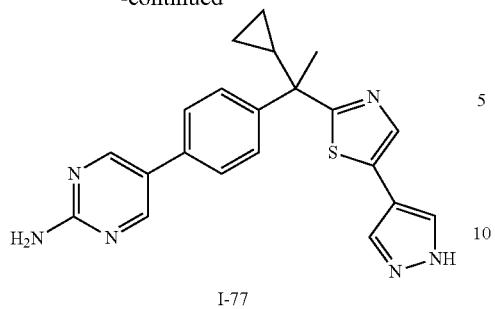

I-77

To a solution of I-72 (700 mg, 2.463 mmol) is added bromoacetaldehyde diethyl acetal (548 mg, 2.781 mmol) and hydrobromic acid (48%) (0.5 mL) in EtOH (10 mL) and stirred at 70° C. for 4 hours. The reaction mixture is concentrated in vacuo. The residue is diluted with EtOAc, washed with saturated aqueous NaHCO$_3$, brine, dried over anhydrous Na$_2$SO$_4$, filtered and concentrated. The residue is purified by flash chromatography (SiO$_2$, 0-20% EtOAc/heptane) to give the title intermediate I-74 (673 mg), m/z: 308, 310 [M, M+2].

I-74 (673 mg, 2.183 mmol) was used as starting material and under the same conditions described in Method 40 the reaction yielded the title intermediate I-75 (762 mg), m/z: 323.3 [M+H].

To a solution of I-75 (670 mg, 2.078 mmol) in CH$_2$Cl$_2$ (2 mL) is added acetic acid glacial (10 mL) and then bromine (664 mg, 4.155 mmol) in CH$_2$Cl$_2$ (1 mL) dropwise. The reaction mixture is stirred at room temperature for 18 hours. The reaction mixture is concentrated to remove HOAc. The residue is diluted with EtOAc, washed with sat. NaHCO$_3$, brine, dried under anhydrous Na$_2$SO$_4$, filtered and concentrated. The residue is purified by flash chromatography (SiO$_2$, 0-5% MeOH/CH$_2$Cl$_2$) to give the title intermediate I-76 (146 mg), m/z: 401, 403 [M, M+2].

To a microwave vial is added I-76 (179 mg, 0.446 mmol), 4-(4,4,5,5-tetramethyl-1,3,2-dioxaborolan-2-yl)-pyrazole-1-carboxylic acid tert-butyl ester (144 mg, 0.49 mmol), tetrakis(triphenylphosphine)palladium(0) (52 mg, 0.045 mmol) and 2M aq. Na$_2$CO$_3$ (0.9 mL, 1.8 mmol) in DMF (3.5 mL). The vial is capped under Ar gas and stirred in a microwave reactor at 120° C. for 1.5 hours. The reaction mixture is concentrated in vacuo, diluted with EtOAc, washed with water, brine, dried under anhydrous Na$_2$SO$_4$, filtered and concentrated. The residue is purified by flash chromatography (SiO$_2$, 0-5% MeOH/CH$_2$Cl$_2$) to give the title intermediate I-77 (100 mg), m/z: 389.2 [M+H].

The following intermediate is also prepared according to Method 50

| Structure | Name | m/z [M, M + 2] |
|---|---|---|
| 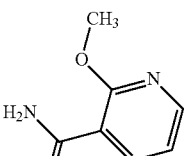 | I-77.1 | N/A |

178

Method 51

Synthesis of 6-methylpyridine-3-carboxamidine (Intermediate 78)

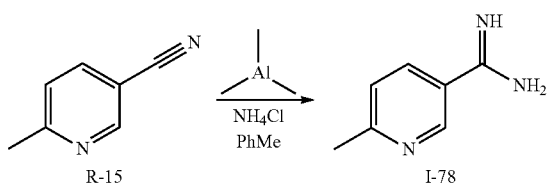

To a solution of ammonium chloride (1.52 g, 28.36 mmol) in anhydrous toluene (5 mL) at 0° C. is added trimethylaluminium (14.2 mL of a 2 M solution in heptane, 28.36 mmol) dropwise. The solution is warmed to room temperature and stirred at that temperature for 1 h and then a solution of R-15 (500 mg, 4.23 mmol) in anhydrous toluene (5 mL) is added. The reaction mixture is stirred at 80° C. for 18 h and cooled to room temperature before pouring onto a stirred suspension of silica (15 g) in DCM. The resulting mixture is stirred at room temperature for 5 minutes and then filtered and rinsed with methanol. The filtrate is concentrated in vacuo to give the title intermediate I-78 (1.20 g) m/z 136.0 [M+H].

The following intermediates are also prepared according to the methods described in Method 51:

| Structure | Name | m/z [M + H] |
|---|---|---|
| 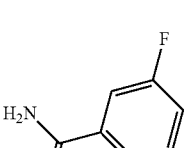 | I-78.1 | 151.9 |
| 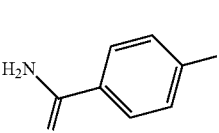 | I-78.2 | 139.0 |
| 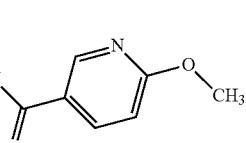 | I-78.3 | 138.9 |
| 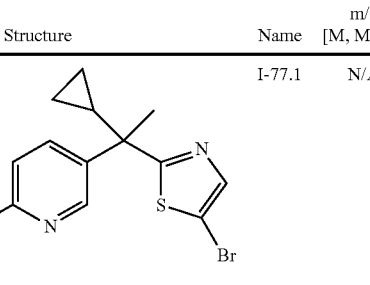 | I-78.4 | 152.0 |

Method 52

Synthesis of 2-[4-(4-bromophenyl)tetrahydropyran-4-yl]-1H-benzimidazole (Intermediate 77)

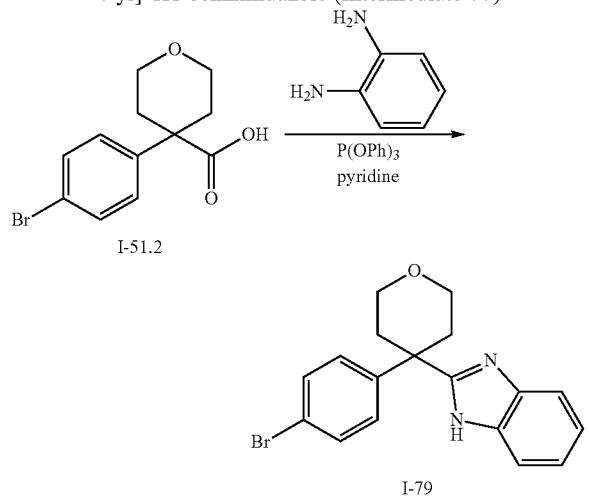

A mixture of I-51.2 (50 mg, 0.175 mmol), phenylenediamine (23 mg, 0.210 mmol), and triphenylphosphite (60 μL, 0.228 mmol) in pyridine (1 mL) is sealed in a vessel and heated at 150° C. for 18 h. After cooling to room temperature the reaction is diluted with DCM and washed with saturated aqueous NaHCO₃. The organics are dried over anhydrous Na₂SO₄ and concentrated in vacuo. Purification is by flash chromatography (SiO₂, DCM to 3% MeOH in DCM) to give the title intermediate I-79 (46 mg) m/z 357.0, 358.8 [M+H].

The following intermediate is also prepared according to the methods described in Method 49:

| Structure | Name | m/z [M + H] |
|---|---|---|
| 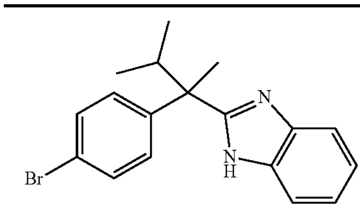 | I-79.1 | 343.0, 345.0 |

Method 53

Synthesis of 2-[1-(4-bromophenyl)cyclobutyl]-1H-imidazo[4,5-b]pyridine (Intermediate 78)

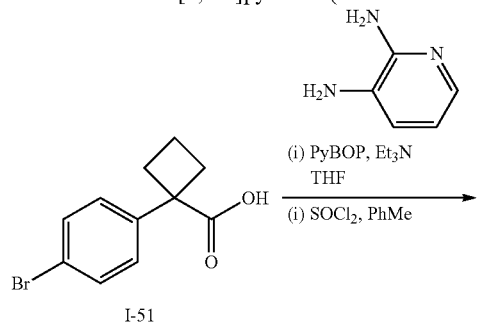

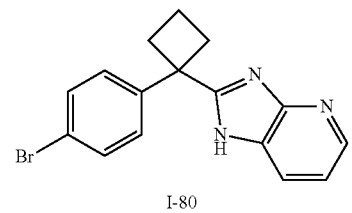

A suspension of I-51 (150 mg, 0.588 mmol), 2,3-diaminopyridine (77 mg, 0.706 mmol), triethylamine (123 μL, 0.882 mmol), and PyBOP (459 mg, 0.882 mmol) in THF (2 mL) is heated at 70° C. in a sealed vessel for 18 h. After cooling to room temperature the reaction is diluted with DCM and washed with saturated aqueous NaHCO₃. The organics are dried over Na₂SO₄, concentrated in vacuo and then re-dissolved in toluene (10 mL). Thionyl chloride (47 μL, 647 mmol) is added, and the reaction heated at 80° C. for 1 h. Further thionyl chloride (47 μL, 647 mmol) is added and the reaction heated at 100° C. for 1 h. After cooling to room temperature, the reaction is diluted with water and EtOAc and the organics dried over Na₂SO₄. The solvent is removed in vacuo and the crude material purified by flash chromatography (SiO₂, DCM to 4% MeOH in DCM) to give the title intermediate I-80 (112 mg) m/z 327.9, 329.9 [M+H].

The following intermediate is also prepared according to the method described in Method 53:

| Structure | Name | m/z [M, M + 2] |
|---|---|---|
| 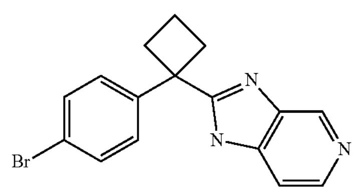 [SMILES: Brc1ccc(C2(c3nc4cnccc4[nH]3)CCC2)cc1] | I-80.1 | 327.9, 329.9 |
| 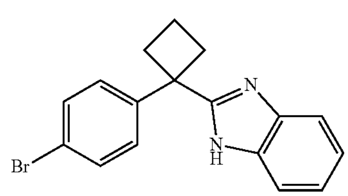 [SMILES: Brc1ccc(C2(c3nc4ccccc4[nH]3)CCC2)cc1] | I-80.2[a] | 326.9, 329.9 |
| 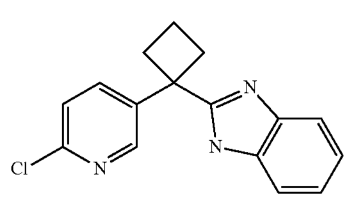 [SMILES: Clc1ccc(C2(c3nc4ccccc4[nH]3)CCC2)cn1] | I-80.3[a] | 284.1, 285.9 |

[a] = 6M HCl takes the place of thionyl chloride, toluene is replaced with a 1:1 mixture of MeOH and dioxane Method 54

Synthesis of 2-[1-(4-bromophenyl)cyclobutyl]-1-methyl-benzimidazole (Intermediate 79)

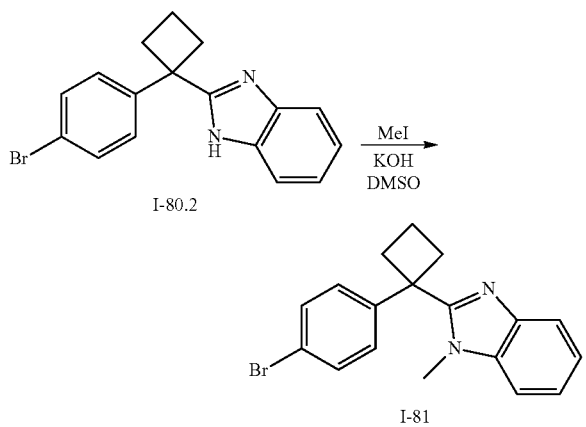

To a solution of I-80.2 (75 mg, 0.229 mmol) in DMSO (1 mL) is added KOH (96 mg, 0.573 mmol) and iodomethane (21 μL, 0.344 mmol). The reaction is stirred at room temperature for 1.5 h and is then partitioned between DCM and saturated aqueous NaHCO₃. The organics are dried over anhydrous Na₂SO₄, and concentrated in vacuo to give the title intermediate I-81 (103 mg) m/z 341.0, 343.0 [M+H].

Method 55

Synthesis of 2-(4-bromophenyl)-2,3-dimethyl-butanehydrazide (Intermediate 83)

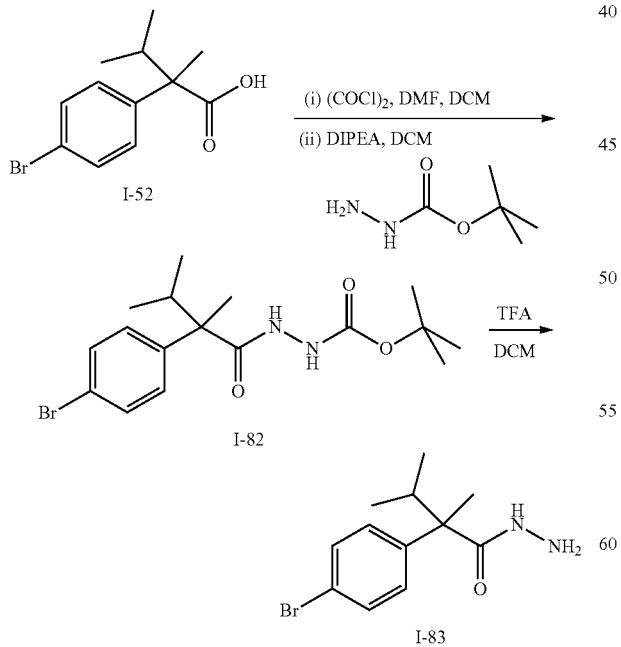

To a solution of I-52 (500 mg, 1.84 mmol) in DCM (18 mL) is added oxalyl chloride (0.47 mL, 5.53 mmol) followed by DMF (2 drops). The mixture is stirred at 45° C. for 2 h then concentrated in vacuo and the residue is dissolved in DCM (18 mL). DIPEA (0.64 mL, 3.68 mmol) is added dropwise, followed by tert-butyl carbazate (267 mg, 2.02 mmol). The reaction is stirred for 1 h at room temperature then saturated aqueous NH₄Cl is added. The organic phase is washed with brine, dried over anhydrous MgSO₄, and concentrated in vacuo. The residue is purified by flash chromatography (SiO₂, 20% EtOAc in cyclohexane) to give the I-82 (0.519 g) m/z 285.0, 286.9 [M+H-boc group].

To a solution of the I-82 (515 mg, 1.34 mmol) in DCM (6.7 mL) is added TFA (6.7 mL). The mixture is stirred at room temperature for 2 h then quenched with saturated aqueous NaHCO₃. The organic layer is dried over anhydrous MgSO₄ and concentrated in vacuo to give the title intermediate I-83 (384 mg) m/z 284.9, 286.9 [M+H].

The following intermediate is also prepared according to the methods described in Method 55:

| Structure | Name | m/z [M, M + 2] |
|---|---|---|
| 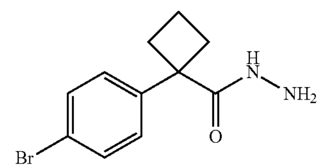 | I-83.1 | 269.0, 271.0 |
| 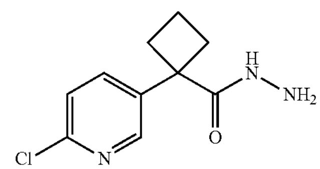 [SMILES: NNC(=O)C1(c2ccc(Cl)nc2)CCC1] | I-83.2 | 226.0, 228.0 |

Method 56

Synthesis of 4-(4-bromophenyl)tetrahydropyran-4-carbohydrazide (Intermediate 84)

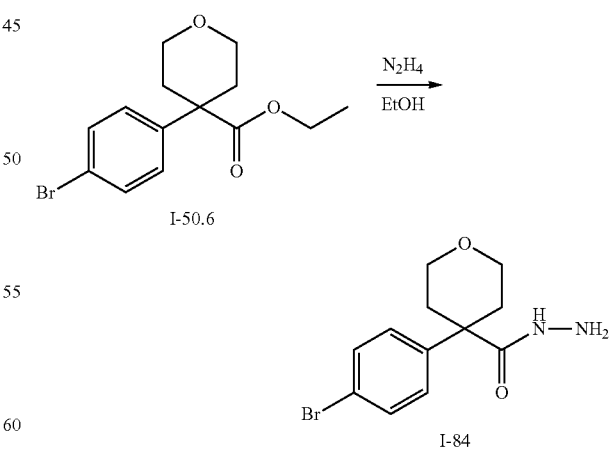

To a solution of I-50.6 (410 mg, 1.31 mmol) in ethanol (13 mL) is added hydrazine hydrate (hydrazine 64%, 0.64 mL, 13.1 mmol) and the solution stirred at room temperature for 4 days then at 100° C. for a further 2 days with the addition of more hydrazine hydrate (hydrazine 64%, 0.64 mL, 13.1 mmol). The reaction mixture is then stirred in a pressure vessel at 100° C. with the addition of more hydrazine hydrate (hydrazine 64%, 0.64 mL, 13.1 mmol) for 10 days. The mixture is concentrated in vacuo and partitioned between DCM and brine and filtered through a hydrophobic frit. The combined organics are concentrated in vacuo and purified by flash chromatography (SiO₂, 20% EtOAc in cyclohexane to 10% MeOH in EtOAc) to give I-84 (94 mg).

Method 57

Synthesis of 3-[5-[1-(4-bromophenyl)cyclobutyl]-4H-1,2,4-triazol-3-yl]pyridine (Intermediate 85)

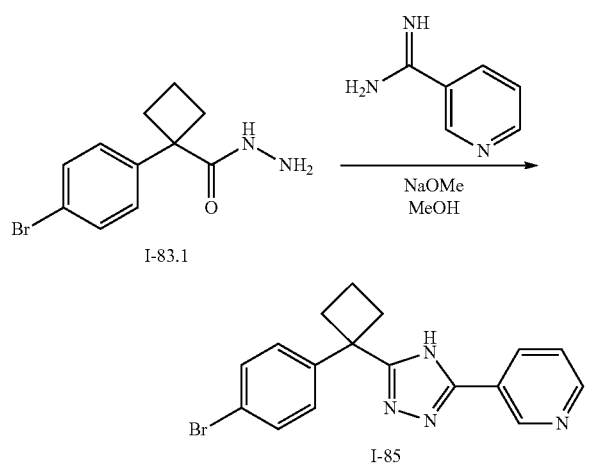

A solution of I-83.1 (250 mg, 0.93 mmol), pyridine-3-carboximidamide (843 mg, 5.34 mmol) and sodium methoxide (375 mg, 6.94 mmol) in methanol (10 mL) is stirred at 70° C. in a pressure vessel for 18 h. An additional amount of the pyridine-3-carboximidamide (422 mg, 2.67 mmol) and sodium methoxide (188 mg, 3.47 mmol) is added and the reaction stirred at 70° C. for a further 24 h. The reaction mixture is cooled and concentrated in vacuo and partitioned between EtOAc and water. The organics are dried with anhydrous Na₂SO₄, concentrated in vacuo, and the crude material purified by flash chromatography (SiO₂, 2% MeOH in DCM) to give I-85 (130 mg).

The following intermediate is also prepared according to the methods described in Method 57:

| Structure | Name | m/z [M + H] |
|---|---|---|
| 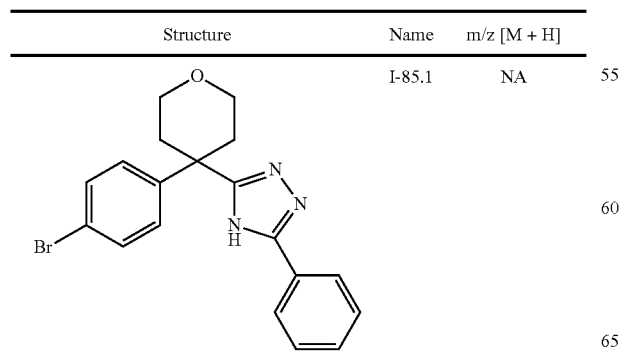 | I-85.1 | NA |
| 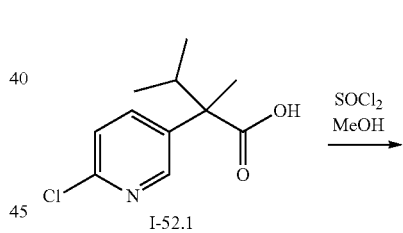 | I-85.2 | NA |
| 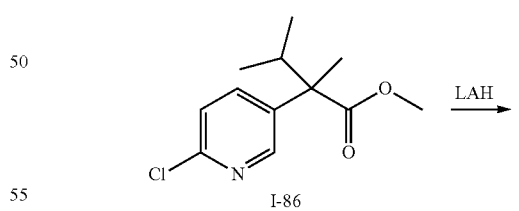 | I-85.3 | NA |

Method 58

Synthesis of (1Z)-2-(6-chloro-3-pyridyl)-N-hydroxy-2,3-dimethyl-butanimidoyl chloride (Intermediate 90)

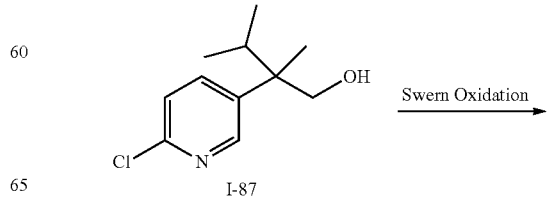

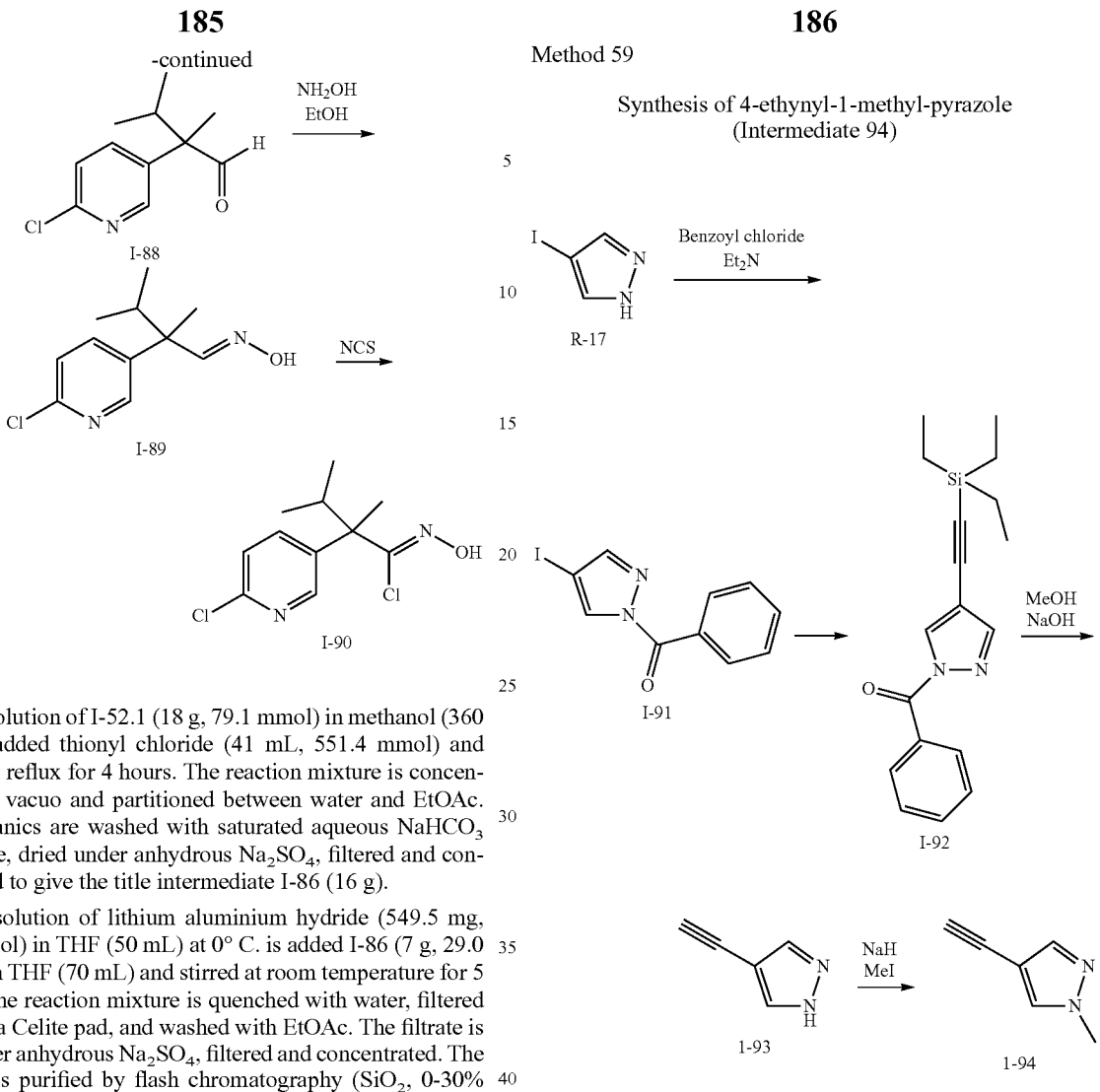

Method 59

Synthesis of 4-ethynyl-1-methyl-pyrazole (Intermediate 94)

To a solution of I-52.1 (18 g, 79.1 mmol) in methanol (360 mL) is added thionyl chloride (41 mL, 551.4 mmol) and stirred at reflux for 4 hours. The reaction mixture is concentrated in vacuo and partitioned between water and EtOAc. The organics are washed with saturated aqueous $NaHCO_3$ and brine, dried under anhydrous $Na_2SO_4$, filtered and concentrated to give the title intermediate I-86 (16 g).

To a solution of lithium aluminium hydride (549.5 mg, 14.5 mmol) in THF (50 mL) at 0° C. is added I-86 (7 g, 29.0 mmol) in THF (70 mL) and stirred at room temperature for 5 hours. The reaction mixture is quenched with water, filtered through a Celite pad, and washed with EtOAc. The filtrate is dried over anhydrous $Na_2SO_4$, filtered and concentrated. The residue is purified by flash chromatography ($SiO_2$, 0-30% EtOAc/petether) to give the title intermediate I-87 (4 g).

To a solution of I-87 (25 g, 117.0 mmol) in $CH_2Cl_2$ (550 mL) is added triethylamine (84.5 mL, 584.9 mmol), DMSO (91.4 mL, 1169.8 mmol), and sulfurtrioxide pyridene complex (74.48 g, 467.9 mmol) and stirred at room temperature for 4 hours. The reaction mixture is quenched with water and extracted with heptane. The organic layer is separated, washed with brine, dried under anhydrous $Na_2SO_4$, filtered and concentrated. The residue is purified by flash chromatography ($SiO_2$, 0-30% EtOAc/petether) to give the title intermediate I-88 (19 g).

To a solution of I-88 (5 g, 23.6 mmol) in ethanol (50 mL) is added hydroxylamine (50% wt in water) (1.56 mL, 23.6 mmol) and stirred at room temperature for 30 minutes. The reaction mixture is concentrated in vacuo. The residue is purified by flash chromatography ($SiO_2$, 0-20% EtOAc/petether) to give the title intermediate I-89 (4 g), m/z: 227.1 [M+H].

To a solution of I-89 (500 mg, 2.2 mmol) in $CH_2Cl_2$ (10 mL) at 0° C. is added N-chlorosuccinimide (294.5 mg, 2.2 mmol) and stirred at 0° C. for 3 hours. The reaction mixture is concentrated in vacuo, and the residue is diluted with EtOAc, washed with brine, dried under anhydrous $Na_2SO_4$, filtered and concentrated. The residue is purified by flash chromatography ($SiO_2$, 0-20% EtOAc/petether) to give the title intermediate I-90 (300 mg), m/z: 261.1 [M+H].

To a solution of R-17 (5 g, 25.8 mmol) in toluene (25 mL) is added triethylamine (3.73 mL, 25.8 mmol) and benzoyl chloride (3.0 mL, 25.8 mmol) and stirred at 100° C. for 4 hours. The reaction mixture is filtered, and partitioned between water and EtOAc. The filtrate was washed with water, brine, dried under anhydrous $Na_2SO_4$, filtered and concentrated. The crude product is crystallized from hexane to give the title intermediate 1-91 (5 g).

To a solution of I-91 (1 g, 3.4 mmol) in diisopropylamine (30 mL) is added triethylsillylacetylene (939.4 mg, 6.7 mmol). The reaction mixture is de-gassed with argon for 30 minutes, then added Copper (I) iodide (63.88 mg, 0.3 mmol) and bis(triphenylphosphine)palladium(II)chloride (117.74 mg, 0.2 mmol). The reaction mixture is de-gassed with argon for 30 minutes and then stirred at room temperature for 16 hours. The reaction mixture is concentrated in vacuo, diluted with EtOAc, washed with water, brine, dried under anhydrous $Na_2SO_4$, filtered and concentrated. The residue is purified by flash chromatography ($SiO_2$, 0-20% EtOAc/petether) to give the title intermediate I-92 (300 mg).

To a solution of I-92 (800 mg, 2.6 mmol) in methanol (10 mL) is added aqueous sodium hydroxide solution (2N) (6 mL) and stirred at room temperature for 16 hours. The reaction mixture is acidified to pH=5 by conc. HCl and concentrated in vacuo. The residue is diluted with EtOAc, washed with water, brine, dried under anhydrous $Na_2SO_4$, filtered and concentrated. The residue is purified by flash chromatography (SiO$_2$, 0-20% EtOAc/petether) to give the title intermediate I-93 (150 mg), m/z: 92.9 [M+H].

To a solution of I-93 (150 mg, 1.63 mmol) in DMF (2 mL) at 0° C. is added sodium hydride (60%) (72 mg, 1.96 mmol) and stirred at 0° C. for 1 hour, followed by the addition of methyl iodide (0.11 mL, 1.63 mmol). The reaction mixture is stirred at 0° C. for 30 minutes. The reaction mixture is quenched with ice water, extracted with EtOAc. The organic layer is separated, washed with water, brine, dried under anhydrous Na$_2$SO$_4$, filtered and concentrated to give the title intermediate I-94 (150 mg), m/z: 107 [M+H].

The following intermediate was synthesized in a similar fashion from the appropriate reagents:

| Structure | Name | m/z [M + H] |
|---|---|---|
| 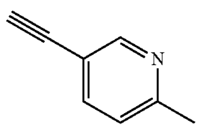 | I-94.1 | NA |

Method 60

Synthesis of 3-[1-(6-chloro-3-pyridyl)-1,2-dimethyl-propyl]-5-(1-methylpyrazol-4-yl)isoxazole (Intermediate 95)

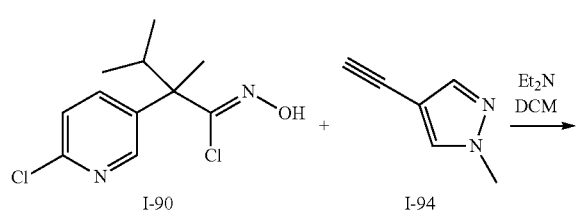

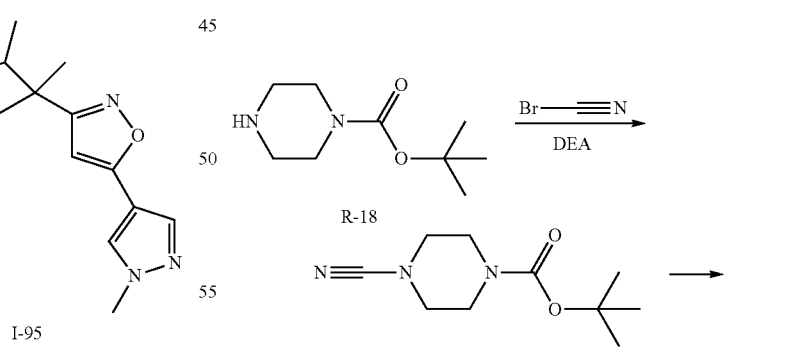

To a solution of I-90 (369 mg, 1.4 mmol) and I-94 (150 mg, 1.4 mmol) in CH$_2$Cl$_2$ (2 mL) is added triethylamine (0.22 mL, 1.6 mmol)) and stirred at room temperature for 14 hours. The reaction mixture is concentrated in vacuo and purified by flash chromatography (SiO$_2$, 0-30% EtOAc/petether) to give the title intermediate I-95 (100 mg), m/z: 331.3 [M+H].

The following intermediates were synthesized in a similar fashion from the appropriate reagents:

| Structure | Name | m/z [M + H] |
|---|---|---|
| 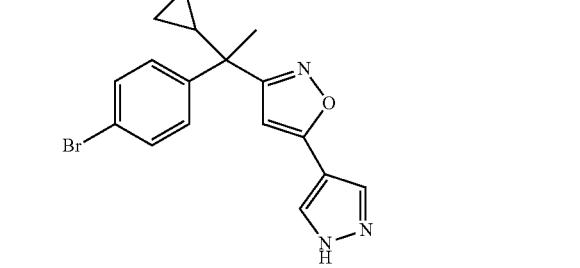 | I-95.1 | 360.2 |
| 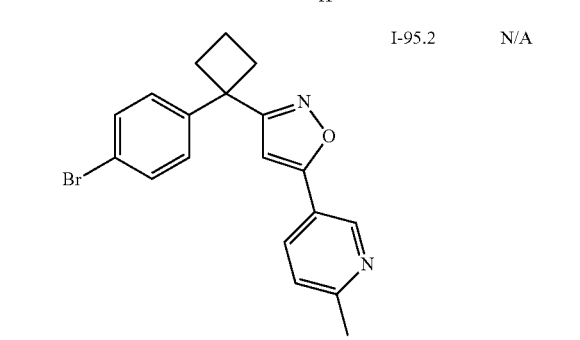 | I-95.2 | N/A |
| 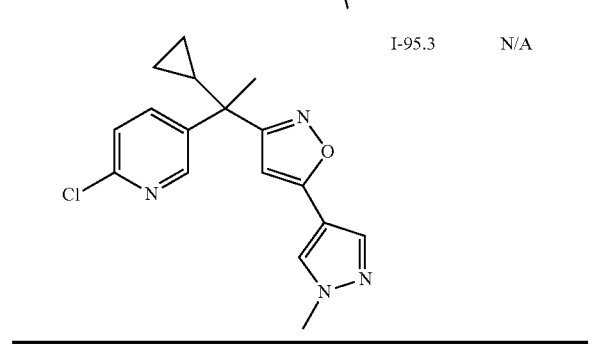 | I-95.3 | N/A |

Method 61

Synthesis of tert-butyl 4-[(E)-N'-hydroxycarbamim-idoyl]piperazine-1-carboxylate (Intermediate 97)

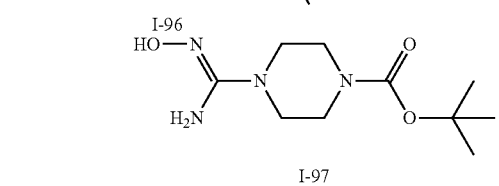

To a solution of R-18 (3.0 g, 16.1 mmol) in CH$_2$Cl$_2$ (5 mL) is added DEA (3.3 mL, 18.5 mmol) and 3.0M cyanogenbromide (5.9 mL, 17.7 mmol) and stirred at 0° C. for 30 min. The reaction mixture is poured into H2O and extracted with EtOAc. The organic layer is washed with water, brine, then dried with ahydrous MgSO4, and concentrated in vacuo to give I-96 (3.5 g).

To a solution of I-96 (3.40 g, 16.1 mmol) in EtOH (15 mL) is added TEA (2.4 mL, 16.9 mmol) and hydroxylamine hydrochloride (1.2 g, 16.9 mmol) at room temperature and stirred for 30 min at 80° C. The reaction mixture is cooled to room temperature and partitioned between EtOAc and water, dried with anhydrous MgSO4, filtered, and concentrated in vacuo. The crude residue is purified with heptane/EtOAc (0-100%) to give I-97 (3.0 g).

Method 62

Synthesis of tert-butyl 4-[5-[1-(4-bromophenyl)-1-methyl-propyl]-1,2,4-oxadiazol-3-yl]piperazine-1-carboxylate (Intermediate 98)

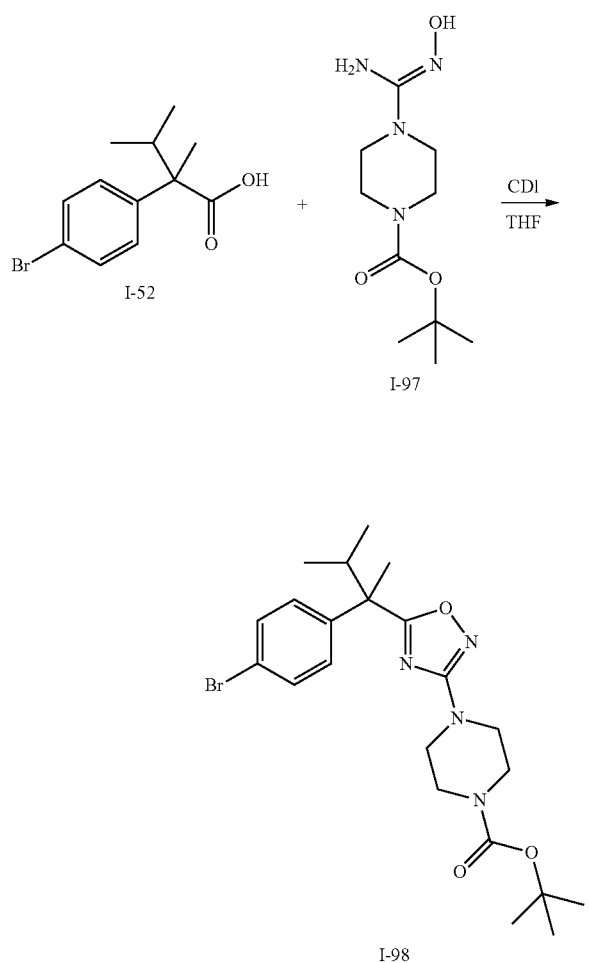

To a suspension of I-52 (200 mg, 0.738 mmol) in THF (2 mL) is added CDI (119 mg; 0.738 mmol). The mixture was heated at 55° C. for 1 hour. I-97 (180 mg; 0.738 mmol) is added to the reaction mixture and heated at 55° C. for 1 hour, then heated in microwave at 150° C. for 40 mins. The reaction mixture is concentrated in vacuo and purified by flash chromatography (SiO$_2$, EA/Hep) which gives I-98 (46 mg).

Method 63

Synthesis of N'-hydroxy-1-methyl-pyrazole-4-carboxamidine (Intermediate 99)

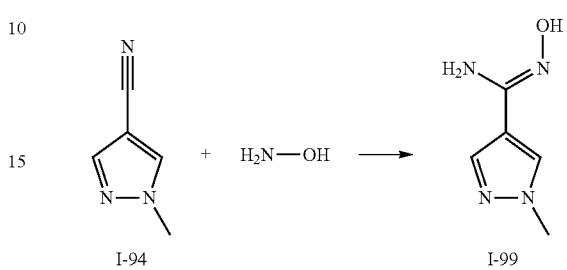

To a solution of I-94 (200 mg, 1.867 mmol) in ethanol (5 mL) is added 50% hydroxyamine aqueous solution (3.65 ml, 59.7 mmol) and is stirred at 85° C. overnight. The reaction mixture is concentrated in vacuo and dissolved in a mixture of water and acetonitrile. It is then dried in a lyophilizer overnight to give I-99 (429 mg).

The following intermediates were synthesized in a similar fashion from the appropriate reagents:

| Structure | Name | m/z [M + H] |
|---|---|---|
| 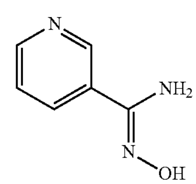 | I-99.1 | NA |

Method 64

Synthesis of 5-[1-(6-chloro-3-pyridyl)-1,2-dimethyl-propyl]-3-(1-methylpyrazol-4-yl)-1,2,4-oxadiazole (Intermediate 100)

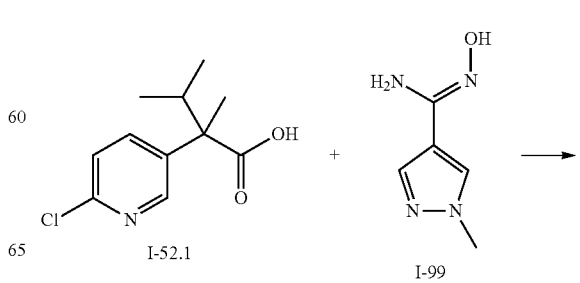

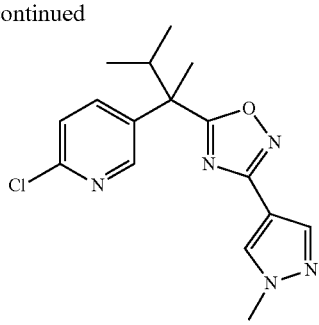

I-100

To a suspension of I-52.1 (200 mg; 0.878 mmol) in THF was added CDI (142 mg; 0.878 mmol) and heated at 55° C. for 20 mins. 1-99 (202 mg; 0.878 mmol) is added to the reaction mixture and heated at 55° C. for 1 hour. The RM is concentrated in vacuo and directly purified by Biotage using EA/Hep as eluent mixtures to give I-100.
Method 65

Synthesis of 5-[1-(4-bromophenyl)-1,2-dimethyl-propyl]-3-(3-pyridyl)-1,2,4-oxadiazole (Intermediate 100)

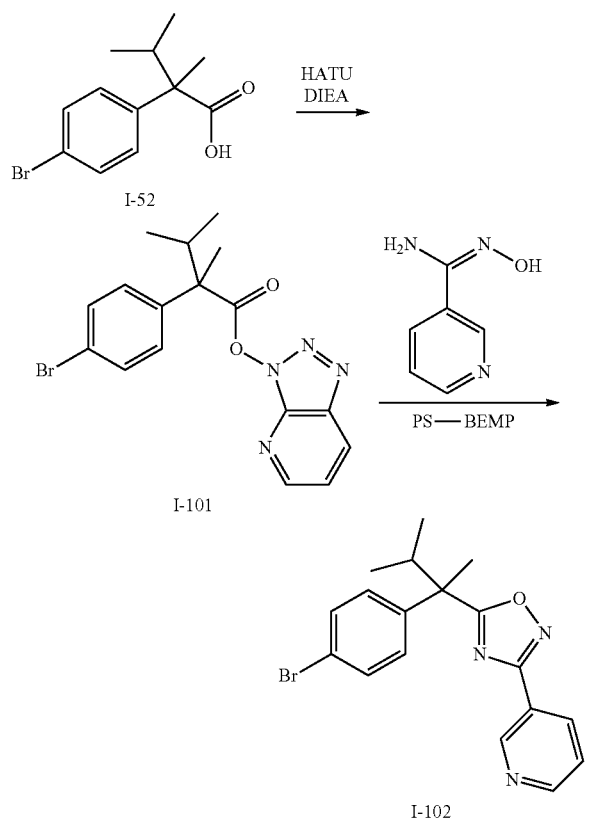

To a solution of I-52 (2.0 g, 7.37 mmol) in DMF (50 mL) is added HATU (4.18 g, 11.0 mmol) followed by DIEA (3.36 g, 26.0 mmol) and the solution is stirred at room temperature for 30 minutes. The reaction mixture is diluted with EtOAc, washed with water, and dried over anhydrous MgSO₄, filtered and concentrated in vacuo. The residue is purified by flash chromatography (SiO2, 0-50% EtOAc/hexanes) to give I-101 (2.3 g).

To a solution of I-101 (26.0 mg, 0.067 mmol) in THF (1 mL) is added I-99.1 (12.3 mg, 0.090 mmol) and PS-BEMP (55.0 mg, 0.110 mmol) and heated in the microwave at 120° C. for 30 min. The mixture is filtered, concentrated in vacuo, and purified by flash chromatography (SiO₂, EtOAc/hexanes) to give I-102 (18 mg).
Method 66

Synthesis of 5-[1-(4-bromophenyl)cyclobutyl]-3-(3-pyridyl)-1,2,4-oxadiazole (Intermediate 101)

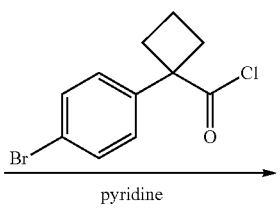

I-99.1

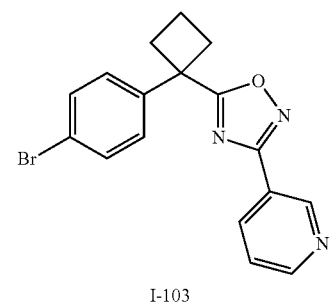

I-103

To a suspension of I-99.1 (350 mg, 2.6 mmol) in pyridine (2.5 mL) in a pressure vessel is added the acid chloride intermediate (835 mg, 3.1 mmol) and the reaction mixture is stirred at room temperature for 10 minutes. The reaction mixture is then stirred at 110° C. for 18 h. The reaction mixture is concentrated in vacuo and saturated aqueous NaHCO₃ is added until the mixture is basic. The product is extracted into EtOAc and the organics washed with water and dried with Na₂SO₄. The solvent is removed in vacuo and the crude product purified by flash chromatography (SiO₂, 20% EtOAc in heptane) to give I-103 (65 mg, 7%).
Method 67

Synthesis of 3-[1-(4-bromophenyl)-1,2-dimethyl-propyl]-5-phenyl-1H-1,2,4-triazole (Intermediate 104) and 2-[1-(4-bromophenyl)-1,2-dimethyl-propyl]-5-phenyl-1,3,4-oxadiazole (Intermediate 105)

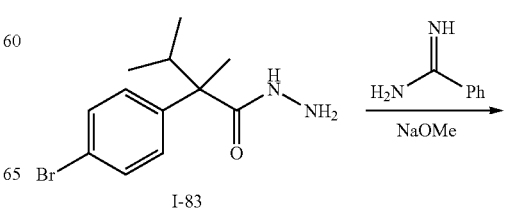

I-83

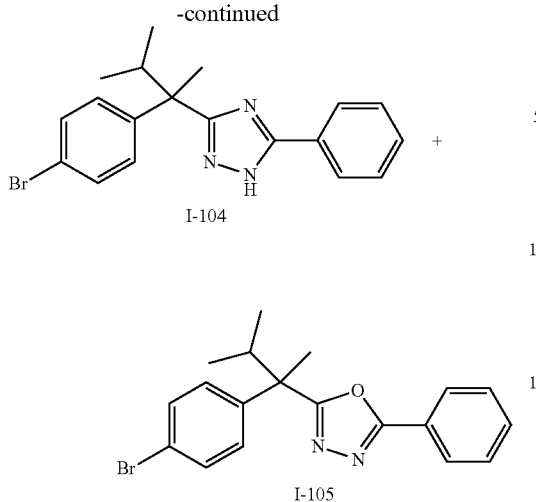

A solution of I-83 (250 mg, 1.05 mmol), benzamidine hydrochloride (316 mg, 2.01 mmol) and sodium methoxide (167 mg, 3.09 mmol) in ethanol (4 mL) in a microwave vessel is stirred at 100° C. for 2 h under microwave irradiation. An additional amount of benzamidine hydrochloride (138 mg, 0.88 mmol) and sodium methoxide (94 mg, 1.74 mmol) is added and the reaction stirred at 100° C. for a further 2 h under microwave irradiation. The reaction mixture is cooled and concentrated in vacuo and partitioned between EtOAc and water. The combined organics are dried over anhydrous MgSO$_4$ and concentrated in vacuo. The residue is purified by flash chromatography (SiO$_2$, 20% EtOAc in cyclohexane) to give I-104 (215 mg) and I-105 (38 mg).

Method 68

Synthesis of 2-[1-(4-bromophenyl)cyclobutyl]-5-phenyl-1,3,4-oxadiazole (Intermediate 106)

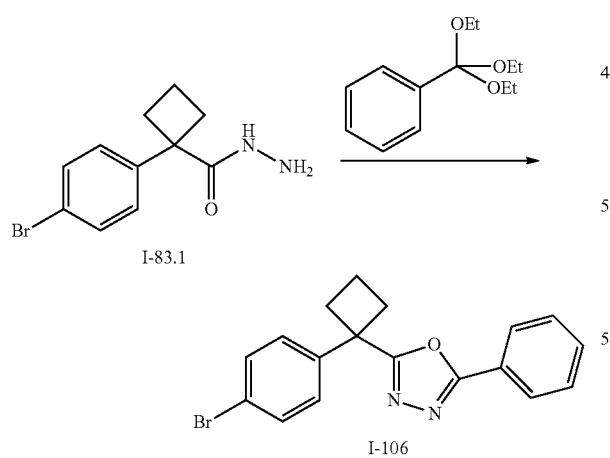

I-83.1 (150 mg, 0.56 mmol) and triethylorthobenzoate (0.19 mL, 0.84 mmol) are combined in a microwave vessel and the reaction is stirred at 135° C. for 3 h under microwave irradiation (power 100 W). The reaction mixture is purified by flash chromatography (SiO$_2$, 10% EtOAc in heptane) to give I-106 (138 mg).

Method 69

Synthesis of 2-[1-(4-bromophenyl)cyclobutyl]-5-phenyl-1,3,4-oxadiazole (Intermediate 107)

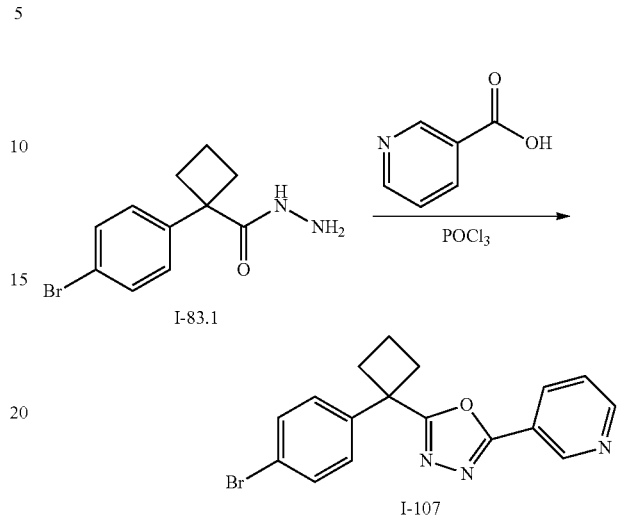

I-83.1 (180 mg, 0.67 mmol), nicotinic acid (83 mg, 0.67 mmol) and phosphorus oxychloride (2 mL) are combined in a microwave vessel and stirred at 110° C. for 20 minutes under microwave irradiation (power 100 W). The reaction mixture is then added slowly to 2 M aqueous NaOH until basic and extracted into EtOAc. The combined organics are washed with water and dried over anhydrous Na$_2$SO$_4$. The solvent is removed in vacuo and the crude material purified by flash chromatography (SiO$_2$, 20% to 25% EtOAc in heptane) to give I-107 (110 mg).

Method 70

Synthesis of 2-[1-[4-(5-methoxy-3-pyridyl)phenyl]-2-methyl-propyl]thiazole (Intermediate 108)

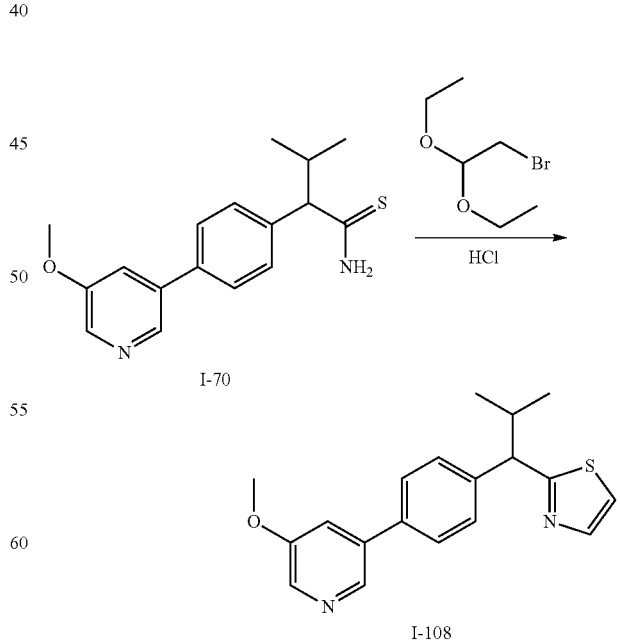

To a round bottom flask was added I-70 (991 mg, 3.30 mmol) in ethanol (30 mL), followed by the addition of bromoacetaldehyde diethyl acetal (1950 mg, 9.90 mmol) and 4N HCl in 1,4-dioxane (4 mL, 16 mmol). The reaction mixture was stirred at 70° C. for 24 hours. The reaction mixture was concentrated in vacuo. The residue was diluted with EtOAc washed with water and sat. NaHCO₃ and brine. The organic layer was dried under anhy. Na₂SO₄, filtered and concentrated. The residue was purified by flash chromatography (SiO₂, 10-50% EtOAc/heptane) to give the title intermediate I-108 (790 mg).
Method 71

Synthesis of methyl 5-[1-[4-(2-aminopyrimidin-5-yl)phenyl]cyclobutyl]-4-bromo-1H-pyrrole-2-carboxylate (Intermediate 109)

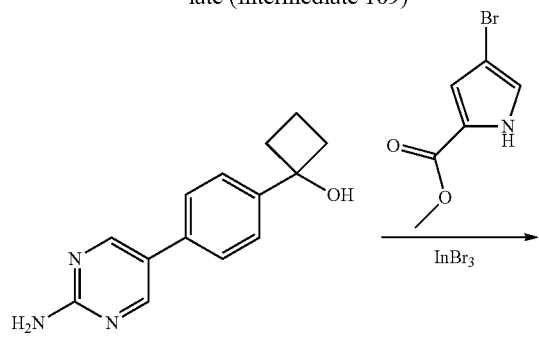

I-66.1

I-109

To a solution of I-66.1 (100 mgs, 0.41 mmol) in CH₂Cl₂ (10 mL) is added indium bromide (44 mgs, 0.12 mmol) and 4-bromo-1H-pyrrole-2-carboxylic acid methyl ester (127 mgs, 0.62 mmol) at room temperature for 24 hours. The reaction is concentrated and the residue extracted with sat. aq. NaHCO₃ and CH₂Cl₂. The combined organic layer is dried with anhydrous Mg₂SO₄, filtered, and concentrated in vacuo. The residue is purified by flash chromatography (SiO₂, 0-10% MeOH in CH₂Cl₂) to give the title intermediate I-109 (20 mg).
Method 72

Synthesis of 2-[1,2-dimethyl-1-[4-(3-pyridyloxy)phenyl]propyl]-5-methyl-pyridine (Example 111)

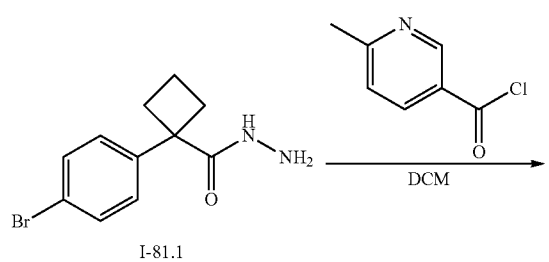

I-81.1

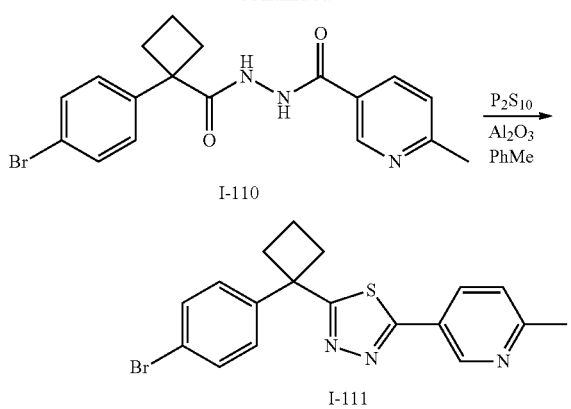

I-110

I-111

To a suspension of methylnicotinic acid (500 mg, 3.6 mmol) in DCM (30 mL) is added oxalyl chloride (0.93 mL, 10.9 mmol) dropwise followed by DMF (1 drop). The reaction mixture is stirred at room temperature for 1 h and then concentrated in vacuo to give methylnicotinoyl chloride in a quantitative yield. A solution of I-83.1 (250 mg, 0.93 mmol) and methylnicotinoyl chloride (159.0 mg, 1.02 mmol) in DCM is stirred at room temperature for 1 h with the addition of more methylnicotinoyl chloride (28.9 mg, 0.19 mmol). The reaction mixture is then diluted with saturated aqueous NaHCO₃ and the combined organics are dried over Na₂SO₄, The solvent is removed in vacuo to give I-110 (360 mg, quantitative).

Finely ground phosphorus pentasulfide (37.5 mg, 84.35 mmol) and aluminium oxide (62.5 mg, 0.61 mol) are added to a solution of I-110 (100 mg, 0.26 mmol) in toluene (5 mL) and the mixture is stirred at 75° C. for 18 h. After cooling to room temperature the mixture is diluted with saturated aqueous NaHCO₃ and the organics are extracted. Extraction is repeated with DCM and EtOAc and the combined organics are filtered to remove inorganics and concentrated in vacuo. The residue is purified by flash chromatography (SiO₂, 30% EtOAc in heptane) to give I-111 (50 mg).

Final Compounds

Method 73

Synthesis of methyl 5-[1-[4-(2-aminopyrimidin-5-yl)phenyl]cyclobutyl]-1H-pyrrole-2-carboxylate (Intermediate 167)

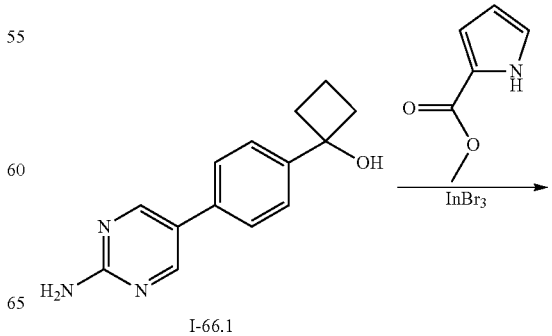

I-66.1

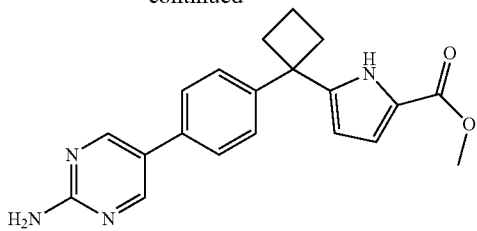

Ex 167

Example 167 was made using Method 71.
The following compounds are synthesized in a similar fashion from the appropriate intermediates:
Example 169
Example 177
Method 74

Synthesis of 3-[1-[4-(2-aminopyrimidin-5-yl)phenyl]cyclobutyl]-N-methyl-1H-indole-7-carboxamide (Example 6)

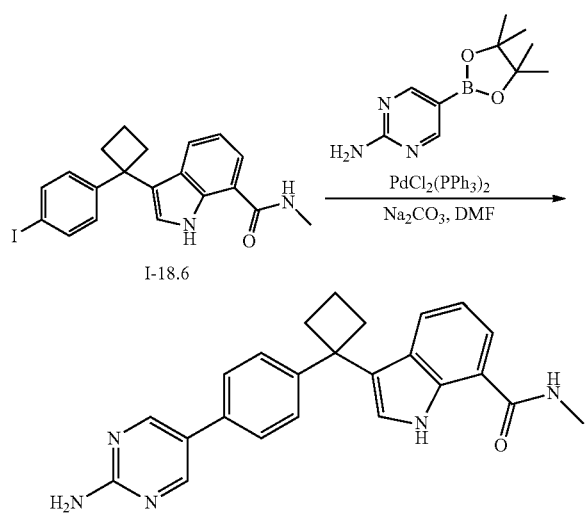

To a suspension of I-19.6 (150 mg, 0.35 mmol), 2-aminopyrimidine-5-boronic acid pinacol ester (93 mg, 0.42 mmol) and 2 M aqueous $Na_2CO_3$ (0.35 mL, 0.70 mmol) in DMF (1.5 mL) is added bis(triphenylphosphino)palladium (II) chloride (25 mg, 0.03 mmol). The reaction vessel is sealed under $N_2$ and heated to 80° C. for 30 min. On cooling to room temperature the reaction mixture is filtered through Celite and the solvent removed in vacuo. The residue is taken up in DCM and washed with saturated $NaHCO_3$ and brine then dried over $Na_2SO_4$. The solvent is removed in vacuo to leave a residue which is purified by flash chromatography ($SiO_2$, 3% MeOH in DCM) to give Example 6 (82 mg). LCMS (ESMS): Rt 3.89 min (Method F) m/z 398.42 $(M+H)^+$.

The following compounds are synthesized in a similar fashion from the appropriate intermediates:
Example 1-7
Example 8: The reaction is run using 2-aminopyrimidine-5-boronic acid for 3 hours, with bromo taking the place of iodo as the halide Example 9-13
Example 14-16: The reaction is run using 2-aminopyrimidine-5-boronic acid and a DMF/MeOH (1 ml/0.3 mL) solvent mixture and is heated to 90° C.
Example 17-20: The reaction is run in THF and refluxed overnight
Example 22: The reaction is run in THF and refluxed overnight Example 25

The reaction is run using Ex 24 as intermediate starting material and 2-(hydroxymethylpyridine-5-boronic acid in a microwave reactor at 100° C. for 1 hour Example 27: The reaction is run using 3-methoxy-5-pyridineboronic acid pinacol ester, $PdCl_2dppf$, dppf and 4:1 EtOH/toluene as solvent at 95° C. for 2 hours
Example 28-29: The reaction is run using 2-aminopyrimidine-5-boronic acid, $PdCl_2dppf$, dppf and 4:1 EtOH/toluene as solvent at 95° C. for 2 hours
Example 31-35: The reaction is run using 2-aminopyrimidine-5-boronic acid, $PdCl_2dppf$, dppf and 4:1 EtOH/toluene as solvent at 95° C. for 2 hours
Example 39-43: The reaction is run using 2-aminopyrimidine-5-boronic acid, $PdCl_2dppf$, dppf and 4:1 EtOH/toluene as solvent at 95° C. for 2 hours
Example 45: The reaction is run using 2-aminopyrimidine-5-boronic acid, $PdCl_2dppf$, dppf and 4:1 EtOH/toluene as solvent at 95° C. for 2 hours
Example 48-52: The reaction is run using 2-aminopyrimidine-5-boronic acid, $PdCl_2dppf$, dppf and 4:1 EtOH/toluene as solvent at 95° C. for 2 hours
Example 54: The reaction is run using 2-aminopyrimidine-5-boronic acid, $PdCl_2dppf$, dppf and 4:1 EtOH/toluene as solvent at 95° C. for 2 hours
Example 56-63: The reaction is run using 2-aminopyrimidine-5-boronic acid, $PdCl_2dppf$, dppf and 4:1 EtOH/toluene as solvent at 95° C. for 2 hours
Example 66: The reaction is run using 2-amino-5-(4,4,5,5-tetramethyl-1,3,2-dioxaborolane-2-yl)pyridine, $PdCl_2dppf$, dppf and 4:1 EtOH/toluene as solvent at 95° C. for 2 hours
Example 67-70: The reaction is run using 2-aminopyrimidine-5-boronic acid, $PdCl_2dppf$, dppf and 4:1 EtOH/toluene as solvent at 95° C. for 2 hours
Example 71: The reaction is run using 2-amino-5-(4,4,5,5-tetramethyl-1,3,2-dioxaborolane-2-yl)pyridine, $PdCl_2dppf$, dppf and 4:1 EtOH/toluene as solvent at 95° C. for 2 hours
Example 72-75: The reaction is run using 2-aminopyrimidine-5-boronic acid, $PdCl_2dppf$, dppf and 4:1 EtOH/toluene as solvent at 95° C. for 2 hours
Example 77-83: The reaction is run using 2-aminopyrimidine-5-boronic acid, $PdCl_2dppf$, dppf and 4:1 EtOH/toluene as solvent at 95° C. for 2 hours
Example 85-99: The reaction is run using 2-aminopyrimidine-5-boronic acid, $PdCl_2dppf$, dppf and 4:1 EtOH/toluene as solvent at 95° C. for 2 hours
Example 100: The reaction is run using Ex 24 as intermediate starting material in a microwave at 110° C. for 1 hour
Example 101: The reaction is run in the microwave at 120° C. for 30 min.
Example 102-111: The reaction is run using 2-aminopyrimidine-5-boronic acid, $PdCl_2dppf$, dppf and 4:1 EtOH/toluene as solvent at 95° C. for 2 hours Example 112
Example 113-117: The reaction is run using 2-aminopyrimidine-5-boronic acid, PdCl$_2$dppf, dppf and 4:1 EtOH/toluene as solvent at 95° C. for 2 hours
Example 119-121: The reaction is run using 2-aminopyrimidine-5-boronic acid, PdCl$_2$dppf, dppf and 4:1 EtOH/toluene as solvent at 95° C. for 2 hours
Example 122-128
Example 129: The reaction is run using 2-aminopyrimidine-5-boronic acid, PdCl$_2$dppf, dppf and 4:1 EtOH/toluene as solvent at 95° C. for 2 hours
Example 130: The reaction is run using 5-(4,4,5,5-tetramethyl-[1,3,2]dioxaborolan-2-yl)-1H-pyrrolo[2,3-B]pyridine, PdCl$_2$dppf, dppf and 4:1 EtOH/toluene as solvent at 95° C. for 2 hours
Example 131-135
Example 136: The reaction is run using 2-aminopyrimidine-5-boronic acid, PdCl$_2$dppf, dppf and 4:1 EtOH/toluene as solvent at 95° C. for 2 hours
Example 137-138
Example 139: The reaction is run using 2-aminopyrimidine-5-boronic acid, PdCl$_2$dppf, dppf and 4:1 EtOH/toluene as solvent at 95° C. for 2 hours
Example 140
Example 141-145: The reaction is run using 2-aminopyrimidine-5-boronic acid, PdCl$_2$dppf, dppf and 4:1 EtOH/toluene as solvent at 95° C. for 2 hours
Example 146-152
Example 153: The reaction is run using 2-aminopyrimidine-5-boronic acid, PdCl$_2$dppf, dppf and 4:1 EtOH/toluene as solvent at 95° C. for 2 hours
Example 154-156
Example 157: The reaction is run using 2-aminopyrimidine-5-boronic acid in a pressure tube at 90° C. for 1 hour
Example 158: The reaction is run using THF as solvent and is heated at reflux for 6 hours
Example 159-160
Example 161: The reaction is run using THF as solvent and heated in the microwave at 110° C. for 1 hour
Example 164: The reaction is run using THF as solvent and refluxed overnight, using bromo in place of iodo as the halide
Example 166: The reaction is run in the microwave for 1 hour at 100° C., using 1-107 as the reagent
Example 171: The reaction is run using THF as solvent at 80° C. overnight, using bromo in place of iodo as the halide
Example 175: Used bromo in place of iodo as the halide
Example 176: The reaction is run in the microwave for 1 hour at 100° C., using 1-107 as the reagent
Example 178: The reaction is run in the microwave at 120° C. for 1 hour
Example 179: The reaction is run in the microwave for 1 hour at 100° C., using 1-107 as the reagent
Example 182: The reaction is run in the microwave at 100° C. for 1 hour, using Ex 177 as SM
Example 183-184: The reaction is run using THF as solvent and heated in the microwave at 110° C. for 45 min
Example 187: The reaction is run using THF as solvent and heated in the microwave at 110° C. for 45 min
Example 190: The reaction is run using THF as solvent and refluxed overnight Method 75

Synthesis of methyl 4-[1-[4-(2-aminopyrimidin-5-yl)phenyl]cyclobutyl]-1H-pyrrole-3-carboxylate (Example 162)

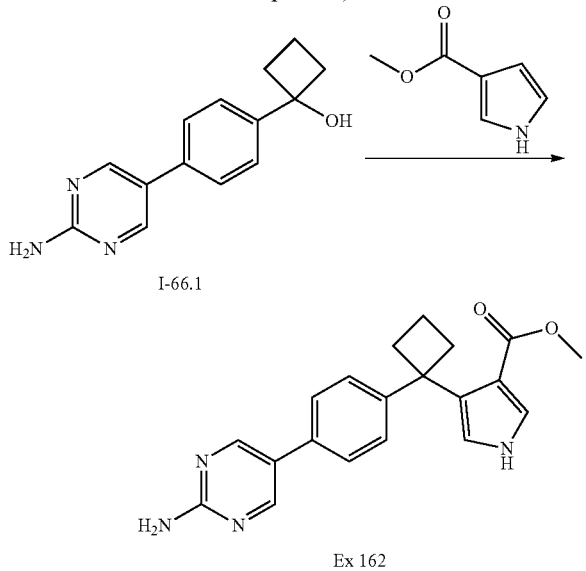

To a solution of I-66.1 (100 mg, 0.41 mmol) in nitromethane (5 mL) is added iron (III) chloride (20.16 mg, 0.12 mmol) and methyl-1H-pyrazole-3-carboxylate (62.2 mg, 0.497 mmol) and is stirred at room temperature for 24 hours. The reaction is concentrated in vacuo, and the residue is partitioned between saturated aqueous NaHCO$_3$ and EtOAc. The combined organics are dried with Mg$_2$SO$_4$, filtered, and concentrated in vacuo. The residue is purified by flash chromatography (SiO$_2$, 0-10% MeOH in CH$_2$Cl$_2$) to give the title compound 162 (5 mg).

The following compounds are synthesized in a similar fashion from the appropriate intermediates:
Example 163
Example 165
Example 174
Example 188-189
Example 193

Method 76

Synthesis of [2-amino-5-[4-[1-(1H-indol-3-yl)cyclobutyl]phenyl]-3-pyridyl]methanol (Example 118)

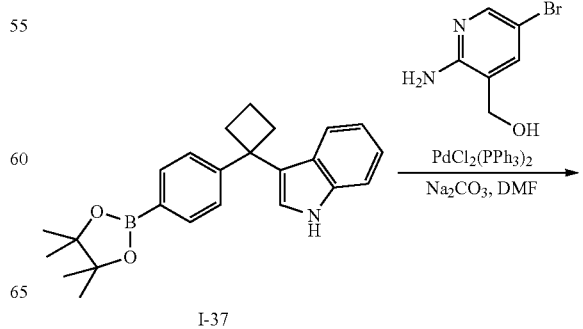

-continued

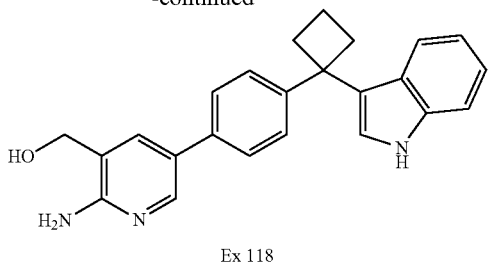

Ex 118

The reaction is run using the same procedure as in Method 71.

Method 77

Synthesis of 3-[1-[4-(2-aminopyrimidin-5-yl)phenyl]-1,2-dimethyl-propyl]-1H-indole-7-carboxylic acid (Example 84)

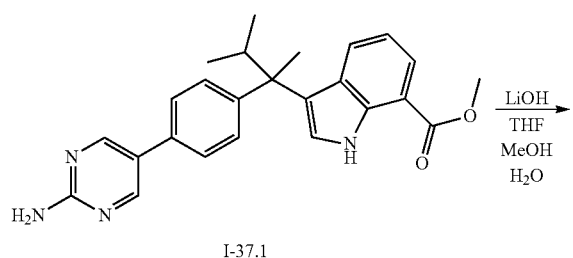

I-37.1

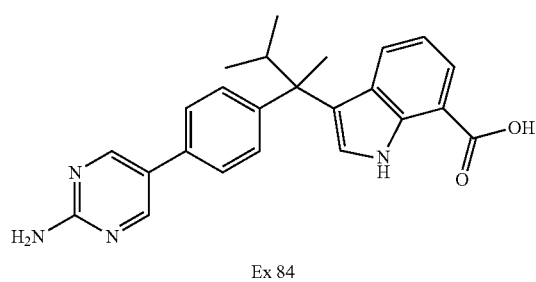

Ex 84

To a solution of I-37.1 (100 mg, 0.24 mmol) in a mixture of MeOH (2 mL), THF (2 mL) and water (2 mL) is added lithium hydroxide monohydrate (201 mg, 4.8 mmol). The solution is stirred at room temperature for 1 d. The solvent is removed in vacuo and the residue diluted in water. The aqueous phase is acidified with 6 M HCl and extracted with DCM. The organics are dried over anhydrous $Na_2SO_4$ and concentrated in vacuo. The crude material is purified by preparative HPLC to give the title compound Ex 84 (3 mg).

The following compounds are synthesized in a similar fashion from the appropriate intermediates:
Example 47
Example 55

Method 78

Synthesis of 5-[3-[1-[4-(2-aminopyrimidin-5-yl)phenyl]-1,2-dimethyl-propyl]-1H-indol-6-yl]-1,3,4-oxadiazol-2-amine (Example 65)

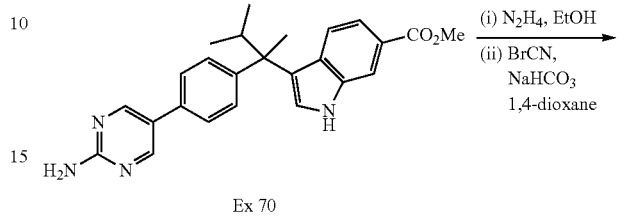

Ex 70

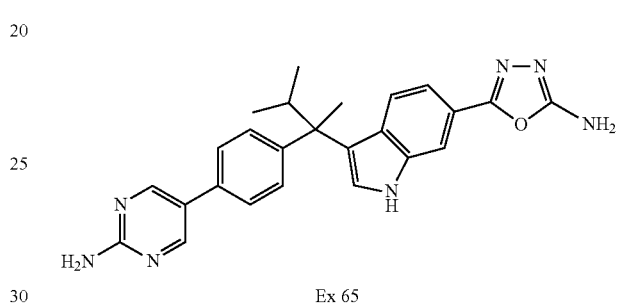

Ex 65

To a solution of Ex 70 (100 mg, 0.24 mmol) in EtOH (5 mL) is added hydrazine hydrate (69 mg, 2.17 mmol) and the solution heated to reflux for 2.5 h. The solvent is removed in vacuo and the residue partitioned between EtOAc and water. The organic phase is separated and washed with brine, dried over $Na_2SO_4$ and the solvent removed in vacuo. The residue is re-dissolved in 1,4-dioxane (3 mL) and $NaHCO_3$ (28 mg, 0.26 mmol) added followed by BrCN (28 mg, 0.26 mmol). The reaction is stirred at room temperature for 18 h then poured onto saturated aqueous $NaHCO_3$ and extracted with EtOAc. The combined organics are washed with brine and dried over anhydrous $Na_2SO_4$, and the solvent removed in vacuo to give the title compound Ex 65 (39 mg).

The following compounds are synthesized in a similar fashion from the appropriate intermediates:
Example 76

Method 79

Synthesis of 3-[1,2-dimethyl-1-[4-(2-pyridylmethoxy)phenyl]propyl]-1H-indole-6-carboxylic acid (Example 64)

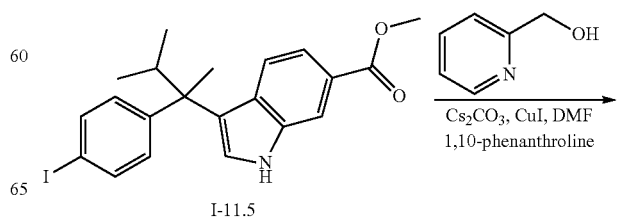

I-11.5

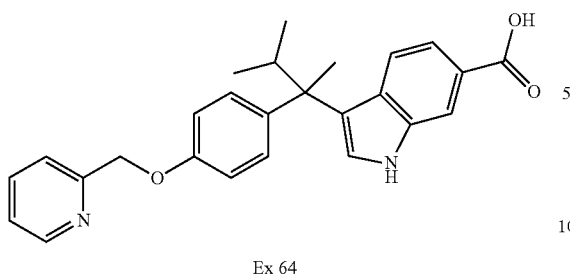

Ex 64

A suspension of I-11.5 (200 mg, 0.447 mmol), 2-(hydroxymethyl)pyridine (244 mg, 2.24 mmol), CuI (26 mg, 0.134 mmol), 1,10-phenanthroline (24 mg, 0.134 mmol) and Cs$_2$CO$_3$ (728 mg, 2.24 mmol) is heated to 110° C. for 18 h. On cooling to room temperature the reaction mixture is taken up in DCM. The organic phase is washed with saturated aqueous NaHCO$_3$ and dried over Na$_2$SO$_4$. The solvent is removed in vacuo and the crude material purified by preparative HPLC to give the title compound Ex 64 (21 mg).

Method 80

Synthesis of 2-[6-[[3-[1,2-dimethyl-1-[4-(2-pyridylmethoxy)phenyl]propyl]indol-1-yl]methyl]-3-pyridyl]propan-2-ol (Example 46)

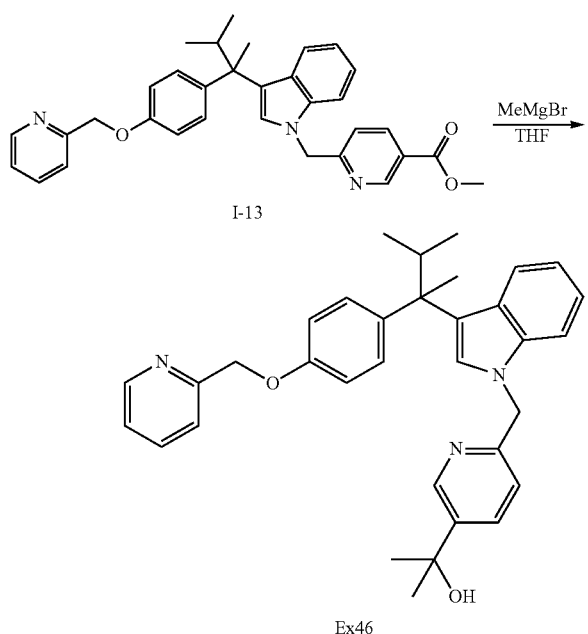

To a solution of I-13 (136 mg, 0.26 mmol) in THF (1.3 mL) is added methyl magnesium bromide (0.393 mL of a 1.4 M solution in 0.55 mmol). After stifling at room temperature for 2 h the reaction mixture is diluted with DCM and washed with saturated aqueous NaHCO$_3$. The organics are dried over Na$_2$SO$_4$ and concentrated in vacuo. The residue is purified by flash chromatography (SiO$_2$, DCM to 5% MeOH in DCM) followed by preparative HPLC (Low pH method) to give the title compound Ex 46 (6 mg) as a TFA salt.

Method 81

Synthesis of 23-[1,2-dimethyl-1-[4-(2-pyridylmethoxy)phenyl]propyl]-1-methyl-indole-6-carboxylic acid (Example 36)

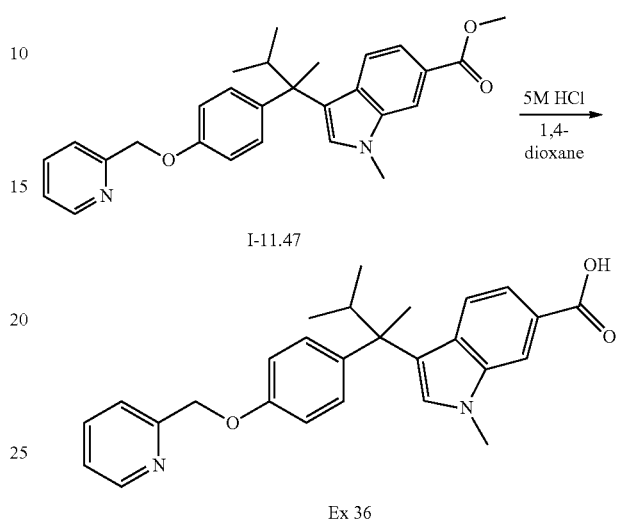

A suspension of I-11.47 (200 mg, 0.45 mmol) in 5 M HCl (2 mL) and 1,4-dioxane (2 mL) is heated to 80° C. for 18 h. The reaction mixture is concentrated in vacuo and the residue triturated with MeCN to give the crude title compound as the HCl salt (225 mg). A portion of the material is purified by preparative HPLC to give the title compound Ex 36.

Method 82

Synthesis of 3-[1,2-dimethyl-1-[4-(2-pyridylmethoxy)phenyl]propyl]-1-methyl-indole-6-carboxamide (Example 38)

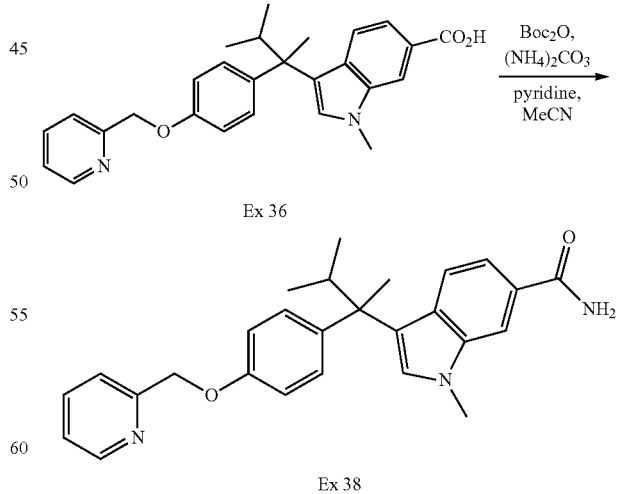

To a suspension of Ex 36 (99 mg, 0.23 mmol) in anhydrous MeCN (2.5 mL) is added di-tert-butyl dicarbonate (66 mg, 0.30 mmol), ammonium carbonate (22 mg, 0.28 mmol) and pyridine (23 μL, 0.28 mmol). After stirring the reaction for 18 h the solvent is removed in vacuo and the residue is purified by preparative HPLC (Neutral method) to give the title compound Ex 38 (14 mg).
Method 83

Synthesis of 3-[1,2-dimethyl-1-[4-(2-pyridyl-methoxy)phenyl]propyl]-1-methyl-N-pyridazin-3-yl-indole-6-carboxamide (Example 37)

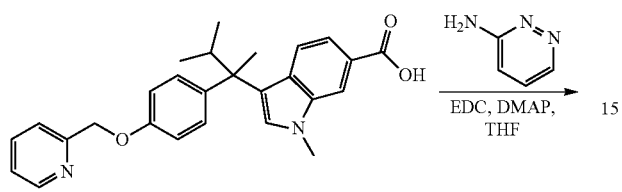

Ex 36

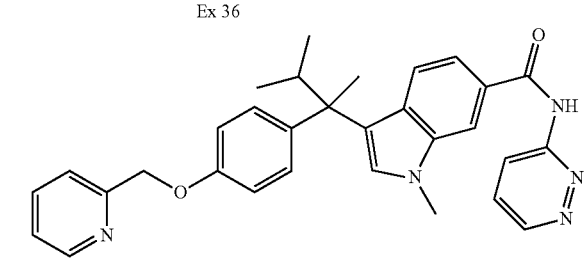

Ex 37

A solution of Ex 36 (98 mg, 0.23 mmol), 3-aminopyridazine (24 mg, 0.25 mmol), EDC hydrochloride (55 mg, 0.29 mmol) and N,N-dimethylaminopyridine (5 mg, 0.05 mmol) in THF (1 mL) is stirred for 18 h at room temperature. The solvent is evaporated in vacuo and the crude material purified by preparative HPLC to give the title compound Ex 37 (10 mg).
Method 84

Synthesis of 5-[4-[2,2-dimethyl-1-(1-methylindazol-3-yl)propyl]phenyl]pyrimidin-2-amine (Example 44)

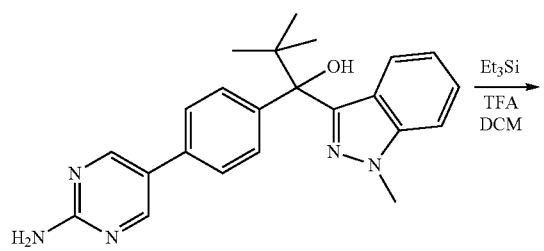

I-39.2

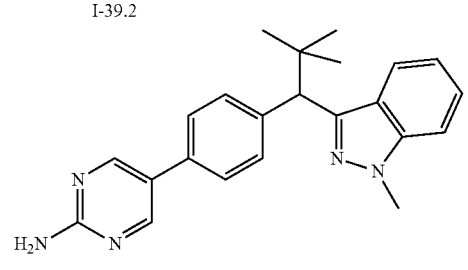

Ex 44

To a solution of I-39.2 (84 mg, 0.217 mmol) in DCM (2 mL) is added triethylsilane (38 µL, 0.238 mmol) and trifluoroacetic acid (0.161 mL, 2.17 mmol). After stirring at room temperature for 18 h the reaction mixture is quenched with saturated aqueous NaHCO$_3$ and extracted with DCM. The combined organics are dried over anhydrous Na$_2$SO$_4$ and concentrated in vacuo. The residue is purified by preparative HPLC to give the title compound Ex 44 (2.1 mg).
Method 85

Synthesis of 5-[4-[1-methoxy-2,2-dimethyl-1-(1-methylindazol-3-yl)propyl]phenyl]pyrimidin-2-amine (Example 53)

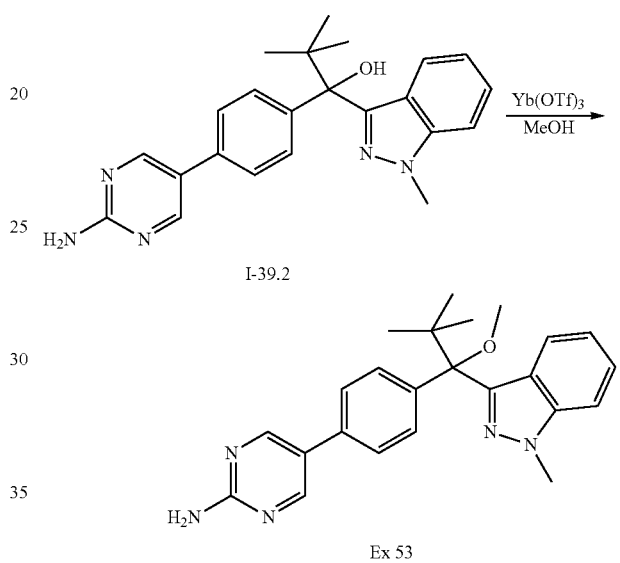

I-39.2

Ex 53

To a solution of I-39.2 (87 mg, 0.23 mmol) in methanol (2 mL) is added ytterbium triflate (7.0 mg, 0.011 mmol). The mixture is heated at 100° C. for 18 h in a sealed vessel then filtered and purified by preparative HPLC to give the title compound Ex 53 (9.2 mg).
Method 86

Synthesis of 5-[4-[(1R)-1-cyclopropyl-1-[4-(1-methylpyrazol-4-yl)oxazol-2-yl]ethyl]phenyl]pyrimidin-2-amine (Example 185) and 5-[4-[(1S)-1-cyclopropyl-1-[4-(1-methylpyrazol-4-yl)oxazol-2-yl]ethyl]phenyl]pyrimidin-2-amine (Example 186)

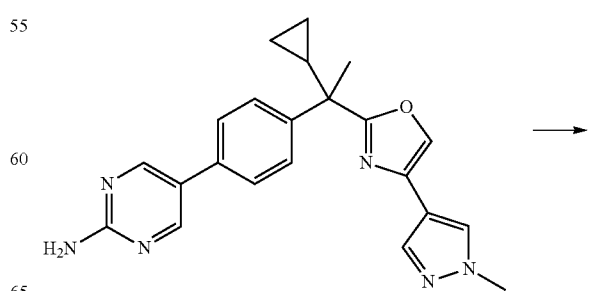

171

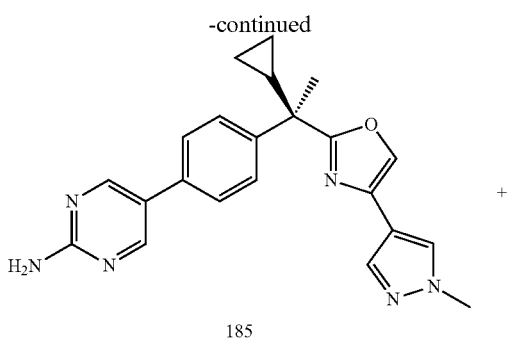

185

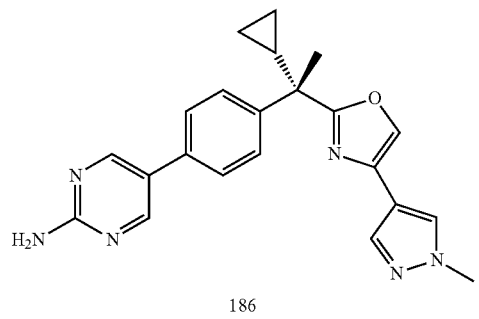

186

Compound 171 (167 mg, 0.432 mmol) was purified by chiralpak AD-H column, 20×2500 mm, eluted with 95% EtOH:heptane (0.5% DEA) @ 6.5 ml/min, 45° C., to give the title compound Ex 185 (68 mg) and Ex 186 (67 mg).

The following compounds are synthesized in a similar fashion from the appropriate intermediates:
Example 26
Example 30
Example 191-192
Example 195-198, 200, 201, 203, 204, 207, 208, 210, 211
Method 87

Synthesis of 5-bromo-2-[1-[4-(5-methoxy-3-pyridyl)phenyl]-2-methyl-propyl]thiazole Example 24

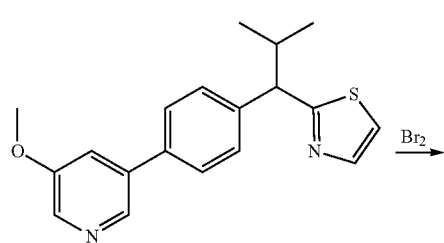

I-106

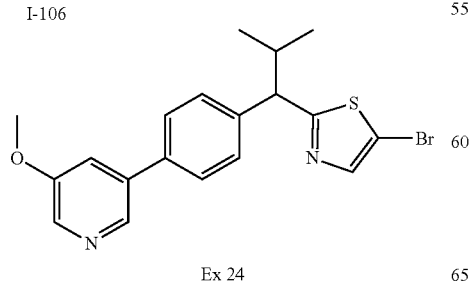

Ex 24

To a round bottom flask was added I-106 (830 mg, 2.56 mmol) in HOAc (15 mL) and CH$_2$Cl$_2$ (5 mL), followed by the addition of Br$_2$ (820 mg, 5.13 mmol). The reaction mixture was stirred at room temperature for 18 hours. The reaction mixture was concentrated in vacuo. The residue was diluted with EtOAc, washed with sat. NaHCO$_3$ and brine The organic layer was dried under anhy. Na$_2$SO$_4$, filtered and concentrated. The residue was purified by flash chromatography (SiO$_2$, 0-30% EtOAc/heptane) to give the title intermediate Ex 24 (470 mg).

Method 88

Synthesis of 2-[4-[2-[1-[4-(2-aminopyrimidin-5-yl)phenyl]-1-cyclopropyl-ethyl]thiazol-5-yl]pyrazol-1-yl]-N,N-dimethyl-acetamide (Example 170)

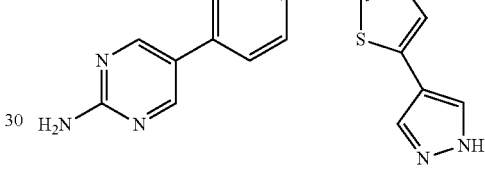

I-75

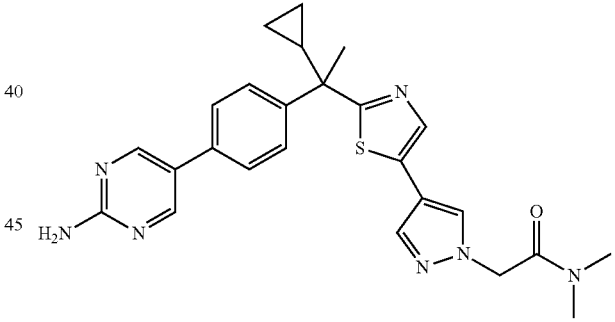

Ex 170

To a vial was added I-75 (25 mg, 0.064 mmol), 2-chloro-N,N-dimethyl-acetamide (16 mg, 0.132 mmol) and K$_2$CO$_3$ (18 mg, 0.13 mmol) in DMF (1.5 mL). The reaction mixture was stirred at 50° C. for 18 hours. The reaction mixture was concentrated in vacuo. The residue was diluted with EtOAc, washed with water, brine, dried under anhydrous Na$_2$SO$_4$, filtered and concentrated. The residue was purified by flash chromatography (SiO$_2$, 0-5% MeOH/CH$_2$Cl$_2$) to give the title compound Ex 170 (23 mg).

The following final compounds were synthesized in a similar fashion from the appropriate reagents and intermediates:
Example 172-173
Example 180-181
Example 194, 202, 205, 209

Method 89

Synthesis of 5-[4-[1,2-dimethyl-1-(3-piperazin-1-yl-1,2,4-oxadiazol-5-yl)propyl]phenyl]pyrimidin-2-amine; formic acid (Example 21)

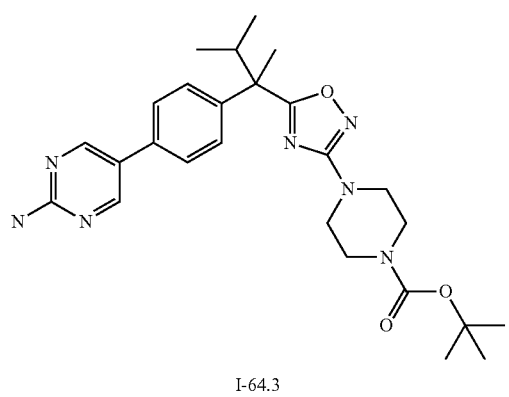

I-64.3

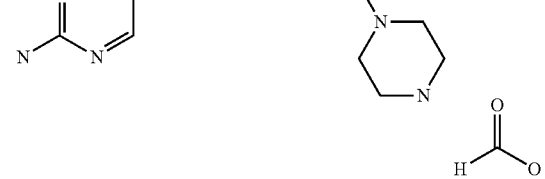

21

I-66.3 (54 mg, 0.109 mmol) was dissolved in 1 mL of DCM and 4N HCl in dioxane (0.273 ml, 1.090 mmol) was added and the RM was stirred at RT overnight. RM was concentrated in vacuo and 51 mg light yellow foam was obtained which gave Ex 21 (22 mg).

Final Compound Table

TABLE 2

| Example | Structure | Synthesis Method | Retention time (min) | m/z [M + H]+ | LCMS method |
|---|---|---|---|---|---|
| 1 | 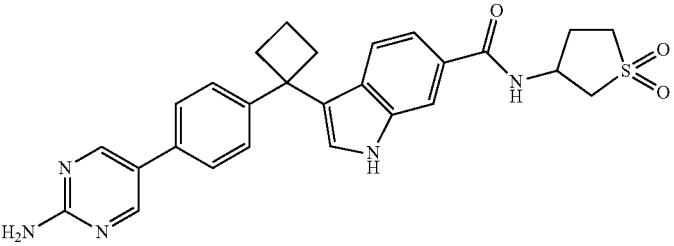 [SMILES: Nc1ncc(-c2ccc(C3(c4c[nH]c5cc(C(=O)NC6CCS(=O)(=O)C6)ccc45)CCC3)cc2)cn1] | 74 | 3.61 | 502.31 | A |
| 2 | 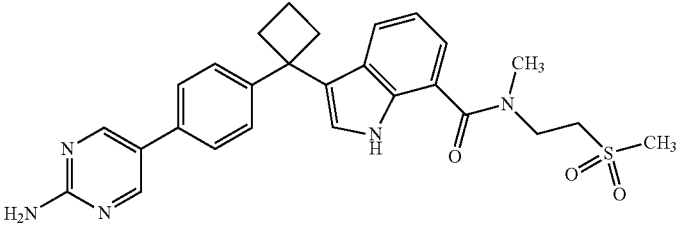 [SMILES: CN(CCS(C)(=O)=O)C(=O)c1cccc2c(C3(c4ccc(-c5cnc(N)nc5)cc4)CCC3)c[nH]c12] | 74 | 3.75 | 504.45 | A |
| 3 | 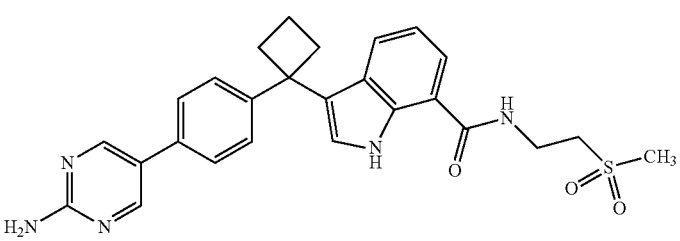 [SMILES: CS(=O)(=O)CCNC(=O)c1cccc2c(C3(c4ccc(-c5cnc(N)nc5)cc4)CCC3)c[nH]c12] | 74 | 3.78 | 490.34 | A |

TABLE 2-continued

| Example | Structure | Synthesis Method | Retention time (min) | m/z [M + H]+ | LCMS method |
|---|---|---|---|---|---|
| 4 | 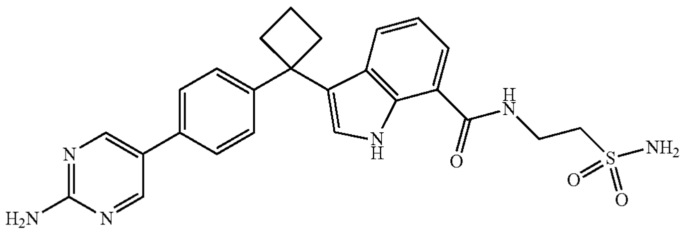 [SMILES: Nc1ncc(-c2ccc(C3(c4c[nH]c5c(C(=O)NCCS(N)(=O)=O)cccc45)CCC3)cc2)cn1] | 74 | 3.67 | 491.35 | A |
| 5 | 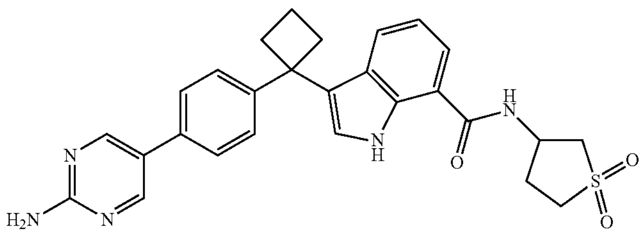 [SMILES: Nc1ncc(-c2ccc(C3(c4c[nH]c5c(C(=O)NC6CCS(=O)(=O)C6)cccc45)CCC3)cc2)cn1] | 74 | 3.89 | 502.27 | A |
| 6 | 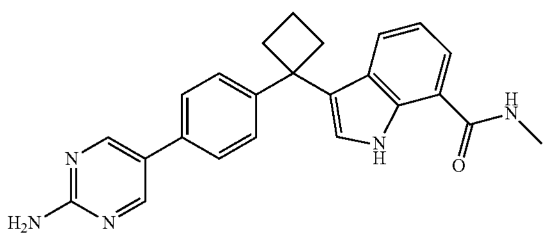 [SMILES: CNC(=O)c1cccc2c(C3(c4ccc(-c5cnc(N)nc5)cc4)CCC3)c[nH]c12] | 74 | 3.89 | 398.42 | A |
| 7 | 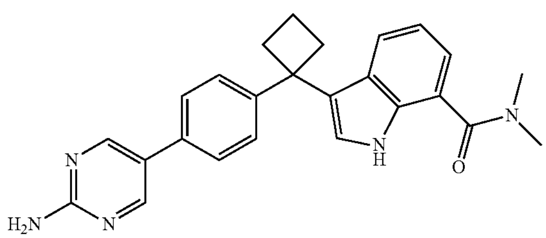 [SMILES: CN(C)C(=O)c1cccc2c(C3(c4ccc(-c5cnc(N)nc5)cc4)CCC3)c[nH]c12] | 74 | 3.88 | 412.43 | A |
| 8 | 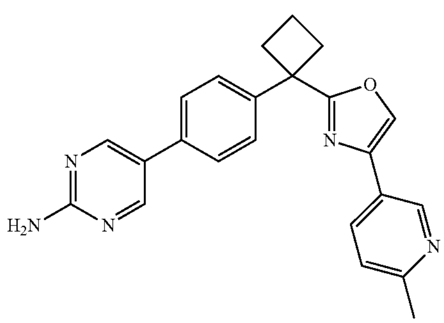 [SMILES: Cc1ccc(-c2coc(C3(c4ccc(-c5cnc(N)nc5)cc4)CCC3)n2)cn1] | 74 | 3.11 | 384.23 | A |
| 9 | 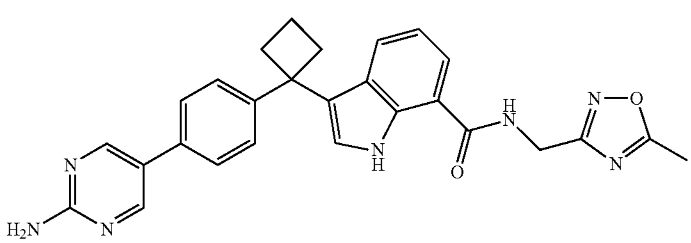 [SMILES: Cc1nc(CNC(=O)c2cccc3c(C4(c5ccc(-c6cnc(N)nc6)cc5)CCC4)c[nH]c23)no1] | 74 | 4.06 | 480.3 | A |

TABLE 2-continued
| Example | Structure | Synthesis Method | Retention time (min) | m/z [M + H]+ | LCMS method |
|---|---|---|---|---|---|
| 10 | 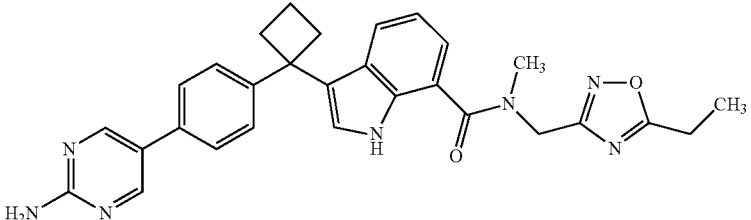 | 74 | 4.29 | 508.49 | A |
| 11 | 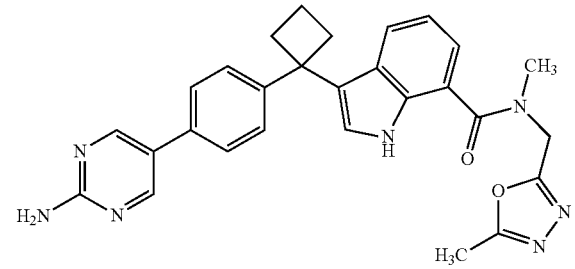 [SMILES: Cc1nnc(CN(C)C(=O)c2cccc3c(C4(c5ccc(-c6cnc(N)nc6)cc5)CCC4)c[nH]c23)o1] | 74 | 3.88 | 494.5 | A |
| 12 | 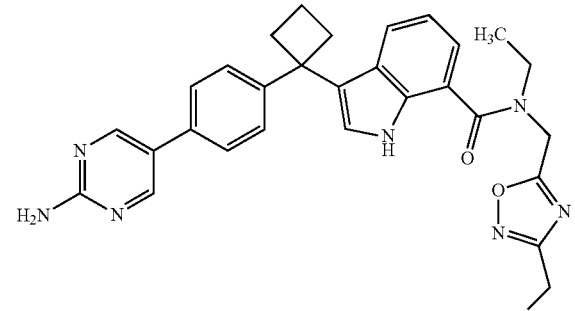 | 74 | 4.49 | 522.49 | A |
| 13 | 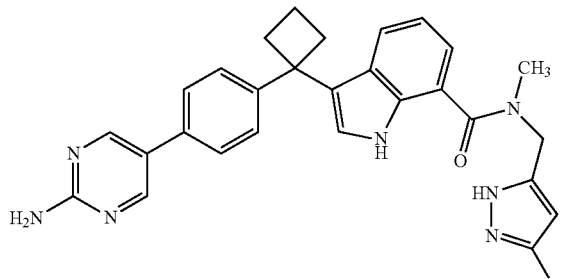 | 74 | 3.94 | 492.46 | A |
| 14 | 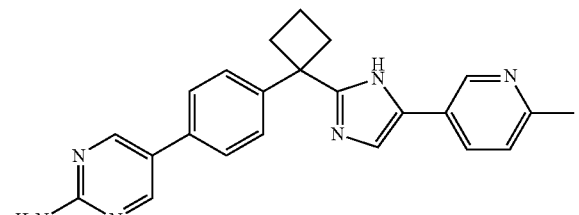 | 74 | 2.58 | 383.28 | A |

TABLE 2-continued

| Example | Structure | Synthesis Method | Retention time (min) | m/z [M + H]+ | LCMS method |
|---|---|---|---|---|---|
| 15 | 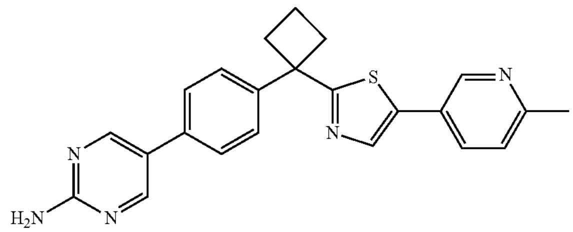 | 74 | 3.53 | 400.23 | A |
| 16 | 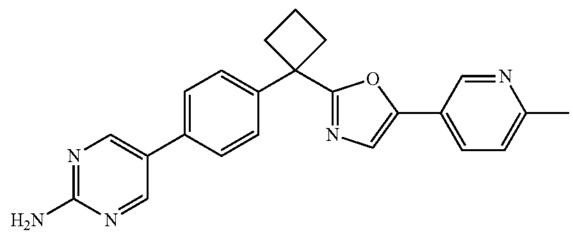 [SMILES: Cc1ccc(-c2cnc(C3(c4ccc(-c5cnc(N)nc5)cc4)CCC3)s2)cn1] | 74 | 3.11 | 384.23 | A |
| 17 | 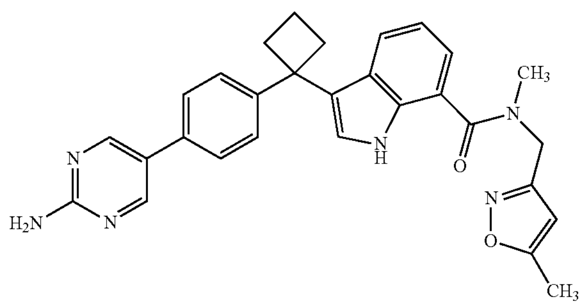 [SMILES: Cc1cc(CN(C)C(=O)c2cccc3c(C4(c5ccc(-c6cnc(N)nc6)cc5)CCC4)c[nH]c23)no1] | 74 | 4.29 | 493.46 | A |
| 18 | 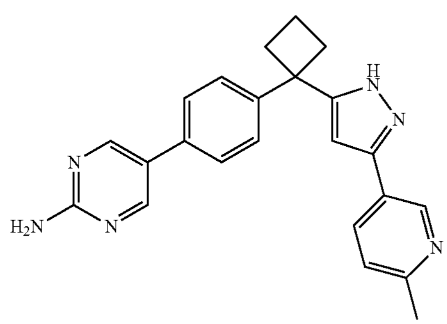 [SMILES: Cc1ccc(-c2cc(C3(c4ccc(-c5cnc(N)nc5)cc4)CCC3)[nH]n2)cn1] | 74 | 1.00 | 383 | F |
| 19 | 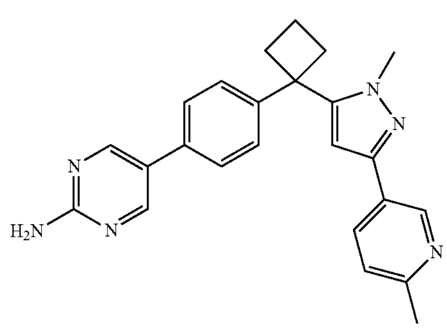 [SMILES: Cc1ccc(-c2cc(C3(c4ccc(-c5cnc(N)nc5)cc4)CCC3)n(C)n2)cn1] | 74 | 1.03 | 397 | F |

TABLE 2-continued
| Example | Structure | Synthesis Method | Retention time (min) | m/z [M + H]+ | LCMS method |
|---|---|---|---|---|---|
| 20 | 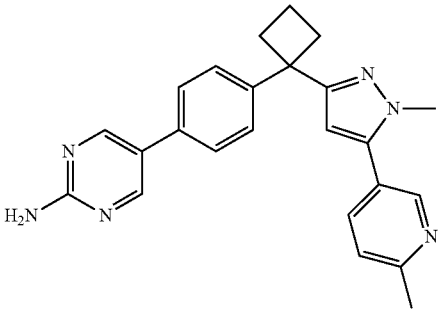 [SMILES: Cc1ccc(-c2cc(C3(c4ccc(-c5cnc(N)nc5)cc4)CCC3)nn2C)cn1] | 74 | 1.16 | 397 | F |
| 21 | 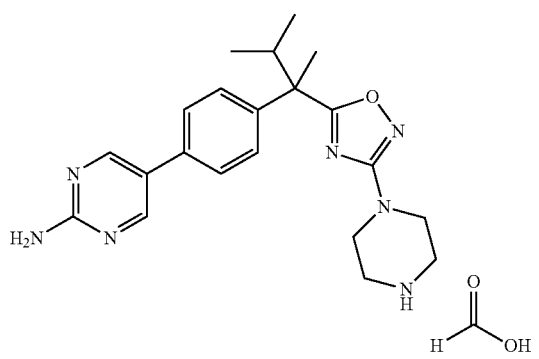 | 89 | 1.11 | 394 | F |
| 22 | 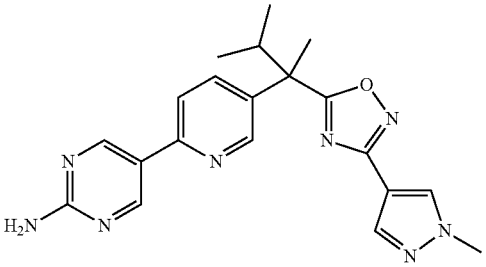 [SMILES: CC(C)C(C)(c1ccc(-c2cnc(N)nc2)nc1)c1nc(-c2cnn(C)c2)no1] | 74 | 1.37 | 391 | E |
| 24 | 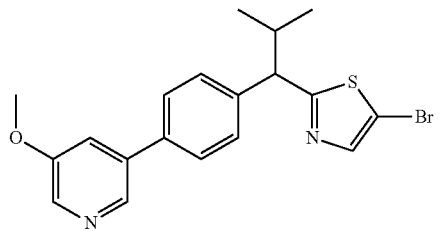 [SMILES: COc1cncc(-c2ccc(C(c3ncc(Br)s3)C(C)C)cc2)c1] | 87 | NA | 403.7, 405.4 | F |
| 25 | 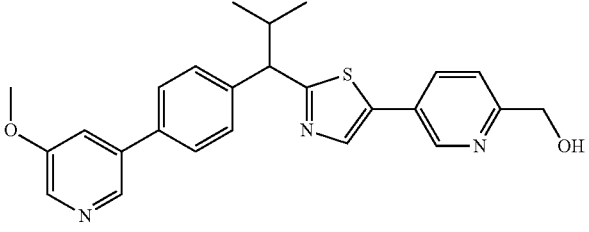 [SMILES: COc1cncc(-c2ccc(C(c3ncc(-c4ccc(CO)nc4)s3)C(C)C)cc2)c1] | 74 | NA | 432.8 | F |

TABLE 2-continued
| Example | Structure | Synthesis Method | Retention time (min) | m/z [M + H]+ | LCMS method |
|---|---|---|---|---|---|
| 26 | 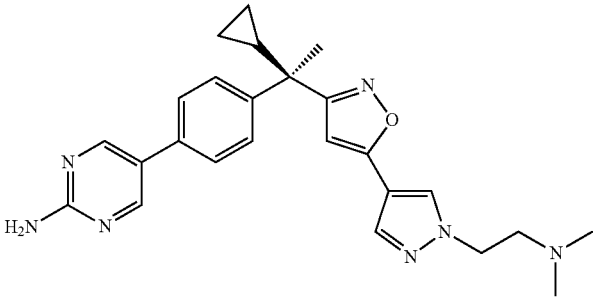 [SMILES: CN(C)CCn1cc(-c2cc([C@@](C)(c3ccc(-c4cnc(N)nc4)cc3)C3CC3)no2)cn1] | 86 | 1.15 | 444.4 | F |
| 27 | 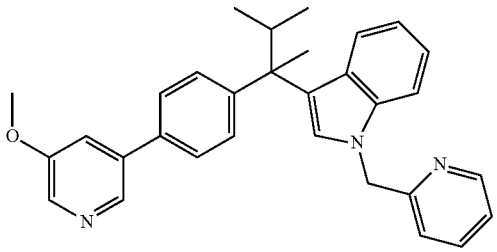 [SMILES: COc1cncc(-c2ccc(C(C)(c3cn(Cc4ccccn4)c4ccccc34)C(C)C)cc2)c1] | 74 | 4.80 | 462.2 | A |
| 28 | 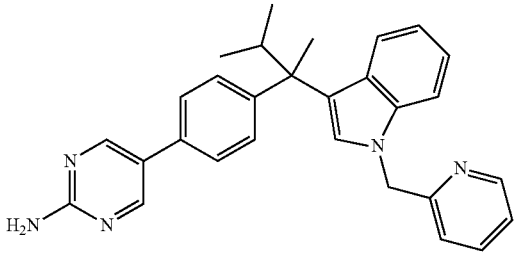 [SMILES: CC(C)C(C)(c1ccc(-c2cnc(N)nc2)cc1)c1cn(Cc2ccccn2)c2ccccc12] | 74 | 4.50 | 448.32 | A |
| 29 | 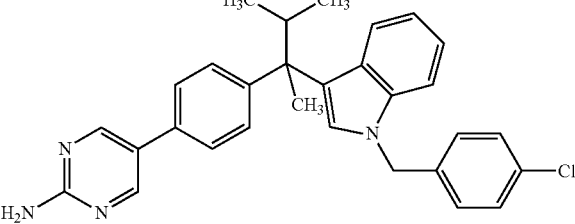 | 74 | 5.43 | 481.29/ 483.29 | A |
| 30 | 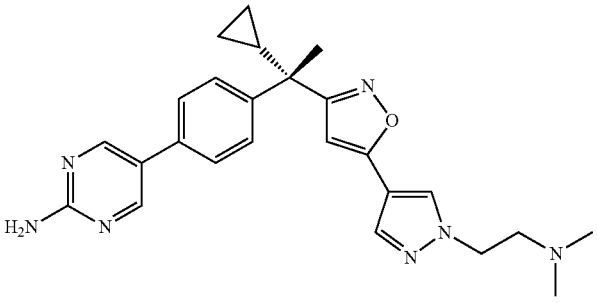 [SMILES: CN(C)CCn1cc(-c2cc([C@](C)(c3ccc(-c4cnc(N)nc4)cc3)C3CC3)no2)cn1] | 86 | 1.15 | 444.4 | F |

TABLE 2-continued

| Example | Structure | Synthesis Method | Retention time (min) | m/z [M + H]⁺ | LCMS method |
|---|---|---|---|---|---|
| 31 | 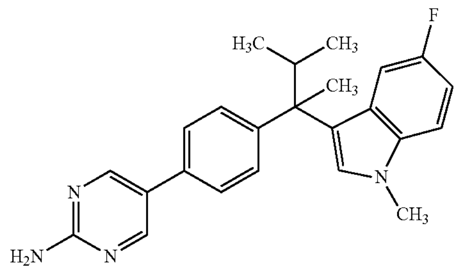 [SMILES: CC(C)C(C)(c1ccc(-c2cnc(N)nc2)cc1)c1cn(C)c2ccc(F)cc12] | 74 | 4.88 | 389.42 | A |
| 32 | 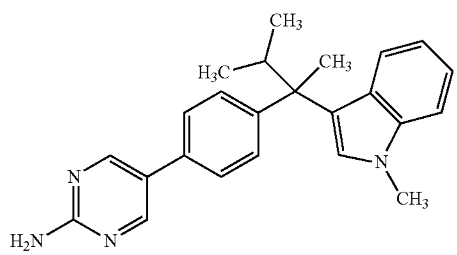 [SMILES: CC(C)C(C)(c1ccc(-c2cnc(N)nc2)cc1)c1cn(C)c2ccccc12] | 74 | 4.86 | 374.28 | A |
| 33 | 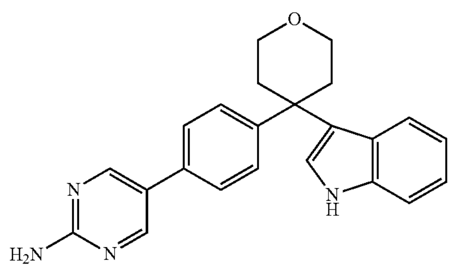 [SMILES: Nc1ncc(-c2ccc(C3(c4c[nH]c5ccccc45)CCOCC3)cc2)cn1] | 74 | 3.58 | 374.31 | A |
| 34 | 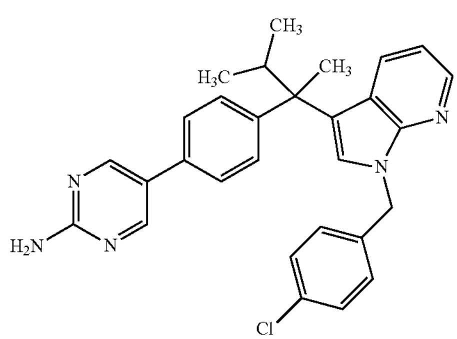 [SMILES: CC(C)C(C)(c1ccc(-c2cnc(N)nc2)cc1)c1cn(Cc2ccc(Cl)cc2)c2ncccc12] | 74 | 5.25 | 482.17/ 484.17 | A |
| 35 | 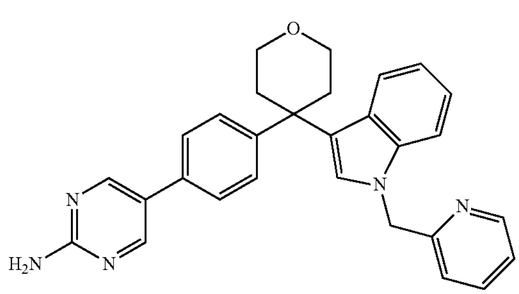 [SMILES: Nc1ncc(-c2ccc(C3(c4cn(Cc5ccccn5)c5ccccc45)CCOCC3)cc2)cn1] | 74 | 3.63 | 462.22 | A |

TABLE 2-continued

| Example | Structure | Synthesis Method | Retention time (min) | m/z [M + H]+ | LCMS method |
|---|---|---|---|---|---|
| 36 | 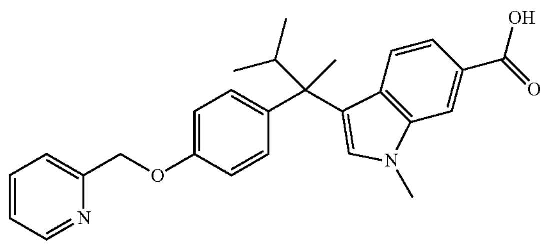 [SMILES: CC(C)C(C)(c1ccc(OCc2ccccn2)cc1)c1cn(C)c2cc(C(=O)O)ccc12] | 81 | 4.51 | 429.23 | A |
| 37 | 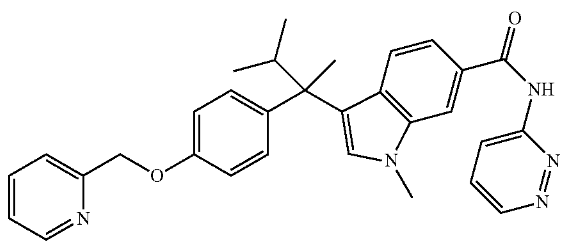 [SMILES: CC(C)C(C)(c1ccc(OCc2ccccn2)cc1)c1cn(C)c2cc(C(=O)Nc3cccnn3)ccc12] | 83 | 4.62 | 506.26 | A |
| 38 | 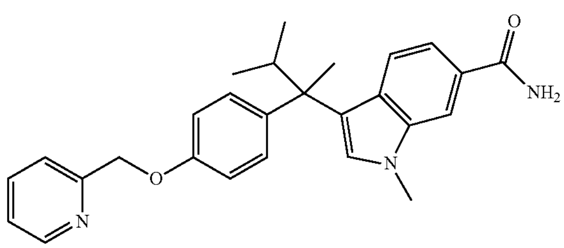 [SMILES: CC(C)C(C)(c1ccc(OCc2ccccn2)cc1)c1cn(C)c2cc(C(N)=O)ccc12] | 82 | 4.15 | 428.22 | A |
| 39 | 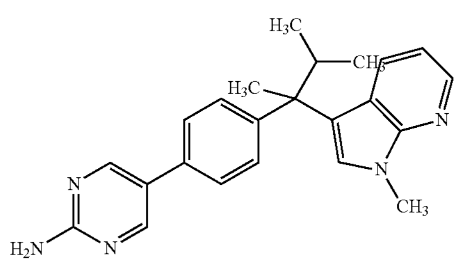 [SMILES: CC(C)C(C)(c1ccc(-c2cnc(N)nc2)cc1)c1cn(C)c2ncccc12] | 74 | 4.04 | 372.2 | A |
| 40 | 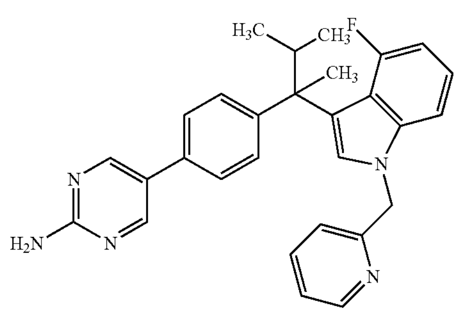 [SMILES: CC(C)C(C)(c1ccc(-c2cnc(N)nc2)cc1)c1cn(Cc2ccccn2)c2cccc(F)c12] | 74 | 4.61 | 466.27 | A |

TABLE 2-continued

| Example | Structure | Synthesis Method | Retention time (min) | m/z [M + H]$^+$ | LCMS method |
|---|---|---|---|---|---|
| 41 | 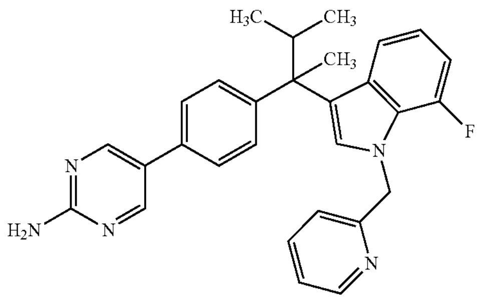 [SMILES: CC(C)C(C)(c1ccc(-c2cnc(N)nc2)cc1)c1cn(Cc2ccccn2)c2c(F)cccc12] | 74 | 4.68 | 466.27 | A |
| 42 | 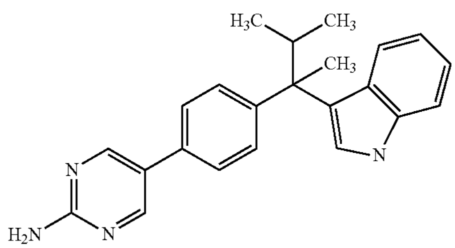 [SMILES: CC(C)C(C)(c1ccc(-c2cnc(N)nc2)cc1)c1c[nH]c2ccccc12] | 74 | 4.45 | 357.19 | A |
| 43 | 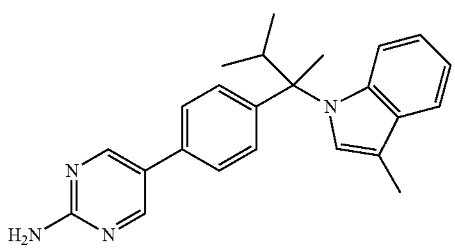 [SMILES: Cc1cn(C(C)(c2ccc(-c3cnc(N)nc3)cc2)C(C)C)c2ccccc12] | 74 | 4.79 | 374.17 | A |
| 44 | 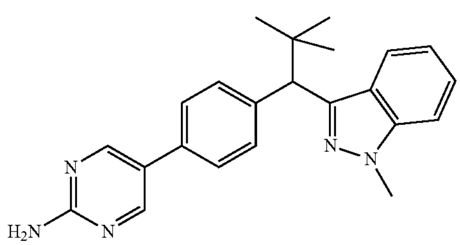 [SMILES: Cn1nc(C(c2ccc(-c3cnc(N)nc3)cc2)C(C)(C)C)c2ccccc21] | 84 | 4.92 | 374.18 | A |
| 45 | 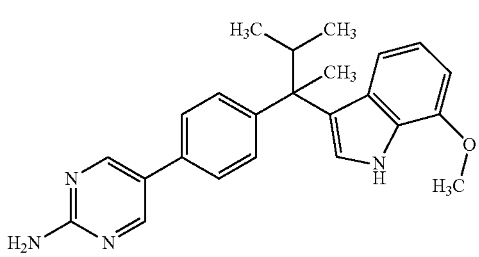 [SMILES: COc1cccc2c(C(C)(c3ccc(-c4cnc(N)nc4)cc3)C(C)C)c[nH]c12] | 74 | 4.53 | 387.17 | A |

TABLE 2-continued

| Example | Structure | Synthesis Method | Retention time (min) | m/z [M + H]+ | LCMS method |
|---|---|---|---|---|---|
| 46 | 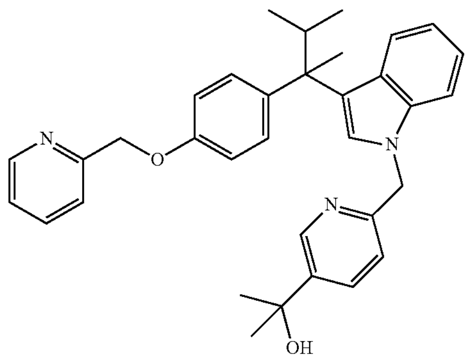 [SMILES: CC(C)C(C)(c1ccc(OCc2ccccn2)cc1)c1cn(Cc2ccc(C(C)(C)O)cn2)c2ccccc12] | 80 | 4.66 | 520.31 | A |
| 47 | 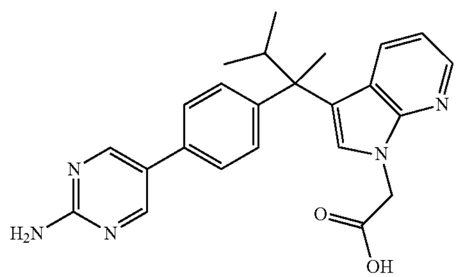 [SMILES: CC(C)C(C)(c1ccc(-c2cnc(N)nc2)cc1)c1cn(CC(=O)O)c2ncccc12] | 77 | 3.69 | 416.19 | A |
| 48 | 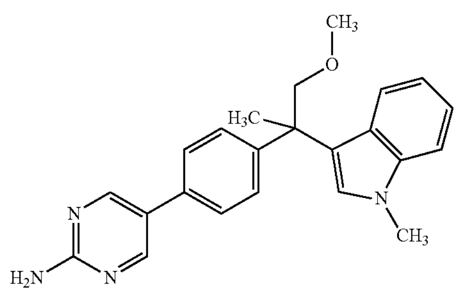 | 74 | 4.25 | 373.18 | A |
| 49 | 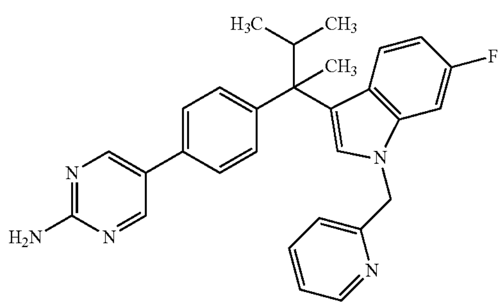 [SMILES: CC(C)C(C)(c1ccc(-c2cnc(N)nc2)cc1)c1cn(Cc2ccccn2)c2cc(F)ccc12] | 74 | 4.68 | 466.2 | A |
| 50 | 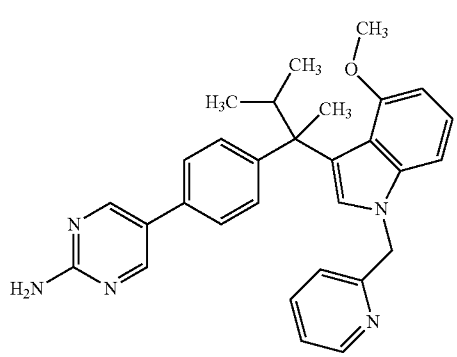 [SMILES: COc1cccc2c1c(C(C)(c1ccc(-c3cnc(N)nc3)cc1)C(C)C)cn2Cc1ccccn1] | 74 | 4.66 | 478.23 | A |

TABLE 2-continued
| Example | Structure | Synthesis Method | Retention time (min) | m/z [M + H]+ | LCMS method |
|---|---|---|---|---|---|
| 51 | 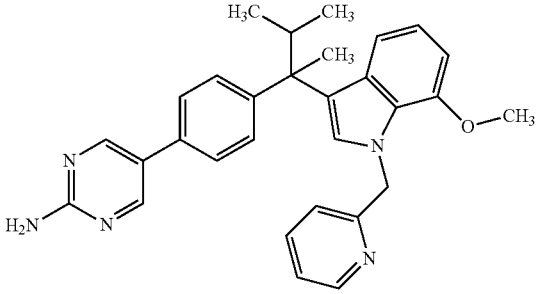 [SMILES: COc1cccc2c(C(C)(c3ccc(-c4cnc(N)nc4)cc3)C(C)C)cn(Cc3ccccn3)c12] | 74 | 4.38 | 478.23 | A |
| 52 | 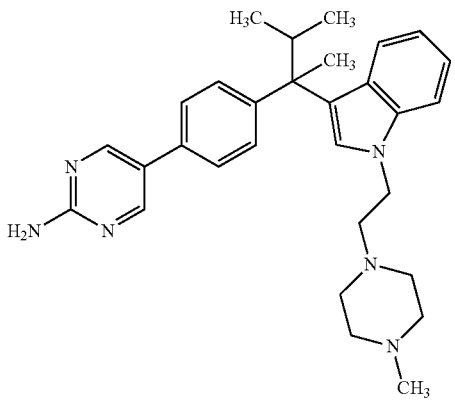 [SMILES: CC(C)C(C)(c1ccc(-c2cnc(N)nc2)cc1)c1cn(CCN2CCN(C)CC2)c2ccccc12] | 74 | 3.29 | 483.33 | A |
| 53 | 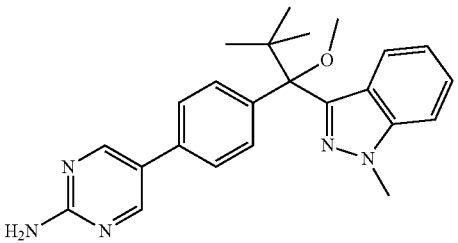 [SMILES: COC(c1ccc(-c2cnc(N)nc2)cc1)(c1nn(C)c2ccccc12)C(C)(C)C] | 85 | 5.26 | 402.20 | A |
| 54 | 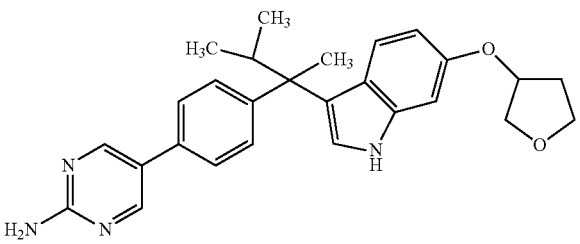 [SMILES: CC(C)C(C)(c1ccc(-c2cnc(N)nc2)cc1)c1c[nH]c2cc(OC3CCOC3)ccc12] | 74 | 4.60 | 443.21 | A |
| 55 | 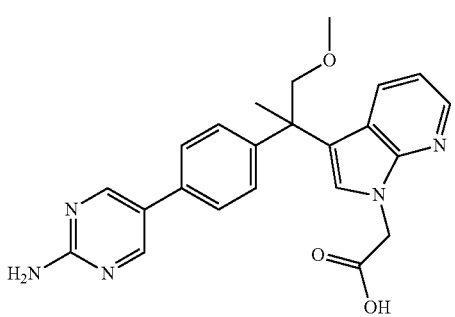 [SMILES: COCC(C)(c1ccc(-c2cnc(N)nc2)cc1)c1cn(CC(=O)O)c2ncccc12] | 77 | 3.24 | 418.16 | A |

TABLE 2-continued

| Example | Structure | Synthesis Method | Retention time (min) | m/z [M + H]+ | LCMS method |
|---|---|---|---|---|---|
| 56 | 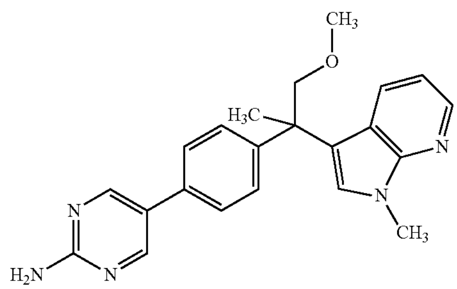 [SMILES: COCC(C)(c1ccc(-c2cnc(N)nc2)cc1)c1cn(C)c2ncccc12] | 74 | 3.46 | 373.13 | A |
| 57 | 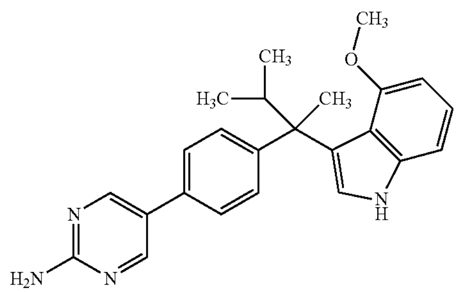 [SMILES: COc1cccc2[nH]cc(C(C)(c3ccc(-c4cnc(N)nc4)cc3)C(C)C)c12] | 74 | 4.54 | 387.23 | A |
| 58 | 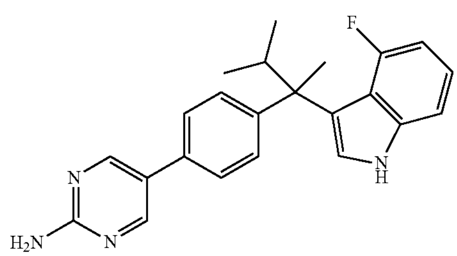 [SMILES: CC(C)C(C)(c1ccc(-c2cnc(N)nc2)cc1)c1c[nH]c2cccc(F)c12] | 74 | 4.44 | 375.14 | A |
| 59 | 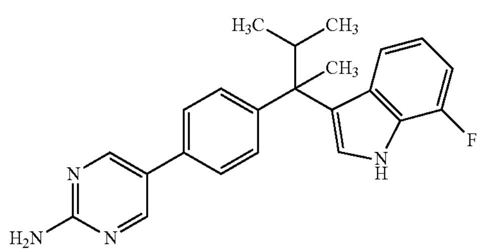 [SMILES: CC(C)C(C)(c1ccc(-c2cnc(N)nc2)cc1)c1c[nH]c2c(F)cccc12] | 74 | 4.62 | 375.15 | A |
| 60 | 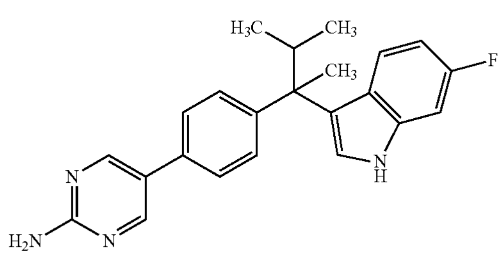 [SMILES: CC(C)C(C)(c1ccc(-c2cnc(N)nc2)cc1)c1c[nH]c2cc(F)ccc12] | 74 | 4.53 | 375.14 | A |

TABLE 2-continued

| Example | Structure | Synthesis Method | Retention time (min) | m/z [M + H]+ | LCMS method |
|---|---|---|---|---|---|
| 61 | 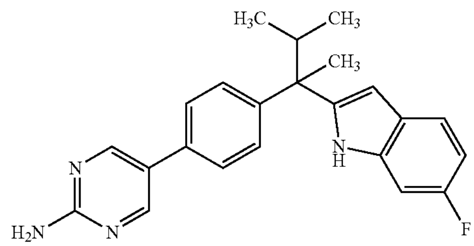 [SMILES: CC(C)C(C)(c1ccc(-c2cnc(N)nc2)cc1)c1cc2ccc(F)cc2[nH]1] | 74 | 4.88 | 375.18 | A |
| 62 | 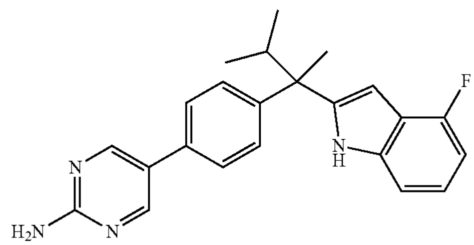 [SMILES: CC(C)C(C)(c1ccc(-c2cnc(N)nc2)cc1)c1cc2c(F)cccc2[nH]1] | 74 | 4.73 | 375.14 | A |
| 63 | 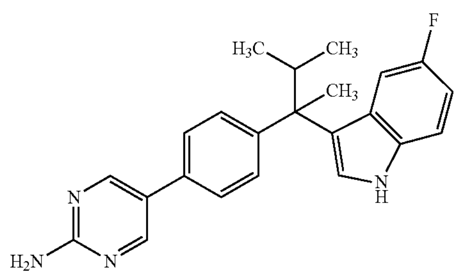 [SMILES: CC(C)C(C)(c1ccc(-c2cnc(N)nc2)cc1)c1c[nH]c2ccc(F)cc12] | 74 | 4.50 | 375.2 | A |
| 64 | 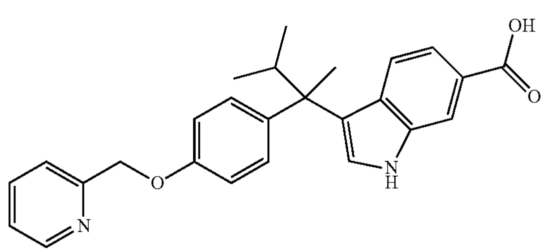 [SMILES: CC(C)C(C)(c1ccc(OCc2ccccn2)cc1)c1c[nH]c2cc(C(=O)O)ccc12] | 79 | 4.29 | 415.14 | A |
| 65 | 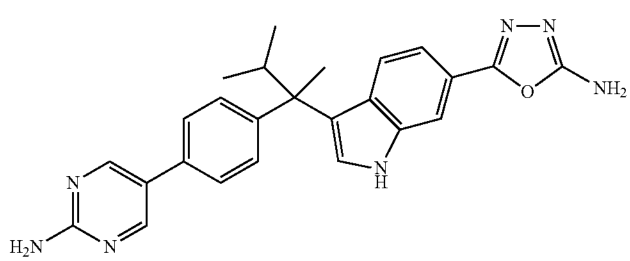 [SMILES: CC(C)C(C)(c1ccc(-c2cnc(N)nc2)cc1)c1c[nH]c2cc(-c3nnc(N)o3)ccc12] | 78 | 3.75 | 440.2 | A |
| 66 | 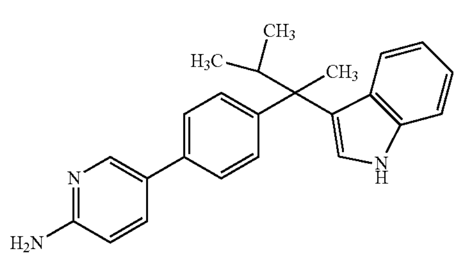 [SMILES: CC(C)C(C)(c1ccc(-c2ccc(N)nc2)cc1)c1c[nH]c2ccccc12] | 74 | 3.48 | 356.18 | A |

TABLE 2-continued

| Example | Structure | Synthesis Method | Retention time (min) | m/z [M + H]+ | LCMS method |
|---|---|---|---|---|---|
| 67 | 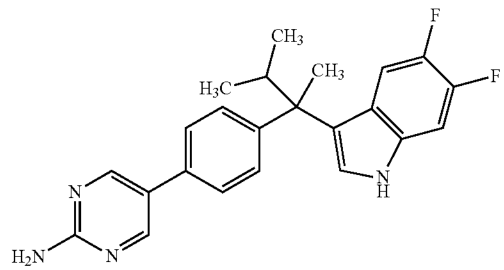 [SMILES: CC(C)C(C)(c1ccc(-c2cnc(N)nc2)cc1)c1c[nH]c2cc(F)c(F)cc12] | 74 | 4.69 | 393.15 | A |
| 68 | 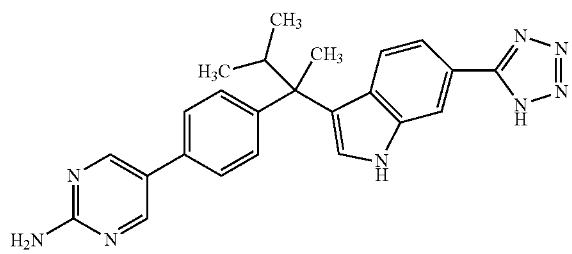 [SMILES: CC(C)C(C)(c1ccc(-c2cnc(N)nc2)cc1)c1c[nH]c2cc(-c3nnn[nH]3)ccc12] | 74 | 3.88 | 425.14 | A |
| 69 | 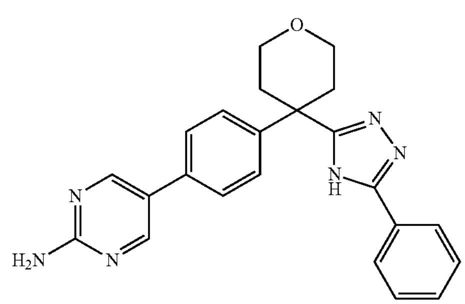 [SMILES: Nc1ncc(-c2ccc(C3(c4nnc(-c5ccccc5)[nH]4)CCOCC3)cc2)cn1] | 74 | 3.36 | 399.19 | A |
| 70 | 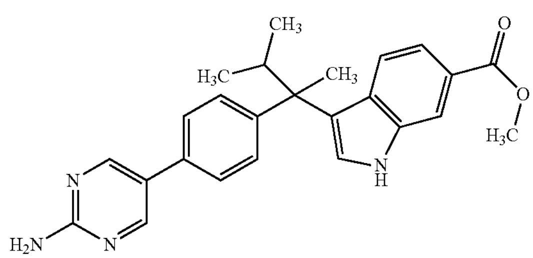 [SMILES: COC(=O)c1ccc2c(C(C)(c3ccc(-c4cnc(N)nc4)cc3)C(C)C)c[nH]c2c1] | 74 | 4.48 | 415.1 | A |
| 74 | 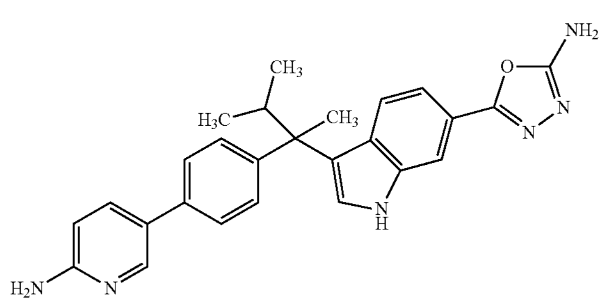 [SMILES: CC(C)C(C)(c1ccc(-c2ccc(N)nc2)cc1)c1c[nH]c2cc(-c3nnc(N)o3)ccc12] | 74 | 3.17 | 439.18 | A |

TABLE 2-continued

| Example | Structure | Synthesis Method | Retention time (min) | m/z [M + H]+ | LCMS method |
|---|---|---|---|---|---|
| 72 | 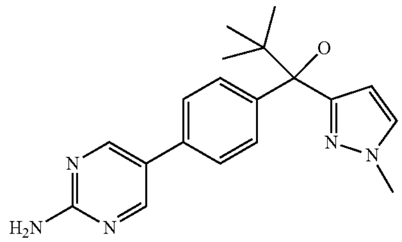 [SMILES: Cn1ccc(C(O)(c2ccc(-c3cnc(N)nc3)cc2)C(C)(C)C)n1] | 74 | 3.89 | 338.17 | A |
| 73 | 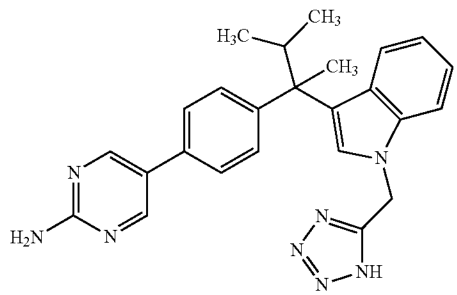 [SMILES: CC(C)C(C)(c1ccc(-c2cnc(N)nc2)cc1)c1cn(Cc2nnn[nH]2)c2ccccc12] | 74 | 4.06 | 439.25 | A |
| 74 | 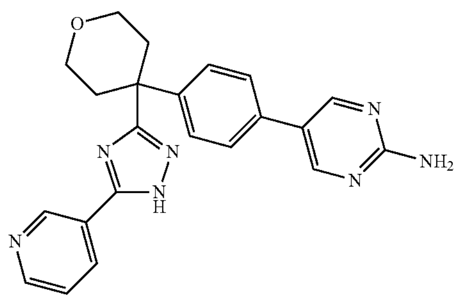 [SMILES: Nc1ncc(-c2ccc(C3(c4n[nH]c(-c5cccnc5)n4)CCOCC3)cc2)cn1] | 74 | 2.62 | 400.11 | A |
| 75 | 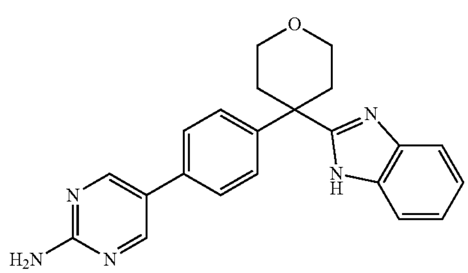 [SMILES: Nc1ncc(-c2ccc(C3(c4nc5ccccc5[nH]4)CCOCC3)cc2)cn1] | 74 | 2.49 | 372.16 | A |
| 76 | 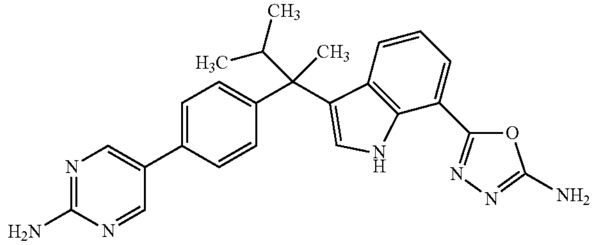 [SMILES: CC(C)C(C)(c1ccc(-c2cnc(N)nc2)cc1)c1c[nH]c2c(-c3nnc(N)o3)cccc12] | 78 | 4.07 | 440.16 | A |

TABLE 2-continued

| Example | Structure | Synthesis Method | Retention time (min) | m/z [M + H]+ | LCMS method |
|---|---|---|---|---|---|
| 77 | 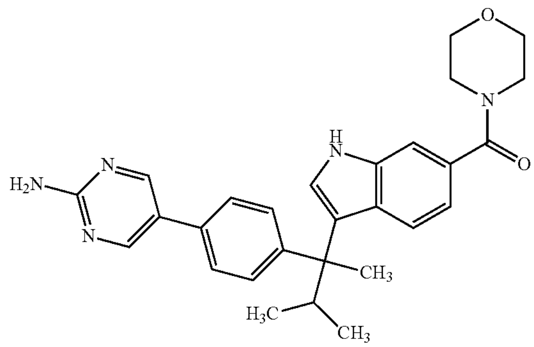 [SMILES: CC(C)C(C)(c1ccc(-c2cnc(N)nc2)cc1)c1c[nH]c2cc(C(=O)N3CCOCC3)ccc12] | 74 | 3.90 | 470.22 | A |
| 78 | 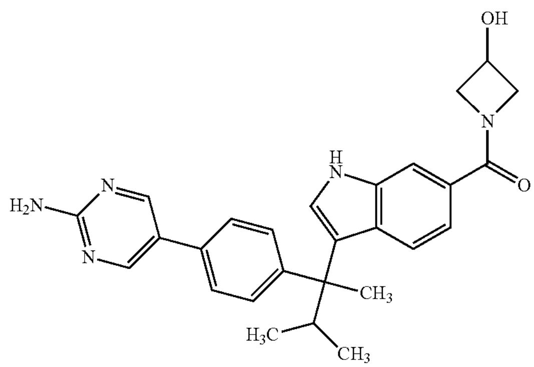 [SMILES: CC(C)C(C)(c1ccc(-c2cnc(N)nc2)cc1)c1c[nH]c2cc(C(=O)N3CC(O)C3)ccc12] | 74 | 3.61 | 456.22 | A |
| 79 | 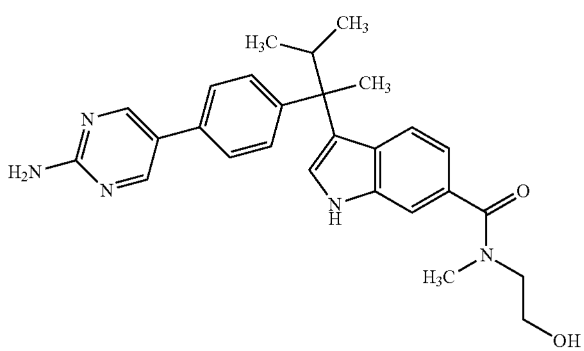 [SMILES: CC(C)C(C)(c1ccc(-c2cnc(N)nc2)cc1)c1c[nH]c2cc(C(=O)N(C)CCO)ccc12] | 74 | 3.64 | 458.23 | A |
| 80 | 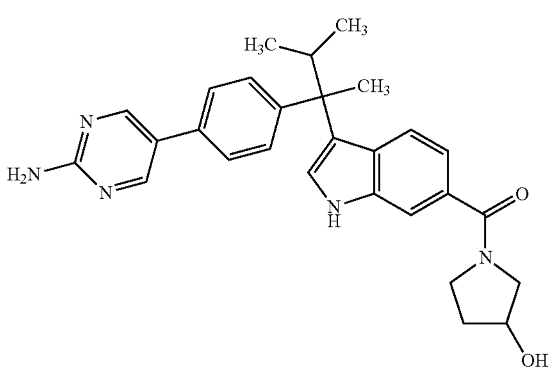 [SMILES: CC(C)C(C)(c1ccc(-c2cnc(N)nc2)cc1)c1c[nH]c2cc(C(=O)N3CCC(O)C3)ccc12] | 74 | 3.61 | 470.23 | A |

TABLE 2-continued

| Example | Structure | Synthesis Method | Retention time (min) | m/z [M + H]+ | LCMS method |
|---|---|---|---|---|---|
| 81 | 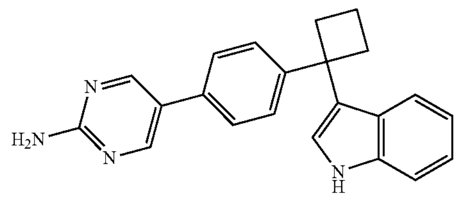 [SMILES: Nc1ncc(-c2ccc(C3(c4c[nH]c5ccccc45)CCC3)cc2)cn1] | 74 | 4.28 | 341.13 | A |
| 82 | 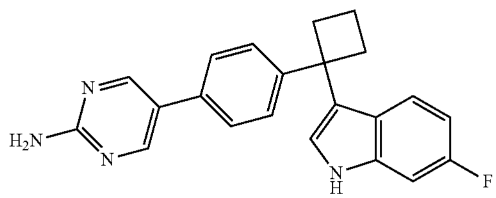 [SMILES: Nc1ncc(-c2ccc(C3(c4c[nH]c5cc(F)ccc45)CCC3)cc2)cn1] | 74 | 4.36 | 358.08 | A |
| 83 | 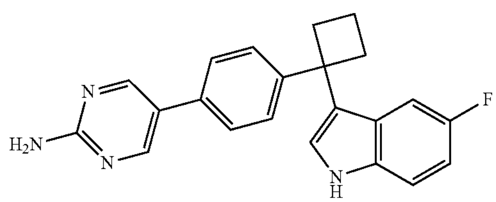 [SMILES: Nc1ncc(-c2ccc(C3(c4c[nH]c5ccc(F)cc45)CCC3)cc2)cn1] | 74 | 4.32 | 359.06 | A |
| 84 | 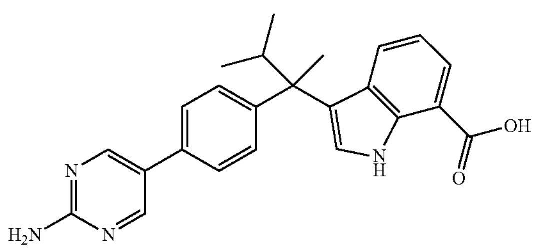 [SMILES: CC(C)C(C)(c1ccc(-c2cnc(N)nc2)cc1)c1c[nH]c2c(C(=O)O)cccc12] | 77 | 4.17 | 401.14 | A |
| 85 | 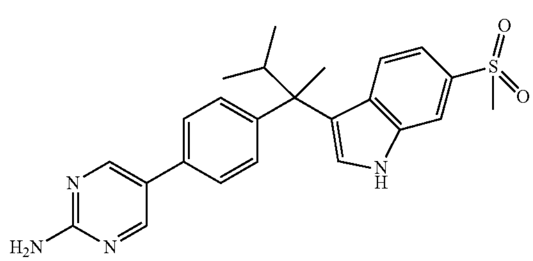 [SMILES: CC(C)C(C)(c1ccc(-c2cnc(N)nc2)cc1)c1c[nH]c2cc(S(C)(=O)=O)ccc12] | 74 | 4.01 | 435.09 | A |
| 86 | 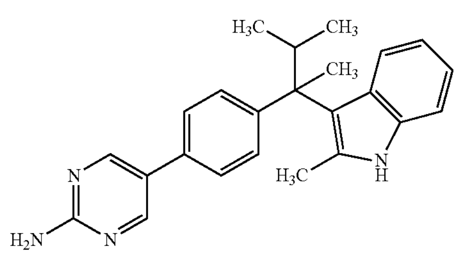 [SMILES: Cc1[nH]c2ccccc2c1C(C)(c1ccc(-c2cnc(N)nc2)cc1)C(C)C] | 74 | 4.70 | 374.17 | A |

TABLE 2-continued

| Example | Structure | Synthesis Method | Retention time (min) | m/z [M + H]+ | LCMS method |
|---|---|---|---|---|---|
| 87 | 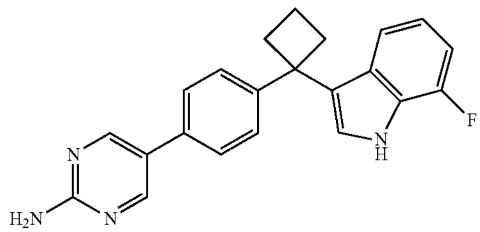 [SMILES: Nc1ncc(-c2ccc(C3(c4c[nH]c5c(F)cccc45)CCC3)cc2)cn1] | 74 | 4.40 | 359.08 | A |
| 88 | 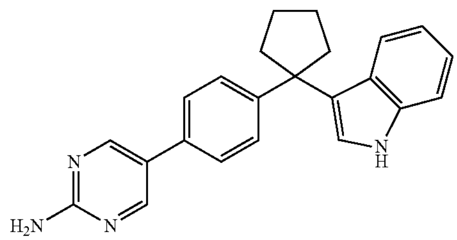 [SMILES: Nc1ncc(-c2ccc(C3(c4c[nH]c5ccccc45)CCCC3)cc2)cn1] | 74 | 4.44 | 355.11 | A |
| 89 | 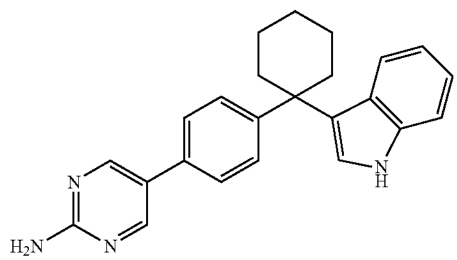 [SMILES: Nc1ncc(-c2ccc(C3(c4c[nH]c5ccccc45)CCCCC3)cc2)cn1] | 74 | 4.63 | 369.15 | A |
| 90 | 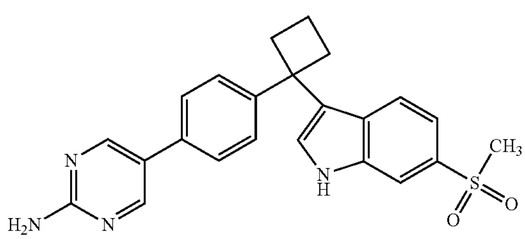 [SMILES: CS(=O)(=O)c1ccc2c(C3(c4ccc(-c5cnc(N)nc5)cc4)CCC3)c[nH]c2c1] | 74 | 3.82 | 419.09 | A |
| 91 | 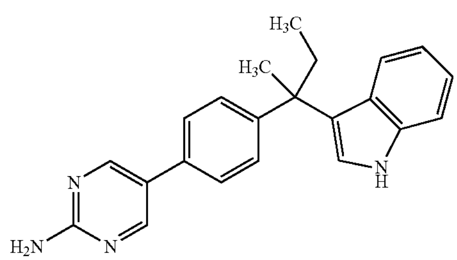 [SMILES: CCC(C)(c1ccc(-c2cnc(N)nc2)cc1)c1c[nH]c2ccccc12] | 74 | 4.35 | 343.15 | A |
| 92 | 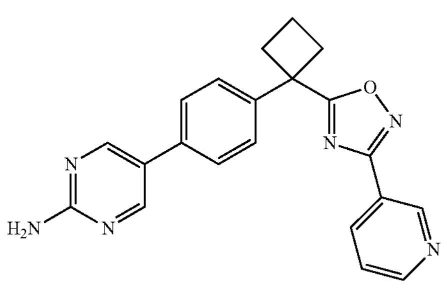 [SMILES: Nc1ncc(-c2ccc(C3(c4nc(-c5cccnc5)no4)CCC3)cc2)cn1] | 74 | 3.91 | 374.11 | A |

TABLE 2-continued
| Example | Structure | Synthesis Method | Retention time (min) | m/z [M + H]+ | LCMS method |
|---|---|---|---|---|---|
| 93 | 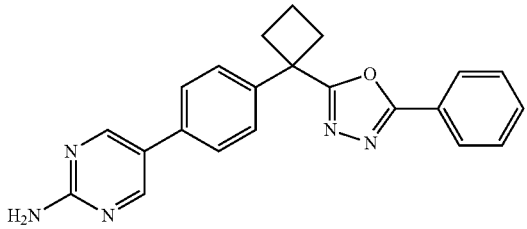 | 74 | 4.06 | 370.16 | A |
| 94 | 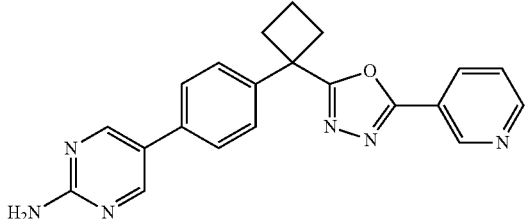 | 74 | 3.50 | 374.03 | A |
| 95 | 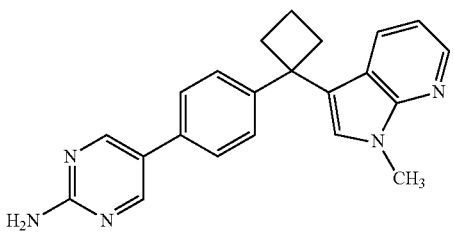 [SMILES: Cn1cc(C2(c3ccc(-c4cnc(N)nc4)cc3)CCC2)c2cccnc21] | 74 | 3.91 | 356.12 | A |
| 96 | 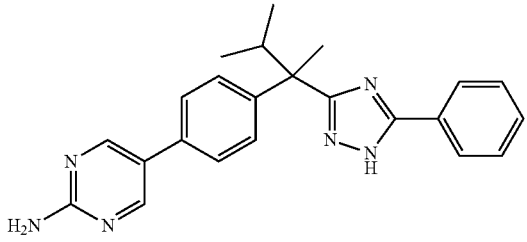 [SMILES: CC(C)C(C)(c1ccc(-c2cnc(N)nc2)cc1)c1n[nH]c(-c2ccccc2)n1] | 74 | 4.03 | 385.15 | A |
| 97 | 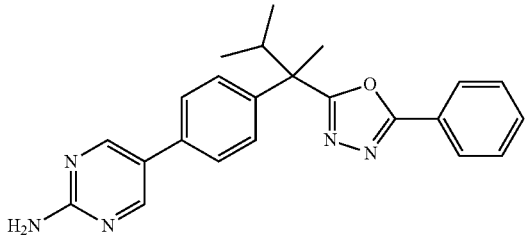 | 74 | 4.36 | 386.16 | A |
| 98 | 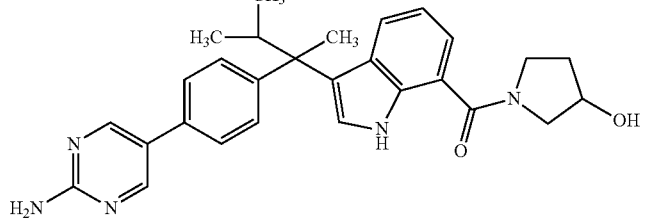 | 74 | 3.79 | 470.24 | A |

TABLE 2-continued
| Example | Structure | Synthesis Method | Retention time (min) | m/z [M + H]+ | LCMS method |
|---|---|---|---|---|---|
| 99 | 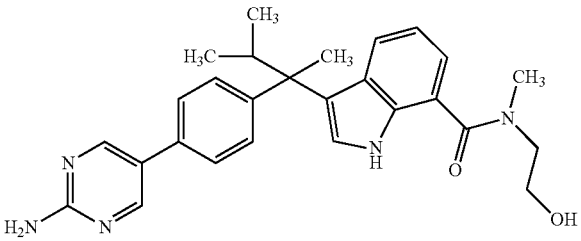 [SMILES: CC(C)C(C)(c1ccc(-c2cnc(N)nc2)cc1)c1c[nH]c2c(C(=O)N(C)CCO)cccc12] | 74 | 3.79 | 458.26 | A |
| 100 | 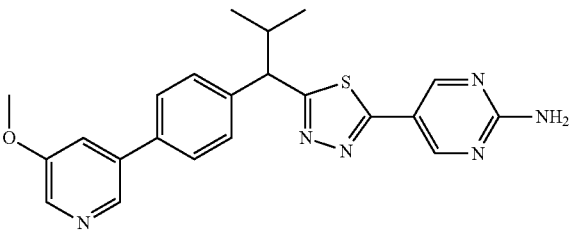 [SMILES: COc1cncc(-c2ccc(C(c3nnc(-c4cnc(N)nc4)s3)C(C)C)cc2)c1] | 74 | NA | 418.7 | F |
| 101 | 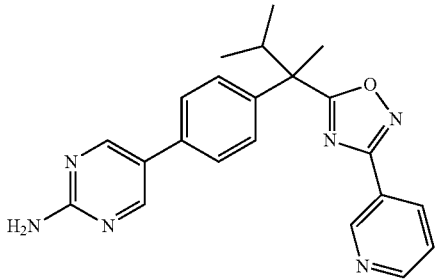 [SMILES: CC(C)C(C)(c1ccc(-c2cnc(N)nc2)cc1)c1nc(-c2cccnc2)no1] | 74 | NA | 387 | F |
| 102 | 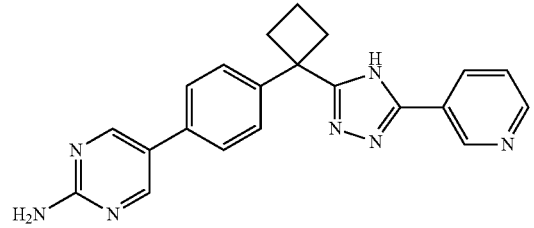 [SMILES: Nc1ncc(-c2ccc(C3(c4nnc(-c5cccnc5)[nH]4)CCC3)cc2)cn1] | 74 | 2.93 | 370.15 | A |
| 103 | 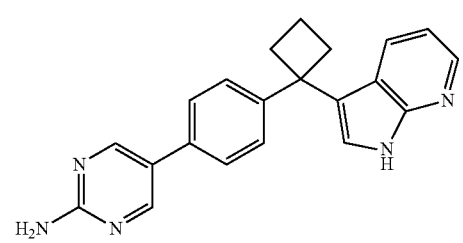 [SMILES: Nc1ncc(-c2ccc(C3(c4c[nH]c5ncccc45)CCC3)cc2)cn1] | 74 | 3.32 | 342.08 | A |
| 104 | 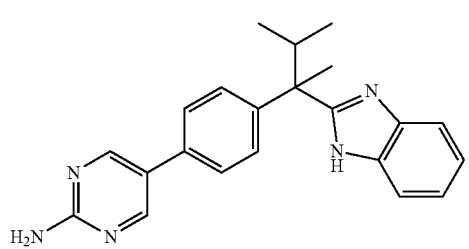 | 74 | 2.79 | 358.12 | A |

TABLE 2-continued
| Example | Structure | Synthesis Method | Retention time (min) | m/z [M + H]+ | LCMS method |
|---|---|---|---|---|---|
| 105 | 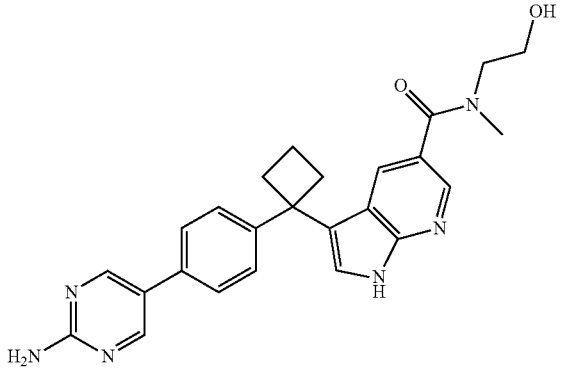 [SMILES: CN(CCO)C(=O)c1cnc2[nH]cc(C3(c4ccc(-c5cnc(N)nc5)cc4)CCC3)c2c1] | 74 | 3.39 | 442.19 | A |
| 106 | 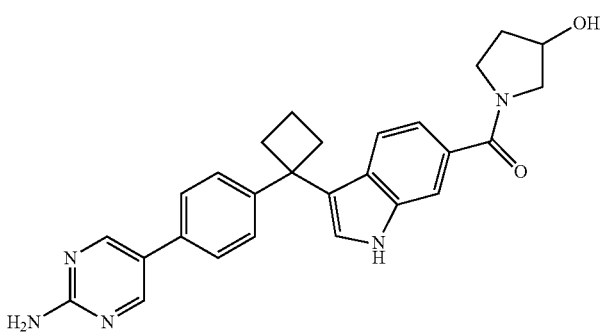 [SMILES: Nc1ncc(-c2ccc(C3(c4c[nH]c5cc(C(=O)N6CCC(O)C6)ccc45)CCC3)cc2)cn1] | 74 | 3.46 | 454.18 | A |
| 107 | 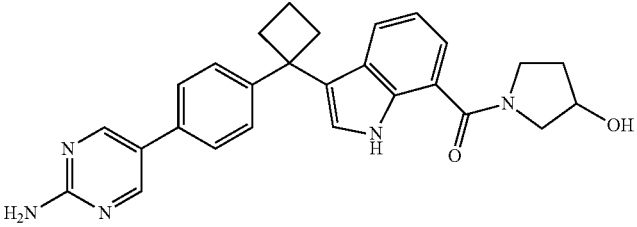 [SMILES: Nc1ncc(-c2ccc(C3(c4c[nH]c5c(C(=O)N6CCC(O)C6)cccc45)CCC3)cc2)cn1] | 74 | 3.66 | 454.23 | A |
| 108 | 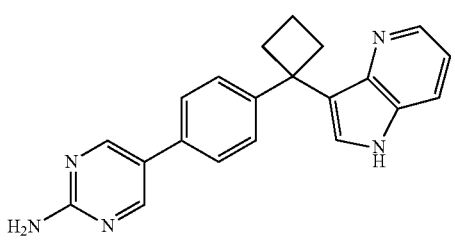 | 74 | 2.72 | 342.08 | A |
| 109 | 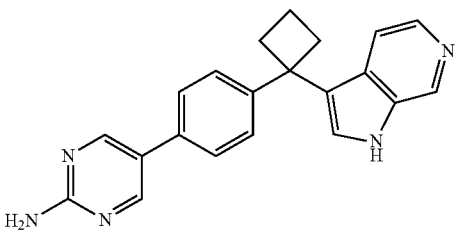 [SMILES: Nc1ncc(-c2ccc(C3(c4c[nH]c5cnccc45)CCC3)cc2)cn1] | 74 | 2.88 | 342.08 | A |

TABLE 2-continued
| Example | Structure | Synthesis Method | Retention time (min) | m/z [M + H]+ | LCMS method |
|---|---|---|---|---|---|
| 110 | 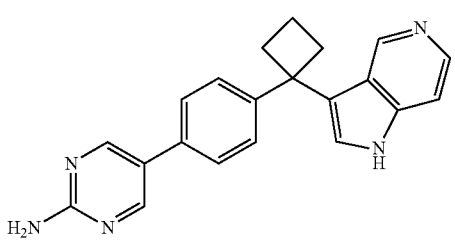 [SMILES: Nc1ncc(-c2ccc(C3(c4c[nH]c5ccncc45)CCC3)cc2)cn1] | 74 | 2.81 | 342.08 | A |
| 111 | 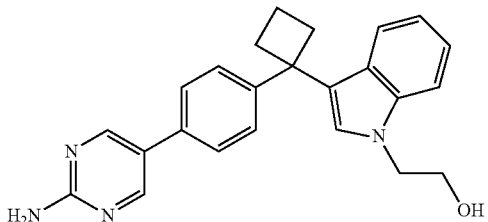 | 74 | 4.10 | 385.08 | A |
| 112 | 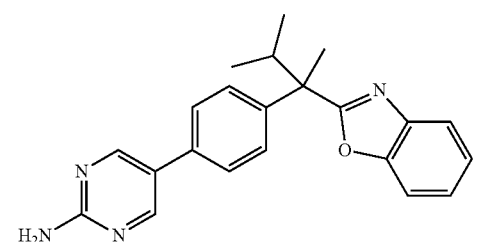 | 74 | 4.56 | 359.14 | A |
| 113 | 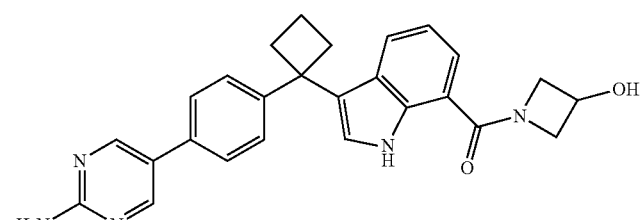 | 74 | 3.68 | 440.15 | A |
| 114 | 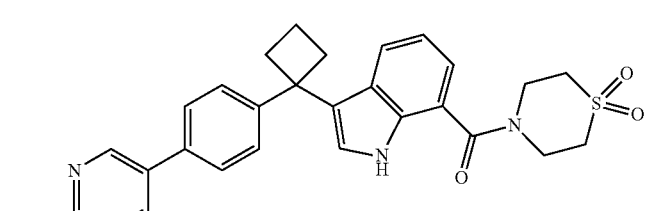 | 74 | 3.80 | 502.11 | A |
| 115 | 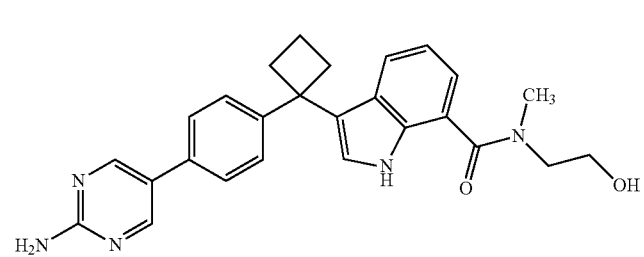 [SMILES: CN(CCO)C(=O)c1cccc2c(C3(c4ccc(-c5cnc(N)nc5)cc4)CCC3)c[nH]c12] | 74 | 3.61 | 442.27 | A |

TABLE 2-continued

| Example | Structure | Synthesis Method | Retention time (min) | m/z [M + H]+ | LCMS method |
|---|---|---|---|---|---|
| 116 | 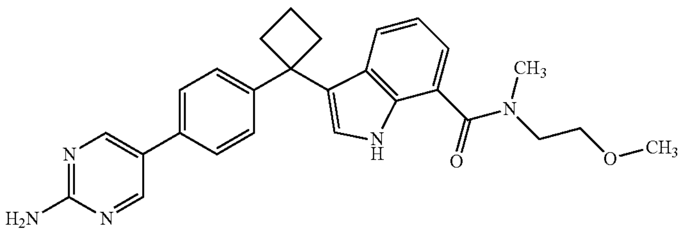 [SMILES: COCCN(C)C(=O)c1cccc2c(C3(c4ccc(-c5cnc(N)nc5)cc4)CCC3)c[nH]c12] | 74 | 3.96 | 456.4 | A |
| 117 | 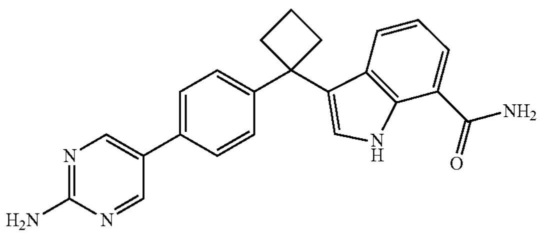 [SMILES: NC(=O)c1cccc2c(C3(c4ccc(-c5cnc(N)nc5)cc4)CCC3)c[nH]c12] | 74 | 3.73 | 384.14 | A |
| 118 | 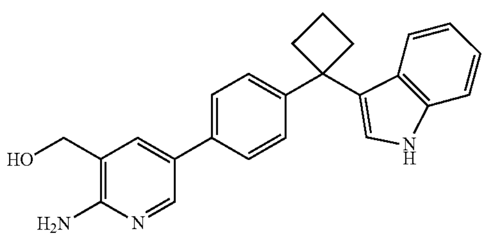 [SMILES: Nc1ncc(-c2ccc(C3(c4c[nH]c5ccccc45)CCC3)cc2)cc1CO] | 76 | 3.23 | 370.13 | A |
| 119 | 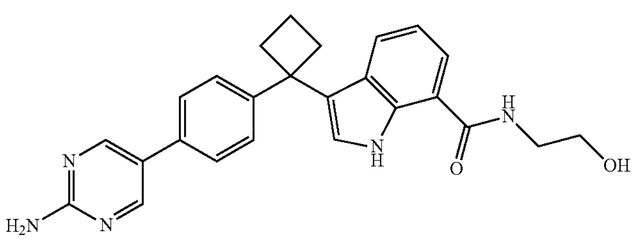 [SMILES: Nc1ncc(-c2ccc(C3(c4c[nH]c5c(C(=O)NCCO)cccc45)CCC3)cc2)cn1] | 74 | 3.62 | 428.16 | A |
| 120 | 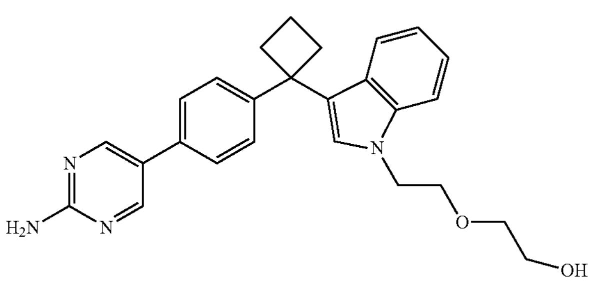 [SMILES: Nc1ncc(-c2ccc(C3(c4cn(CCOCCO)c5ccccc45)CCC3)cc2)cn1] | 74 | 4.05 | 429.17 | A |
| 121 | 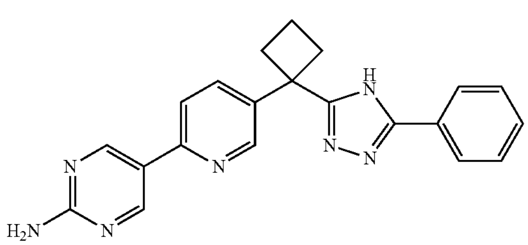 [SMILES: Nc1ncc(-c2ccc(C3(c4nnc(-c5ccccc5)[nH]4)CCC3)cn2)cn1] | 74 | 3.27 | 370.10 | A |

TABLE 2-continued

| Example | Structure | Synthesis Method | Retention time (min) | m/z [M + H]+ | LCMS method |
|---|---|---|---|---|---|
| 122 | 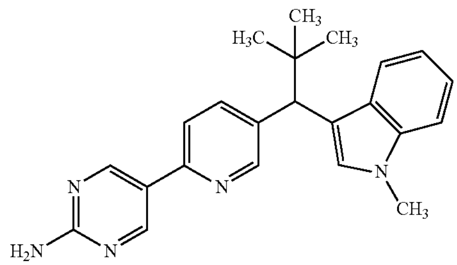 [SMILES: Cn1cc(C(c2ccc(-c3cnc(N)nc3)nc2)C(C)(C)C)c2ccccc21] | 74 | 4.29 | 372.18 | A |
| 123 | 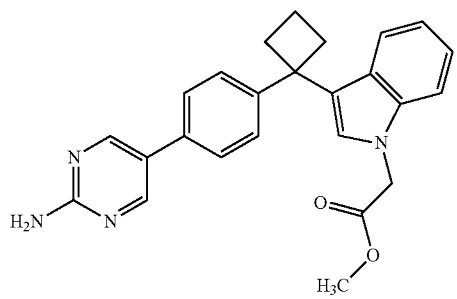 [SMILES: COC(=O)Cn1cc(C2(c3ccc(-c4cnc(N)nc4)cc3)CCC2)c2ccccc21] | 74 | 4.44 | 413.11 | A |
| 124 | 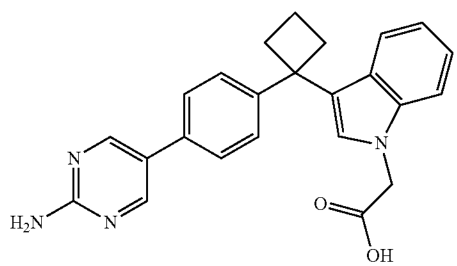 [SMILES: Nc1ncc(-c2ccc(C3(c4cn(CC(=O)O)c5ccccc45)CCC3)cc2)cn1] | 74 | 3.98 | 399.13 | A |
| 125 | 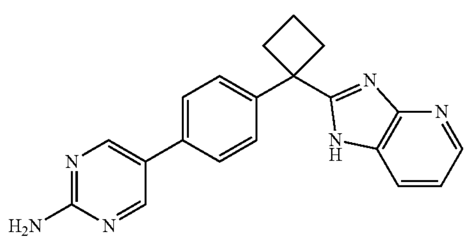 [SMILES: Nc1ncc(-c2ccc(C3(c4nc5ncccc5[nH]4)CCC3)cc2)cn1] | 74 | 2.66 | 343.13 | A |
| 126 | 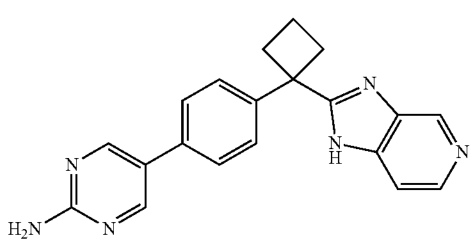 [SMILES: Nc1ncc(-c2ccc(C3(c4nc5cnccc5[nH]4)CCC3)cc2)cn1] | 74 | 2.50 | 343.09 | A |
| 127 | 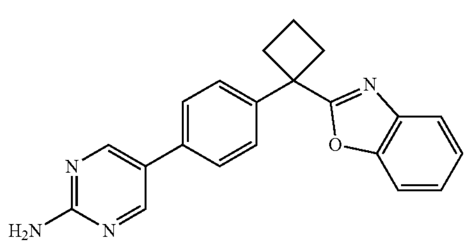 | 74 | 4.24 | 343.09 | A |

TABLE 2-continued

| Example | Structure | Synthesis Method | Retention time (min) | m/z [M + H]+ | LCMS method |
|---|---|---|---|---|---|
| 128 | 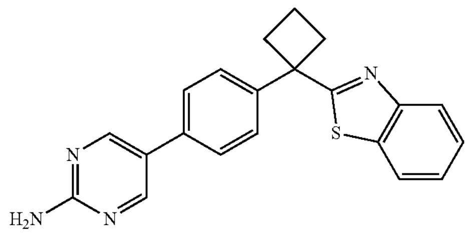 | 74 | 4.55 | 359.08 | A |
| 129 | 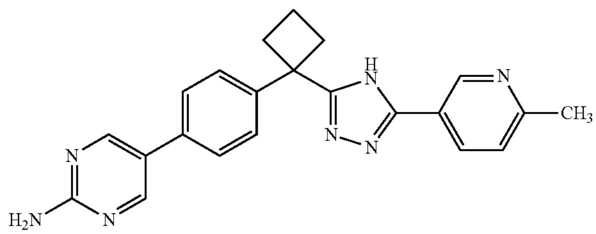 [SMILES: Cc1ccc(-c2nnc(C3(c4ccc(-c5cnc(N)nc5)cc4)CCC3)[nH]2)cn1] | 74 | 2.77 | 384.13 | A |
| 130 | 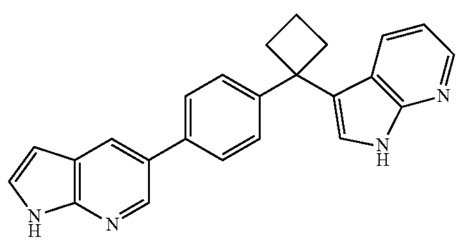 [SMILES: c1cnc2[nH]cc(C3(c4ccc(-c5cnc6[nH]ccc6c5)cc4)CCC3)c2c1] | 74 | 3.83 | 365.12 | A |
| 131 | 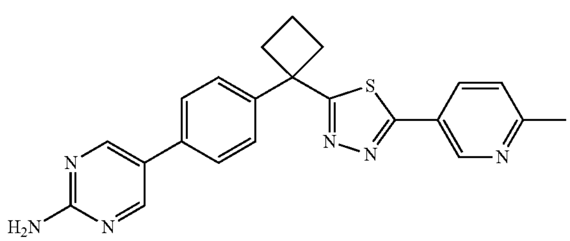 [SMILES: Cc1ccc(-c2nnc(C3(c4ccc(-c5cnc(N)nc5)cc4)CCC3)s2)cn1] | 74 | 3.65 | 401.08 | A |
| 132 | 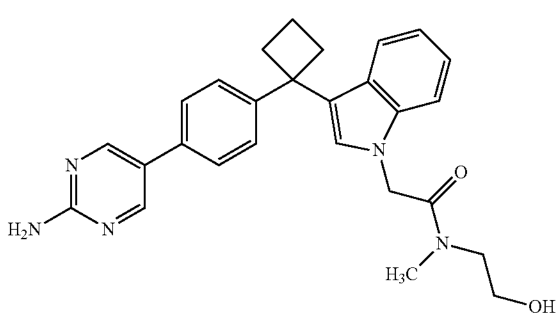 [SMILES: CN(CCO)C(=O)Cn1cc(C2(c3ccc(-c4cnc(N)nc4)cc3)CCC2)c2ccccc21] | 74 | 3.76 | 456.37 | A |

TABLE 2-continued

| Example | Structure | Synthesis Method | Retention time (min) | m/z [M + H]+ | LCMS method |
|---|---|---|---|---|---|
| 133 | 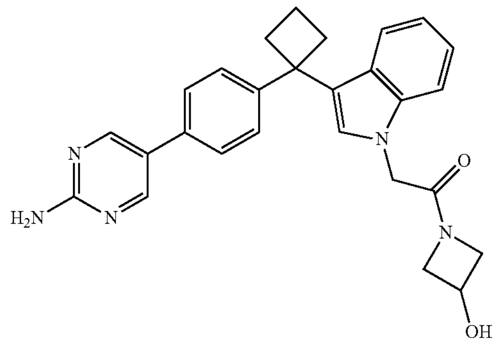 [SMILES: Nc1ncc(-c2ccc(C3(c4cn(CC(=O)N5CC(O)C5)c5ccccc45)CCC3)cc2)cn1] | 74 | 3.67 | 454.28 | A |
| 134 | Chiral | 74 | 3.64 | 454.24 | A |
| 135 | Chiral | 74 | 3.64 | 454.25 | A |
| 136 | 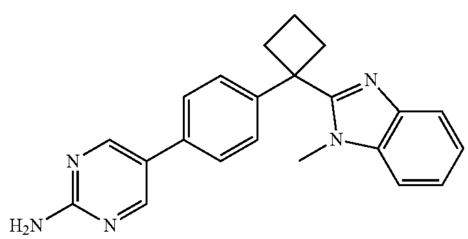 [SMILES: Cn1c(C2(c3ccc(-c4cnc(N)nc4)cc3)CCC2)nc2ccccc21] | 74 | 2.79 | 356.12 | A |
| 137 | 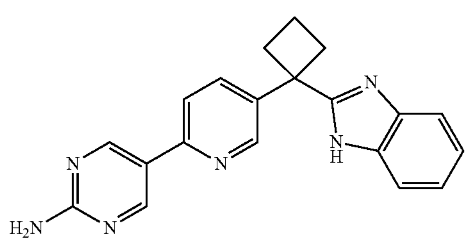 [SMILES: Nc1ncc(-c2ccc(C3(c4nc5ccccc5[nH]4)CCC3)cn2)cn1] | 74 | 2.53 | 343.09 | A |
| 138 | 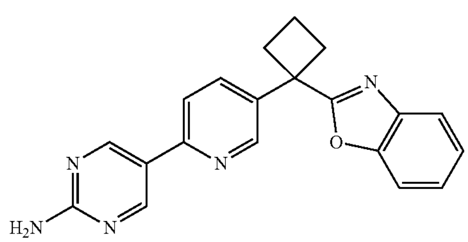 [SMILES: Nc1ncc(-c2ccc(C3(c4nc5ccccc5o4)CCC3)cn2)cn1] | 74 | 3.86 | 344.09 | A |

TABLE 2-continued
| Example | Structure | Synthesis Method | Retention time (min) | m/z [M + H]+ | LCMS method |
|---|---|---|---|---|---|
| 139 | 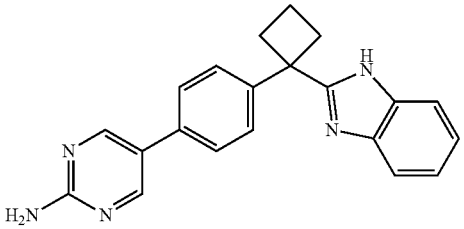 | 74 | 2.74 | 342.14 | A |
| 140 | 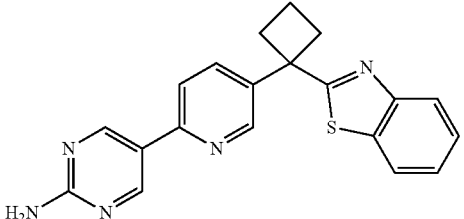 | 74 | 4.19 | 360.09 | A |
| 141 | 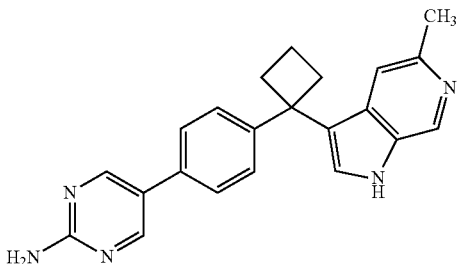 | 74 | 2.95 | 356.12 | A |
| 142 | 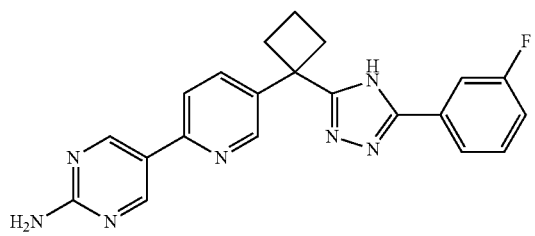 [SMILES: Nc1ncc(-c2ccc(C3(c4nnc(-c5cccc(F)c5)[nH]4)CCC3)cn2)cn1] | 74 | 3.57 | 388.11 | A |
| 143 | 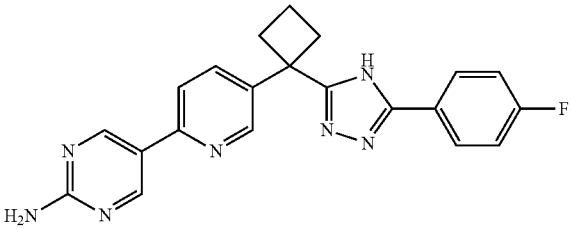 [SMILES: Nc1ncc(-c2ccc(C3(c4nnc(-c5ccc(F)cc5)[nH]4)CCC3)cn2)cn1] | 74 | 3.51 | 388.11 | A |
| 144 | 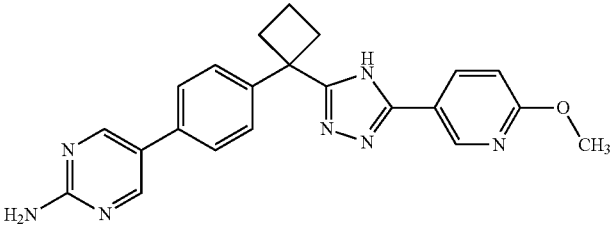 [SMILES: COc1ccc(-c2nnc(C3(c4ccc(-c5cnc(N)nc5)cc4)CCC3)[nH]2)cn1] | 74 | 3.57 | 400.14 | A |

TABLE 2-continued

| Example | Structure | Synthesis Method | Retention time (min) | m/z [M + H]+ | LCMS method |
|---|---|---|---|---|---|
| 145 | 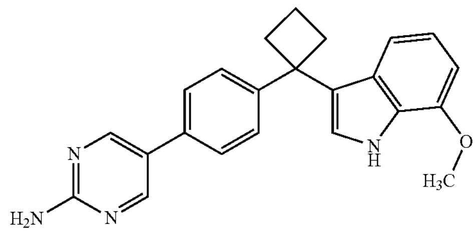 [SMILES: COc1cccc2c(C3(c4ccc(-c5cnc(N)nc5)cc4)CCC3)c[nH]c12] | 74 | 3.29 | 372.11 | A |
| 146 | 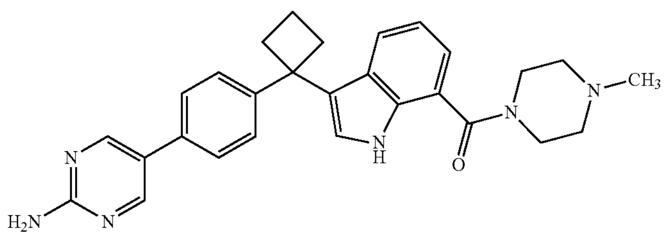 [SMILES: CN1CCN(C(=O)c2cccc3c(C4(c5ccc(-c6cnc(N)nc6)cc5)CCC4)c[nH]c23)CC1] | 74 | 3.03 | 467.22 | A |
| 147 | 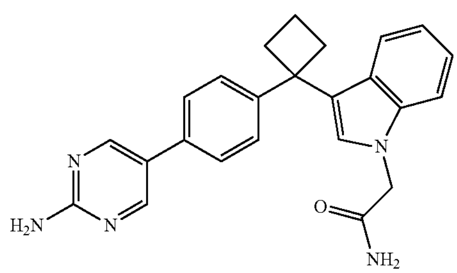 [SMILES: NC(=O)Cn1cc(C2(c3ccc(-c4cnc(N)nc4)cc3)CCC2)c2ccccc21] | 74 | 3.83 | 398.18 | A |
| 148 | 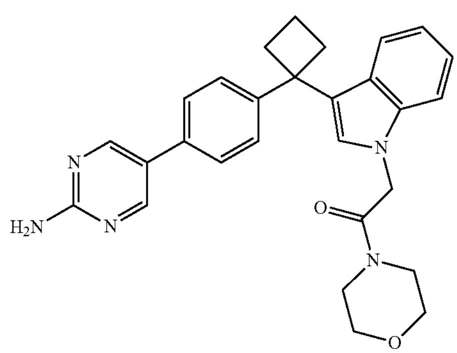 [SMILES: Nc1ncc(-c2ccc(C3(c4cn(CC(=O)N5CCOCC5)c5ccccc45)CCC3)cc2)cn1] | 74 | 4.05 | 468.29 | A |
| 149 | 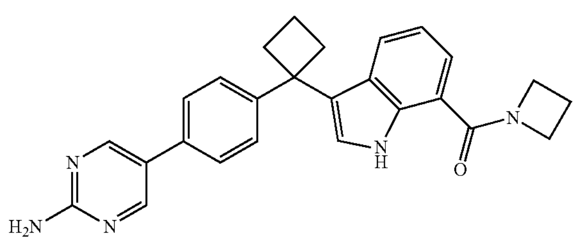 [SMILES: Nc1ncc(-c2ccc(C3(c4c[nH]c5c(C(=O)N6CCC6)cccc45)CCC3)cc2)cn1] | 74 | 4.25 | 424.27 | A |

TABLE 2-continued

| Example | Structure | Synthesis Method | Retention time (min) | m/z [M + H]+ | LCMS method |
| --- | --- | --- | --- | --- | --- |
| 150 | 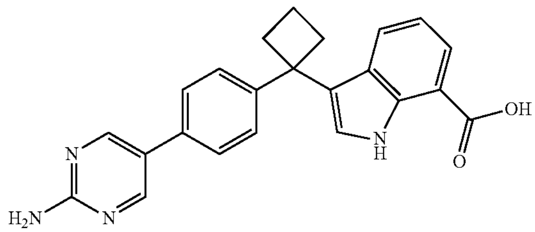 [SMILES: Nc1ncc(-c2ccc(C3(c4c[nH]c5c(C(=O)O)cccc45)CCC3)cc2)cn1] | 74 | 3.98 | 385.08 | A |
| 151 | 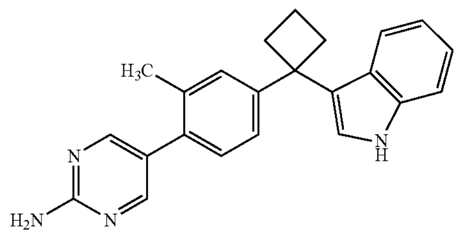 [SMILES: Cc1cc(C2(c3c[nH]c4ccccc34)CCC2)ccc1-c1cnc(N)nc1] | 74 | 4.34 | 355.17 | A |
| 152 | 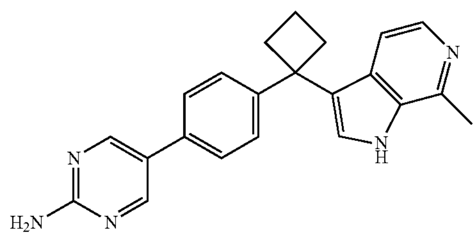 [SMILES: Cc1nccc2c(C3(c4ccc(-c5cnc(N)nc5)cc4)CCC3)c[nH]c12] | 74 | 2.82 | 356.17 | A |
| 153 | 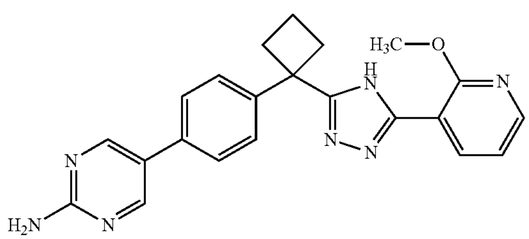 [SMILES: COc1ncccc1-c1nnc(C2(c3ccc(-c4cnc(N)nc4)cc3)CCC2)[nH]1] | 74 | 3.61 | 400.14 | A |
| 154 | 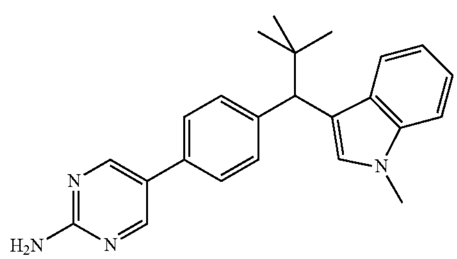 | 74 | 4.88 | 374.08 | A |
| 155 | 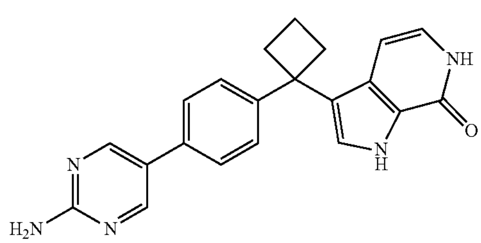 [SMILES: Nc1ncc(-c2ccc(C3(c4c[nH]c5c(=O)[nH]ccc45)CCC3)cc2)cn1] | 74 | 3.44 | 358.04 | A |

TABLE 2-continued

| Example | Structure | Synthesis Method | Retention time (min) | m/z [M + H]+ | LCMS method |
|---|---|---|---|---|---|
| 156 | 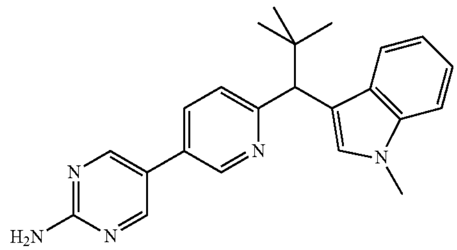 [SMILES: Cn1cc(C(c2ccc(-c3cnc(N)nc3)cn2)C(C)(C)C)c2ccccc21] | 74 | 3.83 | 372.18 | A |
| 157 | 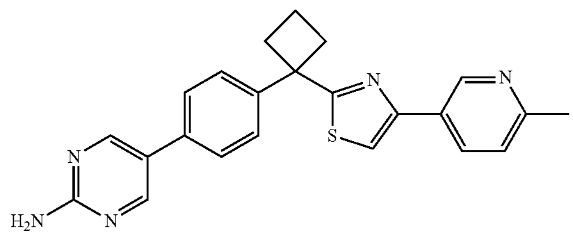 [SMILES: Cc1ccc(-c2csc(C3(c4ccc(-c5cnc(N)nc5)cc4)CCC3)n2)cn1] | 74 | 3.25 | 400.12 | A |
| 158 | 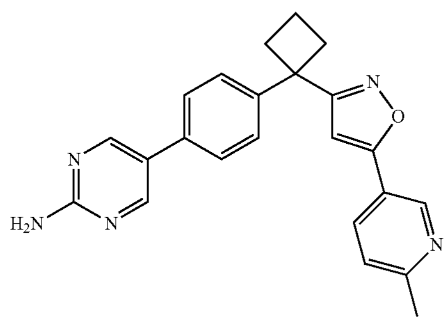 [SMILES: Cc1ccc(-c2cc(C3(c4ccc(-c5cnc(N)nc5)cc4)CCC3)no2)cn1] | 74 | 1.49 | 384.73 | E |
| 159 | 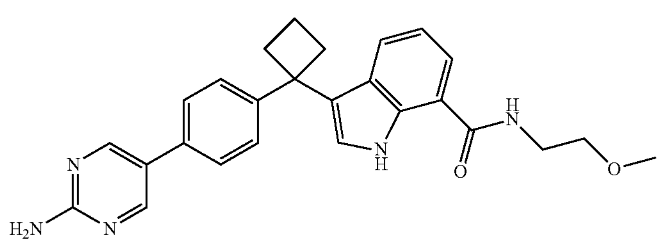 [SMILES: COCCNC(=O)c1cccc2c(C3(c4ccc(-c5cnc(N)nc5)cc4)CCC3)c[nH]c12] | 74 | 4.11 | 442.31 | A |
| 160 | 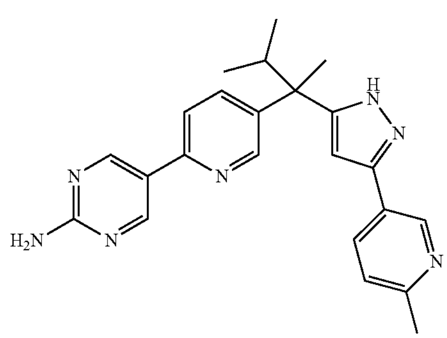 [SMILES: Cc1ccc(-c2cc(C(C)(c3ccc(-c4cnc(N)nc4)nc3)C(C)C)[nH]n2)cn1] | 74 | 0.95 | 400.4 | F |

TABLE 2-continued
| Example | Structure | Synthesis Method | Retention time (min) | m/z [M + H]+ | LCMS method |
|---|---|---|---|---|---|
| 161 | 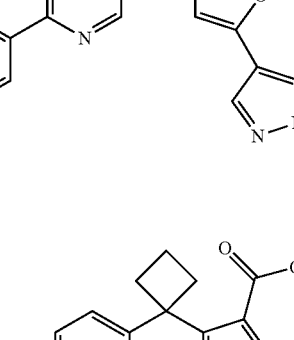 | 74 | 1.35 | 390 | F |
| 162 | 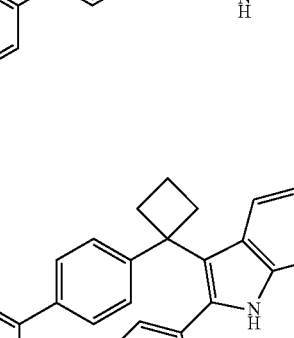 | 75 | 1.36 | 349.4 | E |
| 163 | 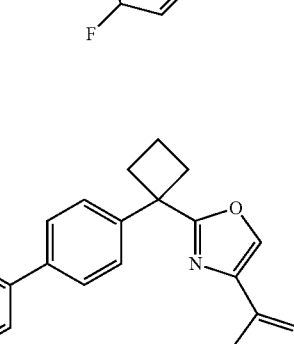 | 75 | 1.66 | 434.5 | E |
| 164 | 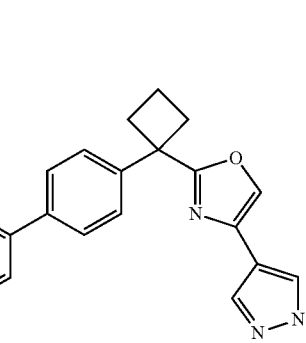 | 74 | 0.77 | 374.3 | E |
| 165 | 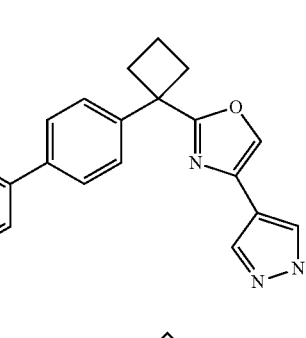 | 75 | 1.53 | 399.4 | E |

TABLE 2-continued

| Example | Structure | Synthesis Method | Retention time (min) | m/z [M + H]+ | LCMS method |
|---|---|---|---|---|---|
| 166 | 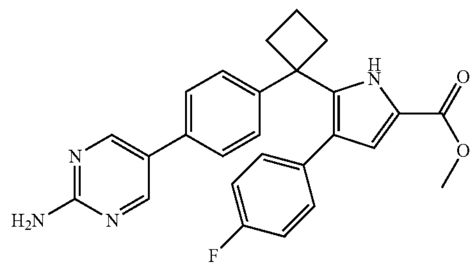 [SMILES: COC(=O)c1cc(-c2ccc(F)cc2)c(C2(c3ccc(-c4cnc(N)nc4)cc3)CCC2)[nH]1] | 74 | 1.57 | 443.4 | F |
| 167 | 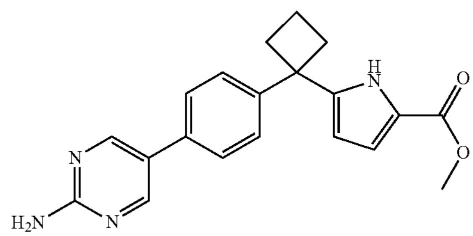 [SMILES: COC(=O)c1ccc(C2(c3ccc(-c4cnc(N)nc4)cc3)CCC2)[nH]1] | 73 | 1.42 | 349.4 | F |
| 168 | 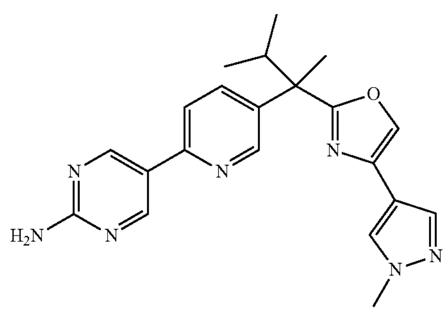 [SMILES: CC(C)C(C)(c1ccc(-c2cnc(N)nc2)nc1)c1nc(-c2cnn(C)c2)co1] | 74 | 1.27 | 390.23 | D |
| 169 | 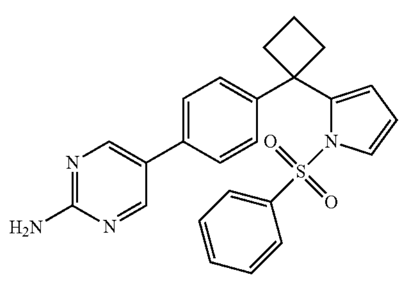 [SMILES: Nc1ncc(-c2ccc(C3(c4cccn4S(=O)(=O)c4ccccc4)CCC3)cc2)cn1] | 73 | 2.27 | 431.23 | D |
| 170 | 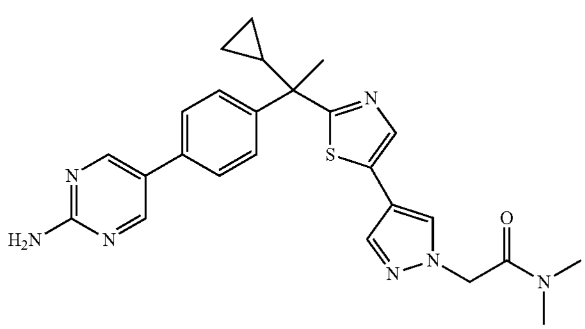 [SMILES: CN(C)C(=O)Cn1cc(-c2cnc(C(C)(c3ccc(-c4cnc(N)nc4)cc3)C3CC3)s2)cn1] | 88 | 0.78 | 474.3 | E |

TABLE 2-continued

| Example | Structure | Synthesis Method | Retention time (min) | m/z [M + H]+ | LCMS method |
|---|---|---|---|---|---|
| 171 | 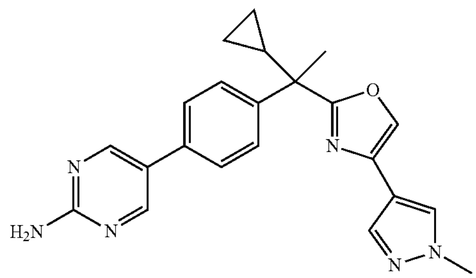 [SMILES: Cn1cc(-c2coc(C(C)(c3ccc(-c4cnc(N)nc4)cc3)C3CC3)n2)cn1] | 74 | 0.81 | 387.3 | E |
| 172 | 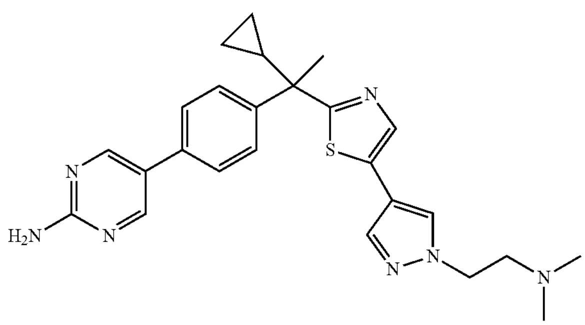 [SMILES: CN(C)CCn1cc(-c2cnc(C(C)(c3ccc(-c4cnc(N)nc4)cc3)C3CC3)s2)cn1] | 88 | 0.61 | 460.3 | E |
| 173 | 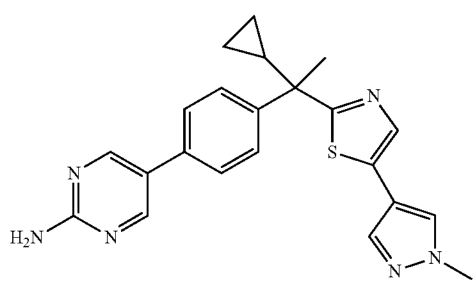 [SMILES: Cn1cc(-c2cnc(C(C)(c3ccc(-c4cnc(N)nc4)cc3)C3CC3)s2)cn1] | 88 | 0.83 | 403.2 | E |
| 174 | 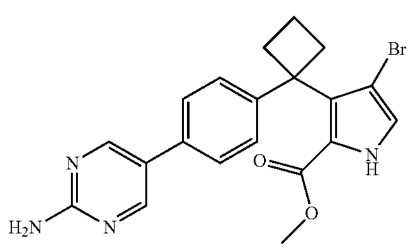 [SMILES: COC(=O)c1[nH]cc(Br)c1C1(c2ccc(-c3cnc(N)nc3)cc2)CCC1] | 75 | 0.93 | 429.2 | E |
| 175 | 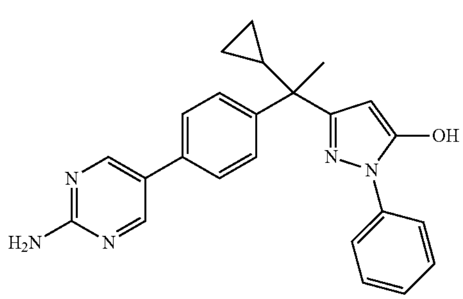 [SMILES: CC(c1ccc(-c2cnc(N)nc2)cc1)(c1cc(O)n(-c2ccccc2)n1)C1CC1] | 74 | 0.90 | 398.3 | E |

TABLE 2-continued

| Example | Structure | Synthesis Method | Retention time (min) | m/z [M + H]+ | LCMS method |
|---|---|---|---|---|---|
| 176 | 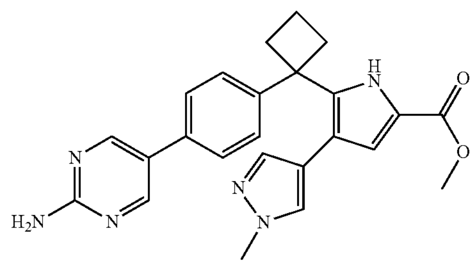 [SMILES: COC(=O)c1cc(-c2cnn(C)c2)c(C2(c3ccc(-c4cnc(N)nc4)cc3)CCC2)[nH]1] | 74 | 0.80 | 429.3 | E |
| 177 | 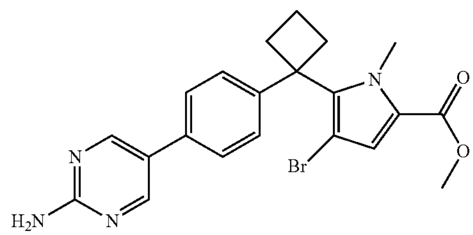 [SMILES: COC(=O)c1cc(Br)c(C2(c3ccc(-c4cnc(N)nc4)cc3)CCC2)n1C] | 73 | 1.10 | 443.1 | E |
| 178 | 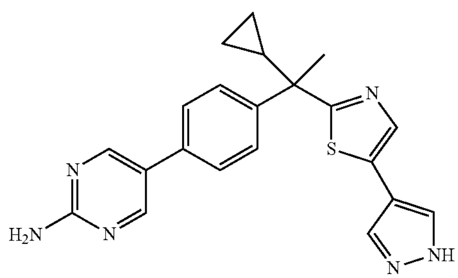 [SMILES: CC(c1ccc(-c2cnc(N)nc2)cc1)(c1ncc(-c2cn[nH]c2)s1)C1CC1] | 74 | 0.80 | 375.19 | E |
| 179 | 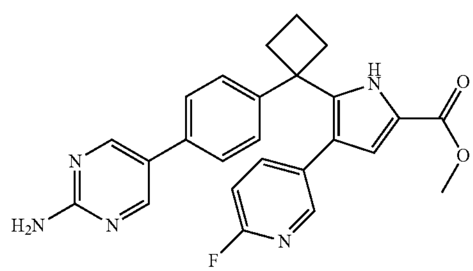 [SMILES: COC(=O)c1cc(-c2ccc(F)nc2)c(C2(c3ccc(-c4cnc(N)nc4)cc3)CCC2)[nH]1] | 74 | 1.47 | 444.4 | F |
| 180 | 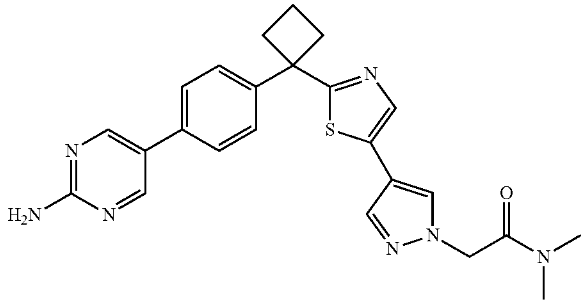 [SMILES: CN(C)C(=O)Cn1cc(-c2cnc(C3(c4ccc(-c5cnc(N)nc5)cc4)CCC3)s2)cn1] | 88 | 0.73 | 460.3 | E |

TABLE 2-continued

| Example | Structure | Synthesis Method | Retention time (min) | m/z [M + H]⁺ | LCMS method |
|---|---|---|---|---|---|
| 181 | 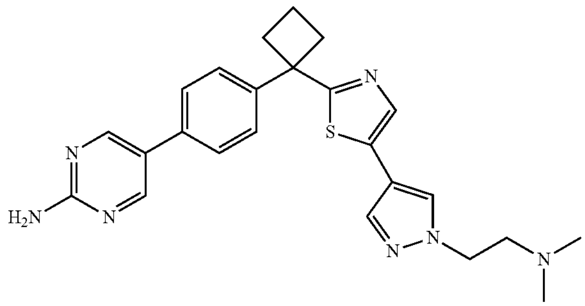 [SMILES: CN(C)CCn1cc(-c2cnc(C3(c4ccc(-c5cnc(N)nc5)cc4)CCC3)s2)cn1] | 88 | 0.58 | 446.3 | E |
| 182 | 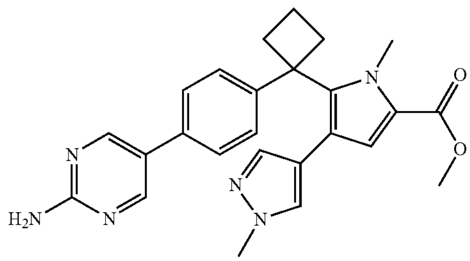 [SMILES: COC(=O)c1cc(-c2cnn(C)c2)c(C2(c3ccc(-c4cnc(N)nc4)cc3)CCC2)n1C] | 74 | 1.52 | 443.4 | F |
| 183 | 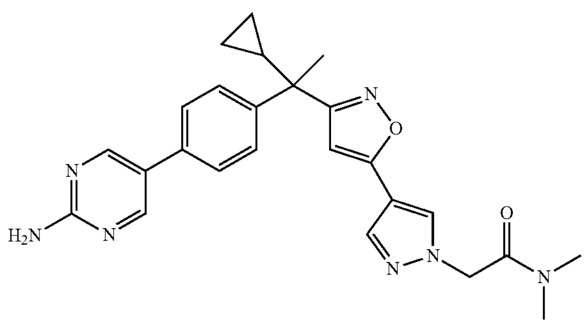 [SMILES: CN(C)C(=O)Cn1cc(-c2cc(C(C)(c3ccc(-c4cnc(N)nc4)cc3)C3CC3)no2)cn1] | 74 | 1.37 | 458.4 | F |
| 184 | 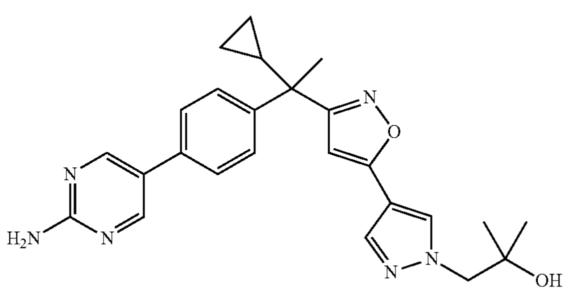 [SMILES: CC(C)(O)Cn1cc(-c2cc(C(C)(c3ccc(-c4cnc(N)nc4)cc3)C3CC3)no2)cn1] | 74 | 1.42 | 445.4 | F |
| 185 | 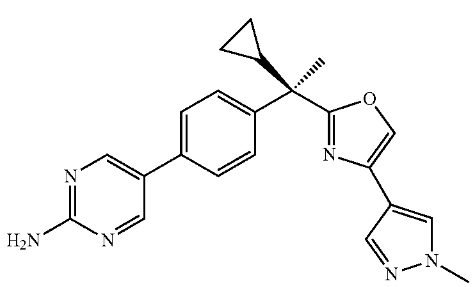 [SMILES: Cn1cc(-c2coc([C@@](C)(c3ccc(-c4cnc(N)nc4)cc3)C3CC3)n2)cn1] | 83 | 0.77 | 387.2 | E |

TABLE 2-continued

| Example | Structure | Synthesis Method | Retention time (min) | m/z [M + H]+ | LCMS method |
|---|---|---|---|---|---|
| 186 | 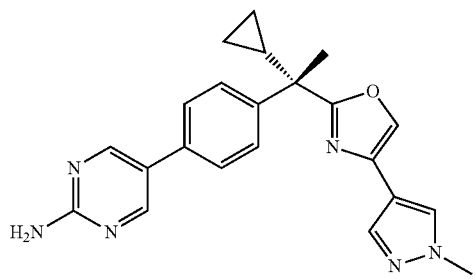 [SMILES: Cn1cc(-c2coc([C@](C)(c3ccc(-c4cnc(N)nc4)cc3)C3CC3)n2)cn1] | 83 | 0.82 | 387.4 | E |
| 187 | 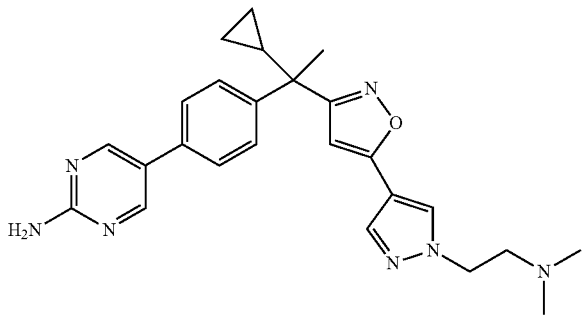 [SMILES: CN(C)CCn1cc(-c2cc(C(C)(c3ccc(-c4cnc(N)nc4)cc3)C3CC3)no2)cn1] | 74 | 1.12 | 444.4 | F |
| 188 | 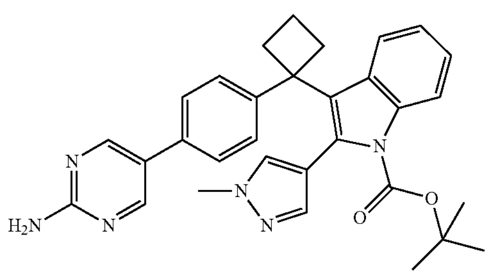 [SMILES: Cn1cc(-c2c(C3(c4ccc(-c5cnc(N)nc5)cc4)CCC3)c3ccccc3n2C(=O)OC(C)(C)C)cn1] | 75 | 1.67 | 521.4 | E |
| 189 | 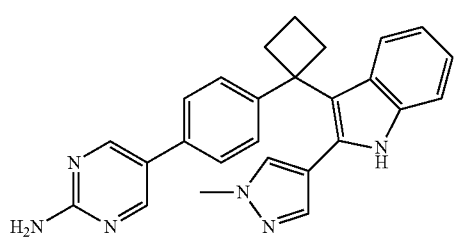 [SMILES: Cn1cc(-c2[nH]c3ccccc3c2C2(c3ccc(-c4cnc(N)nc4)cc3)CCC2)cn1] | 75 | 1.51 | 421.4 | E |
| 190 | 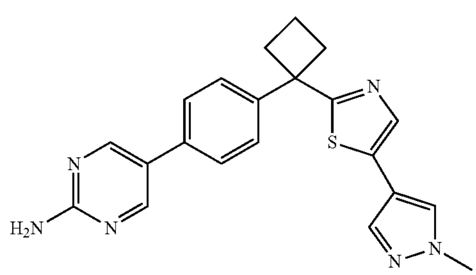 [SMILES: Cn1cc(-c2cnc(C3(c4ccc(-c5cnc(N)nc5)cc4)CCC3)s2)cn1] | 74 | 0.57 | 389.2 | E |

TABLE 2-continued

| Example | Structure | Synthesis Method | Retention time (min) | m/z [M + H]+ | LCMS method |
|---|---|---|---|---|---|
| 191 | 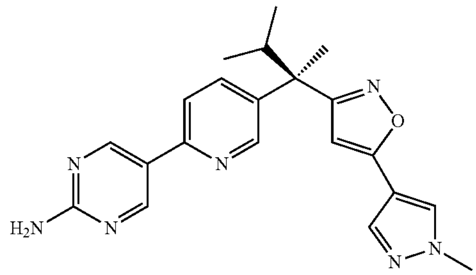 [SMILES: CC(C)[C@](C)(c1ccc(-c2cnc(N)nc2)nc1)c1cc(-c2cnn(C)c2)on1] | 86 | 1.35 | 390.4 | F |
| 192 | 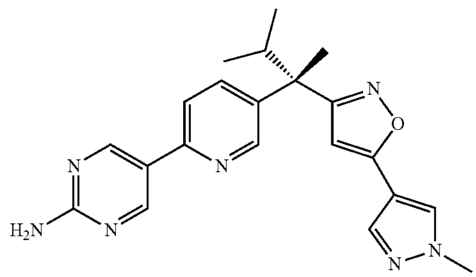 [SMILES: CC(C)[C@@](C)(c1ccc(-c2cnc(N)nc2)nc1)c1cc(-c2cnn(C)c2)on1] | 86 | 1.35 | 390.4 | F |
| 193 | 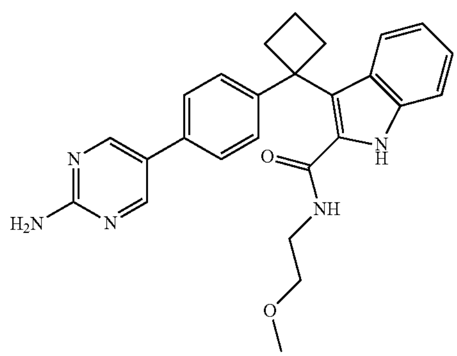 [SMILES: COCCNC(=O)c1[nH]c2ccccc2c1C1(c2ccc(-c3cnc(N)nc3)cc2)CCC1] | 75 | 1.45 | 442.4 | E |
| 194 | 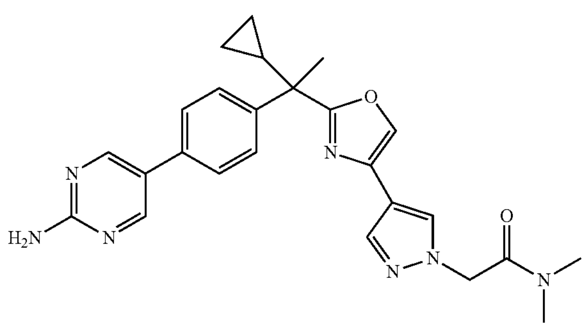 | 88 | 0.68 | 458.2 | E |
| 195 | 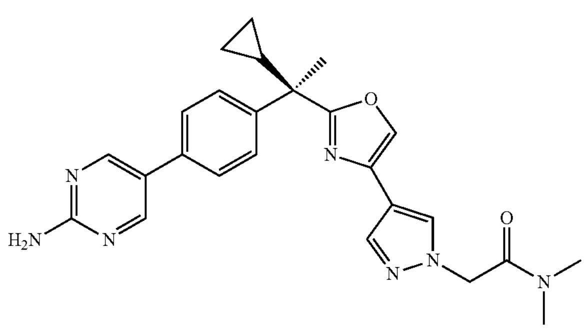 [SMILES: CN(C)C(=O)Cn1cc(-c2coc([C@@](C)(c3ccc(-c4cnc(N)nc4)cc3)C3CC3)n2)cn1] | 86 | 0.72 | 458.3 | E |

TABLE 2-continued
| Example | Structure | Synthesis Method | Retention time (min) | m/z [M + H]+ | LCMS method |
|---|---|---|---|---|---|
| 196 | 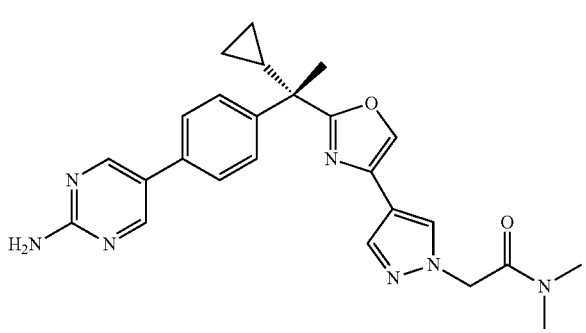 [SMILES: CN(C)C(=O)Cn1cc(-c2coc([C@](C)(c3ccc(-c4cnc(N)nc4)cc3)C3CC3)n2)cn1] | 86 | 0.72 | 458.3 | E |
| 197 | 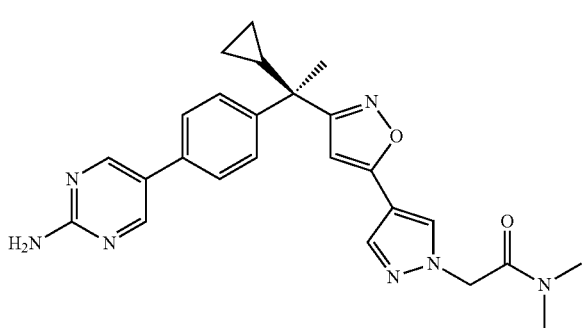 [SMILES: CN(C)C(=O)Cn1cc(-c2cc([C@@](C)(c3ccc(-c4cnc(N)nc4)cc3)C3CC3)no2)cn1] | 86 | 0.74 | 458.3 | E |
| 198 | 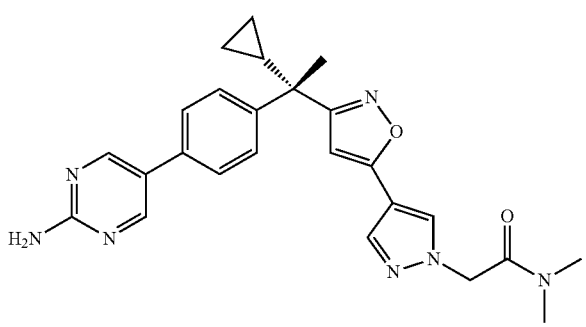 [SMILES: CN(C)C(=O)Cn1cc(-c2cc([C@](C)(c3ccc(-c4cnc(N)nc4)cc3)C3CC3)no2)cn1] | 86 | 0.74 | 458.3 | E |
| 199 | 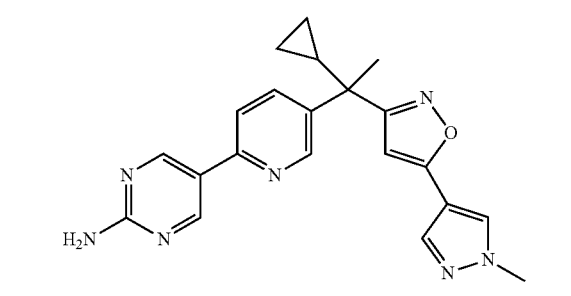 [SMILES: Cn1cc(-c2cc(C(C)(c3ccc(-c4cnc(N)nc4)nc3)C3CC3)no2)cn1] | 43 | 0.66 | 388.3 | E |
| 200 | 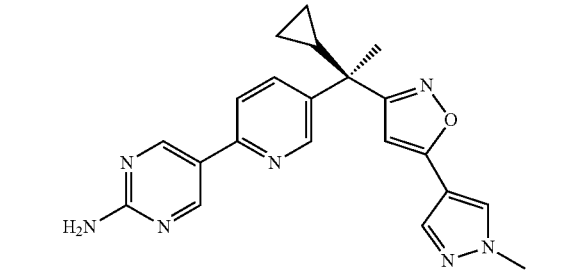 [SMILES: Cn1cc(-c2cc([C@@](C)(c3ccc(-c4cnc(N)nc4)nc3)C3CC3)no2)cn1] | 86 | 0.66 | 388.3 | E |

TABLE 2-continued

| Example | Structure | Synthesis Method | Retention time (min) | m/z [M + H]+ | LCMS method |
|---|---|---|---|---|---|
| 201 | 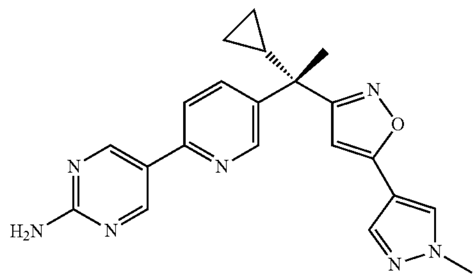 [SMILES: Cn1cc(-c2cc([C@](C)(c3ccc(-c4cnc(N)nc4)nc3)C3CC3)no2)cn1] | 86 | 0.66 | 388.3 | E |
| 202 | 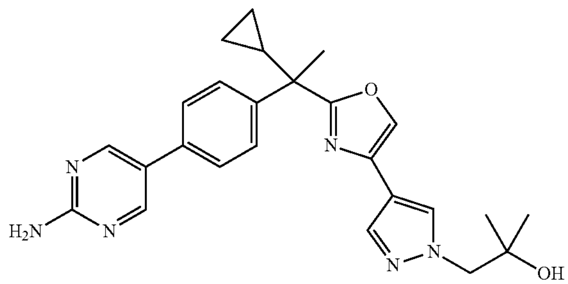 | 88 | 0.77 | 445.7 | E |
| 203 | 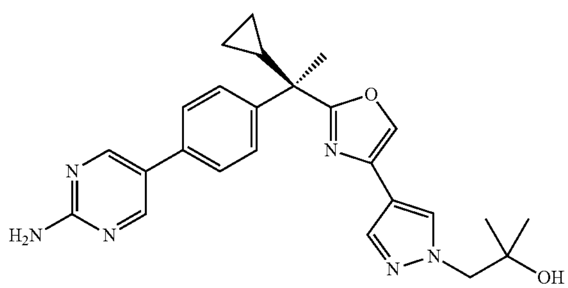 | 86 | 0.77 | 445.7 | E |
| 204 | 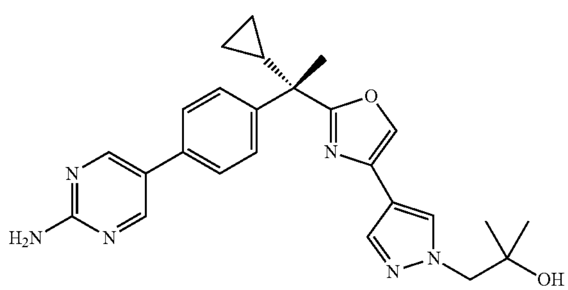 [SMILES: CC(C)(O)Cn1cc(-c2coc([C@](C)(c3ccc(-c4cnc(N)nc4)cc3)C3CC3)n2)cn1] | 86 | 0.77 | 445.7 | E |
| 205 | 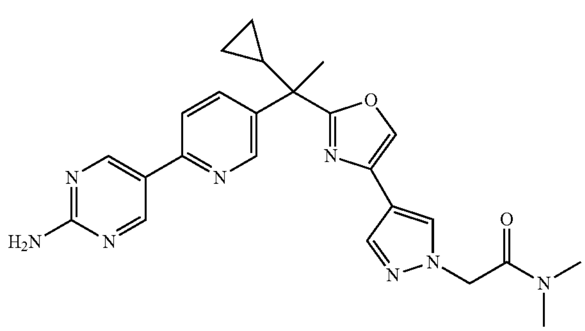 [SMILES: CN(C)C(=O)Cn1cc(-c2coc(C(C)(c3ccc(-c4cnc(N)nc4)nc3)C3CC3)n2)cn1] | 88 | 0.61 | 459.7 | E |

TABLE 2-continued

| Example | Structure | Synthesis Method | Retention time (min) | m/z [M + H]+ | LCMS method |
|---|---|---|---|---|---|
| 206 | 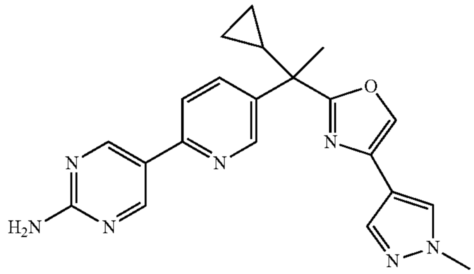 [SMILES: Cn1cc(-c2coc(C(C)(c3ccc(-c4cnc(N)nc4)nc3)C3CC3)n2)cn1] | 43 | 0.65 | 388.1 | E |
| 207 | 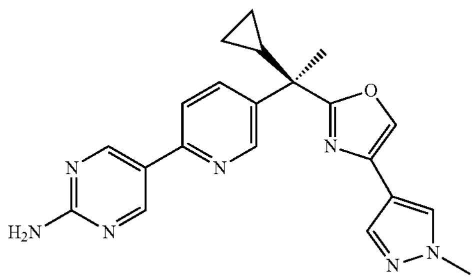 [SMILES: Cn1cc(-c2coc([C@@](C)(c3ccc(-c4cnc(N)nc4)nc3)C3CC3)n2)cn1] | 86 | 0.66 | 388.6 | E |
| 208 | 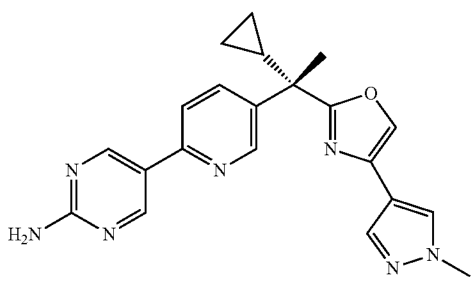 [SMILES: Cn1cc(-c2coc([C@](C)(c3ccc(-c4cnc(N)nc4)nc3)C3CC3)n2)cn1] | 86 | 0.66 | 388.6 | E |
| 209 | 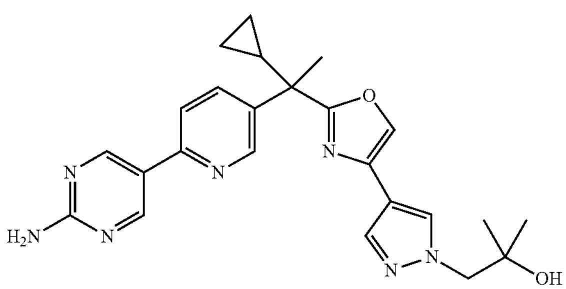 [SMILES: CC(C)(O)Cn1cc(-c2coc(C(C)(c3ccc(-c4cnc(N)nc4)nc3)C3CC3)n2)cn1] | 88 | 0.67 | 446.7 | E |
| 210 | 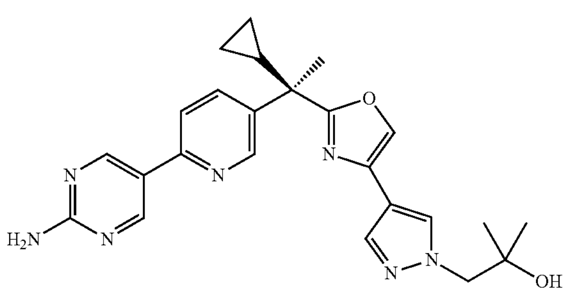 | 86 | 0.67 | 446.7 | E |

TABLE 2-continued

| Example | Structure | Synthesis Method | Retention time (min) | m/z [M + H]+ | LCMS method |
|---|---|---|---|---|---|
| 211 | 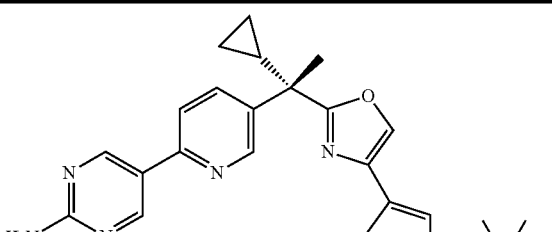 | 86 | 0.67 | 446.7 | E |
| 212 | 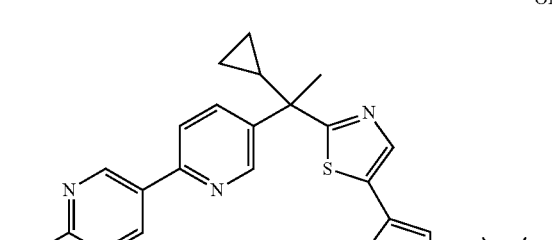 | 50 | 0.69 | 462.6 | E |

Assessment of Biological Properties

1. Binding Assay

Compounds are assessed for the ability to bind to FLAP in a binding assay that measures compound-specific displacement of an iodinated ($^{125}$I) FLAP inhibitor via a Scintillation Proximity Assay format (adapted from S. Charleson et al., Mol. Pharmacol., 1992, 41, 873-879).

Cell pellets produced from sf9 insect cells expressing recombinant human FLAP protein are resuspended in buffer A [15 mM Tris-HCl (pH 7.5), 2 mM MgCl$_2$, 0.3 mM EDTA, 1 mM PMSF]. The cells are lysed with a Dounce homogenizer and the material is centrifuged at 10,000×g for 10 minutes. The supernatant is then collected and centrifuged at 100,000×g for 60 minutes. To prepare membrane protein for an assay, an aliquot of the 100,000×g pellet is resuspended in 1 ml of buffer A, Dounce homogenized, and finally subjected to polytron mixing (30 seconds). Membrane protein (25 μl, 5 μg) is mixed with WGA SPA beads (Amersham) and stirred for 1 h. To an assay plate (Perkin Elmer FlexiPlate) is added 25 μl of test compound prepared in Binding buffer [100 mM Tris (pH 7.5), 140 mM NaCl, 5% glycerol, 2 mM EDTA, 0.5 mM TCEP, 0.05% Tween 20], 25 μl of [$^{125}$I]L-691,831 (an iodinated analog of MK-591, Charleson et al. Mol. Pharmacol., 41, 873-879, 1992) and finally 50 μl of the bead/protein mixture. (final concentrations: beads, 200 μg/well; protein, 5 μg/well; [$^{125}$I] probe, 0.08 nM/well (17 nCi/well). The plates are shaken for 2 h before reading on a Microbeta plate reader. Non-specific binding is determined by the addition of 10 μM cold L-691,831 compound.

In general, the preferred potency range (IC$_{50}$) of compounds in the above assay is between 0.1 nM to 10 μM, the more preferred potency range is 0.1 nM to 1 μM, and the most preferred potency range is 0.1 nM to 100 nM.

2. Whole Blood Assay:

Compounds are additionally tested in a human whole blood assay to determine their ability to inhibit the synthesis of LTB$_4$ in a cellular system. Compounds are combined with heparinized human whole blood and incubated for 15 minutes at 37° C. Calcimycin (20 μM final, prepared in phosphate-buffered saline, pH 7.4) is then added and the mixture is incubated for another 30 minutes at 37° C. The samples are centrifuged for 5 min at low speed (1500×g) and the plasma layer is removed. Plasma LTB$_4$ concentrations are then measured using an antibody-based homogenous time-resolved fluorescence method (CisBio, Bedford, Mass.).

Method of Use

The compounds of the invention are effective inhibitors of 5-lipoxygenase activating protein (FLAP) and thus suggest they inhibit leukotriene production. Therefore, in one embodiment of the invention, there is provided methods of treating leukotriene-mediated disorders using compounds of the invention or their pharmaceutically acceptable salts thereof. In another embodiment, there is provided methods of treating cardiovascular, inflammatory, allergic, pulmonary and fibrotic diseases, renal diseases and cancer using compounds of the invention or their pharmaceutically acceptable salts thereof.

Without wishing to be bound by theory, by inhibiting the activity of FLAP, the compounds of the invention block the production of LTs resulting from the oxidation of arachidonic acid by 5-LO and subsequent metabolism. Thus, the inhibition of FLAP activity is an attractive means for preventing and treating a variety of diseases mediated by LTs. These include:
Cardiovascular diseases including atherosclerosis, myocardial infarction, stroke, aortic aneurysm, sickle cell crisis, ischemia-reperfusion injury, pulmonary arterial hypertension and sepsis;
Allergic diseases including asthma, allergic rhinitis, rhinosinusitis, atopic dermatitis and urticaria;
Fibrotic diseases including airway remodeling in asthma, idiopathic pulmonary fibrosis, scleroderma, asbestosis;
Pulmonary syndromes including adult respiratory distress syndrome, viral bronchiolitis, obstructive sleep apnea, chronic obstructive pulmonary disease, cystic fibrosis, and bronchopulmonary dysplasia;

Inflammatory diseases including rheumatoid arthritis, osteoarthritis, gout, glomerulonephritis, interstitial cystitis, psoriasis, inflammatory bowel disease, inflammatory pain, multiple sclerosis, systemic lupus erythematosus, transplant rejection, inflammatory and allergic ocular diseases;
Cancer including solid tumors, leukemias and lymphomas; and
Renal diseases such as glomerulonephritis.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy*, 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; H. C. Ansel and N. G. Popovish, *Pharmaceutical Dosage Forms and Drug Delivery Systems*, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

Combination Therapy

The compounds of the invention may be administered alone or in combination with at least one additional active agent. Thus, in one embodiment, the invention relates to a pharmaceutical composition comprising one or more compounds of the invention in combination with at least one additional agent. In another embodiment, the invention relates a method of treating diseases mediated by $LTB_4$, the method comprising administering a therapeutically effective amount of one or more compounds of the invention in combination with at least one additional agent.

Nonlimiting examples of additional active agents include statins (or HMG-CoA reductase inhibitors); cholesterol ester transfer protein (CETP) inhibitors (or antagonists); fibrates, niacin derivatives, Lp-PLA2-inhibitors (e.g., darapladib, varespladib), antiplatelets and anticoagulants.

In one embodiment, the additional active agent is a statin. In another embodiment, the additional active agent is a statin selected from the group consisting of atorvastatin, fluvastatin, lovastatin, pitavastatin, pravastatin, rosuvastatin, and simvastatin.

In one embodiment, the additional active agent is a CETP inhibitor. In another embodiment, the additional active agent is a CETP inhibitor selected from the group consisting of anacetrapib, dalcetrapib, evacetrapib, TA-8995 (Mitsubishi Tanabe Pharma), ATH-03 (Affris), DRL-17822 (Dr. Reddy's). In yet another embodiment, the additional active is selected from dalcetrapib and anacetrapib.

What is claimed is:
1. A compound of formula I, wherein:

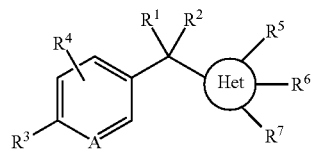

A is carbon;
$R^1$ and $R^2$ together with the carbon atom to which they are attached form a $C_{3-10}$ carbocyclic ring, wherein each carbocycle is optionally independently substituted with one to two groups selected from $C_{1-6}$ alkyl and halogen;
$R^3$ is a 5-11 membered heteroaryl ring containing one to three nitrogen, wherein the heteroaryl ring is optionally independently substituted with one to three groups selected from $C_{1-5}$alkyl, —O—$C_{1-5}$alkyl, $C_{1-3}$ alkylhydroxy, halogen, hydroxy, amino, $C_{1-6}$ alkylamino and $C_{1-3}$ dialkylamino;
$R^4$ is hydrogen, $C_{1-3}$ alkyl, halogen or nitrile;
HET is indolyl
$R^5$, $R^6$ and $R^7$ are each independently selected from
  (a) —H,
  (b) —OH,
  (c) halogen,
  (d) —CN, (e) $C_{1-6}$alkyl optionally substituted with one to three —OH, —O—$C_{1-6}$alkyl, —N($R^8$)($R^9$), —O—$C_{1-6}$alkyl-OH, —$CO_2R^8$, —C(O)N($R^8$)($R^9$) or —S(O)$_n$ $C_{1-6}$alkyl, aryl optionally substituted with halogen, 5-11 membered heteroaryl ring optionally substituted with $C_{1-4}$ alkyl-OH, 3-8 membered heterocycle optionally substituted with $C_{1-4}$ alkyl,
(f) —O—$C_{1-6}$alkyl optionally substituted with 5-11 membered heteroaryl ring,
(g) —O-heterocycle
(h) —N($R^8$)($R^9$),
(i) —S(O)$_n$$C_{1-6}$alkyl,
(j) —S(O)$_n$aryl,
(k) —$CO_2R^8$,
(l) —C(O)N($R^8$)($R^9$),
(m) —S(O)$_2$N($R^8$)($R^9$),
(n') oxo,
(o) —C(O)—$C_{1-3}$ alkyl
(p) $C_{3-10}$ carbocycle,
(q) a 3-10 membered heterocyclic group optionally substituted with one to three $C_{1-6}$ alkyl groups,
(r) a 5-11 membered heteroaryl group optionally substituted with one to three substituents selected from $C_{1-4}$ alkyl, $C_{1-4}$ alkyl-OH, —O—$C_{1-4}$ alkyl, $C_{1-4}$ alkyl-N($R^8$)($R^9$), $C_{1-4}$ alkyl-C(O)N($R^8$)($R^9$), —N($R^8$)($R^9$) and halogen,
(s) aryl optionally substituted with halogen;
$R^8$ and $R^9$ are each independently selected from —H, —$C_{1-6}$alkyl, —C(O)$C_{1-6}$alkyl, and a 3-6 membered heterocyclic group, each of which is optionally independently substituted with one to three $C_{1-6}$alkyl groups, —OH, —C(O)N($R^{10}$)($R^{11}$), —S(O)$_n$$C_{1-6}$alkyl, —S(O)$_n$N($R^{10}$)($R^{11}$), CN, a 3-6 membered heterocyclic group which is optionally substituted with one to two groups selected from $C_{1-3}$ alkyl, —O$C_{1-6}$alkyl, and oxo;
or
$R^8$ and $R^9$ taken together with the nitrogen ring to which they are attached form a heterocyclyl ring optionally substituted with one to three —OH, CN, —O$C_{1-6}$alkyl or oxo;
$R^{10}$ and $R^{11}$ are each independently selected from —H and —$C_{1-6}$alkyl;
n is 0, 1 or 2;
or a pharmaceutically acceptable salt thereof.

2. The compound according to claim 1, wherein:
A is carbon;
$R^1$ and $R^2$ together with the carbon atom to which they are attached form a cyclopropyl, cyclobutyl, cyclopentyl, cylohexyl ring each optionally independently substituted with one to two groups selected from $C_{1-3}$ alkyl and halogen;
$R^3$ is pyrimidinyl, wherein the heteroaryl ring is optionally independently substituted with one to three groups selected from $C_{1-3}$ alkyl, —O—$C_{1-3}$ alkyl, $C_{1-3}$ alkylhydroxy, halogen, hydroxy, amino, $C_{1-3}$alkylamino and $C_{1-3}$ dialkylamino;
$R^4$ is hydrogen, methyl or fluoro;
HET is indolyl;
$R^5$, $R^6$ and $R^7$ are each independently selected from
(a) —H,
(b) —OH,
(c) halogen,
(d) —CN,
(e) $C_{1-6}$alkyl optionally substituted with one to three —OH, —O—$C_{1-6}$alkyl, —N($R^8$)($R^9$), —$CO_2R^8$, —C(O)N($R^8$)($R^9$) or —S(O)$_n$$C_{1-6}$alkyl, aryl optionally substituted with halogen, 5-11 membered heteroaryl ring optionally substituted with $C_{1-4}$ alkyl-OH, 3-8 membered heterocycle optionally substituted with $C_{1-4}$ alkyl,
(f) —O—$C_{1-6}$alkyl optionally substituted with 5-11 membered heteroaryl ring,
(g) —O-heterocycle
(h) —N($R^8$)($R^9$),
(i) —S(O)$_n$$C_{1-6}$alkyl,
(j) —S(O)$_n$aryl,
(k) —$CO_2R^8$,
(l) —C(O)N($R^8$)($R^9$),
(m) —S(O)$_2$N($R^8$)($R^9$),
(n') oxo,
(o) —C(O)—$C_{1-3}$ alkyl
(p) $C_{3-10}$ carbocycle,
(q) a 3-10 membered heterocyclic group optionally substituted with one to three $C_{1-6}$ alkyl groups,
(r) a 5-11 membered heteroaryl group optionally substituted with one to three substituents selected from $C_{1-4}$ alkyl, $C_{1-4}$ alkyl-OH, —O—$C_{1-4}$ alkyl, $C_{1-4}$ alkyl-N($R^8$)($R^9$), $C_{1-4}$ alkyl-C(O)N($R^8$)($R^9$), —N($R^8$)($R^9$) and halogen,
(s) aryl optionally substituted with halogen;
$R^8$ and $R^9$ are each independently selected from —H, —$C_{1-6}$alkyl, —C(O)$C_{1-6}$alkyl, and a 3-6 membered heterocyclic group, each of which is optionally independently substituted with one to three $C_{1-6}$alkyl groups, —OH, —O—$C_{1-6}$alkyl, —C(O)N($R^{10}$)($R^{11}$), —S(O)$_n$$C_{1-6}$alkyl, —S(O)N($R^{10}$)($R^{11}$), CN, a 3-6 membered heterocyclic group which is optionally substituted with one to two groups selected from $C_{1-3}$ alkyl, —O$C_{1-6}$ alkyl, and oxo;
or
$R^8$ and $R^9$ taken together with the nitrogen ring to which they are attached form a heterocyclyl ring optionally substituted with one to three —OH, CN, —O$C_{1-6}$alkyl or oxo;
$R^{10}$ and $R^{11}$ are each independently selected from —H and —$C_{1-6}$alkyl;
n is 1 or 2;
or a pharmaceutically acceptable salt thereof.

3. The compound according to claim 1, wherein:
$R^1$ and $R^2$ together with the carbon atom to which they are attached form a cyclopropyl, cyclobutyl, cyclopentyl, or cylohexyl ring;
or a pharmaceutically acceptable salt thereof.

4. The compound according to claim 1, wherein:
$R^3$ is pyrimidinyl, wherein the heteroaryl ring is optionally independently substituted with one to three groups selected from $C_{1-3}$ alkyl, —O—$C_{1-3}$ alkyl, $C_{1-3}$ alkylhydroxy, halogen, hydroxy, amino, $C_{1-3}$alkylamino and $C_{1-3}$dialkylamino;
or a pharmaceutically acceptable salt thereof.

5. The compound according to claim 1, wherein:
$R^4$ is hydrogen or methyl;
or a pharmaceutically acceptable salt thereof.

6. The compound according to claim 1, wherein:
$R^5$, $R^6$ and $R^7$ are each independently selected from
(a) —H,
(b) —OH,
(c) halogen,
(d) —CN,
(e) $C_{1-6}$alkyl optionally substituted with one to three —OH, —O—$C_{1-6}$alkyl, —N($R^8$)($R^9$), —O—$C_{1-6}$alkyl-OH, —$CO_2R^8$, —C(O)N($R^8$)($R^9$) or —S(O)$_2$ $C_{1-3}$alkyl, phenyl optionally substituted with halogen, pyridinyl optionally substituted with $C_{1-4}$ alkyl-OH, tetrazolyl, piperazinyl optionally substituted with a methyl group,
(f) —O—$C_{1-6}$alkyl optionally substituted with a quinolinyl or isoquinolinyl ring,
(g) —O-heterocycle wherein the heterocycle is tetrahydrofuranyl or tetrahydropyranyl,
(h) —N($R^8$)($R^9$),
(i) —S(O)$_2C_{1-3}$ alkyl,
(j) —S(O)$_2$ phenyl,
(k) —CO$_2R^8$,
(l) —C(O)N($R^8$)($R^9$),
(m) —S(O)$_2$N($R^8$)($R^9$),
(n') oxo,
(o) —C(O)—$C_{1-3}$ alkyl
(p) $C_{3-10}$ carbocycle,
(q) a piperazinyl group optionally substituted with a methyl group,
(r) a 5-11 membered heteroaryl group selected from pyridinyl, pyrimidinyl, pyrazolyl, oxadiazolyl and tetrazolyl wherein each heteroaryl ring is optionally substituted with one to three substituents selected from $C_{1-4}$ alkyl, $C_{1-2}$ alkyl-OH, —O—$C_{1-2}$ alkyl, $C_{1-2}$alkyl-N($R^8$)($R^9$), $C_{1-4}$ alkyl-C(O)N($R^8$)($R^9$), —N($R^8$)($R^9$) and halogen,
(s) phenyl ring optionally substituted with halogen;
$R^8$ and $R^9$ are each independently selected from —H, —$C_{1-6}$alkyl, —C(O)$C_{1-6}$alkyl, and a 3-6 membered heterocyclic group, each of which is optionally independently substituted with one to three $C_{1-6}$alkyl groups, —OH, —O—$C_{1-6}$alkyl, —C(O)N($R^{10}$)($R^{11}$), —S(O)$_2$ $C_{1-6}$alkyl,
—S(O)$_2$N($R^{10}$)($R^{11}$), a 3-6 membered heterocyclic group which is optionally substituted with one to two groups selected from $C_{1-3}$ alkyl, —OC$_{1-3}$alkyl, and oxo;
or
$R^8$ and $R^9$ taken together with the nitrogen ring to which they are attached form a heterocyclyl ring optionally substituted with one to three —OH, CN, —OC$_{1-3}$alkyl or oxo;
$R^{10}$ and $R^{11}$ are each independently selected from —H and —$C_{1-4}$alkyl;
or a pharmaceutically acceptable salt thereof.

7. The compound according to claim 1, wherein:
A is carbon;
$R^1$ and $R^2$ together with the carbon atom to which they are attached form a cyclopropyl, cyclobutyl, cyclopentyl, or cylohexyl ring; or
$R^3$ is pyrimidinyl optionally independently substituted with one to three groups selected from $C_{1-3}$ alkyl, —O—$C_{1-3}$ alkyl, $C_{1-3}$ alkylhydroxy, halogen, hydroxy, amino, $C_{1-3}$alkylamino and $C_{1-3}$dialkylamino;
$R^4$ is hydrogen;
HET is indolyl;
$R^5$, $R^6$ and $R^7$ are each independently selected from
(a) —H,
(b) —OH,
(c) halogen,
(d) —CN,
(e) $C_{1-6}$alkyl optionally substituted with one to three —OH, —O—$C_{1-6}$alkyl, —N($R^8$)($R^9$), —O—$C_{1-6}$ alkyl-OH, —CO$_2R^8$, —C(O)N($R^8$)($R^9$) or —S(O)$_2$ $C_{1-3}$alkyl, phenyl optionally substituted with halogen, pyridinyl optionally substituted with $C_{1-4}$ alkyl-OH, tetrazolyl, piperazinyl optionally substituted with a methyl group,
(f) —O—$C_{1-6}$alkyl optionally substituted with a quinolinyl or isoquinolinyl ring,
(g) —O-heterocycle wherein the heterocycle is tetrahydrofuranyl or tetrahydropyranyl,
(h) —N($R^8$)($R^9$),
(i) —S(O)$_2C_{1-3}$alkyl,
(j) —S(O)$_2$ phenyl,
(k) —CO$_2R^8$,
(l) —C(O)N($R^8$)($R^9$),
(m) —S(O)$_2$N($R^8$)($R^9$),
(n') oxo,
(o) —C(O)—$C_{1-3}$ alkyl
(p) $C_{3-10}$ carbocycle,
(q) a piperazinyl group optionally substituted with a methyl group,
(r) a 5-11 membered heteroaryl group selected from pyridinyl, pyrimidinyl, pyrazolyl, oxadiazolyl and tetrazolyl wherein each heteroaryl ring is optionally substituted with one to three substituents selected from $C_{1-4}$ alkyl, $C_{1-2}$ alkyl-OH, —O—$C_{1-2}$ alkyl, $C_{1-2}$alkyl-N($R^8$)($R^9$), $C_{1-4}$ alkyl-C(O)N($R^8$)($R^9$), —N($R^8$)($R^9$) and halogen,
(s) phenyl ring optionally substituted with halogen;
$R^8$ and $R^9$ are each independently selected from —H, —$C_{1-6}$alkyl, —C(O)$C_{1-6}$alkyl, and a 3-6 membered heterocyclic group, each of which is optionally independently substituted with one to three $C_{1-6}$alkyl groups, —OH, —O—$C_{1-6}$alkyl, —C(O)N($R^{10}$)($R^{11}$), —S(O)$_2$ $C_{1-6}$alkyl,
—S(O)$_2$N($R^{10}$)($R^{11}$) a 3-6 membered heterocyclic group which is optionally substituted with one to two groups selected from $C_{1-3}$ alkyl, —OC$_{1-3}$alkyl, and oxo;
or
$R^8$ and $R^9$ taken together with the nitrogen ring to which they are attached form a heterocyclyl ring optionally substituted with one to three —OH, CN, —OC$_{1-3}$alkyl or oxo;
$R^{10}$ and $R^{11}$ are each independently selected from —H and —$C_{1-4}$alkyl;
or a pharmaceutically acceptable salt thereof.

8. A compound selected from a group consisting of:

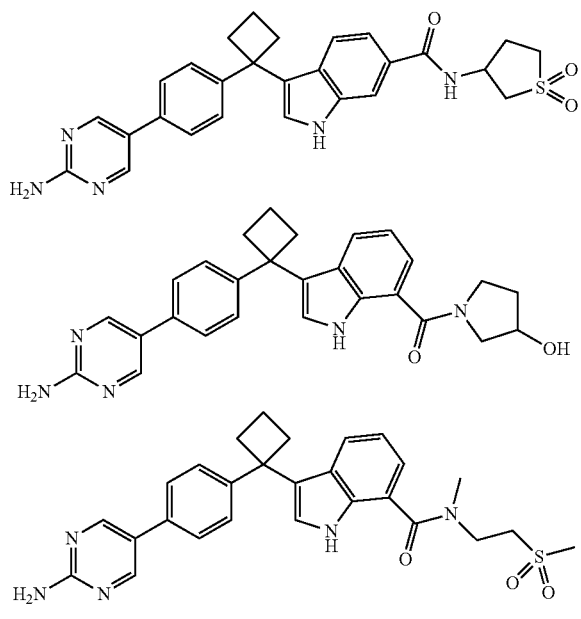

297
-continued
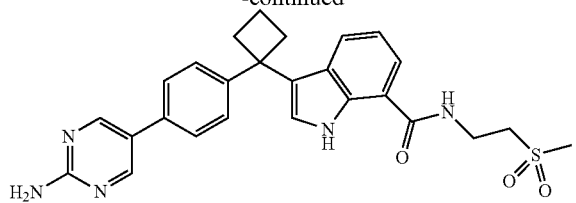
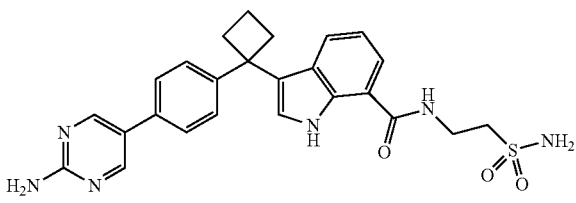
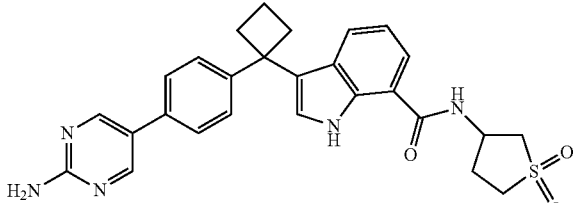
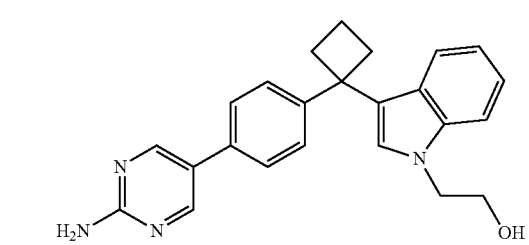
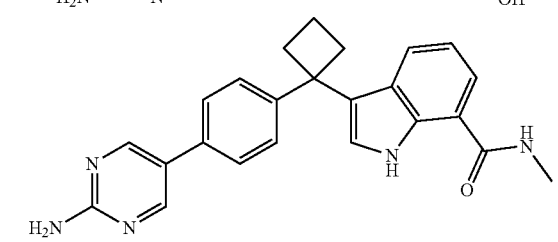
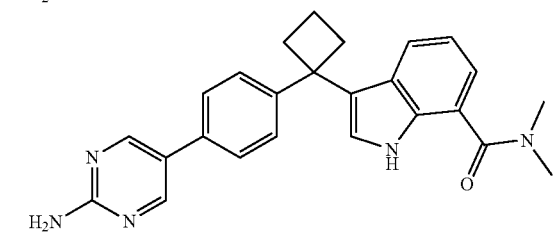
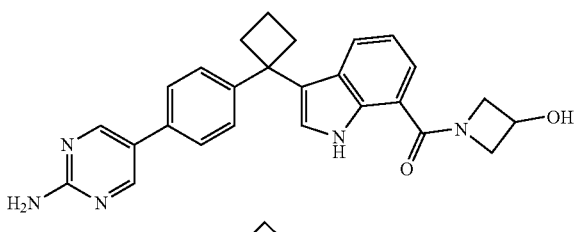
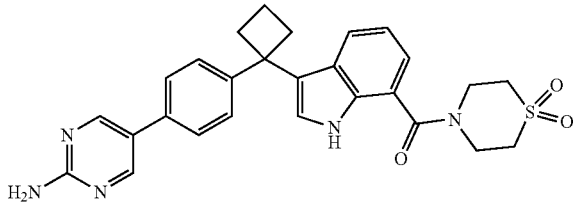
298
-continued
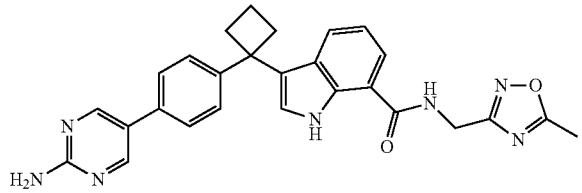
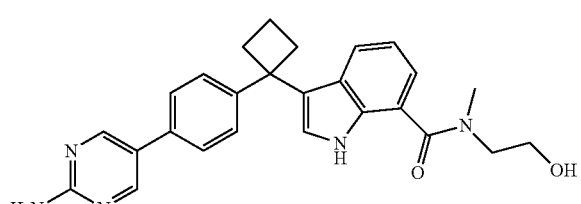
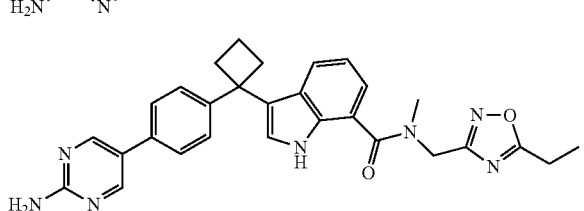
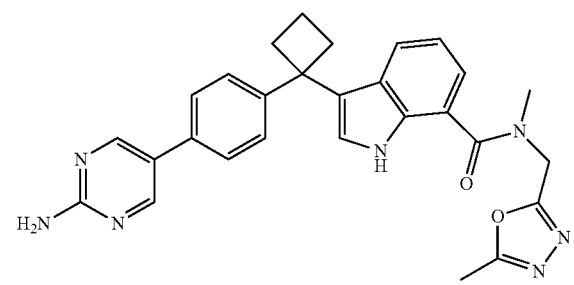
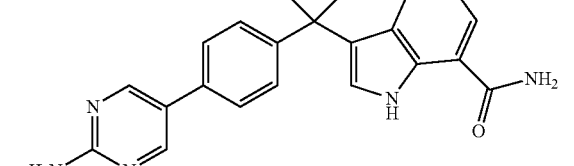
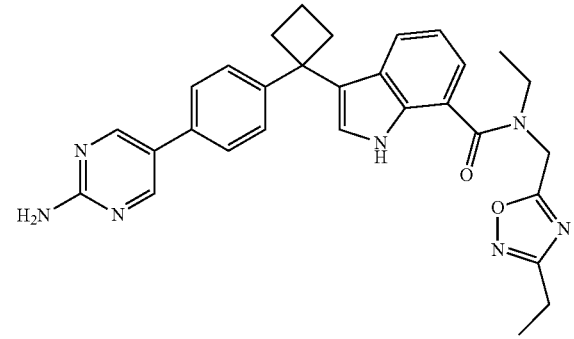

299
-continued
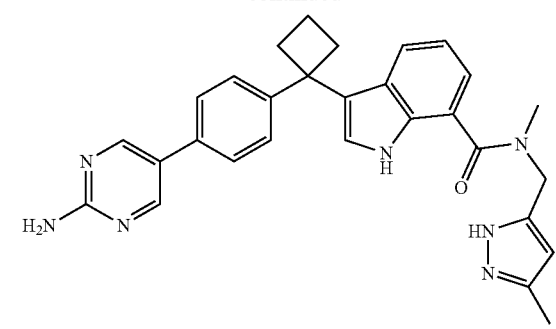
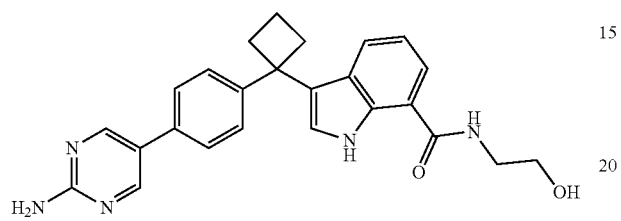
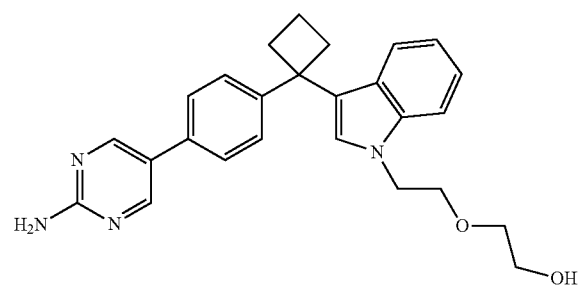
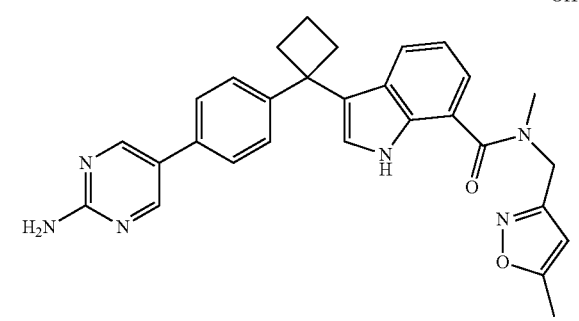
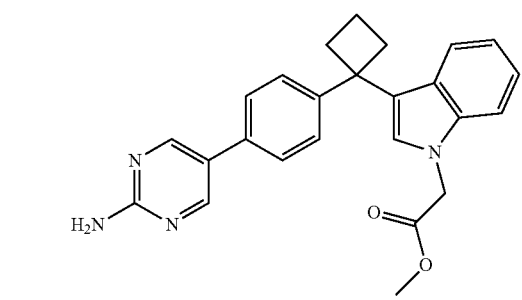
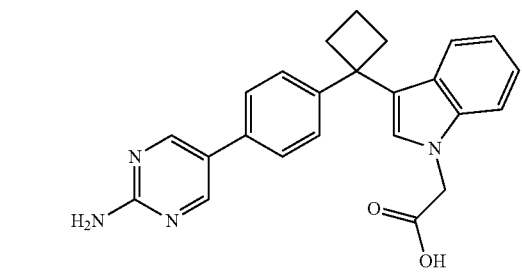
300
-continued
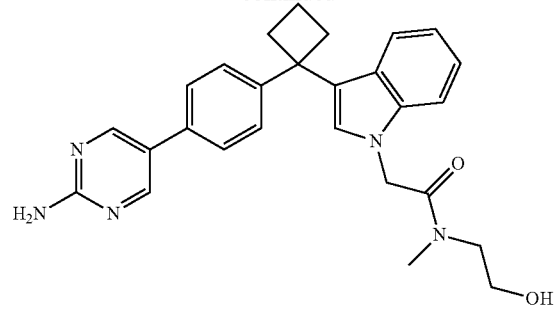 [SMILES: CN(CCO)C(=O)Cn1cc(C2(c3ccc(-c4cnc(N)nc4)cc3)CCC2)c2ccccc21]
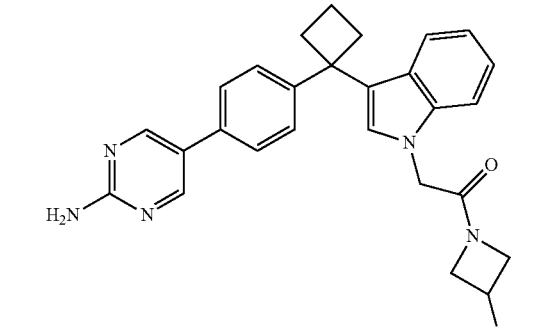
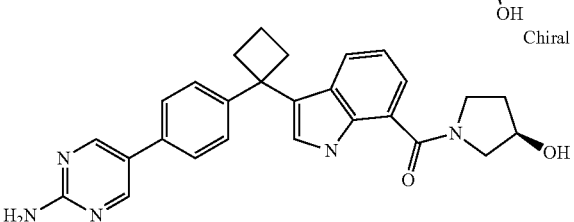
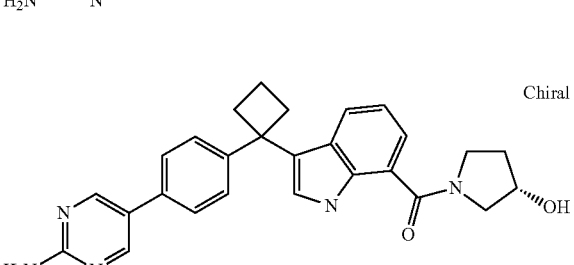
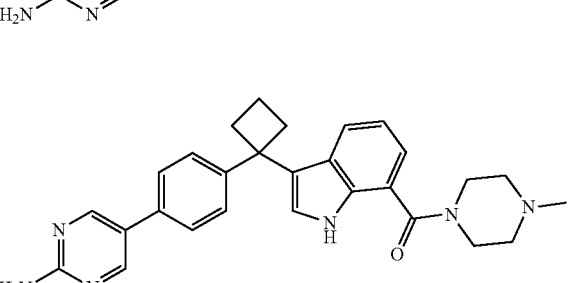
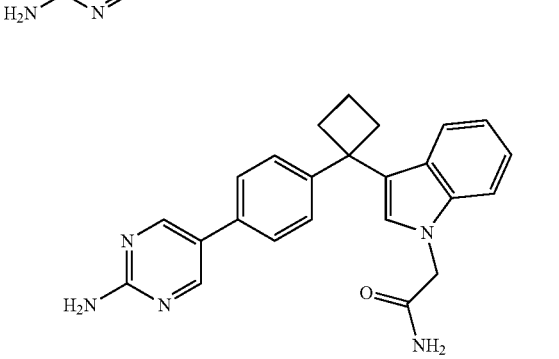

301
-continued
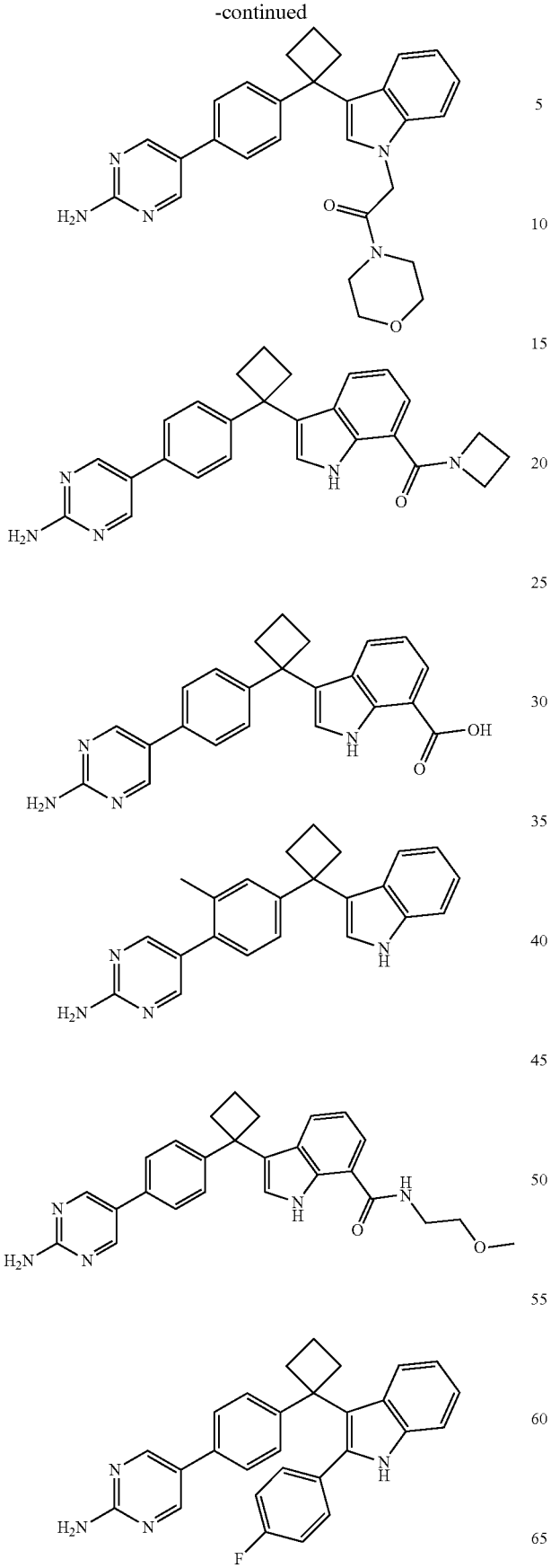
302
-continued
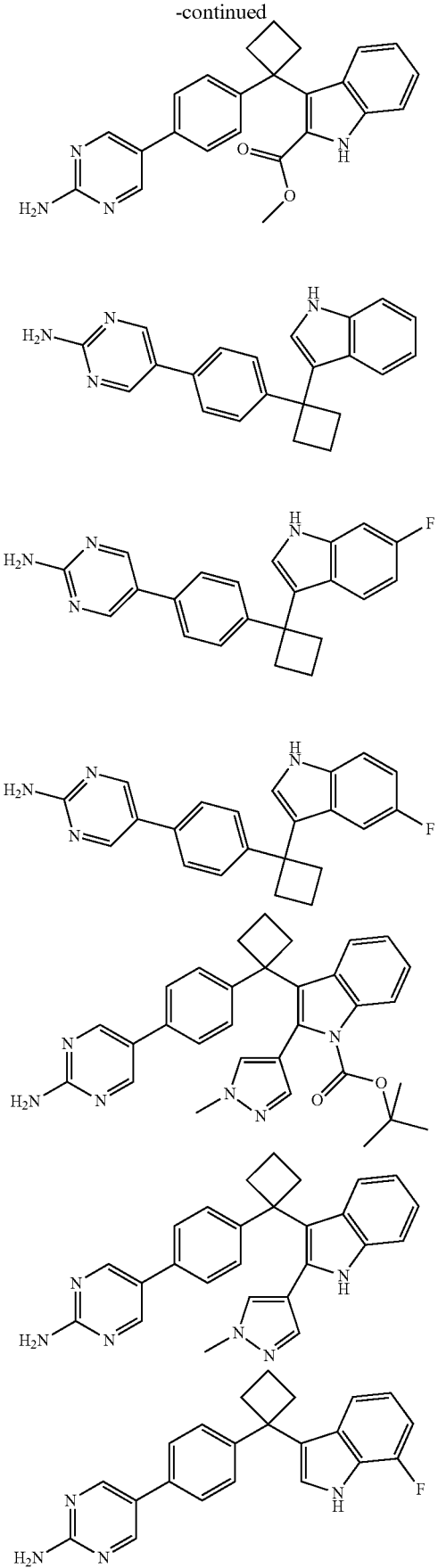

303
-continued
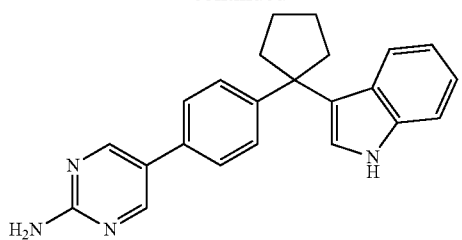
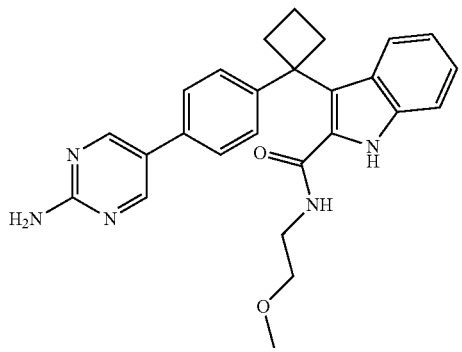
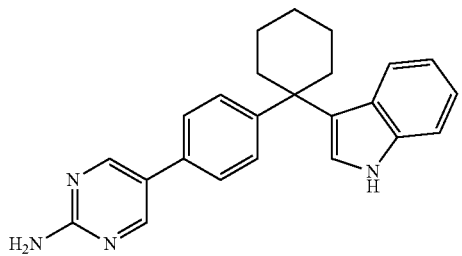
304
-continued
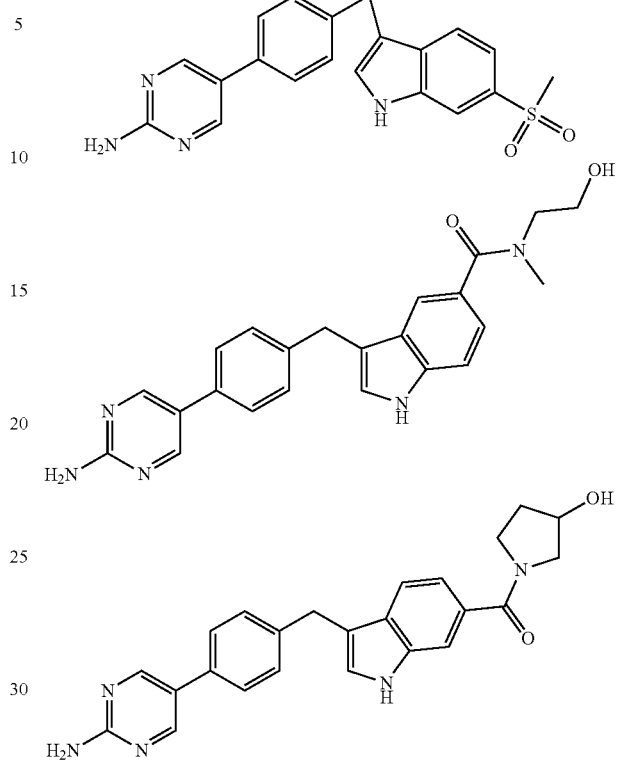
or pharmaceutically acceptable salts thereof.
9. A pharmaceutical composition comprising a compound according to claim 1, or a pharmaceutically acceptable salt thereof, and a pharmaceutically acceptable excipient and/or carrier.
* * * * *